United States Patent
Hong et al.

(10) Patent No.: US 11,542,339 B2
(45) Date of Patent: Jan. 3, 2023

(54) ANTI-CD43 ANTIBODY AND USE THEREOF FOR CANCER TREATMENT

(71) Applicant: Aprogen Medicines Inc., Seongnam-si (KR)

(72) Inventors: Kwon Pyo Hong, Cheongju-si (KR); Sangsoon Yoon, Seoul (KR); Irene Koukoulas, Watsonia North (AU); Vincent Batori, Munich (DE); Briony Cristiano, Gaithersburg, MA (US); David S Wilson, Jr., Redwood City, CA (US); George Kopsidas, Preston (AU)

(73) Assignee: APROGEN INC., Seongnam-si (KR)

( * ) Notice: Subject to any disclaimer, the term of this patent is extended or adjusted under 35 U.S.C. 154(b) by 262 days.

(21) Appl. No.: 16/871,280

(22) Filed: May 11, 2020

(65) Prior Publication Data

US 2020/0392240 A1 Dec. 17, 2020

Related U.S. Application Data

(62) Division of application No. 15/767,179, filed as application No. PCT/KR2016/011428 on Oct. 12, 2016, now Pat. No. 10,676,531.

(60) Provisional application No. 62/240,276, filed on Oct. 12, 2015.

(30) Foreign Application Priority Data

Apr. 28, 2016 (AU) ................................ 2016901555

(51) Int. Cl.
| | |
|---|---|
| *C07K 16/28* | (2006.01) |
| *A61K 39/395* | (2006.01) |
| *A61K 47/68* | (2017.01) |
| *A61P 35/00* | (2006.01) |
| *A61K 39/00* | (2006.01) |
| *A61K 45/06* | (2006.01) |
| *G01N 33/50* | (2006.01) |
| *G01N 33/574* | (2006.01) |
| *A61K 38/16* | (2006.01) |

(52) U.S. Cl.
CPC .......... *C07K 16/2896* (2013.01); *A61K 39/00* (2013.01); *A61K 39/395* (2013.01); *A61K 45/06* (2013.01); *A61K 47/6803* (2017.08); *A61P 35/00* (2018.01); *G01N 33/50* (2013.01); *G01N 33/574* (2013.01); *A61K 38/16* (2013.01); *A61K 2039/505* (2013.01); *A61K 2300/00* (2013.01); *C07K 2317/24* (2013.01); *C07K 2317/34* (2013.01); *C07K 2317/41* (2013.01); *C07K 2317/565* (2013.01); *C07K 2317/622* (2013.01); *C07K 2317/72* (2013.01); *C07K 2317/732* (2013.01); *C07K 2317/734* (2013.01); *C07K 2317/77* (2013.01); *C07K 2319/55* (2013.01)

(58) Field of Classification Search
CPC .............. A61K 39/395; A61K 39/3955; A61K 47/6803; A61K 47/6849; A61K 2039/505; A61P 35/00; C07K 2317/24; C07K 2317/565; C07K 2317/732; C07K 2317/734; C07K 2319/55
See application file for complete search history.

(56) References Cited

U.S. PATENT DOCUMENTS

| | | | | |
|---|---|---|---|---|
| 5,879,911 A * | 3/1999 | Park | ........................ | A61P 35/00 530/391.1 |
| 7,622,560 B2 * | 11/2009 | Park | .................... | A61K 47/6815 424/139.1 |
| 2007/0207142 A1 * | 9/2007 | Crowley | .............. | C07K 14/705 424/139.1 |

OTHER PUBLICATIONS

Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Padlan, Advances in Protein Chemistry, 1996, 49:57-133.*
Berglund etal, Protein Science, 2008, 17:606-613.*
Kim et al., Immune Network 2014, 14(3): 164-170.*
Goel et al., Plasticity within the Antigen Combining Site May Manifestos Molecular Mimicry in the Humoral Immune Response, The Journal of Immunology, 2004, 173(12):7358-7367.*

* cited by examiner

*Primary Examiner* — Hong Sang
(74) *Attorney, Agent, or Firm* — Lex IP Meister, PLLC

(57) ABSTRACT

Provided is an antibody for treating a cancer, more specifically, an anti-CD43 antibody binding to an extracellular domain of CD43, compositions for treating a cancer or inhibiting a cancer stem cell comprising the antibody as an active ingredient, and methods for screening an agent of inhibiting a cancer stem cell.

9 Claims, 48 Drawing Sheets

Specification includes a Sequence Listing.

Effect of JL1-SAP on colony-forming cells of AML blasts

Colony-forming cell assay huJL-1 257-10 Vk

```
1--------10---------20---------30---------40---------50---------60
DTQMTQSPSSVSASVGDRVTITCRTSQDISNYLNWYQQKPGKAPKLLIYNTSRLHSGVPS
```

```
--------70---------80---------90--------100----107
RFSGSGSGTDFTLTISSLQPEDFATYYCQQSNMFPYTFGQGTKLEIK
```
(SEQ ID NO: 105)

huJL-1 257-10 VH

```
1--------10---------20---------30---------40---------50---------60
QVQLVQSGAEVKKPGASVKVSCKASGYTFNGYFMNWVRQAPGQGLERMGRINPNNGDSFY
```

```
--------70---------80---------90--------100---------110---------120
NQKFQGRVTMTRDTSTSTVYMELPSLRSEDTAVYYCAREGYYGGRGYALDYWGQGTLVTV
```

```
122
SS
```
(SEQ ID NO: 6)

1: wild type, 2: N50A, 3: N50Q, 4: S52A

SEQUENCE LISTING

```
<160> NUMBER OF SEQ ID NOS: 134

<210> SEQ ID NO 1
<211> LENGTH: 366
<212> TYPE: DNA
<213> ORGANISM: Artificial Sequence
<220> FEATURE:
<223> OTHER INFORMATION: Synthetic (Quickchange mutant Combo A heavy
      chain variable region (VH) nucleotide sequence)

<400> SEQUENCE: 1
caggtgcagc tggtgcagag cggcgccgag gtgaagaaac ctggcgccag cgtgaaggtg        60
tcctgcaagg ccagcggcta cagcatcggc ggctactaca tgaactgggt gcgccaggct       120
cctggacagg gcctggaatg gatgggccgg atcaacccca cagcggcga cagcttctac        180 aaccagaaat tcaagggcag ggtgaccacg acccgcgaca ccagcaccag caccatgtac       240
atggaactga gcagcctgag aagcgaggac accgccgtgt actactgcgc cagagagggc       300
tattacggcg gcagaggcta cgccctggat tactgggccc agggcaccct ggtgaccgtg       360
tcctcc                                                                  366

<210> SEQ ID NO 2
<211> LENGTH: 122
<212> TYPE: PRT
<213> ORGANISM: Artificial Sequence
<220> FEATURE:
<223> OTHER INFORMATION: Synthetic (Quickchange mutant Combo A VH amino
      acid sequence)

<400> SEQUENCE: 2

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Ser Ile Gly Gly Tyr
            20                  25                  30

Tyr Met Asn Trp Val Arg Gln Ala Pro Gly Gln Gly Leu Glu Trp Met
            35                  40                  45

Gly Arg Ile Asn Pro Asn Ser Gly Asp Ser Phe Tyr Asn Gln Lys Phe
50                      55                  60

Lys Gly Arg Val Thr Thr Thr Arg Asp Thr Ser Thr Ser Thr Met Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
            115                 120

<210> SEQ ID NO 3
<211> LENGTH: 324
<212> TYPE: DNA
<213> ORGANISM: Artificial Sequence
<220> FEATURE:
<223> OTHER INFORMATION: Synthetic (Quickchange mutant Combo A light
      chain variable region (VL) nucleotide sequence)

<400> SEQUENCE: 3
gacatccaga tgacccggag ccctagcagc gtgtccgcca gcgtgggcgg cagagtgccc      60
atcacctgtc ggaccagcca ggacatcagc aactacctga actggtatca gcagaagccc    120
gacggcaccg tcaagctgct gatctacaac accagccggc tgcacagcgg cgtgccaagc    180
agattcagcg gcagcggctc cggcaccgac ttcaccctga ccatcagctc cctgcagccc    240
gaggacttcg ccacctacta ctgccagcag agcaacatgt tcccctacac cttcggccag    300
ggtatcaagc tggagatcaa gcgt                                           324

<210> SEQ ID NO 4
<211> LENGTH: 108
<212> TYPE: PRT
<213> ORGANISM: Artificial Sequence
<220> FEATURE:
<223> OTHER INFORMATION: Synthetic (Quickchange mutant Combo A VL amino
      acid sequence)

<400> SEQUENCE: 4

Asp Ile Gln Met Thr Arg Ser Pro Ser Ser Val Ser Ala Ser Val Gly
1               5                   10                  15

Gly Arg Val Pro Ile Thr Cys Arg Thr Ser Gln Asp Ile Ser Asn Tyr
            20                  25                  30

Leu Asn Trp Tyr Gln Gln Lys Pro Asp Gly Thr Val Lys Leu Leu Ile
            35                  40                  45

Tyr Asn Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Ile Lys Leu Glu Ile Lys Arg
            100                 105

<210> SEQ ID NO 5
```

<211> LENGTH: 366
<212> TYPE: DNA
<213> ORGANISM: Artificial Sequence
<220> FEATURE:
<223> OTHER INFORMATION: Synthetic (257-10 (Round 2 variant) VH
      nucleotide sequence)

<400> SEQUENCE: 5

```
caggtgcagc tggtgcagag cggcgccgag gtgaagaagc ccggcgccag cgtcaaggtg    60
tcctgcaagg ccagcggcta caccttcaac ggctacttca tgaactgggt gaggcaggcc   120
cctgggcagg gactggagcg gatgggccgc atcaaccccc acaacggcga cagcttctac   180
aaccagaagt tccagggccg cgtcaccatg acccgcgaca ccagcaccag caccgtgtac   240
atggagctgc ccagcctgcg cagcgaggac accgccgtgt actactgcgc cagggagggc   300
tactacggcg gcagaggcta cgccctggac tactggggcc agggcaccct ggtgaccgtg   360
tcctcc                                                              366
```

<210> SEQ ID NO 6
<211> LENGTH: 122
<212> TYPE: PRT
<213> ORGANISM: Artificial Sequence
<220> FEATURE:
<223> OTHER INFORMATION: Synthetic (257-10 (Round 2 variant) VH amino
      acid sequence)

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Gly Tyr
            20                  25                  30

Phe Met Asn Trp Val Arg Gln Ala Pro Gly Gln Gly Leu Glu Arg Met
        35                  40                  45

Gly Arg Ile Asn Pro Asn Asn Gly Asp Ser Phe Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Pro Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120

<210> SEQ ID NO 7
<211> LENGTH: 325
<212> TYPE: DNA
<213> ORGANISM: Artificial Sequence
<220> FEATURE:
<223> OTHER INFORMATION: Synthetic (257-10 (Round 2 variant) VL
      nucleotide sequence)

<400> SEQUENCE: 7

```
gacacccaga tgacccagag ccccttcttct gtctccgcca gcgtgggcga ccgcgtgacc    60
atcacctgcc gcaccagcca ggacatcagc aactacctga ctggtatca gcagaagccc   120
ggcaaggccc ccaagctgct gatctacaac accagcaggc tccactctgg agtccccagc   180
cgcttctccg gctccgggtc tggaaccgac ttcaccctga ccatcagctc cctgcagccc   240
gaggacttcg ccacctacta ctgccagcag agcaacatgt tcccctacac cttcgggcag   300
```
gggaccaagc tggagatcaa gcgta                                              325

<210> SEQ ID NO 8
<211> LENGTH: 108
<212> TYPE: PRT
<213> ORGANISM: Artificial Sequence
<220> FEATURE:
<223> OTHER INFORMATION: Synthetic (257-10 (Round 2 variant) VL amino
      acid sequence)

<400> SEQUENCE: 8

Asp Thr Gln Met Thr Gln Ser Pro Ser Ser Val Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Thr Lys Leu Glu Ile Lys Arg
            100                 105

<210> SEQ ID NO 9
<211> LENGTH: 366
<212> TYPE: DNA
<213> ORGANISM: Artificial Sequence
<220> FEATURE:
<223> OTHER INFORMATION: Synthetic (456-D10 VH nucleotide sequence)

<400> SEQUENCE: 9
caggtgcagc tggtgcagag cggcgccgag gtgaagaagc ccggcgccag cgtcaaggtg    60
tcctgcaagg ccagcggcta caccttcaac ggctacttca tgaactgggt gaggcaggcc   120
cctgggcagg gactggagcg gatgggccgc atcaaccccaacaacggcga cagcttctac    180 aaccagaagt tccagggccg cgtcaccatg acccgcgaca ccagcaccag caccgtgtac   240
atggagctgc ccagcctgcg cagcgaggac accgccgtgt actactgcgc cagggagggc   300
tactacggcg gcagaggcta cgccctggac tactggggcc agggcaccct ggtgaccgtg   360
tcctcc                                                               366

<210> SEQ ID NO 10
<211> LENGTH: 122
<212> TYPE: PRT
<213> ORGANISM: Artificial Sequence
<220> FEATURE:
<223> OTHER INFORMATION: Synthetic (456-D10 VH amino acid)

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Gly Tyr
            20                  25                  30

Phe Met Asn Trp Val Arg Gln Ala Pro Gly Gln Gly Leu Glu Arg Met
        35                  40                  45

Gly Arg Ile Asn Pro Asn Asn Gly Asp Ser Phe Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Pro Ser Leu Arg Ser Glu Asp Thr Ala Val Tyr Tyr Cys
                85                  90                  95

Ala Arg Glu Gly Tyr Tyr Gly Arg Gly Tyr Ala Leu Asp Tyr Trp
            100                 105                 110

Gly Gln Gly Thr Leu Val Thr Val Ser Ser
        115                 120

<210> SEQ ID NO 11
<211> LENGTH: 324
<212> TYPE: DNA
<213> ORGANISM: Artificial Sequence
<220> FEATURE:
<223> OTHER INFORMATION: Synthetic (456-D10 VL nucleotide sequence)

<400> SEQUENCE: 11
gacacccaga tgacccagag cccttcttct gtctccgcca gcgtgggcga ccgcgtgacc      60
atcacctgcc gcaccagcca ggacatcagc aactacctga actggtatca gcaggagccc     120
ggcaaggccc ccaagctgct gatctacaac accagcaggc tccactctgg agtccccagc     180
cgcttctccg gctccgggtc tggaaccgac ttcaccctga ccatcagctc cctgcagccc     240
gaggacttcg ccacctacta ctgccagcag agcaacatgt tccctacac cttcgggcag      300 gggaccaagc tggagatcaa gcgg                                            324

<210> SEQ ID NO 12
<211> LENGTH: 108
<212> TYPE: PRT
<213> ORGANISM: Artificial Sequence
<220> FEATURE:
<223> OTHER INFORMATION: Synthetic (456-D10 VL amino acid sequence)

<400> SEQUENCE: 12

Asp Thr Gln Met Thr Gln Ser Pro Ser Ser Val Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Glu Pro Gly Lys Ala Pro Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Thr Lys Leu Glu Ile Lys Arg
            100                 105

<210> SEQ ID NO 13
<211> LENGTH: 366
<212> TYPE: DNA
<213> ORGANISM: Artificial Sequence
<220> FEATURE:
<223> OTHER INFORMATION: Synthetic (324-B10 VH nucleotide sequence)

<400> SEQUENCE: 13
caggtgcagc tggtgcagag cggcgccgag gtgaagaaac ctggcgccag cgtgaaggtg      60
tcctgcaagg ccagcggcta cagcatcggc ggctactaca tgaactgggt cgccaggct     120

```
cctggacagg gcctggaatg gatgggccgg atcaaccccaa acagcggcga cagcttctac    180
aaccagaaat tcaagggcag ggtgaccatg acccgcgaca ccagcaccag caccgtgtac    240
atggaactga gcagcctgag aagcgaggac accgccgtgt actactgcgc cagagagggc    300
tattacggcg gcagaggcta cgccctggat tactggggcc agggcaccct ggtgaccgtg    360
tcctcc                                                                366
```

```
<210> SEQ ID NO 14
<211> LENGTH: 122
<212> TYPE: PRT
<213> ORGANISM: Artificial Sequence
<220> FEATURE:
<223> OTHER INFORMATION: Synthetic (324-B10 VH amino acid sequence)

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ile Gly Gly Tyr
            20                  25                  30

Tyr Met Asn Trp Val Arg Gln Ala Pro Gly Gln Gly Leu Glu Trp Met
        35                  40                  45

Gly Arg Ile Asn Pro Asn Ser Gly Asp Ser Phe Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120
```

```
<210> SEQ ID NO 15
<211> LENGTH: 324
<212> TYPE: DNA
<213> ORGANISM: Artificial Sequence
<220> FEATURE:
<223> OTHER INFORMATION: Synthetic (324-B10 VL nucleotide sequence)

<400> SEQUENCE: 15
gacattcaga tgacccggag ccctagcagc gtgtccgcca gcgtgggcga cagagtgtcc    60
atcacctgtc ggaccagcca ggacatcagc aactacctga ctggtatca gcagaagccc    120 gacggcaccg tcaagctgct gatctacaac accagccggc tgcacagcgg cgtgccaagc    180
agattcagcg gcagcggctc cggcaccgac ttcaccctga ccatcagctc cctgcagccc    240
gaggacttcg ccacctacta ctgccagcag agcaacatgt tcccctacac cttcggccag    300
ggtatcaagc tggagatcaa gcgg                                            324
```

```
<210> SEQ ID NO 16
<211> LENGTH: 108
<212> TYPE: PRT
<213> ORGANISM: Artificial Sequence
<220> FEATURE:
<223> OTHER INFORMATION: Synthetic (324-B10 VL amino acid sequence)

<400> SEQUENCE: 16

Asp Ile Gln Met Thr Arg Ser Pro Ser Ser Val Ser Ala Ser Val Gly
1               5                   10                  15
```

Asp Arg Val Ser Ile Thr Cys Arg Thr Ser Gln Asp Ile Ser Asn Tyr
            20                  25                  30

Leu Asn Trp Tyr Gln Gln Lys Pro Asp Gly Thr Val Lys Leu Leu Ile
         35                  40                  45

Tyr Asn Thr Ser Arg Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Met Phe Pro Tyr
                 85                  90                  95

Thr Phe Gly Gln Gly Ile Lys Leu Glu Ile Lys Arg
            100                 105

<210> SEQ ID NO 17
<211> LENGTH: 366
<212> TYPE: DNA
<213> ORGANISM: Artificial Sequence
<220> FEATURE:
<223> OTHER INFORMATION: Synthetic (361-C11 VH nucleotide sequence)

<400> SEQUENCE: 17
caggtgcagc tggtgcagag cggcgccgag gtgaagaaac tggcgccag cgtgaaggtg      60 tcctgcaagg ccagcggcta cagcatcggc ggctacttca tgaactgggt gcgccaggct    120
cctggacagg gcctggaatg gatgggccgg atcaaccca acaacggcga cagcttctac    180
aaccagaaat tcaagggcag ggtgaccatg acccgcgaca ccagcaccag caccgtgtac    240
atggaactga gcagcctgag aagcgaggac accgccgtgt actactgcgc cagagagggc    300
tattacggcg gcagaggcta cgccctggat tactggggcc agggcacccct ggtgaccgtg    360 tcctcc                                                               366

<210> SEQ ID NO 18
<211> LENGTH: 122
<212> TYPE: PRT
<213> ORGANISM: Artificial Sequence
<220> FEATURE:
<223> OTHER INFORMATION: Synthetic (361-C11 VH amino acid sequence)

<400> SEQUENCE: 18

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Ile Gly Gly Tyr
            20                  25                  30

Phe Met Asn Trp Val Arg Gln Ala Pro Gly Gln Gly Leu Glu Trp Met
         35                  40                  45

Gly Arg Ile Asn Pro Asn Asn Gly Asp Ser Phe Tyr Asn Gln Lys Phe
     50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120

<210> SEQ ID NO 19

<211> LENGTH: 324
<212> TYPE: DNA
<213> ORGANISM: Artificial Sequence
<220> FEATURE:
<223> OTHER INFORMATION: Synthetic (361-C11 VL nucleotide sequence)

<400> SEQUENCE: 19

| | |
|---|---|
| gacattcaga tgacccggag ccctagcagc gtgtccgcca gcgtgggcgg cagagtgtcc | 60 |
| atcacctgtc ggaccagcca ggacatcagc aactacctga actggtatca gcagaagccc | 120 |
| gacggcaccg tcaagctgct gatctacaac accagccggc tgcacagcgg cgtgccaagc | 180 |
| agattcagcg gcagcggctc cggcaccgac ttcaccctga ccatcagctc cctgcagccc | 240 |
| gaggacttcg ccacctacta ctgccagcag agcaacatgt tcccctacac cttcggccag | 300 |
| ggtatcaagc tggagatcaa gcgg | 324 |

<210> SEQ ID NO 20
<211> LENGTH: 108
<212> TYPE: PRT
<213> ORGANISM: Artificial Sequence
<220> FEATURE:
<223> OTHER INFORMATION: Synthetic (361-C11 VL amino acid sequence)

<400> SEQUENCE: 20

Asp Ile Gln Met Thr Arg Ser Pro Ser Ser Val Ser Ala Ser Val Gly
1               5                   10                  15

Gly Arg Val Ser Ile Thr Cys Arg Thr Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Ile Lys Leu Glu Ile Lys Arg
            100                 105

<210> SEQ ID NO 21
<211> LENGTH: 366
<212> TYPE: DNA
<213> ORGANISM: Artificial Sequence
<220> FEATURE:
<223> OTHER INFORMATION: Synthetic (368-G07 VH nucleotide sequence)
<220> FEATURE:
<221> NAME/KEY: misc_feature
<222> LOCATION: (63)
<223> OTHER INFORMATION: n is any one of a, t, c, and g

<400> SEQUENCE: 21

| | |
|---|---|
| caggtgcagc tggtgcagag cggcgccgag gtgaagaaac tggcgccag cgtgaaggtg | 60 |
| tcntgcaagg ccagcggcta cagcatcggc ggctacttca tgaactgggt cgccaggct | 120 |
| cctggacagg gcctggaatg gatgggccgg atcaaccca caacggcga cagcttctac | 180 |
| aaccagaaat tcaagggcag ggtgaccatg acccgcgaca ccagcaccag caccgtgtac | 240 |
| atggaactga gcagcctgag aagcgaggac accgccgtgt actactgcgc cagagagggc | 300 |
| tattacggcg gcagaggcta cgccctggat tactggggcc agggcaccct ggtgaccgtg | 360 |
| tcctcc | 366 |

<210> SEQ ID NO 22
<211> LENGTH: 122
<212> TYPE: PRT
<213> ORGANISM: Artificial Sequence
<220> FEATURE:
<223> OTHER INFORMATION: Synthetic (368-G07 VH amino acid sequence)

<400> SEQUENCE: 22

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ile Gly Gly Tyr
            20                  25                  30

Phe Met Asn Trp Val Arg Gln Ala Pro Gly Gln Gly Leu Glu Trp Met
        35                  40                  45

Gly Arg Ile Asn Pro Asn Asn Gly Asp Ser Phe Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Arg Gly Tyr Ala Leu Asp Tyr Trp
            100                 105                 110

Gly Gln Gly Thr Leu Val Thr Val Ser Ser
        115                 120
```

<210> SEQ ID NO 23
<211> LENGTH: 324
<212> TYPE: DNA
<213> ORGANISM: Artificial Sequence
<220> FEATURE:
<223> OTHER INFORMATION: Synthetic (368-G07 VL nucleotide sequence)

<400> SEQUENCE: 23

```
gacattcaga tgacccggag ccctagcagc gtgtccgcca gcgtgggcga cagagtgccc      60
atcacctgtc ggaccagcca ggacatcagc aactacctga actggtatca gcagaagccc     120
gacggcaccg tcaagctgct gatctacaac accagccggc tgcacagcgg cgtgccaagc     180
agattcagcg gcagcggctc cggcaccgac ttcaccctga ccatcagctc cctgcagccc     240
gaggacttcg ccacctacta ctgccagcag agcaacatgt tccctacac cttcggccag     300 ggtatcaagc tggagatcaa gcgg                                             324
```

<210> SEQ ID NO 24
<211> LENGTH: 108
<212> TYPE: PRT
<213> ORGANISM: Artificial Sequence
<220> FEATURE:
<223> OTHER INFORMATION: Synthetic (368-G07 VL amino acid sequence)

<400> SEQUENCE: 24

```
Asp Ile Gln Met Thr Arg Ser Pro Ser Ser Val Ser Ala Ser Val Gly
1               5                   10                  15

Asp Arg Val Pro Ile Thr Cys Arg Thr Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
```

|  |  |  |  |  |  |  |  | 65 |  |  |  | 70 |  |  |  | 75 |  |  |  | 80 |  |
|---|---|---|---|---|---|---|---|---|---|---|---|---|---|---|---|---|---|---|---|---|---|

Glu Asp Phe Ala Thr Tyr Tyr Cys Gln Gln Ser Asn Met Phe Pro Tyr
                          85                    90                    95

Thr Phe Gly Gln Gly Ile Lys Leu Glu Ile Lys Arg
                100                    105

<210> SEQ ID NO 25
<211> LENGTH: 366
<212> TYPE: DNA
<213> ORGANISM: Artificial Sequence
<220> FEATURE:
<223> OTHER INFORMATION: Synthetic (369-F05 VH nucleotide sequence)

<400> SEQUENCE: 25

```
caggtgcagc tggtgcagag cggcgccgag gtgaagaaac ctggcgccag cgtgaaggtg      60
tcctgcaagg ccagcggcta cagcatcggc ggctacttca tgaactgggt gcgccaggct     120
cctggacagg gcctggaatg gatgggccgg atcaacccca caacggcga cagcttctac     180
aaccagaaat tcaagggcag ggtgaccatg acccgcgaca ccagcaccag caccatgtac     240
atggaactga gcagcctgag aagcgaggac accgccgtgt actactgcgc cagagagggc     300
tattacggcg gcagaggcta cgccctggat tactggggcc agggcaccct ggtgaccgtg     360
tcctcc                                                                 366
```

<210> SEQ ID NO 26
<211> LENGTH: 122
<212> TYPE: PRT
<213> ORGANISM: Artificial Sequence
<220> FEATURE:
<223> OTHER INFORMATION: Synthetic (369-F05 VH amino acid sequence)

<400> SEQUENCE: 26

Gln Val Gln Leu Val Gln Ser Gly Ala Glu Val Lys Lys Pro Gly Ala
1                 5                    10                    15

Ser Val Lys Val Ser Cys Lys Ala Ser Gly Tyr Ser Ile Gly Gly Tyr
            20                    25                    30

Phe Met Asn Trp Val Arg Gln Ala Pro Gly Gln Gly Leu Glu Trp Met
          35                    40                    45

Gly Arg Ile Asn Pro Asn Asn Gly Asp Ser Phe Tyr Asn Gln Lys Phe
  50                    55                    60

Lys Gly Arg Val Thr Met Thr Arg Asp Thr Ser Thr Ser Thr Met Tyr
65                70                    75                    80

Met Glu Leu Ser Ser Leu Arg Ser Glu Asp Thr Ala Val Tyr Tyr Cys
          85                    90                    95

Ala Arg Glu Gly Tyr Tyr Gly Gly Arg Gly Tyr Ala Leu Asp Tyr Trp
            100                   105                110

Gly Gln Gly Thr Leu Val Thr Val Ser Ser
          115                    120

<210> SEQ ID NO 27
<211> LENGTH: 324
<212> TYPE: DNA
<213> ORGANISM: Artificial Sequence
<220> FEATURE:
<223> OTHER INFORMATION: Synthetic (369-F05 VL nucleotide sequenc)

<400> SEQUENCE: 27

```
gacattcaga tgacccggag ccctagcagc gtgtccgcca gcgtgggcga cagagtgtcc      60
atcacctgtc ggaccagcca ggacatcagc aactacctga actggtatca gcagaagccc     120
```

```
gacggcaccg tcaagctgct gatctacaac accagccggc tgcacagcgg cgtgccaagc    180
agattcagcg gcagcggctc cggcaccgac ttcaccctga ccatcagctc cctgcagccc    240
gaggacttcg ccacctacta ctgccagcag agcaacatgt tcccctacac cttcggccag    300
ggtatcaagc tggagatcaa gcgg                                           324
```

<210> SEQ ID NO 28
<211> LENGTH: 108
<212> TYPE: PRT
<213> ORGANISM: Artificial Sequence
<220> FEATURE:
<223> OTHER INFORMATION: Synthetic (369-F05 VL amino acid sequence)

<400> SEQUENCE: 28

```
Asp Ile Gln Met Thr Arg Ser Pro Ser Ser Val Ser Ala Ser Val Gly
1               5                   10                  15

Asp Arg Val Ser Ile Thr Cys Arg Thr Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Ile Lys Leu Glu Ile Lys Arg
            100                 105
```

<210> SEQ ID NO 29
<211> LENGTH: 366
<212> TYPE: DNA
<213> ORGANISM: Artificial Sequence
<220> FEATURE:
<223> OTHER INFORMATION: Synthetic (361-H05 VH nucleotide sequence)

<400> SEQUENCE: 29

```
caggtgcagc tggtgcagag cggcgccgag gtgaagaaac ctggcgccag cgtgaaggtg    60
tcctgcaagg ccagcggcta cagcatcggc ggctacttca tgaactgggt cgcgcaggct    120
cctggacagg gcctggaatg gatgggccgg atcaacccca caacggcga cagcttctac    180 aaccagaaat tcaagggcag ggtgaccacg acccgcgaca ccagcaccag caccgtgtac    240
atggaactga gcagcctgag aagcgaggac accgccgtgt actactgcgc cagagagggc    300
tattacggcg gcagaggcta cgccctggat tactggggcc agggcaccct ggtgactgtg    360
tcctcc                                                               366
```

<210> SEQ ID NO 30
<211> LENGTH: 122
<212> TYPE: PRT
<213> ORGANISM: Artificial Sequence
<220> FEATURE:
<223> OTHER INFORMATION: Synthetic (361-H05 VH amino acid sequence)

<400> SEQUENCE: 30

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ile Gly Gly Tyr
            20                  25                  30
```

```
Phe Met Asn Trp Val Arg Gln Ala Pro Gly Gln Gly Leu Glu Trp Met
         35                  40                  45

Gly Arg Ile Asn Pro Asn Asn Gly Asp Ser Phe Tyr Asn Gln Lys Phe
     50                  55                  60

Lys Gly Arg Val Thr Thr Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Gly Tyr Tyr Gly Arg Gly Tyr Ala Leu Asp Tyr Trp
                100                 105                 110

Gly Gln Gly Thr Leu Val Thr Val Ser Ser
            115                 120

<210> SEQ ID NO 31
<211> LENGTH: 324
<212> TYPE: DNA
<213> ORGANISM: Artificial Sequence
<220> FEATURE:
<223> OTHER INFORMATION: Synthetic (361-H05 VL nucleotide sequence)

<400> SEQUENCE: 31
gacattcaga tgacccggag ccctagcagc gtgtccgcca gcgtgggcga cagagtatcc      60
atcacctgtc ggaccagcca ggacatcagc aactacctga actggtatca gcagaagccc    120
gacggcaccg tcaagctgct gatctacaac accagccggc tgcacagcgg cgtgccaagc    180
agattcagcg gcagcggctc cggcaccgac ttcaccctga ccatcagctc cctgcagccc    240
gaggacttcg ccacctacta ctgccagcag agcaacatgt tcccctacac cttcggccag    300
ggtatcaagc tggagatcaa gcgg                                           324

<210> SEQ ID NO 32
<211> LENGTH: 108
<212> TYPE: PRT
<213> ORGANISM: Artificial Sequence
<220> FEATURE:
<223> OTHER INFORMATION: Synthetic (361-H05 VL amino acid sequence)

<400> SEQUENCE: 32

Asp Ile Gln Met Thr Arg Ser Pro Ser Ser Val Ser Ala Ser Val Gly
 1               5                  10                  15

Asp Arg Val Ser Ile Thr Cys Arg Thr Ser Gln Asp Ile Ser Asn Tyr
             20                  25                  30

Leu Asn Trp Tyr Gln Gln Lys Pro Asp Gly Thr Val Lys Leu Leu Ile
         35                  40                  45

Tyr Asn Thr Ser Arg Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Met Phe Pro Tyr
                 85                  90                  95

Thr Phe Gly Gln Gly Ile Lys Leu Glu Ile Lys Arg
            100                 105

<210> SEQ ID NO 33
<211> LENGTH: 1356
<212> TYPE: DNA
<213> ORGANISM: Artificial Sequence
<220> FEATURE:
<223> OTHER INFORMATION: Synthetic (murine anti-CD43 (mJL-1) IgG Heavy
```

Chain (HC) DNA sequence)

<400> SEQUENCE: 33

```
gaggttcagc tgcagcagtc tggtcctgag ctggtgaagc ctggggcttc agtgaagatt      60
tcctgcaagg cctctggtta ctcaattggt ggctacttta tgaactgggt gaagcagagc     120
cacggcaaga gccctgagtg gattgggcgt attaatccta caatggtga ttctttctac     180
aaccagaaat tcaagggcac ggccacattg actgttgacc gctcttctga cacagtccac     240
atggaggtcc tgagcctgac atctgaggac tctgcagtct attattgtgg ccgcgaaggt     300
tactacggtg ggcgaggcta tgctttggac tactggggtc aaggcacctc ggtcaccgtc     360
tcctcagcta gcaccaaggg cccatcggtc ttccccctgg caccctcctc caagagcacc     420
tctgggggca gcgcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga cagagagtt     660
gagcccaaat cttgtgacaa aactcacaca tgcccaccgt gcccagcacc tgaactcctg     720
gggggaccgt cagtcttcct cttccccccca aacccaagg acaccctcat gatctcccgg     780
acccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagccctcc cagcccccat cgagaaaacc    1020
atctccaaag ccaaagggca gccccgagaa ccacaggtgt acaccctgcc cccatcccgg    1080
gatgagctga ccaagaacca ggtcagcctg acctgcctgg tcaaaggctt ctatcccagc    1140
gacatcgccg tggagtggga gagcaatggg cagccggaga caactacaa gaccacgcct    1200
cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga agagcctctc cctgtctccg ggtaaa                              1356
```

<210> SEQ ID NO 34
<211> LENGTH: 452
<212> TYPE: PRT
<213> ORGANISM: Artificial Sequence
<220> FEATURE:
<223> OTHER INFORMATION: Synthetic (murine anti-CD43 (mJL-1) IgG HC
      amino acid sequence)

<400> SEQUENCE: 34

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Ile Gly Gly Tyr
            20                  25                  30

Phe Met Asn Trp Val Lys Gln Ser His Gly Lys Ser Pro Glu Trp Ile
        35                  40                  45

Gly Arg Ile Asn Pro Asn Asn Gly Asp Ser Phe Tyr Asn Gln Lys Phe
    50                  55                  60

Lys Gly Thr Ala Thr Leu Thr Val Asp Arg Ser Ser Asp Thr Val His
65                  70                  75                  80

Met Glu Val Leu Ser Leu Thr Ser Glu Asp Ser Ala Val Tyr Tyr Cys
                85                  90                  95
```

Gly Arg Glu Gly Tyr Tyr Gly Arg Gly Tyr Ala Leu Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 35
<211> LENGTH: 5734
<212> TYPE: DNA
<213> ORGANISM: Artificial Sequence
<220> FEATURE:
<223> OTHER INFORMATION: Synthetic (murine anti-CD43 (mJL-1) IgG HC Full
      vector used to express (pTT5 based))

<400> SEQUENCE: 35

```
gtacatttat attggctcat gtccaatatg accgccatgt tgacattgat tattgactag    60
ttattaatag taatcaatta cggggtcatt agttcatagc ccatatatgg agttccgcgt   120
tacataactt acggtaaatg gcccgcctgg ctgaccgccc aacgaccccc gcccattgac   180
gtcaataatg acgtatgttc ccatagtaac gccaataggg actttccatt gacgtcaatg   240
ggtggagtat ttacggtaaa ctgcccactt ggcagtacat caagtgtatc atatgccaag   300 tccgcccct attgacgtca atgacggtaa atggcccgcc tggcattatg cccagtacat   360
gaccttacgg gactttccta cttggcagta catctacgta ttagtcatcg ctattaccat   420
ggtgatgcgg ttttggcagt acaccaatgg gcgtggatag cggtttgact cacggggatt   480
tccaagtctc caccccattg acgtcaatgg gagtttgttt tggcaccaaa atcaacggga   540
ctttccaaaa tgtcgtaata accccgcccc gttgacgcaa atgggcggta ggcgtgtacg   600
gtgggaggtc tatataagca gagctcgttt agtgaaccgt cagatcctca ctctcttccg   660
catcgctgtc tgcagggcc agctgttggg ctcgcggttg aggacaaact cttcgcggtc   720
tttccagtac tcttggatcg gaaacccgtc ggcctccgaa cggtactccg ccaccgaggg   780
acctgagcga gtccgcatcg accggatcgg aaaacctctc gagaaaggcg tctaaccagt   840
cacagtcgca aggtaggctg agcaccgtgg cgggcggcag cgggtggcgg tcggggttgt   900
ttctggcgga ggtgctgctg atgatgtaat taaagtaggc ggtcttgaga cggcggatgg   960
tcgaggtgag gtgtggcagg cttgagatcc agctgttggg gtgagtactc cctctcaaaa  1020
gcgggcatta cttctgcgct aagattgtca gtttccaaaa acgaggagga tttgatattc  1080
acctggcccg atctggccat acacttgagt gacaatgaca tccactttgc ctttctctcc  1140
acaggtgtcc actcccaggt ccaagtttgc cgccaccatg gcttggatga tgcttctcct  1200
cggactcctt gcgtacggat caggagaggt tcagctgcag cagtctggtc ctgagctggt  1260
gaagcctggg gcttcagtga agatttcctg caaggcctct ggttactcaa ttggtggcta  1320
ctttatgaac tgggtgaagc agagccacgg caagagccct gagtggattg ggcgtattaa  1380
tcctaacaat ggtgattctt ctacaaccaa gaaattcaag ggcacggcca cattgactgt  1440
tgaccgctct tctgacacag tccacatgga ggtcctgagc ctgacatctg aggactctgc  1500
agtctattat tgtggccgcg aaggttacta cggtggcgaa ggctatgctt tggactactg  1560
gggtcaaggc acctcggtca ccgtctcctc agctagcacc aagggcccat cggtcttccc  1620
cctggcaccc tcctccaaga gcacctctgg gggcacagcg gccctgggct gcctggtcaa  1680
ggactacttc cccgaaccgg tgacggtgtc gtggaactca ggcgccctga ccagcggcgt  1740
gcacaccttc ccggctgtcc tacagtcctc aggactctac tccctcagca gcgtggtgac  1800
cgtgccctcc agcagcttgg gcacccagac ctacatctgc aacgtgaatc acaagcccag  1860
caacaccaag gtggacaaga gagttgagcc caaatcttgt gacaaaactc acacatgccc  1920
accgtgccca gcacctgaac tcctgggggg accgtcagtc ttcctcttcc ccccaaaacc  1980
caaggacacc ctcatgatct cccggacccc tgaggtcaca tgcgtggtgg tggacgtgag  2040
ccacgaagac cctgaggtca agttcaactg gtacgtggac ggcgtggagg tgcataatgc  2100
caagacaaag ccgcgggagg agcagtacaa cagcacgtac cgtgtggtca gcgtcctcac  2160
cgtcctgcac caggactggc tgaatggcaa ggagtacaag tgcaaggtct ccaacaaagc  2220
cctcccagcc cccatcgaga aaaccatctc caaagccaaa gggcagcccc gagaaccaca  2280
ggtgtacacc ctgcccccat cccgggatga gctgaccaag aaccaggtca gcctgacctg  2340
```

```
cctggtcaaa ggcttctatc ccagcgacat cgccgtggag tgggagagca atgggcagcc    2400
ggagaacaac tacaagacca cgcctcccgt gctggactcc gacggctcct tcttcctcta    2460
cagcaagctc accgtggaca agagcaggtg gcagcagggg aacgtcttct catgctccgt    2520
gatgcatgag gctctgcaca accactacac gcagaagagc ctctccctgt ctccgggtaa    2580
ataggatccc ccgacctcga cctctggcta ataaggaaaa tttattttca ttgcaatagt    2640
gtgttggaat ttttgtgtc tctcactcgg aaggacatat ggagggcaa atcatttggt      2700 cgagatccct cggagatctc tagctagagg atcgatcccc gccccggacg aactaaacct    2760
gactacgaca tctctgcccc ttcttcgcgg ggcagtgcat gtaatccctt cagttggttg    2820
gtacaacttg ccaactgaac cctaaacggg tagcatatgc ttcccgggta gtagtatata    2880
ctatccagac taaccctaat tcaatagcat atgttaccca acgggaagca tatgctatcg    2940
aattagggtt agtaaaaggg tcctaaggaa cagcgatgta ggtgggcggg ccaagatagg    3000
ggcgcgattg ctgcgatctg gaggacaaat tacacacact tgcgcctgag cgccaagcac    3060
agggttgttg gtcctcatat tcacgaggtc gctgagagca cggtgggcta atgttgccat    3120
gggtagcata tactacccaa atatctggat agcatatgct atcctaatct atatctgggt    3180
agcataggct atcctaatct atatctgggt agcatatgct atcctaatct atatctgggt    3240
agtatatgct atcctaatt atatctgggt agcataggct atcctaatct atatctgggt     3300
agcatatgct atcctaatct atatctgggt agtatatgct atcctaatct gtatccgggt    3360
agcatatgct atcctaatag agattagggt agtatatgct atcctaatt atatctgggt     3420 agcatatact acccaaatat ctggatagca tatgctatcc taatctatat ctgggtagca    3480
tatgctatcc taatctatat ctgggtagca taggctatcc taatctatat ctgggtagca    3540
tatgctatcc taatctatat ctgggtagta tgctatcc taatttatat ctgggtagca      3600
taggctatcc taatctatat ctgggtagca tatgctatcc taatctatat ctgggtagta    3660
tatgctatcc taatctgtat ccgggtagca tatgctatcc tcatgataag ctgtcaaaca    3720
tgagaattaa ttcttgaaga cgaaagggcc tcgtgatacg cctattttta taggttaatg    3780
tcatgataat aatggtttct tagacgtcag gtggcacttt cggggaaat gtgcgcggaa     3840 cccctatttg tttatttttc taaatacatt caaatatgta tccgctcatg agacaataac    3900
cctgataaat gcttcaataa tattgaaaaa ggaagagtat gagtattcaa catttccgtg    3960
tcgcccttat cccttttttt gcggcatttt gccttcctgt ttttgctcac ccagaaacgc    4020
tggtgaaagt aaaagatgct gaagatcagt tgggtgcacg agtgggttac atcgaactgg    4080
atctcaacag cggtaagatc cttgagagtt ttcgccccga agaacgtttt ccaatgatga    4140
gcacttttaa agttctgcta tgtggcgcgg tattatcccg tgttgacgcc gggcaagagc    4200
aactcggtcg ccgcatacac tattctcaga atgacttggt tgagtactca ccagtcacag    4260
aaaagcatct tacggatggc atgacagtaa gagaattatg cagtgctgcc ataaccatga    4320
gtgataacac tgcggccaac ttacttctga caacgatcgg aggaccgaag gagctaaccg    4380
cttttttgca caacatgggg gatcatgtaa ctcgccttga tcgttgggaa ccggagctga    4440
atgaagccat accaaacgac gagcgtgaca ccacgatgcc tgcagcaatg gcaacaacgt    4500
tgcgcaaact attaactggc gaactactta ctctagcttc ccggcaacaa ttaatagact    4560
ggatggaggc ggataaagtt gcaggaccac ttctgcgctc ggcccttccg gctggctggt    4620
ttattgctga taaatctgga gccggtgagc gtgggtctcg cggtatcatt gcagcactgg    4680
ggccagatgg taagccctcc cgtatcgtag ttatctacac gacggggagt caggcaacta    4740
```

```
tggatgaacg aaatagacag atcgctgaga taggtgcctc actgattaag cattggtaac    4800
tgtcagacca agtttactca tatatacttt agattgattt aaaacttcat ttttaattta    4860
aaaggatcta ggtgaagatc cttttttgata atctcatgac caaaatccct taacgtgagt    4920
tttcgttcca ctgagcgtca gacccgtag aaaagatcaa aggatcttct tgagatcctt    4980 ttttctgcg cgtaatctgc tgcttgcaaa caaaaaaacc accgctacca gcggtggttt    5040
gtttgccgga tcaagagcta ccaactcttt tccgaaggt aactggcttc agcagagcgc    5100
agataccaaa tactgttctt ctagtgtagc cgtagttagg ccaccacttc aagaactctg    5160
tagcaccgcc tacatacctc gctctgctaa tcctgttacc agtggctgct gccagtggcg    5220
ataagtcgtg tcttaccggg ttggactcaa gacgatagtt accggataag gcgcagcggt    5280
cgggctgaac ggggggttcg tgcacacagc ccagcttgga gcgaacgacc tacaccgaac    5340
tgagatacct acagcgtgag ctatgagaaa gcgccacgct tcccgaaggg agaaaggcgg    5400
acaggtatcc ggtaagcggc agggtcggaa caggagagcg cacgagggag cttccagggg    5460
gaaacgcctg gtatctttat agtcctgtcg ggtttcgcca cctctgactt gagcgtcgat    5520
ttttgtgatg ctcgtcaggg gggcggagcc tatggaaaaa cgccagcaac gcggcctttt    5580
tacggttcct ggccttttgc tggccttttg ctcacatgtt ctttcctgcg ttatcccctg    5640
attctgtgga taaccgtatt accgcctttg agtgagctga taccgctcgc cgcagccgaa    5700
cgaccgagcg cagcgagtca gtgagcgagg aagc                               5734

<210> SEQ ID NO 36
<211> LENGTH: 642
<212> TYPE: DNA
<213> ORGANISM: Artificial Sequence
<220> FEATURE:
<223> OTHER INFORMATION: Synthetic (murine anti-CD43 (mJL-1) IgG Light
      Chain (LC) DNA sequence)

<400> SEQUENCE: 36
gatatccaga tgacacagac tacatcctcc ctgtctgcct ctctgggcga ccgcgtcacc      60
atcagctgcc ggacaagtca ggacattagc aattatttga actggtatca gcagaaacca     120
gatggtactg ttaaactcct gatctataac acatcacgct tgcactcagg cgtcccatca     180
cggttcagtg gcagcgggtc tggtacagat tattcccctca ccattcgcaa cctgaacaa     240 aaagatattg ccacttactt ttgccaacag agcaatatgt ttccgtacac gttcgggggg     300
gggaccaagc tggaaatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg    540 ctgagcaaag cagactacga gaacacaaa gtctacgcct gcgaagtcac ccatcagggc     600
ctgagttcac cggtgacaaa gagcttcaac aggggagagt gt                        642

<210> SEQ ID NO 37
<211> LENGTH: 214
<212> TYPE: PRT
<213> ORGANISM: Artificial Sequence
<220> FEATURE:
<223> OTHER INFORMATION: Synthetic (murine anti-CD43 (mJL-1) IgG LC
      amino acid sequence)

<400> SEQUENCE: 37
```

-continued

```
Asp Ile Gln Met Thr Gln Thr Thr Ser Ser Leu Ser Ala Ser Leu Gly
1               5                   10                  15

Asp Arg Val Thr Ile Ser Cys Arg Thr Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Tyr Ser Leu Thr Ile Arg Asn Leu Glu Gln
65                  70                  75                  80

Lys Asp Ile Ala Thr Tyr Phe Cys Gln Gln Ser Asn Met Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 38
<211> LENGTH: 5038
<212> TYPE: DNA
<213> ORGANISM: Artificial Sequence
<220> FEATURE:
<223> OTHER INFORMATION: Synthetic (murine anti-CD43 (mJL-1) IgG LC Full vector used to express (pTT5 based))

<400> SEQUENCE: 38

```
gtacatttat attggctcat gtccaatatg accgccatgt tgacattgat tattgactag      60
ttattaatag taatcaatta cggggtcatt agttcatagc ccatatatgg agttccgcgt     120
tacataactt acggtaaatg gcccgcctgg ctgaccgccc aacgaccccc gcccattgac     180
gtcaataatg acgtatgttc ccatagtaac gccaataggg actttccatt gacgtcaatg     240
ggtggagtat ttacggtaaa ctgcccactt ggcagtacat caagtgtatc atatgccaag     300
tccgccccct attgacgtca atgacggtaa atggcccgcc tggcattatg cccagtacat     360
gaccttacgg gactttccta cttggcagta catctacgta ttagtcatcg ctattaccat     420
ggtgatgcgg ttttggcagt acaccaatgg cgtggatag cggtttgact cacggggatt     480
tccaagtctc cacccattg acgtcaatgg gagtttgttt tggcaccaaa atcaacggga     540
ctttccaaaa tgtcgtaata accccgcccc gttgacgcaa atgggcggta ggcgtgtacg     600
gtgggaggtc tatataagca gagctcgttt agtgaaccgt cagatcctca ctctcttccg     660
catcgctgtc tgcgagggcc agctgttggg ctcgcggttg aggacaaaact cttcgcggtc     720
tttccagtac tcttggatcg gaaacccgtc ggcctccgaa cggtactccg ccaccgaggg     780
```

```
acctgagcga gtccgcatcg accggatcgg aaaacctctc gagaaaggcg tctaaccagt    840
cacagtcgca aggtaggctg agcaccgtgg cgggcggcag cgggtggcgg tcggggttgt    900
ttctggcgga ggtgctgctg atgatgtaat taaagtaggc ggtcttgaga cggcggatgg    960
tcgaggtgag gtgtggcagg cttgagatcc agctgttggg gtgagtactc cctctcaaaa   1020
gcgggcatta cttctgcgct aagattgtca gtttccaaaa acgaggagga tttgatattc   1080
acctggcccg atctggccat acacttgagt gacaatgaca tccactttgc ctttctctcc   1140
acaggtgtcc actcccaggt ccaagtttgc cgccaccatg gatatgaggg taccagcaca   1200
acttctcgga ttactattgt tatggctgcg aggtgcgcgc tgtgtatatcc agatgacaca   1260 gactacatcc tccctgtctg cctctctggg cgaccgcgtc accatcagct gccggacaag   1320
tcaggacatt agcaattatt tgaactggta tcagcagaaa ccagatggta ctgttaaact   1380
cctgatctat aacacatcac gcttgcactc aggcgtccca tcacggttca gtggcagcgg   1440
gtctggtaca gattattccc tcaccattcg caacctggaa caaaaagata ttgccactta   1500
cttttgccaa cagagcaata tgtttccgta cacgttcggg ggggggacca agctggaaat   1560
caagcgtacg gtggctgcac catctgtctt catcttcccg ccatctgatg agcagttgaa   1620
atctggaact gcctctgttg tgtgcctgct gaataacttc tatcccagag aggccaaagt   1680
acagtggaag gtggataacg ccctccaatc gggtaactcc caggagagtg tcacagagca   1740
ggacagcaag gacagcacct acagcctcag cagcaccctg acgctgagca aagcagacta   1800
cgagaaacac aaagtctacg cctgcgaagt cacccatcag ggcctgagtt caccggtgac   1860 aaaagagcttc aacaggggag agtgttagga tcccccgacc tcgacctctg gctaataaag   1920
gaaatttatt ttcattgcaa tagtgtgttg aatttttttg tgtctctcac tcggaaggac   1980
atatgggagg gcaaatcatt tggtcgagat ccctcggaga tctctagcta gaggatcgat   2040
ccccgccccg gacgaactaa acctgactac gacatctctg ccccttcttc gcggggcagt   2100
gcatgtaatc ccttcagttg gttggtacaa cttgccaact gaaccctaaa cgggtagcat   2160
atgcttcccg ggtagtagta tatactatcc agactaaccc taattcaata gcatatgtta   2220
cccaacggga agcatatgct atcgaattag ggttagtaaa agggtcctaa ggaacagcga   2280
tgtaggtggg cgggccaaga tagggggcgcg attgctgcga tctggaggac aaattacaca   2340
cacttgcgcc tgagcgccaa gcacagggtt gttggtcctc atattcacga ggtcgctgag   2400
agcacggtgg gctaatgttg ccatgggtag catatactac ccaaatatct ggatagcata   2460
tgctatccta atctatatct gggtagcata ggctatccta atctatatct gggtagcata   2520
tgctatccta atctatatct gggtagtata tgctatccta atttatatct gggtagcata   2580
ggctatccta atctatatct gggtagcata tgctatccta atctatatct gggtagtata   2640
tgctatccta atctgtatcc gggtagcata tgctatccta atagagatta gggtagtata   2700
tgctatccta atttatatct gggtagcata tactacccaa atatctggat agcatatgct   2760
atcctaatct atatctgggt agcatatgct atcctaatct atatctgggt agcataggct   2820
atcctaatct atatctgggt agcatatgct atcctaatct atatctgggt agtatatgct   2880
atcctaattt atatctgggt agcataggct atcctaatct atatctgggt agcatatgct   2940
atcctaatct atatctgggt agtatatgct atcctaatct gtatccgggt agcatatgct   3000
atcctcatga taagctgtca aacatgagaa ttaattcttg aagacgaaag gcctcgtga   3060 tacgcctatt tttataggtt aatgtcatga taataatggt tcttagacg tcaggtggca   3120 cttttcgggg aaatgtgcgc ggaacccccta tttgtttatt tttctaaata cattcaaata   3180
```

```
tgtatccgct catgagacaa taaccctgat aaatgcttca ataatattga aaaaggaaga    3240
gtatgagtat tcaacatttc cgtgtcgccc ttattcccct ttttgcggca ttttgccttc    3300 ctgttttttgc tcacccagaa acgctggtga agtaaaaga tgctgaagat cagttgggtg    3360
cacgagtggg ttacatcgaa ctggatctca acagcggtaa gatccttgag agttttcgcc    3420
ccgaagaacg ttttccaatg atgagcactt ttaaagttct gctatgtggc gcggtattat    3480
cccgtgttga cgccgggcaa gagcaactcg gtcgccgcat acactattct cagaatgact    3540
tggttgagta ctcaccagtc acagaaaagc atcttacgga tggcatgaca gtaagagaat    3600
tatgcagtgc tgccataacc atgagtgata acactgcggc caacttactt ctgacaacga    3660
tcggaggacc gaaggagcta accgcttttt tgcacaacat gggggatcat gtaactcgcc    3720
ttgatcgttg ggaaccggag ctgaatgaag ccataccaaa cgacgagcgt gacaccacga    3780
tgcctgcagc aatggcaaca acgttgcgca aactattaac tggcgaacta cttactctag    3840
cttcccggca acaattaata gactggatgg aggcggataa agttgcagga ccacttctgc    3900
gctcggccct tccggctggc tggtttattg ctgataaatc tggagccggt gagcgtgggt    3960
ctcgcggtat cattgcagca ctggggccag atggtaagcc ctcccgtatc gtagttatct    4020
acacgacggg gagtcaggca actatggatg aacgaaatag acagatcgct gagataggtg    4080
cctcactgat taagcattgg taactgtcag accaagttta ctcatatata ctttagattg    4140
atttaaaact tcatttttaa tttaaaagga tctaggtgaa gatcctttt gataatctca    4200 tgaccaaaat cccttaacgt gagttttcgt tccactgagc gtcagacccc gtagaaaaga    4260
tcaaaggatc ttcttgagat ccttttttc tgcgcgtaat ctgctgcttg caaacaaaaa    4320
aaccaccgct accagcggtg gtttgtttgc cggatcaaga gctaccaact cttttttcga    4380
aggtaactgg cttcagcaga gcgcagatac caaatactgt tcttctagtg tagccgtagt    4440
taggccacca cttcaagaac tctgtagcac cgcctacata cctcgctctg ctaatcctgt    4500
taccagtggc tgctgccagt ggcgataagt cgtgtcttac cgggttggac tcaagacgat    4560
agttaccgga taaggcgcag cggtcgggct gaacggggg ttcgtgcaca cagcccagct    4620
tggagcgaac gacctacacc gaactgagat acctacagcg tgagctatga aaagcgcca    4680 cgcttcccga agggagaaag gcggacaggt atccggtaag cggcagggtc ggaacaggag    4740
agcgcacgag ggagcttcca gggggaaacg cctggtatct ttatagtcct gtcgggttc    4800 gccacctctg acttgagcgt cgattttgt gatgctcgtc aggggggcgg agcctatgga    4860
aaaacgccag caacgcggcc ttttacggt tcctggcctt ttgctggcct tttgctcaca    4920
tgttctttcc tgcgttatcc cctgattctg tggataaccg tattaccgcc tttgagtgag    4980
ctgataccgc tcgccgcagc cgaacgaccg agcgcagcga gtcagtgagc gaggaagc     5038
```

<210> SEQ ID NO 39
<211> LENGTH: 1356
<212> TYPE: DNA
<213> ORGANISM: Artificial Sequence
<220> FEATURE:
<223> OTHER INFORMATION: Synthetic (Sh741JLH IgG HC DNA sequence)

<400> SEQUENCE: 39

```
caggtgcagc tggtgcagag cggcagcgag ctgaagaagc ccggcgccag cgtcaaggtg      60
tcctgcaagg ccagcggcta caccttcacc ggctacttca tgaactgggt gcggcaggcc     120
cctgggcagg gactggagtg gatgggccgc atcaaccca caacggcga cagcttctac     180
```

```
aaccagggct tcaccggccg cttcgtgttc agcctggaca ccagcgtgtc caccgcctac      240
ctgcagatca gcagcctgaa ggccgaggac accgccgtgt actactgcgc cagggagggc      300
tactacggcg gcagaggcta cgccctggac tactggggcc agggcaccct ggtgaccgtg      360
tccagcgcta gcaccaaggg cccatcggtc ttccccctgg caccctcctc caagagcacc      420
tctgggggca cagcggccct gggctgcctg gtcaaggact acttccccga accggtgacg      480
gtgtcgtgga actcaggcgc cctgaccagc ggcgtgcaca ccttcccggc tgtcctacag      540
tcctcaggac tctactccct cagcagcgtg gtgaccgtgc cctccagcag cttgggcacc      600
cagacctaca tctgcaacgt gaatcacaag cccagcaaca ccaaggtgga caagagagtt      660
gagcccaaat cttgtgacaa aactcacaca tgcccaccgt gcccagcacc tgaactcctg      720
gggggaccgt cagtcttcct cttccccoca aacccaagg acaccctcat gatctcccgg       780
acccctgagg tcacatgcgt ggtggtggac gtgagccacg aagaccctga ggtcaagttc      840
aactggtacg tggacggcgt ggaggtgcat aatgccaaga caaagccgcg ggaggagcag      900
tacaacagca cgtaccgtgt ggtcagcgtc ctcaccgtcc tgcaccagga ctggctgaat      960
ggcaaggagt acaagtgcaa ggtctccaac aaagccctcc cagcccccat cgagaaaacc     1020
atctccaaag ccaaagggca gccccgagaa ccacaggtgt acaccctgcc cccatcccgg     1080
gatgagctga ccaagaacca ggtcagcctg acctgcctgg tcaaaggctt ctatcccagc     1140
gacatcgccg tggagtggga gagcaatggg cagccggaga acaactacaa gaccacgcct     1200
cccgtgctgg actccgacgg ctccttcttc ctctacagca agctcaccgt ggacaagagc     1260
aggtggcagc aggggaacgt cttctcatgc tccgtgatgc atgaggctct gcacaaccac     1320
tacacgcaga agagcctctc cctgtctccg ggtaaa                                1356
```

<210> SEQ ID NO 40
<211> LENGTH: 452
<212> TYPE: PRT
<213> ORGANISM: Artificial Sequence
<220> FEATURE:
<223> OTHER INFORMATION: Synthetic (Sh741JLH IgG HC amino acid sequence)

<400> SEQUENCE: 40

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gly Tyr
            20                  25                  30

Phe Met Asn Trp Val Arg Gln Ala Pro Gly Gln Gly Leu Glu Trp Met
        35                  40                  45

Gly Arg Ile Asn Pro Asn Asn Gly Asp Ser Phe Tyr Asn Gln Gly Phe
    50                  55                  60

Thr Gly Arg Phe Val Phe Ser Leu Asp Thr Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160
```

```
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Arg Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
            355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
    435                 440                 445
Ser Pro Gly Lys
    450

<210> SEQ ID NO 41
<211> LENGTH: 1356
<212> TYPE: DNA
<213> ORGANISM: Artificial Sequence
<220> FEATURE:
<223> OTHER INFORMATION: Synthetic (Sh145JLH IgG HC DNA sequence)

<400> SEQUENCE: 41
cagatgcagc tggtgcagag cggcgccgag gtgaagaaaa ccggcagcag cgtcaaggtg      60
tcctgcaagg ccagcggcta caccttcacc ggctacttca tgaactgggt gcgccaggcc     120
cccggccagg ccctggagtg gatgggccgc atcaaccccaa caacggcga cagcttctac     180 aaccagaagt tccaggaccg cgtcaccatc acccgcgacc gcagcatgag caccgcctac     240
atggagctgt ccagcctgcg cagcgaggac accgccatgt actactgcgc cagggagggc     300
tactacggcg gcagaggcta cgccctggac tactggggcc agggcaccct ggtgaccgtg     360
```

```
tccagcgcta gcaccaaggg cccatcggtc ttccccctgg caccctcctc caagagcacc    420 tctggggca cagcggccct gggctgcctg gtcaaggact acttccccga accggtgacg     480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
gagcccaaat cttgtgacaa aactcacaca tgcccaccgt gcccagcacc tgaactcctg    720
gggggaccgt cagtcttcct cttccccca aaacccaagg acaccctcat gatctcccgg     780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaaagggca gccccgagaa ccacaggtgt acaccctgcc cccatcccgg   1080
gatgagctga ccaagaacca ggtcagcctg acctgcctgg tcaaaggctt ctatcccagc   1140
gacatcgccg tggagtggga gagcaatggg cagccggaga acaactacaa gaccacgcct   1200
cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaa                             1356
```

<210> SEQ ID NO 42
<211> LENGTH: 452
<212> TYPE: PRT
<213> ORGANISM: Artificial Sequence
<220> FEATURE:
<223> OTHER INFORMATION: Synthetic (Sh145JLH IgG HC amino acid sequence)

<400> SEQUENCE: 42

```
Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Gly Tyr
            20                  25                  30

Phe Met Asn Trp Val Arg Gln Ala Pro Gly Gln Ala Leu Glu Trp Met
        35                  40                  45

Gly Arg Ile Asn Pro Asn Asn Gly Asp Ser Phe Tyr Asn Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
```

```
            180                 185                 190
Val Pro Ser Ser Ser Leu Gly Thr Gln Thr Tyr Ile Cys Asn Val Asn
                195                 200                 205

His Lys Pro Ser Asn Thr Lys Val Asp Lys Arg Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
        435                 440                 445

Ser Pro Gly Lys
    450

<210> SEQ ID NO 43
<211> LENGTH: 1356
<212> TYPE: DNA
<213> ORGANISM: Artificial Sequence
<220> FEATURE:
<223> OTHER INFORMATION: Synthetic (Sh146JLH IgG HC DNA sequence)

<400> SEQUENCE: 43
caggtgcagc tggtgcagag cggcgccgag gtgaagaagc ccggcgccag cgtcaaggtg    60
tcctgcaagg ccagcggcta caccttcaac ggctacttca tgaactgggt gaggcaggcc   120
cctgggcagg gactggagtg gatgggccgc atcaacccca caacggcga cagcttctac    180 aaccagaagt tccagggccg cgtcaccatg acccgcgaca ccagcaccag caccgtgtac   240
atggagctgt ccagcctgcg cagcgaggac accgccgtgt actactgcgc cagggagggc   300
tactacggcg gcagaggcta cgccctggac tactgggccc agggcaccct ggtgaccgtg   360
tccagcgcta gcaccaaggg cccatcggtc ttccccctgg cacccctcct caagagcacc   420
tctgggggca gcggcccct gggctgcctg gtcaaggact acttccccga accggtgacg   480
```

```
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
gagcccaaat cttgtgacaa aactcacaca tgcccaccgt gcccagcacc tgaactcctg    720
gggggaccgt cagtcttcct cttcccccca aaacccaagg acaccctcat gatctcccgg    780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc    1020
atctccaaag ccaaagggca gccccgagaa ccacaggtgt acaccctgcc cccatcccgg    1080
gatgagctga ccaagaacca ggtcagcctg acctgcctgg tcaaaggctt ctatcccagc    1140
gacatcgccg tggagtggga gagcaatggg cagccggaga acaactacaa gaccacgcct    1200
cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga agagcctctc cctgtctccg ggtaaa                               1356
```

<210> SEQ ID NO 44
<211> LENGTH: 452
<212> TYPE: PRT
<213> ORGANISM: Artificial Sequence
<220> FEATURE:
<223> OTHER INFORMATION: Synthetic (Sh146JLH IgG HC amino acid sequence)

<400> SEQUENCE: 44

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Gly Tyr
            20                  25                  30

Phe Met Asn Trp Val Arg Gln Ala Pro Gly Gln Gly Leu Glu Trp Met
        35                  40                  45

Gly Arg Ile Asn Pro Asn Asn Gly Asp Ser Phe Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

His Lys Pro Ser Asn Thr Lys Val Asp Lys Arg Val Glu Pro Lys Ser
   210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
            245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 45
<211> LENGTH: 1356
<212> TYPE: DNA
<213> ORGANISM: Artificial Sequence
<220> FEATURE:
<223> OTHER INFORMATION: Synthetic (Sh434JLH IgG HC DNA sequence)

<400> SEQUENCE: 45
caggtgcagc tgcaggagag cggccccggc ctggtgaagc ccagccagac cctgagcctg      60
acctgcgccg tctacggagg aagcttcagc ggctacttca tgaactggat caggcagccc     120
cccggcaagg gcctggagtg gatcggccgc atcaaccccc acaacggcga cttcagctac     180
aaccagagcc tgaagagccg cgtgaccatc agcgtggaca ccagcaagaa ccagttcagc     240
ctgaagctgt ccagcgtgac cgccgccgac accgccgtgt actactgcgc cagggagggc     300
tactacggcg gcagaggcta cgccctggac tactggggcc agggcaccct ggtgaccgtg     360
tccagcgcta gcaccaaggg cccatcggtc ttccccctgg cacccTCCTC caagagcacc     420
tctgggggca gcggccccT gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660

-continued

```
gagcccaaat cttgtgacaa aactcacaca tgcccaccgt gcccagcacc tgaactcctg      720
gggggaccgt cagtcttcct cttcccccca aacccaagg  acaccctcat gatctcccgg      780 accccctgagg tcacatgcgt ggtggtggac gtgagccacg aagaccctga ggtcaagttc      840
aactggtacg tggacggcgt ggaggtgcat aatgccaaga caaagccgcg ggaggagcag      900
tacaacagca cgtaccgtgt ggtcagcgtc ctcaccgtcc tgcaccagga ctggctgaat      960
ggcaaggagt acaagtgcaa ggtctccaac aaagccctcc cagcccccat cgagaaaacc     1020
atctccaaag ccaaagggca gccccgagaa ccacaggtgt acaccctgcc cccatcccgg     1080
gatgagctga ccaagaacca ggtcagcctg acctgcctgg tcaaaggctt ctatcccagc     1140
gacatcgccg tggagtggga gagcaatggg cagccggaga acaactacaa gaccacgcct     1200
cccgtgctgg actccgacgg ctccttcttc ctctacagca agctcaccgt ggacaagagc     1260
aggtggcagc aggggaacgt cttctcatgc tccgtgatgc atgaggctct gcacaaccac     1320
tacacgcaga agagcctctc cctgtctccg ggtaaa                               1356
```

<210> SEQ ID NO 46
<211> LENGTH: 452
<212> TYPE: PRT
<213> ORGANISM: Artificial Sequence
<220> FEATURE:
<223> OTHER INFORMATION: Synthetic (Sh434JLH IgG HC amino acid sequence)

<400> SEQUENCE: 46

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Gly Tyr
            20                  25                  30

Phe Met Asn Trp Ile Arg Gln Pro Pro Gly Lys Gly Leu Glu Trp Ile
        35                  40                  45

Gly Arg Ile Asn Pro Asn Asn Gly Asp Phe Ser Tyr Asn Gln Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240
```

```
Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 47
<211> LENGTH: 642
<212> TYPE: DNA
<213> ORGANISM: Artificial Sequence
<220> FEATURE:
<223> OTHER INFORMATION: Synthetic (Sh112JLL IgG LC DNA sequence)

<400> SEQUENCE: 47
gacatccaga tgacccagag ccccagcagc gtgtccgcca gcgtgggcga ccgcgtgacc      60
atcacctgcc gcaccagcca ggacatcagc aactacctga actggtatca gcagaagccc     120
ggcaaggccc ccaagctgct gatctacaac accagccgcc tgcacagcgg cgtgccctcc     180
agattctccg gcagcggatc tggcaccgac ttcaccctga ccatcagcag cctgcagccc     240
gaggacttcg ccacctacta ctgccagcag agcaacatgt tccctacac cttcggccag      300 ggcaccaagc tggagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccttgacg    540 ctgagcaaag cagactacga aaacacaaa gtctacgcct gcgaagtcac ccatcagggc      600
ctgagttcac cggtgacaaa gagcttcaac aggggagagt gt                        642

<210> SEQ ID NO 48
<211> LENGTH: 214
<212> TYPE: PRT
```

<213> ORGANISM: Artificial Sequence
<220> FEATURE:
<223> OTHER INFORMATION: Synthetic (Sh112JLL IgG LC amino acid sequence)

<400> SEQUENCE: 48

```
Asp Ile Gln Met Thr Gln Ser Pro Ser Ser Val Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 49
<211> LENGTH: 751
<212> TYPE: DNA
<213> ORGANISM: Artificial Sequence
<220> FEATURE:
<223> OTHER INFORMATION: Synthetic (murine anti-CD43 (mJL1) scFv DNA sequence)

<400> SEQUENCE: 49

```
ccatggccga ggttcagctg cagcagtctg gtcctgagct ggtgaagcct ggggcttcag     60
tgaagatttc ctgcaaggcc tctggttact caattggtgg ctactttatg aactgggtga    120
agcagagcca cggcaagagc cctgagtgga ttgggcgtat taatcctaac aatggtgatt    180
ctttctacaa ccagaaattc aagggcacgg ccacattgac tgttgaccgc tcttctgaca    240
cagtccacat ggaggtcctg agcctgacat ctgaggactc tgcagtctat tattgtggcc    300
gcgaaggtta ctacggtggg cgagggtatg ctttggacta ctggggtcaa ggcacctcgg    360
tcaccgtctc ctcaggcggc ggagctagcg ggggaggagg atccggaggc gggggatctg    420
atatccagat gacacagact acatcctccc tgtctgcctc tctgggcgac cgcgtcacca    480
tcagctgccg gacaagtcag gacattagca attatttgaa ctggtatcag cagaaaccag    540
atggtactgt taaactcctg atctataaca tcacgctt gcactcaggc gtcccatcac    600
```

```
ggttcagtgg cagcgggtct ggtacagatt attccctcac cattcgcaac ctggaacaaa    660
aagatattgc acttacttt tgccaacaga gcaatatgtt tccgtacacg ttcggggggg     720
ggaccaagct ggaaatcaag cgggcggccg c                                   751
```

```
<210> SEQ ID NO 50
<211> LENGTH: 247
<212> TYPE: PRT
<213> ORGANISM: Artificial Sequence
<220> FEATURE:
<223> OTHER INFORMATION: Synthetic (murine anti-CD43 (mJL1) scFv amino
      acid sequence)

<400> SEQUENCE: 50
```

```
Met Ala Glu Val Gln Leu Gln Gln Ser Gly Pro Glu Leu Val Lys Pro
 1               5                  10                  15

Gly Ala Ser Val Lys Ile Ser Cys Lys Ala Ser Gly Tyr Ser Ile Gly
             20                  25                  30

Gly Tyr Phe Met Asn Trp Val Lys Gln Ser His Gly Lys Ser Pro Glu
         35                  40                  45

Trp Ile Gly Arg Ile Asn Pro Asn Asn Gly Asp Ser Phe Tyr Asn Gln
     50                  55                  60

Lys Phe Lys Gly Thr Ala Thr Leu Thr Val Asp Arg Ser Ser Asp Thr
 65                  70                  75                  80

Val His Met Glu Val Leu Ser Leu Thr Ser Glu Asp Ser Ala Val Tyr
                 85                  90                  95

Tyr Cys Gly Arg Glu Gly Tyr Tyr Gly Gly Arg Gly Tyr Ala Leu Asp
            100                 105                 110

Tyr Trp Gly Gln Gly Thr Ser Val Thr Val Ser Ser Gly Gly Gly Ala
        115                 120                 125

Ser Gly Gly Gly Gly Ser Gly Gly Gly Ser Asp Ile Gln Met Thr
    130                 135                 140

Gln Thr Thr Ser Ser Leu Ser Ala Ser Leu Gly Asp Arg Val Thr Ile
145                 150                 155                 160

Ser Cys Arg Thr Ser Gln Asp Ile Ser Asn Tyr Leu Asn Trp Tyr Gln
                165                 170                 175

Gln Lys Pro Asp Gly Thr Val Lys Leu Leu Ile Tyr Asn Thr Ser Arg
            180                 185                 190

Leu His Ser Gly Val Pro Ser Arg Phe Ser Gly Ser Gly Ser Gly Thr
        195                 200                 205

Asp Tyr Ser Leu Thr Ile Arg Asn Leu Glu Gln Lys Asp Ile Ala Thr
    210                 215                 220

Tyr Phe Cys Gln Gln Ser Asn Met Phe Pro Tyr Thr Phe Gly Gly Gly
225                 230                 235                 240

Thr Lys Leu Glu Ile Lys Arg
                245
```

```
<210> SEQ ID NO 51
<211> LENGTH: 751
<212> TYPE: DNA
<213> ORGANISM: Artificial Sequence
<220> FEATURE:
<223> OTHER INFORMATION: Synthetic (Sh741-112 scFv DNA sequence)

<400> SEQUENCE: 51
ccatggccca ggtgcagctg gtgcagagcg gcagcgagct gaagaagccc ggcgccagcg    60
tcaaggtgtc ctgcaaggcc agcggctaca ccttcaccgg ctacttcatg aactgggtgc   120
```

```
gccaggcccc tgggcaggga ctggagtgga tgggccgcat caaccccaac aacggcgaca      180
gcttctacaa ccagggcttc accggccgct tcgtgttcag cctggacacc agcgtgtcca      240
ccgcctacct gcagatcagc agcctgaagg ccgaggacac cgccgtgtac tactgcgcca      300
gggagggcta ctacggaggg agagggtacg ccctggacta ctggggccag ggcaccctgg      360
tgaccgtgtc ctccggcggc ggaggatccg gaggcggggg atctggggga ggagctagcg      420
acatccagat gacccagagc ccttcttctg tctccgccag cgtgggcgac cgcgtgacca      480
tcacctgccg caccagccag gacatcagca actacctgaa ctggtatcag cagaagcccg      540
gcaaggcccc caagctgctg atctacaaca ccagcaggct ccactctgga gtccccagcc      600
gcttctccgg ctccgggtct ggaaccgact tcaccctgac catcagctcc ctgcagcccg      660
aggacttcgc cacctactac tgccagcaga gcaacatgtt ccctacacc ttcgggcagg      720 ggaccaagct ggagatcaag cgggcggccg c                                    751
```

<210> SEQ ID NO 52
<211> LENGTH: 245
<212> TYPE: PRT
<213> ORGANISM: Artificial Sequence
<220> FEATURE:
<223> OTHER INFORMATION: Synthetic (Sh741-112 scFv amio acid sequence)

<400> SEQUENCE: 52

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gly Tyr
            20                  25                  30

Phe Met Asn Trp Val Arg Gln Ala Pro Gly Gln Gly Leu Glu Trp Met
        35                  40                  45

Gly Arg Ile Asn Pro Asn Asn Gly Asp Ser Phe Tyr Asn Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Ala Ser Asp Ile Gln Met Thr Gln Ser
    130                 135                 140

Pro Ser Ser Val Ser Ala Ser Val Gly Asp Arg Val Thr Ile Thr Cys
145                 150                 155                 160

Arg Thr Ser Gln Asp Ile Ser Asn Tyr Leu Asn Trp Tyr Gln Gln Lys
                165                 170                 175

Pro Gly Lys Ala Pro Lys Leu Leu Ile Tyr Asn Thr Ser Arg Leu His
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser Asn Met Phe Pro Tyr Thr Phe Gly Gln Gly Thr Lys
225                 230                 235                 240

Leu Glu Ile Lys Arg
                245
```

<210> SEQ ID NO 53
<211> LENGTH: 751
<212> TYPE: DNA
<213> ORGANISM: Artificial Sequence
<220> FEATURE:
<223> OTHER INFORMATION: Synthetic (Sh145-112 scFv DNA sequence)

<400> SEQUENCE: 53

```
ccatggccca gatgcagctg gtgcagagcg gcgccgaggt gaagaaaacc ggcagcagcg    60
tcaaggtgtc ctgcaaggcc agcggctaca ccttcaccgg ctacttcatg aactgggtgc   120
gccaggcccc cggccaggcc ctggagtgga tgggccgcat caaccccaac aacggcgaca   180
gcttctacaa ccagaagttc caggaccgcg tcaccatcac ccgcgaccgc agcatgagca   240
ccgcctacat ggagctgtcc agcctgcgca gcgaggacac cgccatgtac tactgcgcca   300
gggagggcta ctacggcggc agaggctacg ccctggacta ctggggccag gcaccctgg   360
tgaccgtgtc ctccggcggc ggaggatccg gaggcggggg atctggggga ggagctagcg   420
acatccagat gacccagagc ccttcttctg tctccgccag cgtgggcgac cgcgtgacca   480
tcacctgccg caccagccag gacatcagca actacctgaa ctggtatcag cagaagcccg   540
gcaaggcccc caagctgctg atctacaaca ccagcaggct ccactctgga gtccccagcc   600
gcttctccgg ctccgggtct ggaaccgact tcaccctgac catcagctcc ctgcagcccg   660
aggacttcgc cacctactac tgccagcaga gcaacatgtt cccctacacc ttcgggcagg   720
ggaccaagct ggagatcaag cgggcggccg c                                  751
```

<210> SEQ ID NO 54
<211> LENGTH: 245
<212> TYPE: PRT
<213> ORGANISM: Artificial Sequence
<220> FEATURE:
<223> OTHER INFORMATION: Synthetic (Sh145-112 scFv amino acid sequence)

<400> SEQUENCE: 54

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Gly Tyr
            20                  25                  30

Phe Met Asn Trp Val Arg Gln Ala Pro Gly Gln Ala Leu Glu Trp Met
        35                  40                  45

Gly Arg Ile Asn Pro Asn Asn Gly Asp Ser Phe Tyr Asn Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ala Ser Asp Ile Gln Met Thr Gln Ser
    130                 135                 140

Pro Ser Ser Val Ser Ala Ser Val Gly Asp Arg Val Thr Ile Thr Cys
145                 150                 155                 160

Arg Thr Ser Gln Asp Ile Ser Asn Tyr Leu Asn Trp Tyr Gln Gln Lys
                165                 170                 175

Pro Gly Lys Ala Pro Lys Leu Leu Ile Tyr Asn Thr Ser Arg Leu His
            180                 185                 190

Ser Gly Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
        210                 215                 220

Cys Gln Gln Ser Asn Met Phe Pro Tyr Thr Phe Gly Gln Gly Thr Lys
225                 230                 235                 240

Leu Glu Ile Lys Arg
            245

<210> SEQ ID NO 55
<211> LENGTH: 751
<212> TYPE: DNA
<213> ORGANISM: Artificial Sequence
<220> FEATURE:
<223> OTHER INFORMATION: Synthetic (Sh146-112 scFv DNA sequence)

<400> SEQUENCE: 55

| | | |
|---|---|---|
| ccatggccca ggtgcagctg gtgcagagcg gcgccgaggt gaagaagccc ggcgccagcg | 60 |
| tcaaggtgtc ctgcaaggcc agcggctaca ccttcaacgg ctacttcatg aactgggtga | 120 |
| ggcaggcccc tgggcaggga ctggagtgga tgggccgcat caaccccaac aacggcgaca | 180 |
| gcttctacaa ccagaagttc cagggccgcg tcaccatgac ccgcgacacc agcaccagca | 240 |
| ccgtgtacat ggagctgtcc agcctgcgca gcgaggacac cgccgtgtac tactgcgcca | 300 |
| gggagggcta ctacggcggc agaggctacg ccctggacta ctggggtcaa ggcaccctgg | 360 |
| tgaccgtgtc cagcggcggc ggaggatccg gaggcggggg atctggggga ggagctagcg | 420 |
| acatccagat gacccagagc ccttcttctg tctccgccag cgtgggcgac cgcgtgacca | 480 |
| tcacctgccg caccagccag gacatcagca actacctgaa ctggtatcag cagaagcccg | 540 |
| gcaaggcccc caagctgctg atctacaaca ccagcaggct ccactctgga gtccccagcc | 600 |
| gcttctccgg ctccgggtct ggaaccgact tcaccctgac catcagctcc ctgcagcccg | 660 |
| aggacttcgc cacctactac tgccagcaga gcaacatgtt ccccctacacc ttcgggcagg | 720 |
| gtacaaagct ggagatcaag cgggcggccg c | 751 |

<210> SEQ ID NO 56
<211> LENGTH: 247
<212> TYPE: PRT
<213> ORGANISM: Artificial Sequence
<220> FEATURE:
<223> OTHER INFORMATION: Synthetic (Sh146-112 scFv amino acid sequence)

<400> SEQUENCE: 56

Met Ala Gln Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Asn
            20                  25                  30

Gly Tyr Phe Met Asn Trp Val Arg Gln Ala Pro Gly Gln Gly Leu Glu
        35                  40                  45

Trp Met Gly Arg Ile Asn Pro Asn Asn Gly Asp Ser Phe Tyr Asn Gln
    50                  55                  60

Lys Phe Gln Gly Arg Val Thr Met Thr Arg Asp Thr Ser Thr Ser Thr
65                  70                  75                  80

Val Tyr Met Glu Leu Ser Ser Leu Arg Ser Glu Asp Thr Ala Val Tyr
                85                  90                  95

Tyr Cys Ala Arg Glu Gly Tyr Gly Gly Arg Gly Tyr Ala Leu Asp
            100                 105                 110

Tyr Trp Gly Gln Gly Thr Leu Val Thr Val Ser Ser Gly Gly Gly
            115                 120                 125

Ser Gly Gly Gly Ser Gly Gly Gly Ala Ser Asp Ile Gln Met Thr
    130                 135                 140

Gln Ser Pro Ser Ser Val Ser Ala Ser Val Gly Asp Arg Val Thr Ile
145                 150                 155                 160

Thr Cys Arg Thr Ser Gln Asp Ile Ser Asn Tyr Leu Asn Trp Tyr Gln
                165                 170                 175

Gln Lys Pro Gly Lys Ala Pro Lys Leu Leu Ile Tyr Asn Thr Ser Arg
            180                 185                 190

Leu His Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Ser Asn Met Phe Pro Tyr Thr Phe Gly Gln Gly
225                 230                 235                 240

Thr Lys Leu Glu Ile Lys Arg
                245

<210> SEQ ID NO 57
<211> LENGTH: 751
<212> TYPE: DNA
<213> ORGANISM: Artificial Sequence
<220> FEATURE:
<223> OTHER INFORMATION: Synthetic (Sh434-112 scFv DNA sequence)

<400> SEQUENCE: 57
ccatggccca ggtgcagctg caggagagcg gccccggcct ggtgaagccc agccagaccc    60
tgagcctgac ctgcgccgtc tacggaggaa gcttcagcgg ctacttcatg aactggatca   120
ggcagccccc cggcaagggc ctggagtgga tcggccgcat caaccccaac aacggcgact   180
tcagctacaa ccagagcctg aagagccgcg tgaccatcag cgtggacacc agcaagaacc   240
agttcagcct gaagctgtcc agcgtgaccg ccgccgacac cgccgtgtac tactgcgcca   300
gggagggcta ctacggcggc agaggctacg ccctggacta ctggggccag ggcaccctgg   360
tgaccgtgtc cagcggcggc ggaggatccg gaggcggggg atctggggga ggagctagcg   420
acatccagat gacccagagc ccttcttctg tctccgccag cgtgggcgac cgcgtgacca   480
tcacctgccg caccagccag gacatcagca actacctgaa ctggtatcag cagaagcccg   540
gcaaggcccc caagctgctg atctacaaca ccagcaggct ccactctgga gtccccagcc   600
gcttctccgg ctccgggtct ggaaccgact tcaccctgac catcagctcc ctgcagcccg   660
aggacttcgc cacctactac tgccagcaga gcaacatgtt ccctacacc ttcgggcagg    720
gtacaaagct ggagatcaag cgggcggccg c                                  751

<210> SEQ ID NO 58
<211> LENGTH: 245
<212> TYPE: PRT
<213> ORGANISM: Artificial Sequence
<220> FEATURE:
<223> OTHER INFORMATION: Synthetic (Sh434-112 scFv amino acid sequence)

<400> SEQUENCE: 58

Gln Val Gln Leu Gln Glu Ser Gly Pro Gly Leu Val Lys Pro Ser Gln
1               5                   10                  15

```
Thr Leu Ser Leu Thr Cys Ala Val Tyr Gly Gly Ser Phe Ser Gly Tyr
         20                  25                  30

Phe Met Asn Trp Ile Arg Gln Pro Pro Gly Lys Gly Leu Glu Trp Ile
         35                  40                  45

Gly Arg Ile Asn Pro Asn Asn Gly Asp Phe Ser Tyr Asn Gln Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Glu Gly Tyr Tyr Gly Arg Gly Tyr Ala Leu Asp Tyr Trp
             100                 105                 110

Gly Gln Gly Thr Leu Val Thr Val Ser Ser Gly Gly Gly Ser Gly
             115                 120                 125

Gly Gly Ser Gly Gly Gly Ala Ser Asp Ile Gln Met Thr Gln Ser
 130                 135                 140

Pro Ser Ser Val Ser Ala Ser Val Gly Asp Arg Val Thr Ile Thr Cys
145                 150                 155                 160

Arg Thr Ser Gln Asp Ile Ser Asn Tyr Leu Asn Trp Tyr Gln Gln Lys
                 165                 170                 175

Pro Gly Lys Ala Pro Lys Leu Leu Ile Tyr Asn Thr Ser Arg Leu His
             180                 185                 190

Ser Gly Val Pro Ser Arg Phe Ser Gly Ser Gly Ser Gly Thr Asp Phe
         195                 200                 205

Thr Leu Thr Ile Ser Ser Leu Gln Pro Glu Asp Phe Ala Thr Tyr Tyr
         210                 215                 220

Cys Gln Gln Ser Asn Met Phe Pro Tyr Thr Phe Gly Gln Gly Thr Lys
225                 230                 235                 240

Leu Glu Ile Lys Arg
             245

<210> SEQ ID NO 59
<211> LENGTH: 1356
<212> TYPE: DNA
<213> ORGANISM: Artificial Sequence
<220> FEATURE:
<223> OTHER INFORMATION: Synthetic (Sh741JLHP45 IgG HC DNA sequence)

<400> SEQUENCE: 59
caggtgcagc tggtgcagag cggcagcgag ctgaagaagc ccggcgccag cgtcaaggtg      60
tcctgcaagg ccagcggcta caccttcacc ggctacttca tgaactgggt cgcgcaggcc     120
cccggacagg ggcccgagtg gatgggccgc atcaacccca caacggcga cagcttctac     180 aaccagggct tcaccggccg cttcgtgttc agcctggaca ccagcgtgtc caccgcctac     240
ctgcagatca gcagcctgaa ggccgaggac accgccgtgt actactgcgc agggagggc     300 tactacggcg gcagaggcta cgccctggac tactggggcc agggcaccct ggtgaccgtg     360
tccagcgcta gcaccaaggg cccatcggtc ttccccctgg caccctcctc caagagcacc     420
tctgggggca gcggccct gggctgcctg gtcaaggact acttcccga accggtgacg     480 gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactcacaca tgcccaccgt gcccagcacc tgaactcctg     720
```

```
gggggaccgt cagtcttcct cttcccccca aaacccaagg acaccctcat gatctcccgg    780 accctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaaagggca gccccgagaa ccacaggtgt acaccctgcc cccatcccgg   1080
gatgagctga ccaagaacca ggtcagcctg acctgcctgg tcaaaggctt ctatcccagc   1140
gacatcgccg tggagtggga gagcaatggg cagccggaga acaactacaa gaccacgcct   1200
cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaa                              1356
```

<210> SEQ ID NO 60
<211> LENGTH: 452
<212> TYPE: PRT
<213> ORGANISM: Artificial Sequence
<220> FEATURE:
<223> OTHER INFORMATION: Synthetic (Sh741JLHP45 IgG HC amino acid
      sequence, wherein the 45th amino acid residue is substituted with
      P)

<400> SEQUENCE: 60

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gly Tyr
            20                  25                  30

Phe Met Asn Trp Val Arg Gln Ala Pro Gly Gln Gly Pro Glu Trp Met
        35                  40                  45

Gly Arg Ile Asn Pro Asn Asn Gly Asp Ser Phe Tyr Asn Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240
```

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 61
<211> LENGTH: 1356
<212> TYPE: DNA
<213> ORGANISM: Artificial Sequence
<220> FEATURE:
<223> OTHER INFORMATION: Synthetic (Sh145JLHP45 IgG HC DNA sequence)

<400> SEQUENCE: 61
cagatgcagc tggtgcagag cggcgccgag gtgaagaaaa ccggcagcag cgtcaaggtg     60
tcctgcaagg ccagcggcta caccttcacc ggctacttca tgaactgggt gaggcaggcc    120
cctggacagg cccccgagtg gatgggccgc atcaaccccacaacggcga cagcttctac    180 aaccagaagt tccaggaccg cgtcaccatc acccgcgacc gcagcatgag caccgcctac    240
atggagctgt ccagcctgcg cagcgaggac accgccatgt actactgcgc cagggagggc    300
tactacggcg gcagaggcta cgccctggac tactggggcc agggcaccct ggtgaccgtg    360
tccagcgcta gcaccaaggg cccatcggtc ttccccctgg cacctcctc caagagcacc    420 tctgggggca gcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
gagcccaaat cttgtgacaa aactcacaca tgcccaccgt gcccagcacc tgaactcctg    720
gggggaccgt cagtcttcct cttccccca aaacccaagg acaccctcat gatctcccgg    780

```
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagcccctc cagcccccat cgagaaaacc   1020
atctccaaag ccaaagggca gccccgagaa ccacaggtgt acaccctgcc cccatcccgg   1080
gatgagctga ccaagaacca ggtcagcctg acctgcctgg tcaaaggctt ctatcccagc   1140
gacatcgccg tggagtggga gagcaatggg cagccggaga caactacaa gaccacgcct    1200 cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga gagcctctc cctgtctccg ggtaaa                              1356
```

<210> SEQ ID NO 62
<211> LENGTH: 452
<212> TYPE: PRT
<213> ORGANISM: Artificial Sequence
<220> FEATURE:
<223> OTHER INFORMATION: Synthetic (Sh145JLHP45 IgG HC variant (residue
     45 is substituted with P) amino acid sequence)

<400> SEQUENCE: 62

```
Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Gly Tyr
            20                  25                  30

Phe Met Asn Trp Val Arg Gln Ala Pro Gly Gln Ala Pro Glu Trp Met
        35                  40                  45

Gly Arg Ile Asn Pro Asn Asn Gly Asp Ser Phe Tyr Asn Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 63
<211> LENGTH: 642
<212> TYPE: DNA
<213> ORGANISM: Artificial Sequence
<220> FEATURE:
<223> OTHER INFORMATION: Synthetic (Sh112JLV44 IgG LC variant DNA
      sequence)

<400> SEQUENCE: 63
gacatccaga tgacccagag ccccagcagc gtgtccgcca gcgtgggcga ccgcgtgacc      60
atcacctgcc gcaccagcca ggacatcagc aactacctga actggtatca gcagaagccc     120
ggcaaggccg tgaagctgct gatctacaac accagccgcc tgcacagcgg cgtgccctcc     180
agattctccg gcagcggatc tggcaccgac ttcaccctga ccatcagcag cctgcagccc     240
gaggacttcg ccacctacta ctgccagcag agcaacatgt tccctacac cttcggccag      300 ggcaccaagc tggagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagttcac cggtgacaaa gagcttcaac aggggagagt gt                        642

<210> SEQ ID NO 64
<211> LENGTH: 214
<212> TYPE: PRT
<213> ORGANISM: Artificial Sequence
<220> FEATURE:
<223> OTHER INFORMATION: Synthetic (Sh112JLV44 IgG LC variant (residue
```

44 is substituted with V) amino acid sequence)

<400> SEQUENCE: 64

Asp Ile Gln Met Thr Gln Ser Pro Ser Ser Val Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 1356
<212> TYPE: DNA
<213> ORGANISM: Artificial Sequence
<220> FEATURE:
<223> OTHER INFORMATION: Synthetic (DNA sequence CDhRZ7VHKb (Conv.
      Humanized variants IgG))

<400> SEQUENCE: 65
gaggtgcagc tggtccagag cggcgccgag gtcaagaagc tggcgccac cgtcaagatc        60 agctgcaagg ccagcggcta caccttcagc ggctacttca tgaactgggt ccgccaggcc      120
ccaggcaagg gactggagtg gatgggccgc atcaacccca caacggcga cagcttctac       180 aaccagaagt tcaagggccg cgtcaccatc accgccgaca ccagcaccga caccggctac      240
ctggagctgt ccagcctgag aagcgaggac accgccgtgt actactgtgc cgccgagggc      300
tactacggcg gcagaggcta cgccctggac tactggggcc agggcaccct ggtgtccgtg      360
agcagcgcta gcaccaaggg cccatcggtc ttccccctgg cacctcctc caagagcacc       420 tctggggca cagcggccct gggctgcctg gtcaaggact acttccccga accggtgacg       480
gtgtcgtgga actcaggcgc cctgaccagc ggcgtgcaca ccttcccggc tgtcctacag      540
tcctcaggac tctactccct cagcagcgtg gtgaccgtgc cctccagcag cttgggcacc      600
cagacctaca tctgcaacgt gaatcacaag cccagcaaca ccaaggtgga caagagagtt      660

```
gagcccaaat cttgtgacaa aactcacaca tgcccaccgt gcccagcacc tgaactcctg    720
gggggaccgt cagtcttcct cttcccccca aacccaagg acaccctcat gatctcccgg    780
accctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc    1020
atctccaaag ccaaagggca gccccgagaa ccacaggtgt acaccctgcc cccatcccgg    1080
gatgagctga ccaagaacca ggtcagcctg acctgcctgg tcaaaggctt ctatcccagc    1140
gacatcgccg tggagtggga gagcaatggg cagccggaga caactacaa gaccacgcct    1200
cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga agagcctctc cctgtctccg ggtaaa                              1356
```

<210> SEQ ID NO 66
<211> LENGTH: 452
<212> TYPE: PRT
<213> ORGANISM: Artificial Sequence
<220> FEATURE:
<223> OTHER INFORMATION: Synthetic (Amino acid sequence CDhRZ7VHKb
      (Conv. Humanized variants IgG))

<400> SEQUENCE: 66

```
Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Gly Tyr
                20                  25                  30

Phe Met Asn Trp Val Arg Gln Ala Pro Gly Lys Gly Leu Glu Trp Met
            35                  40                  45

Gly Arg Ile Asn Pro Asn Asn Gly Asp Ser Phe Tyr Asn Gln Lys Phe
        50                  55                  60

Lys Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Glu Gly Tyr Tyr Gly Arg Gly Tyr Ala Leu Asp Tyr Trp
                100                 105                 110

Gly Gln Gly Thr Leu Val Ser Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240
```

Gly Gly Pro Ser Val Phe Leu Phe Pro Pro Lys Pro Lys Asp Thr Leu
              245                 250                 255

Met Ile Ser Arg Thr Pro Glu Val Thr Cys Val Val Val Asp Val Ser
              260                 265                 270

His Glu Asp Pro Glu Val Lys Phe Asn Trp Tyr Val Asp Gly Val Glu
              275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
              340                 345                 350

Val Tyr Thr Leu Pro Pro Ser Arg Asp Glu Leu Thr Lys Asn Gln Val
              355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
              420                 425                 430

Met His Glu Ala Leu His Asn His Tyr Thr Gln Lys Ser Leu Ser Leu
              435                 440                 445

Ser Pro Gly Lys
    450

<210> SEQ ID NO 67
<211> LENGTH: 1356
<212> TYPE: DNA
<213> ORGANISM: Artificial Sequence
<220> FEATURE:
<223> OTHER INFORMATION: Synthetic (DNA sequence CDhRZ7VH_KbR73 (Conv.
      Humanized variants IgG))

<400> SEQUENCE: 67
gaggtgcagc tggtccagag cggcgccgag gtcaagaagc tggcgccac cgtcaagatc      60 agctgcaagg ccagcggcta cacctcagc ggctacttca tgaactgggt ccgccaggcc     120
ccaggcaagg gactggagtg gatgggccgc atcaacccca caacggcga cagcttctac     180 aaccagaagt tcaagggccg cgtcaccatc accgccgacc gcagcaccga caccggctac     240
ctggagctgt ccagcctgag aagcgaggac accgccgtgt actactgtgc cgccgagggc     300
tactacggcg cagaggcta cgccctggac tactggggcc agggcaccct ggtgtccgtg     360
agcagcgcta gcaccaaggg cccatcggtc ttccccctgg cacctcctc caagagcacc     420 tctgggggca gcggcccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactcacaca tgcccaccgt gcccagcacc tgaactcctg     720
gggggaccgt cagtcttcct cttccccca aaacccaagg acaccctcat gatctccgg     780

-continued

```
acccctgagg tcacatgcgt ggtggtggac gtgagccacg aagaccctga ggtcaagttc      840
aactggtacg tggacggcgt ggaggtgcat aatgccaaga caaagccgcg ggaggagcag      900
tacaacagca cgtaccgtgt ggtcagcgtc ctcaccgtcc tgcaccagga ctggctgaat      960
ggcaaggagt acaagtgcaa ggtctccaac aaagccctcc cagcccccat cgagaaaacc     1020
atctccaaag ccaaagggca gccccgagaa ccacaggtgt acaccctgcc cccatcccgg     1080
gatgagctga ccaagaacca ggtcagcctg acctgcctgg tcaaaggctt ctatcccagc     1140
gacatcgccg tggagtggga gagcaatggg cagccggaga caactacaa gaccacgcct      1200 cccgtgctgg actccgacgg ctccttcttc ctctacagca agctcaccgt ggacaagagc     1260
aggtggcagc aggggaacgt cttctcatgc tccgtgatgc atgaggctct gcacaaccac     1320
tacacgcaga agagcctctc cctgtctccg ggtaaa                               1356
```

<210> SEQ ID NO 68
<211> LENGTH: 452
<212> TYPE: PRT
<213> ORGANISM: Artificial Sequence
<220> FEATURE:
<223> OTHER INFORMATION: Synthetic (Amino acid sequence CDhRZ7VH_KbR73
      (Conv. Humanized variants IgG))

<400> SEQUENCE: 68

```
Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Gly Tyr
            20                  25                  30

Phe Met Asn Trp Val Arg Gln Ala Pro Gly Lys Gly Leu Glu Trp Met
        35                  40                  45

Gly Arg Ile Asn Pro Asn Asn Gly Asp Ser Phe Tyr Asn Gln Lys Phe
    50                  55                  60

Lys Gly Arg Val Thr Ile Thr Ala Asp Arg Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Glu Gly Tyr Tyr Gly Gly Arg Gly Tyr Ala Leu Asp Tyr Trp
            100                 105                 110

Gly Gln Gly Thr Leu Val Ser Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 69
<211> LENGTH: 1356
<212> TYPE: DNA
<213> ORGANISM: Artificial Sequence
<220> FEATURE:
<223> OTHER INFORMATION: Synthetic (DNA sequence CDhL7IVHKb (Conv.
      Humanized variants IgG))

<400> SEQUENCE: 69
gaggtgcagc tggtcgagag cggcggggc ctggtgcagc ctggcggcag cctgcgcctg      60
agctgcgccg ccagcggctt caccttcacc ggctacttca tgaactgggt ccgccaggcc    120
ccagggaaag gcctggagtg ggtggcccgc atcaaccca caacggcga cagcttctac      180 aaccagaagt tcaagggccg cttcaccctg agcgtggacc gcagcaagaa caccctgtac    240
ctgcagatga cagcctgag ggccgaggac accgccgtgt actactgcgc cagagagggc    300
tactacggcg cagaggcta cgccctggac tactggggcc agggcaccct ggtcaccgtg    360
tccagcgcta gcaccaaggg cccatcggtc ttccccctgg caccctcctc caagagcacc    420
tctgggggca gcggccct gggctgcctg gtcaaggact acttccccga accggtgacg     480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
gagcccaaat cttgtgacaa aactcacaca tgcccaccgt gcccagcacc tgaactcctg    720
gggggaccgt cagtcttcct cttccccca aaacccaagg acaccctcat gatctcccgg    780
acccctgagg tcacatgcgt ggtggtggac gtgagccacg aagaccctga ggtcaagttc    840
```

```
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaaagggca gccccgagaa ccacaggtgt acaccctgcc cccatcccgg   1080
gatgagctga ccaagaacca ggtcagcctg acctgcctgg tcaaaggctt ctatcccagc   1140
gacatcgccg tggagtggga gagcaatggg cagccggaga caactacaa gaccacgcct    1200 cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaa                             1356
```

<210> SEQ ID NO 70
<211> LENGTH: 452
<212> TYPE: PRT
<213> ORGANISM: Artificial Sequence
<220> FEATURE:
<223> OTHER INFORMATION: Synthetic (Amino acid sequence CDhL7IVHKb
      (Conv. Humanized variants IgG))

<400> SEQUENCE: 70

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Tyr
            20                  25                  30

Phe Met Asn Trp Val Arg Gln Ala Pro Gly Lys Gly Leu Glu Trp Val
        35                  40                  45

Ala Arg Ile Asn Pro Asn Asn Gly Asp Ser Phe Tyr Asn Gln Lys Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
    435                 440                 445

Ser Pro Gly Lys
    450

<210> SEQ ID NO 71
<211> LENGTH: 1356
<212> TYPE: DNA
<213> ORGANISM: Artificial Sequence
<220> FEATURE:
<223> OTHER INFORMATION: Synthetic (DNA sequence CDhRZ7VHAM (Conv.
      Humanized variants IgG))

<400> SEQUENCE: 71
gaggtgcagc tggtccagag cggcgccgag gtcaagaagc tggcgccac cgtcaagatc      60 agctgcaagg ccagcggcta cagcatcggc ggctacttca tgaactgggt ccgccaggcc    120
ccaggcaagg gactggagtg gatgggccgc atcaaccca caacggcga cagcttctac      180 aaccagaagt tcaagggccg cgtcaccatc accgccgaca ccagcaccga caccggctac   240
ctggagctgt ccagcctgag aagcgaggac accgccgtgt actactgtgc cgccgagggc   300
tactacggcg gcagaggcta cgccctggac tactggggcc agggcaccct ggtgtccgtg   360
agcagcgcta gcaccaaggg cccatcggtc ttccccctgg cacctcctc caagagcacc    420 tctgggggca gcggccct gggctgcctg gtcaaggact acttccccga accggtgacg      480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacc   600
cagacctaca tctgcaacgt gaatcacaag cccagcaaca ccaaggtgga caagagagtt    660
gagcccaaat cttgtgacaa aactcacaca tgcccaccgt gcccagcacc tgaactcctg    720
gggggaccgt cagtcttcct cttccccca aaacccaagg acaccctcat gatctcccgg    780 accctgagg tcacatgcgt ggtggtggac gtgagccacg aagaccctga ggtcaagttc    840
aactggtacg tggacggcgt ggaggtgcat aatgccaaga caaagccgcg ggaggagcag   900
tacaacagca cgtaccgtgt ggtcagcgtc ctcaccgtcc tgcaccagga ctggctgaat    960

```
ggcaaggagt acaagtgcaa ggtctccaac aaagccctcc cagcccccat cgagaaaacc    1020
atctccaaag ccaagggca gccccgagaa ccacaggtgt acaccctgcc cccatcccgg     1080
gatgagctga ccaagaacca ggtcagcctg acctgcctgg tcaaaggctt ctatcccagc    1140
gacatcgccg tggagtggga gagcaatggg cagccggaga acaactacaa gaccacgcct    1200
cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga agagcctctc cctgtctccg ggtaaa                              1356
```

<210> SEQ ID NO 72
<211> LENGTH: 452
<212> TYPE: PRT
<213> ORGANISM: Artificial Sequence
<220> FEATURE:
<223> OTHER INFORMATION: Synthetic (Amino acid sequence CDhRZ7VHAM
      (Conv. Humanized variants IgG))

<400> SEQUENCE: 72

```
Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Ser Ile Gly Gly Tyr
            20                  25                  30

Phe Met Asn Trp Val Arg Gln Ala Pro Gly Lys Gly Leu Glu Trp Met
        35                  40                  45

Gly Arg Ile Asn Pro Asn Asn Gly Asp Ser Phe Tyr Asn Gln Lys Phe
    50                  55                  60

Lys Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Glu Gly Tyr Tyr Gly Gly Arg Gly Tyr Ala Leu Asp Tyr Trp
            100                 105                 110

Gly Gln Gly Thr Leu Val Ser Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

```
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 73
<211> LENGTH: 1356
<212> TYPE: DNA
<213> ORGANISM: Artificial Sequence
<220> FEATURE:
<223> OTHER INFORMATION: Synthetic (DNA sequence CDhRZ7VHAMR73 (Conv.
      Humanized variants IgG))

<400> SEQUENCE: 73
gaggtgcagc tggtccagag cggcgccgag gtcaagaagc tggcgccac cgtcaagatc       60 agctgcaagg ccagcggcta ctccatcggc ggctacttca tgaactgggt ccgccaggcc      120
ccaggcaagg gactggagtg gatgggccgc atcaacccca caacggcga cagcttctac      180 aaccagaagt tcaagggccg cgtcaccatc accgccgacc gcagcaccga caccggctac      240
ctggagctgt ccagcctgag aagcgaggac accgccgtgt actactgtgc cgccgagggc      300
tactacggcg gcagaggcta cgccctggac tactggggcc agggcaccct ggtgtccgtg      360
agcagcgcta gcaccaaggg cccatcggtc ttccccctgg cacctcctc caagagcacc      420 tctgggggca gcggccct gggctgcctg gtcaaggact acttccccga accggtgacg      480
gtgtcgtgga actcaggcgc cctgaccagc ggcgtgcaca ccttcccggc tgtcctacag      540
tcctcaggac tctactccct cagcagcgtg gtgaccgtgc cctccagcag cttgggcacc      600
cagacctaca tctgcaacgt gaatcacaag cccagcaaca ccaaggtgga caagagagtt      660
gagcccaaat cttgtgacaa aactcacaca tgcccaccgt gcccagcacc tgaactcctg      720
gggggaccgt cagtcttcct cttccccca aaacccaagg acaccctcat gatctcccgg      780
acccctgagg tcacatgcgt ggtggtggac gtgagccacg aagaccctga ggtcaagttc      840
aactggtacg tggacggcgt ggaggtgcat aatgccaaga caaagccgcg ggaggagcag      900
tacaacagca cgtaccgtgt ggtcagcgtc ctcaccgtcc tgcaccagga ctggctgaat      960
ggcaaggagt acaagtgcaa ggtctccaac aaagccctcc cagcccccat cgagaaaacc     1020
```

```
atctccaaag ccaaagggca gccccgagaa ccacaggtgt acaccctgcc cccatcccgg    1080
gatgagctga ccaagaacca ggtcagcctg acctgcctgg tcaaaggctt ctatcccagc    1140
gacatcgccg tggagtggga gagcaatggg cagccggaga caactacaa gaccacgcct     1200 cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga gagcctctc cctgtctccg ggtaaa                                1356
```

<210> SEQ ID NO 74
<211> LENGTH: 452
<212> TYPE: PRT
<213> ORGANISM: Artificial Sequence
<220> FEATURE:
<223> OTHER INFORMATION: Synthetic (Amino acid sequence CDhRZ7VHAMR73
      (Conv. Humanized variants IgG))

<400> SEQUENCE: 74

```
Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Ser Ile Gly Gly Tyr
                20                  25                  30

Phe Met Asn Trp Val Arg Gln Ala Pro Gly Lys Gly Leu Glu Trp Met
            35                  40                  45

Gly Arg Ile Asn Pro Asn Asn Gly Asp Ser Phe Tyr Asn Gln Lys Phe
        50                  55                  60

Lys Gly Arg Val Thr Ile Thr Ala Asp Arg Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Glu Gly Tyr Tyr Gly Gly Arg Gly Tyr Ala Leu Asp Tyr Trp
            100                 105                 110

Gly Gln Gly Thr Leu Val Ser Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300
```

| | | | | | | | | | | | |
|---|---|---|---|---|---|---|---|---|---|---|---|
|Tyr|Arg|Val|Val|Ser|Val|Leu|Thr|Val|Leu|His|Gln|Asp|Trp|Leu|Asn|
|305| | | | |310| | | | |315| | | | |320|

Gly Lys Glu Tyr Lys Cys Lys Val Ser Asn Lys Ala Leu Pro Ala Pro
                          325                          330                          335

Ile Glu Lys Thr Ile Ser Lys Ala Lys Gly Gln Pro Arg Glu Pro Gln
                  340                          345                          350

Val Tyr Thr Leu Pro Pro Ser Arg Asp Glu Leu Thr Lys Asn Gln Val
      355                          360                          365

Ser Leu Thr Cys Leu Val Lys Gly Phe Tyr Pro Ser Asp Ile Ala Val
    370                        375                        380

Glu Trp Glu Ser Asn Gly Gln Pro Glu Asn Asn Tyr Lys Thr Thr Pro
385                      390                          395                      400

Pro Val Leu Asp Ser Asp Gly Ser Phe Phe Leu Tyr Ser Lys Leu Thr
              405                          410                        415

Val Asp Lys Ser Arg Trp Gln Gln Gly Asn Val Phe Ser Cys Ser Val
            420                      425                        430

Met His Glu Ala Leu His Asn His Tyr Thr Gln Lys Ser Leu Ser Leu
        435                      440                        445

Ser Pro Gly Lys
    450

```
<210> SEQ ID NO 75
<211> LENGTH: 1356
<212> TYPE: DNA
<213> ORGANISM: Artificial Sequence
<220> FEATURE:
<223> OTHER INFORMATION: Synthetic (DNA sequence CDhL7IVHAM (Conv.
      Humanized variants IgG))

<400> SEQUENCE: 75
gaggtgcagc tggtcgagag cggcggggc ctggtgcagc ctggcggcag cctgcgcctg      60
agctgcgccg ccagcggcta ctccatcggc ggctacttca tgaactgggt ccgccaggcc     120
ccagggaaag gcctggagtg ggtggcccgc atcaacccca caacggcga cagcttctac      180 aaccagaagt tcaagggccg cttcaccctg agcgtggacc gcagcaagaa caccctgtac     240
ctgcagatga cagcctgag ggccgaggac accgccgtgt actactgcgc cagagagggc     300
tactacggcg gcagaggcta cgccctggac tactggggcc agggcaccct ggtcaccgtg     360
tccagcgcta gcaccaaggg cccatcggtc ttccccctgg cacctcctc caagagcacc     420 tctggggca gcggccct gggctgcctg gtcaaggact acttcccga accggtgacg         480 gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactcacaca tgcccaccgt gcccagcacc tgaactcctg     720
gggggaccgt cagtcttcct cttccccca aaacccaagg acaccctcat gatctcccgg     780
acccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagccctcc cagccccat cgagaaaacc     1020 atctccaaag ccaaggca gccccgagaa ccacaggtgt acaccctgcc cccatcccgg     1080
gatgagctga ccaagaacca ggtcagcctg acctgcctgg tcaaaggctt ctatcccagc     1140
```

```
gacatcgccg tggagtggga gagcaatggg cagccggaga acaactacaa gaccacgcct   1200
cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga gagcctctc cctgtctccg ggtaaa                              1356
```

<210> SEQ ID NO 76
<211> LENGTH: 452
<212> TYPE: PRT
<213> ORGANISM: Artificial Sequence
<220> FEATURE:
<223> OTHER INFORMATION: Synthetic (Amino acid sequence CDhL7IVHAM
      (Conv. Humanized variants IgG))

<400> SEQUENCE: 76

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Gly Gly Tyr
            20                  25                  30

Phe Met Asn Trp Val Arg Gln Ala Pro Gly Lys Gly Leu Glu Trp Val
        35                  40                  45

Ala Arg Ile Asn Pro Asn Asn Gly Asp Ser Phe Tyr Asn Gln Lys Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320
```

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 77
<211> LENGTH: 642
<212> TYPE: DNA
<213> ORGANISM: Artificial Sequence
<220> FEATURE:
<223> OTHER INFORMATION: Synthetic (DNA sequence CDhRZ7Vk (light chain variant))

<400> SEQUENCE: 77
gacatccaga tgacccagag ccccagcagc gtgtccgcca gcgtgggcga ccgcgtgacc      60
atcacctgcc gcaccagcca ggacatcagc aactacctga actggtatca gcagaagccc     120
ggcaaggccc ccaagctgct gatctacaac accagccgcc tgcacagcgg cgtgccctcc     180
agattctccg gcagcggatc tggcaccgac ttcagcctga ccatcaatag cctgcagccc     240
gaggacttcg ccacctacta ctgccagcag agcaacatgt tccccctcac cttcggcggc     300
ggcaccaagg tggagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagttcac cggtgacaaa gagcttcaac aggggagagt gt                       642

<210> SEQ ID NO 78
<211> LENGTH: 214
<212> TYPE: PRT
<213> ORGANISM: Artificial Sequence
<220> FEATURE:
<223> OTHER INFORMATION: Synthetic (Amino acid sequence CDhRZ7Vk (light chain variant))

<400> SEQUENCE: 78

Asp Ile Gln Met Thr Gln Ser Pro Ser Ser Val Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Pro Lys Leu Leu Ile

```
                35                  40                  45
Tyr Asn Thr Ser Arg Leu His Ser Gly Val Pro Ser Arg Phe Ser Gly
     50                  55                  60

Ser Gly Ser Gly Thr Asp Phe Ser Leu Thr Ile Asn Ser Leu Gln Pro
 65                  70                  75                  80

Glu Asp Phe Ala Thr Tyr Tyr Cys Gln Gln Ser Asn Met Phe Pro Tyr
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 79
<211> LENGTH: 642
<212> TYPE: DNA
<213> ORGANISM: Artificial Sequence
<220> FEATURE:
<223> OTHER INFORMATION: Synthetic (DNA sequence CDhRZ7VkFS (light chain variant))

<400> SEQUENCE: 79

```
gacatccaga tgacccagag ccccagcagc gtgtccgcca gcgtgggcga ccgcgtgacc      60
atcacctgcc gcaccagcca ggacatcagc aactacctga actggtatca gcagaagccc     120
ggcaaggccc ccaagctgct gatctacaac accagccgcc tgcacagcgg cgtgccctcc     180
agattctccg gcagcggatc tggcaccgac ttcagcctga ccatccgcag cctgcagccc     240
aaggacttcg ccacctacta ctgccagcag agcaacatgt tcccctacac cttcggcggc     300
ggcaccaagg tggagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagttcac cggtgacaaa gagcttcaac aggggagagt gt                        642
```

<210> SEQ ID NO 80
<211> LENGTH: 214
<212> TYPE: PRT
<213> ORGANISM: Artificial Sequence
<220> FEATURE:
<223> OTHER INFORMATION: Synthetic (Amino acid sequence CDhRZ7VkFS (light chain variant))

<400> SEQUENCE: 80

```
Asp Ile Gln Met Thr Gln Ser Pro Ser Ser Val Ser Ala Ser Val Gly
 1               5                  10                  15

Asp Arg Val Thr Ile Thr Cys Arg Thr Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asn Thr Ser Arg Leu His Ser Gly Val Pro Ser Arg Phe Ser Gly
     50                  55                  60

Ser Gly Ser Gly Thr Asp Phe Ser Leu Thr Ile Arg Ser Leu Gln Pro
 65                  70                  75                  80

Lys Asp Phe Ala Thr Tyr Tyr Cys Gln Gln Ser Asn Met Phe Pro Tyr
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
     210
```

<210> SEQ ID NO 81
<211> LENGTH: 642
<212> TYPE: DNA
<213> ORGANISM: Artificial Sequence
<220> FEATURE:
<223> OTHER INFORMATION: Synthetic (DNA sequence CDhL7IVk (light chain variant))

<400> SEQUENCE: 81

```
gacatccaga tgacccagag ccccagcagc ctgtccgcca gcgtgggcga ccgcgtgacc      60
atcacctgcc gcaccagcca ggacatcagc aactacctga actggtatca gcagaagccc     120
ggcaaggccc ccaagctgct gatctacaac accagccgcc tgcacagcgg cgtgccctcc     180
agattctccg gcagcggatc tggcaccgac ttcaccctga ccatcagcag cctgcagccc     240
gaggacttcg ccacctacta ctgccagcag agcaacatgt tcccctacac cttcggccag     300
ggcaccaagg tggagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcgaagtcac ccatcagggc     600
ctgagttcac cggtgacaaa gagcttcaac aggggagagt gt                       642
```

<210> SEQ ID NO 82
<211> LENGTH: 214
<212> TYPE: PRT

<213> ORGANISM: Artificial Sequence
<220> FEATURE:
<223> OTHER INFORMATION: Synthetic (Amino acid sequence CDhL7IVk (light
chain variant))

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asn Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 83
<211> LENGTH: 122
<212> TYPE: PRT
<213> ORGANISM: Artificial Sequence
<220> FEATURE:
<223> OTHER INFORMATION: Synthetic (sh146-112 heavy chain variable
region (VH))

<400> SEQUENCE: 83

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Gly Tyr
            20                  25                  30

Phe Met Asn Trp Val Arg Gln Ala Pro Gly Gln Gly Leu Glu Trp Met
        35                  40                  45

Gly Arg Ile Asn Pro Asn Asn Gly Asp Ser Phe Tyr Asn Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
```

```
            100                 105                 110
Gly Gln Gly Thr Leu Val Thr Val Ser Ser
        115                 120

<210> SEQ ID NO 84
<211> LENGTH: 122
<212> TYPE: PRT
<213> ORGANISM: Artificial Sequence
<220> FEATURE:
<223> OTHER INFORMATION: Synthetic (36-10 Q6R heavy chain variable
      region (VH))

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ile Gly Gly Tyr
            20                  25                  30

Phe Met Asn Trp Val Arg Gln Ala Pro Gly Gln Gly Leu Glu Trp Met
        35                  40                  45

Gly Arg Ile Asn Pro Asn Asn Gly Asp Ser Phe Tyr Asn Gln Lys Phe
    50                  55                  60

Lys Gly Arg Val Thr Met Thr Arg Asp Arg Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120

<210> SEQ ID NO 85
<211> LENGTH: 122
<212> TYPE: PRT
<213> ORGANISM: Artificial Sequence
<220> FEATURE:
<223> OTHER INFORMATION: Synthetic (153-28 heavy chain variable region
      (VH))

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ile Gly Gly Tyr
            20                  25                  30

Phe Met Asn Trp Val Arg Gln Ala Pro Gly Gln Gly Leu Glu Trp Met
        35                  40                  45

Gly Arg Ile Asn Pro Asn Asn Gly Asp Ser Phe Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120

<210> SEQ ID NO 86
<211> LENGTH: 122
<212> TYPE: PRT
```

<213> ORGANISM: Artificial Sequence
<220> FEATURE:
<223> OTHER INFORMATION: Synthetic (324-B10 heavy chain variable region (VH))

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ile Gly Gly Tyr
            20                  25                  30

Tyr Met Asn Trp Val Arg Gln Ala Pro Gly Gln Gly Leu Glu Trp Met
        35                  40                  45

Gly Arg Ile Asn Pro Asn Ser Gly Asp Ser Phe Tyr Asn Gln Lys Phe
    50                  55                  60

Lys Gly Arg Val Thr Met Thr Arg Asp Arg Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120

<210> SEQ ID NO 87
<211> LENGTH: 122
<212> TYPE: PRT
<213> ORGANISM: Artificial Sequence
<220> FEATURE:
<223> OTHER INFORMATION: Synthetic (361-C11 heavy chain variable region (VH))

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ile Gly Gly Tyr
            20                  25                  30

Phe Met Asn Trp Val Arg Gln Ala Pro Gly Gln Gly Leu Glu Trp Met
        35                  40                  45

Gly Arg Ile Asn Pro Asn Asn Gly Asp Ser Phe Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120

<210> SEQ ID NO 88
<211> LENGTH: 122
<212> TYPE: PRT
<213> ORGANISM: Artificial Sequence
<220> FEATURE:
<223> OTHER INFORMATION: Synthetic (368-G07 heavy chain variable region (VH))

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ile Gly Gly Tyr
            20                  25                  30

Phe Met Asn Trp Val Arg Gln Ala Pro Gly Gln Gly Leu Glu Trp Met
        35                  40                  45

Gly Arg Ile Asn Pro Asn Asn Gly Asp Ser Phe Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120

<210> SEQ ID NO 89
<211> LENGTH: 122
<212> TYPE: PRT
<213> ORGANISM: Artificial Sequence
<220> FEATURE:
<223> OTHER INFORMATION: Synthetic (369-F05 heavy chain variable region
      (VH))

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ile Gly Gly Tyr
            20                  25                  30

Phe Met Asn Trp Val Arg Gln Ala Pro Gly Gln Gly Leu Glu Trp Met
        35                  40                  45

Gly Arg Ile Asn Pro Asn Asn Gly Asp Ser Phe Tyr Asn Gln Lys Phe
    50                  55                  60

Lys Gly Arg Val Thr Met Thr Arg Asp Thr Ser Thr Ser Thr Met Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120

<210> SEQ ID NO 90
<211> LENGTH: 122
<212> TYPE: PRT
<213> ORGANISM: Artificial Sequence
<220> FEATURE:
<223> OTHER INFORMATION: Synthetic (361-H05 heavy chain variable region
      (VH))

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ile Gly Gly Tyr
            20                  25                  30

Phe Met Asn Trp Val Arg Gln Ala Pro Gly Gln Gly Leu Glu Trp Met
        35                  40                  45

Gly Arg Ile Asn Pro Asn Asn Gly Asp Ser Phe Tyr Asn Gln Lys Phe
    50                  55                  60

Lys Gly Arg Val Thr Thr Thr Arg Asp Thr Ser Ser Thr Val Tyr
65                  70                  75                  80

Met Glu Leu Ser Ser Leu Arg Ser Glu Asp Thr Ala Val Tyr Tyr Cys
            85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120

<210> SEQ ID NO 91
<211> LENGTH: 122
<212> TYPE: PRT
<213> ORGANISM: Artificial Sequence
<220> FEATURE:
<223> OTHER INFORMATION: Synthetic (Quikchange mutant heavy chain
      variable region (VH))

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Ile Gly Gly Tyr
            20                  25                  30

Tyr Met Asn Trp Val Arg Gln Ala Pro Gly Gln Gly Leu Glu Trp Met
        35                  40                  45

Gly Arg Ile Asn Pro Asn Ser Gly Asp Ser Phe Tyr Asn Gln Lys Phe
    50                  55                  60

Lys Gly Arg Val Thr Thr Thr Arg Asp Arg Ser Thr Ser Thr Met Tyr
65                  70                  75                  80

Met Glu Leu Ser Ser Leu Arg Ser Glu Asp Thr Ala Val Tyr Tyr Cys
            85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120

<210> SEQ ID NO 92
<211> LENGTH: 122
<212> TYPE: PRT
<213> ORGANISM: Artificial Sequence
<220> FEATURE:
<223> OTHER INFORMATION: Synthetic (45-37 VH heavy chain variable region
      (VH))

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Gly Tyr
            20                  25                  30

Phe Met Asn Trp Val Arg Gln Ala Pro Gly Gln Gly Leu Glu Arg Met
        35                  40                  45

Gly Arg Ile Asn Pro Asn Asn Gly Asp Ser Phe Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Glu Gly Tyr Tyr Gly Gly Arg Gly Tyr Ala Leu Asp Tyr Trp
            100                 105                 110

```
Gly Gln Gly Thr Leu Val Thr Val Ser Ser
        115                 120

<210> SEQ ID NO 93
<211> LENGTH: 122
<212> TYPE: PRT
<213> ORGANISM: Artificial Sequence
<220> FEATURE:
<223> OTHER INFORMATION: Synthetic (257-10 heavy chain variable region
      (VH))

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Gly Tyr
            20                  25                  30

Phe Met Asn Trp Val Arg Gln Ala Pro Gly Gln Gly Leu Arg Trp Met
        35                  40                  45

Gly Arg Ile Asn Pro Asn Asn Gly Asp Ser Phe Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Pro Ser Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120

<210> SEQ ID NO 94
<211> LENGTH: 122
<212> TYPE: PRT
<213> ORGANISM: Artificial Sequence
<220> FEATURE:
<223> OTHER INFORMATION: Synthetic (456-D10 heavy chain variable region
      (VH))

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Gly Tyr
            20                  25                  30

Phe Met Asn Trp Val Arg Gln Ala Pro Gly Gln Gly Leu Glu Arg Met
        35                  40                  45

Gly Arg Ile Asn Pro Asn Asn Gly Asp Ser Phe Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Pro Ser Leu Arg Ser Glu Asp Thr Ala Val Tyr Tyr Cys
                85                  90                  95

Ala Arg Glu Gly Tyr Tyr Gly Gly Arg Gly Tyr Ala Leu Asp Tyr Trp
            100                 105                 110

Gly Gln Gly Thr Leu Val Thr Val Ser Ser
        115                 120

<210> SEQ ID NO 95
<211> LENGTH: 108
<212> TYPE: PRT
<213> ORGANISM: Artificial Sequence
```

<220> FEATURE:
<223> OTHER INFORMATION: Synthetic (sh146-112 light chain variable
      region (VL))

<400> SEQUENCE: 95

Asp Ile Gln Met Thr Gln Ser Pro Ser Ser Val Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Thr Lys Leu Glu Ile Lys Arg
            100                 105

<210> SEQ ID NO 96
<211> LENGTH: 108
<212> TYPE: PRT
<213> ORGANISM: Artificial Sequence
<220> FEATURE:
<223> OTHER INFORMATION: Synthetic (36-10 Q6R light chain variable
      region (VL))

<400> SEQUENCE: 96

Asp Ile Gln Met Thr Arg Ser Pro Ser Ser Val Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Thr Lys Leu Glu Ile Lys Arg
            100                 105

<210> SEQ ID NO 97
<211> LENGTH: 108
<212> TYPE: PRT
<213> ORGANISM: Artificial Sequence
<220> FEATURE:
<223> OTHER INFORMATION: Synthetic (153-28 light chain variable region
      (VL))

<400> SEQUENCE: 97

Asp Ile Gln Met Thr Arg Ser Pro Ser Ser Val Ser Ala Ser Val Gly
1               5                   10                  15

Asp Arg Val Ser Ile Thr Cys Arg Thr Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

```
Tyr Asn Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Met Phe Pro Tyr
                 85                  90                  95

Thr Phe Gly Gln Gly Ile Lys Leu Glu Ile Lys Arg
                100                 105
```

<210> SEQ ID NO 98
<211> LENGTH: 108
<212> TYPE: PRT
<213> ORGANISM: Artificial Sequence
<220> FEATURE:
<223> OTHER INFORMATION: Synthetic (324-B10 light chain variable region (VL))

<400> SEQUENCE: 98

```
Asp Ile Gln Met Thr Arg Ser Pro Ser Ser Val Ser Ala Ser Val Gly
 1               5                  10                  15

Asp Arg Val Ser Ile Thr Cys Arg Thr Ser Gln Asp Ile Ser Asn Tyr
                20                  25                  30

Leu Asn Trp Tyr Gln Gln Lys Pro Asp Gly Thr Val Lys Leu Leu Ile
             35                  40                  45

Tyr Asn Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Met Phe Pro Tyr
                 85                  90                  95

Thr Phe Gly Gln Gly Ile Lys Leu Glu Ile Lys Arg
                100                 105
```

<210> SEQ ID NO 99
<211> LENGTH: 108
<212> TYPE: PRT
<213> ORGANISM: Artificial Sequence
<220> FEATURE:
<223> OTHER INFORMATION: Synthetic (361-C11 light chain variable region (VL))

<400> SEQUENCE: 99

```
Asp Ile Gln Met Thr Arg Ser Pro Ser Ser Val Ser Ala Ser Val Gly
 1               5                  10                  15

Gly Arg Val Ser Ile Thr Cys Arg Thr Ser Gln Asp Ile Ser Asn Tyr
                20                  25                  30

Leu Asn Trp Tyr Gln Gln Lys Pro Asp Gly Thr Val Lys Leu Leu Ile
             35                  40                  45

Tyr Asn Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Met Phe Pro Tyr
                 85                  90                  95

Thr Phe Gly Gln Gly Ile Lys Leu Glu Ile Lys Arg
                100                 105
```

<210> SEQ ID NO 100
<211> LENGTH: 108

```
<212> TYPE: PRT
<213> ORGANISM: Artificial Sequence
<220> FEATURE:
<223> OTHER INFORMATION: Synthetic (368-G07 light chain variable region
      (VL))

<400> SEQUENCE: 100
```

Asp Ile Gln Met Thr Arg Ser Pro Ser Ser Val Ser Ala Ser Val Gly
1               5                   10                  15

Asp Arg Val Pro Ile Thr Cys Arg Thr Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Ile Lys Leu Glu Ile Lys Arg
            100                 105

```
<210> SEQ ID NO 101
<211> LENGTH: 108
<212> TYPE: PRT
<213> ORGANISM: Artificial Sequence
<220> FEATURE:
<223> OTHER INFORMATION: Synthetic (369-F05 light chain variable region
      (VL))

<400> SEQUENCE: 101
```

Asp Ile Gln Met Thr Arg Ser Pro Ser Ser Val Ser Ala Ser Val Gly
1               5                   10                  15

Asp Arg Val Ser Ile Thr Cys Arg Thr Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Ile Lys Leu Glu Ile Lys Arg
            100                 105

```
<210> SEQ ID NO 102
<211> LENGTH: 108
<212> TYPE: PRT
<213> ORGANISM: Artificial Sequence
<220> FEATURE:
<223> OTHER INFORMATION: Synthetic (361-H05 light chain variable region
      (VL))

<400> SEQUENCE: 102
```

Asp Ile Gln Met Thr Arg Ser Pro Ser Ser Val Ser Ala Ser Val Gly
1               5                   10                  15

Asp Arg Val Ser Ile Thr Cys Arg Thr Ser Gln Asp Ile Ser Asn Tyr
            20                  25                  30

Leu Asn Trp Tyr Gln Gln Lys Pro Asp Gly Thr Val Lys Leu Leu Ile

```
            35                  40                  45
Tyr Asn Thr Ser Arg Leu His Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Asn Met Phe Pro Tyr
                85                  90                  95
Thr Phe Gly Gln Gly Ile Lys Leu Glu Ile Lys Arg
            100                 105

<210> SEQ ID NO 103
<211> LENGTH: 108
<212> TYPE: PRT
<213> ORGANISM: Artificial Sequence
<220> FEATURE:
<223> OTHER INFORMATION: Synthetic (Quikchange mutant light chain
      variable region (VL))

<400> SEQUENCE: 103

Asp Ile Gln Met Thr Arg Ser Pro Ser Ser Val Ser Ala Ser Val Gly
1               5                   10                  15
Gly Arg Val Pro Ile Thr Cys Arg Thr Ser Gln Asp Ile Ser Asn Tyr
            20                  25                  30
Leu Asn Trp Tyr Gln Gln Lys Pro Asp Gly Thr Val Lys Leu Leu Ile
            35                  40                  45
Tyr Asn Thr Ser Arg Leu His Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Asn Met Phe Pro Tyr
                85                  90                  95
Thr Phe Gly Gln Gly Ile Lys Leu Glu Ile Lys Arg
            100                 105

<210> SEQ ID NO 104
<211> LENGTH: 108
<212> TYPE: PRT
<213> ORGANISM: Artificial Sequence
<220> FEATURE:
<223> OTHER INFORMATION: Synthetic (45-37 light chain variable region
      (VL))

<400> SEQUENCE: 104

Asp Thr Gln Met Thr Gln Ser Pro Ser Ser Val Ser Ala Ser Val Gly
1               5                   10                  15
Asp Arg Val Thr Ile Thr Cys Arg Thr Ser Gln Asp Ile Ser Asn Tyr
            20                  25                  30
Leu Asn Trp Tyr Gln Gln Lys Pro Gly Lys Ala Pro Lys Leu Leu Ile
            35                  40                  45
Tyr Asn Thr Ser Arg Leu His Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Asn Met Phe Pro Tyr
                85                  90                  95
Thr Phe Gly Gln Gly Thr Lys Leu Glu Ile Lys Arg
            100                 105
```

```
<210> SEQ ID NO 105
<211> LENGTH: 108
<212> TYPE: PRT
<213> ORGANISM: Artificial Sequence
<220> FEATURE:
<223> OTHER INFORMATION: Synthetic (257-10 light chain variable region
      (VL))

<400> SEQUENCE: 105

Asp Thr Gln Met Thr Gln Ser Pro Ser Ser Val Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Thr Lys Leu Glu Ile Lys Arg
            100                 105

<210> SEQ ID NO 106
<211> LENGTH: 108
<212> TYPE: PRT
<213> ORGANISM: Artificial Sequence
<220> FEATURE:
<223> OTHER INFORMATION: Synthetic (456-D10 light chain variable region
      (VL))

<400> SEQUENCE: 106

Asp Thr Gln Met Thr Gln Ser Pro Ser Ser Val Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Glu Pro Gly Lys Ala Pro Lys Leu Leu Ile
        35                  40                  45

Tyr Asn Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Met Phe Pro Tyr
                85                  90                  95

Thr Phe Gly Gln Gly Thr Lys Leu Glu Ile Lys Arg
            100                 105

<210> SEQ ID NO 107
<211> LENGTH: 107
<212> TYPE: PRT
<213> ORGANISM: Artificial Sequence
<220> FEATURE:
<223> OTHER INFORMATION: Synthetic (Light chain variable region (VL)
      variant (deglycosylated))

<400> SEQUENCE: 107

Asp Thr Gln Met Thr Gln Ser Pro Ser Ser Val Ser Ala Ser Val Gly
1               5                   10                  15

Asp Arg Val Thr Ile Thr Cys Arg Thr Ser Gln Asp Ile Ser Asn Tyr
            20                  25                  30
```

Leu Asn Trp Tyr Gln Gln Lys Pro Gly Lys Ala Pro Lys Leu Leu Ile
            35                  40                  45

Tyr Asn Thr Ala Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Met Phe Pro Tyr
                 85                  90                  95

Thr Phe Gly Gln Gly Thr Lys Leu Glu Ile Lys
            100                 105

<210> SEQ ID NO 108
<211> LENGTH: 107
<212> TYPE: PRT
<213> ORGANISM: Artificial Sequence
<220> FEATURE:
<223> OTHER INFORMATION: Synthetic (Light chain variable region (VL)
      variant (deglycosylated))

<400> SEQUENCE: 108

Asp Thr Gln Met Thr Gln Ser Pro Ser Ser Val Ser Ala Ser Val Gly
 1               5                  10                  15

Asp Arg Val Thr Ile Thr Cys Arg Thr Ser Gln Asp Ile Ser Asn Tyr
                 20                  25                  30

Leu Asn Trp Tyr Gln Gln Lys Pro Gly Lys Ala Pro Lys Leu Leu Ile
            35                  40                  45

Tyr Gln Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Met Phe Pro Tyr
                 85                  90                  95

Thr Phe Gly Gln Gly Thr Lys Leu Glu Ile Lys
            100                 105

<210> SEQ ID NO 109
<211> LENGTH: 107
<212> TYPE: PRT
<213> ORGANISM: Artificial Sequence
<220> FEATURE:
<223> OTHER INFORMATION: Synthetic (Light chain variable region (VL)
      variant (deglycosylated))

<400> SEQUENCE: 109

Asp Thr Gln Met Thr Gln Ser Pro Ser Ser Val Ser Ala Ser Val Gly
 1               5                  10                  15

Asp Arg Val Thr Ile Thr Cys Arg Thr Ser Gln Asp Ile Ser Asn Tyr
                 20                  25                  30

Leu Asn Trp Tyr Gln Gln Lys Pro Gly Lys Ala Pro Lys Leu Leu Ile
            35                  40                  45

Tyr Ala Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Met Phe Pro Tyr
                 85                  90                  95

Thr Phe Gly Gln Gly Thr Lys Leu Glu Ile Lys
            100                 105

```
<210> SEQ ID NO 110
<211> LENGTH: 5
<212> TYPE: PRT
<213> ORGANISM: Artificial Sequence
<220> FEATURE:
<223> OTHER INFORMATION: Synthetic (CDRH1 of anti-CD43 antibody or
      antigen-binding fragment)
<220> FEATURE:
<221> NAME/KEY: MOD_RES
<222> LOCATION: (3)
<223> OTHER INFORMATION: Xaa is Phe (F) or Tyr (Y)

<400> SEQUENCE: 110

Gly Tyr Xaa Met Asn
1               5

<210> SEQ ID NO 111
<211> LENGTH: 5
<212> TYPE: PRT
<213> ORGANISM: Artificial Sequence
<220> FEATURE:
<223> OTHER INFORMATION: Synthetic (CDRH1 of anti-CD43 antibody or
      antigen-binding fragment)

<400> SEQUENCE: 111

Gly Tyr Phe Met Asn
1               5

<210> SEQ ID NO 112
<211> LENGTH: 5
<212> TYPE: PRT
<213> ORGANISM: Artificial Sequence
<220> FEATURE:
<223> OTHER INFORMATION: Synthetic (CDRH1 of anti-CD43 antibody or
      antigen-binding fragment)

<400> SEQUENCE: 112

Gly Tyr Tyr Met Asn
1               5

<210> SEQ ID NO 113
<211> LENGTH: 17
<212> TYPE: PRT
<213> ORGANISM: Artificial Sequence
<220> FEATURE:
<223> OTHER INFORMATION: Synthetic (CDRH2 of anti-CD43 antibody or
      antigen-binding fragment)
<220> FEATURE:
<221> NAME/KEY: MOD_RES
<222> LOCATION: (6)
<223> OTHER INFORMATION: Xaa is Asn (N) or Ser (S)
<220> FEATURE:
<221> NAME/KEY: MOD_RES
<222> LOCATION: (16)
<223> OTHER INFORMATION: Xaa is Gln (Q) or Lys (K)

<400> SEQUENCE: 113

Arg Ile Asn Pro Asn Xaa Gly Asp Ser Phe Tyr Asn Gln Lys Phe Xaa
1               5                   10                  15

Gly

<210> SEQ ID NO 114
<211> LENGTH: 17
<212> TYPE: PRT
<213> ORGANISM: Artificial Sequence
<220> FEATURE:
<223> OTHER INFORMATION: Synthetic (CDRH2 of anti-CD43 antibody or
      antigen-binding fragment)
```

<400> SEQUENCE: 114

Arg Ile Asn Pro Asn Asn Gly Asp Ser Phe Tyr Asn Gln Lys Phe Gln
1               5                   10                  15

Gly

<210> SEQ ID NO 115
<211> LENGTH: 17
<212> TYPE: PRT
<213> ORGANISM: Artificial Sequence
<220> FEATURE:
<223> OTHER INFORMATION: Synthetic (CDRH2 of anti-CD43 antibody or
      antigen-binding fragment)

<400> SEQUENCE: 115

Arg Ile Asn Pro Asn Ser Gly Asp Ser Phe Tyr Asn Gln Lys Phe Gln
1               5                   10                  15

Gly

<210> SEQ ID NO 116
<211> LENGTH: 17
<212> TYPE: PRT
<213> ORGANISM: Artificial Sequence
<220> FEATURE:
<223> OTHER INFORMATION: Synthetic (CDRH2 of anti-CD43 antibody or
      antigen-binding fragment)

<400> SEQUENCE: 116

Arg Ile Asn Pro Asn Asn Gly Asp Ser Phe Tyr Asn Gln Lys Phe Lys
1               5                   10                  15

Gly

<210> SEQ ID NO 117
<211> LENGTH: 17
<212> TYPE: PRT
<213> ORGANISM: Artificial Sequence
<220> FEATURE:
<223> OTHER INFORMATION: Synthetic (CDRH2 of anti-CD43 antibody or
      antigen-binding fragment)

<400> SEQUENCE: 117

Arg Ile Asn Pro Asn Ser Gly Asp Ser Phe Tyr Asn Gln Lys Phe Lys
1               5                   10                  15

Gly

<210> SEQ ID NO 118
<211> LENGTH: 13
<212> TYPE: PRT
<213> ORGANISM: Artificial Sequence
<220> FEATURE:
<223> OTHER INFORMATION: Synthetic (CDRH3 of anti-CD43 antibody or
      antigen-binding fragment)

<400> SEQUENCE: 118

Glu Gly Tyr Tyr Gly Gly Arg Gly Tyr Ala Leu Asp Tyr
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Synthetic (CDRL1 of anti-CD43 antibody or
      antigen-binding fragment)

```
<400> SEQUENCE: 119

Arg Thr Ser Gln Asp Ile Ser Asn Tyr Leu Asn
1               5                   10

<210> SEQ ID NO 120
<211> LENGTH: 7
<212> TYPE: PRT
<213> ORGANISM: Artificial Sequence
<220> FEATURE:
<223> OTHER INFORMATION: Synthetic (CDRL2 of anti-CD43 antibody or
      antigen-binding fragment)
<220> FEATURE:
<221> NAME/KEY: MOD_RES
<222> LOCATION: (1)
<223> OTHER INFORMATION: Xaa is Asn (N) or Gln (Q)
<220> FEATURE:
<221> NAME/KEY: MOD_RES
<222> LOCATION: (3)
<223> OTHER INFORMATION: Xaa is Ser (S) or Ala (A)

<400> SEQUENCE: 120

Xaa Thr Xaa Arg Leu His Ser
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic (CDRL2 of anti-CD43 antibody or
      antigen-binding fragment)

<400> SEQUENCE: 121

Asn Thr Ser Arg Leu His Ser
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic (CDRL2 of anti-CD43 antibody or
      antigen-binding fragment)

<400> SEQUENCE: 122

Asn Thr Ala Arg Leu His Ser
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic (CDRL2 of anti-CD43 antibody or
      antigen-binding fragment)

<400> SEQUENCE: 123

Gln Thr Ser Arg Leu His Ser
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic (CDRL2 of anti-CD43 antibody or
      antigen-binding fragment)

<400> SEQUENCE: 124
```

```
Ala Thr Ser Arg Leu His Ser
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic (CDRL3 of anti-CD43 antibody or
      antigen-binding fragment)

<400> SEQUENCE: 125

Gln Gln Ser Asn Met Phe Pro Tyr
1               5

<210> SEQ ID NO 126
<211> LENGTH: 5
<212> TYPE: PRT
<213> ORGANISM: Artificial Sequence
<220> FEATURE:
<223> OTHER INFORMATION: Synthetic (linker)
<220> FEATURE:
<221> NAME/KEY: MOD_RES
<222> LOCATION: (4)
<223> OTHER INFORMATION: Xaa is Gly (G) or Ala (A)

<400> SEQUENCE: 126

Gly Gly Gly Xaa Ser
1               5

<210> SEQ ID NO 127
<211> LENGTH: 15
<212> TYPE: PRT
<213> ORGANISM: Artificial Sequence
<220> FEATURE:
<223> OTHER INFORMATION: Synthetic (linker)

<400> SEQUENCE: 127

Gly Gly Gly Ala Ser Gly Gly Gly Gly Ser Gly Gly Gly Gly Ser
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Synthetic (linker)

<400> SEQUENCE: 128

Gly Gly Gly Gly Ser Gly Gly Gly Gly Ser Gly Gly Gly Ala Ser
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Synthetic (epitope containing peptide, DN2)

<400> SEQUENCE: 129

Glu Gly Ser Pro Leu Trp Thr Ser Ile Gly Ala Ser Thr Gly Ser Cys
1               5                   10                  15

<210> SEQ ID NO 130
<211> LENGTH: 400
<212> TYPE: PRT
<213> ORGANISM: Artificial Sequence
```

```
<220> FEATURE:
<223> OTHER INFORMATION: Synthetic (human CD43)

<400> SEQUENCE: 130

Met Ala Thr Leu Leu Leu Leu Gly Val Leu Val Val Ser Pro Asp
1               5                   10                  15

Ala Leu Gly Ser Thr Thr Ala Val Gln Thr Pro Thr Ser Gly Glu Pro
            20                  25                  30

Leu Val Ser Thr Ser Glu Pro Leu Ser Ser Lys Met Tyr Thr Thr Ser
            35                  40                  45

Ile Thr Ser Asp Pro Lys Ala Asp Ser Thr Gly Asp Gln Thr Ser Ala
        50                  55                  60

Leu Pro Pro Ser Thr Ser Ile Asn Glu Gly Ser Pro Leu Trp Thr Ser
65                  70                  75                  80

Ile Gly Ala Ser Thr Gly Ser Pro Leu Pro Glu Pro Thr Thr Tyr Gln
                85                  90                  95

Glu Val Ser Ile Lys Met Ser Ser Val Pro Gln Glu Thr Pro His Ala
            100                 105                 110

Thr Ser His Pro Ala Val Pro Ile Thr Ala Asn Ser Leu Gly Ser His
            115                 120                 125

Thr Val Thr Gly Gly Thr Ile Thr Thr Asn Ser Pro Glu Thr Ser Ser
    130                 135                 140

Arg Thr Ser Gly Ala Pro Val Thr Thr Ala Ala Ser Ser Leu Glu Thr
145                 150                 155                 160

Ser Arg Gly Thr Ser Gly Pro Pro Leu Thr Met Ala Thr Val Ser Leu
                165                 170                 175

Glu Thr Ser Lys Gly Thr Ser Gly Pro Pro Val Thr Met Ala Thr Asp
            180                 185                 190

Ser Leu Glu Thr Ser Thr Gly Thr Thr Gly Pro Pro Val Thr Met Thr
            195                 200                 205

Thr Gly Ser Leu Glu Pro Ser Ser Gly Ala Ser Gly Pro Gln Val Ser
    210                 215                 220

Ser Val Lys Leu Ser Thr Met Met Ser Pro Thr Thr Ser Thr Asn Ala
225                 230                 235                 240

Ser Thr Val Pro Phe Arg Asn Pro Asp Glu Asn Ser Arg Gly Met Leu
                245                 250                 255

Pro Val Ala Val Leu Val Ala Leu Leu Ala Val Ile Val Leu Val Ala
            260                 265                 270

Leu Leu Leu Leu Trp Arg Arg Arg Gln Lys Arg Arg Thr Gly Ala Leu
            275                 280                 285

Val Leu Ser Arg Gly Gly Lys Arg Asn Gly Val Val Asp Ala Trp Ala
    290                 295                 300

Gly Pro Ala Gln Val Pro Glu Glu Gly Ala Val Thr Val Thr Val Gly
305                 310                 315                 320

Gly Ser Gly Gly Asp Lys Gly Ser Gly Phe Pro Asp Gly Glu Gly Ser
                325                 330                 335

Ser Arg Arg Pro Thr Leu Thr Thr Phe Phe Gly Arg Arg Lys Ser Arg
            340                 345                 350

Gln Gly Ser Leu Ala Met Glu Glu Leu Lys Ser Gly Ser Gly Pro Ser
            355                 360                 365

Leu Lys Gly Glu Glu Glu Pro Leu Val Ala Ser Glu Asp Gly Ala Val
    370                 375                 380

Asp Ala Pro Ala Pro Asp Glu Pro Glu Gly Gly Asp Gly Ala Ala Pro
385                 390                 395                 400
```

```
<210> SEQ ID NO 131
<211> LENGTH: 6
<212> TYPE: PRT
<213> ORGANISM: Artificial Sequence
<220> FEATURE:
<223> OTHER INFORMATION: Synthetic (epitope)

<400> SEQUENCE: 131

Pro Leu Trp Thr Ser Ile
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic (epitope)

<400> SEQUENCE: 132

Ser Pro Leu Trp Thr Ser Ile
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic (epitope)

<400> SEQUENCE: 133

Gly Ser Pro Leu Trp Thr Ser Ile
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic (epitope)

<400> SEQUENCE: 134

Glu Gly Ser Pro Leu Trp Thr Ser Ile
1               5
```

ANTI-CD43 ANTIBODY AND USE THEREOF FOR CANCER TREATMENT

TECHNICAL FIELD

Provided are an anti-CD43 antibody or antigen-binding fragment thereof binding to an extracellular domain of CD43, a composition for treating cancer comprising the anti-CD43 antibody or antigen-binding fragment thereof as an active ingredient, a composition for inhibiting a cancer stem cell comprising the anti-CD43 antibody binding to an extracellular domain of CD43 as an active ingredient, and a method of screening of an agent of inhibiting a cancer stem cell.

BACKGROUND ART

CD43 is a cell-surface protein expressed in various hematoblasts except erythrocytes. A human CD43, known as sialophorin or leukosialin, is composed of a mucine-like extracellular domain consisting of 235 amino acids, a transmembrane domain consisting of 23 amino acids, and an intracellular domain consisting of 123 amino acids, and the relevant genetic information is encoded in one exon. There are many serine (46 residues) and threonine (47 residues) amino acids in the human extracellular CD43 domain, and most of them possess O-linked glycan (O-glycan). Additionally, N-glycan is also linked to CD43. The structure of O-glycan is known to vary greatly depending on the cell type. CD43 has an intron consisting of 378 base pairs, which divides the exon into two, and the entire transcript material information is encoded in the second exon.

CD43 is synthesized as a precursor of about 40 kDa including N-glycan, and is converted to a material of 115 kDa to 200 kDa through a consecutive mature glycosylation processes. The strictly-controlled glycosylation process after transcription forms characteristic molecular weight isoform proteins depending on the type and these can be expressed differently depending on the cell type.

The glycosylated epitope of CD43 has been known as a specific marker restricted to white blood cells, and its specific utility as a marker for hematologic malignancy has been revealed. For this reason, in many studies, the possibility of using antibodies binding to the glycosylated epitope of CD43 for diagnostic or therapeutic purposes has been explored. The rodent monoclonal antibody recognizing CD43 has been known to induce apoptosis in lineage marker-negative bone marrow hematopoietic progenitor cells that over-express CD34 (Bazil et al. (1996) *Blood*, 87(4):1272-81) and human T-lymphoblastoid cells (Brown et al. (1996) *J. Biol. Chem.* 271:27686-95). However, these antibodies are not effective for detecting or treating cancer cells, since most of them react with the glycosylated epitope located in the CD43 extracellular domain expressed in mature (non-cancerous) hematopoietic cells. Therefore, it is required to develop a more improved material binding to the glycosylated epitope of CD43 for diagnosing, tracing and treating hematologic malignancy.

On the other hand, the cancer stem cell hypothesis, which suggests abnormal stem cells are involved in the occurrence and recurrence of cancer in a hierarchical model, has been known.

All tissues of human body are originated from organ-specific stem cells. The organ-specific stem cells have the ability of self-renewal and differentiation into all cells composing each organ. These organ-specific stem cells are distinguished from embryonic stem cells in that they can only be differentiated into cell types in the specific organ.

The cancer stem cell hypothesis largely consists of two elements. First, the tumor occurs in a stem cell in the tissue, and second, the tumor occurred from the stem cell has basic properties of stem cells.

The cancer stem cell as a cancer cell having a limitless regenerative ability, defined as a cell which can effectively produce tumor when injected into an immune-suppressed mice, and express its unique heterogeneity which the primary tumor possesses well in the formed tumor.

The cancer stem cell hypothesis has become more materialized as the stem cell biology has been recently developed. The cancer stem cell hypothesis took a step forward by the report that human leukemia was reproduced in an immunosuppressed mouse grafted possible cancer stem cells from an acute myelocytic leukemia patient in 1997 (Bonnet D, Dick J E; Human acute myeloid leukemia is organized as a hierarchy that originates from a primitive hematopoietic cell. Nat Med 1997; 3: 730-7).

The various heterogeneity that a malignant tumor exhibits corresponds to the various differentiation potential of stem cells, and the repeatedly occurring drug resistance of cancer cell, despite of a number of target treatments also corresponds to the basic property of stem cells. As the cancer stem cell could form a new tumor mass by self-renewal, even though tumor cells other than cancer stem cells are completely removed by surgery and the chemotherapy, if the cancer stem cell is remained, the cancer becomes recurred again.

Therefore, in order to cure the cancer completely, it is required to develop a technology to inhibit or remove the cancer stem cell.

DISCLOSURE

Technical Problem

Other embodiment provides a pharmaceutical composition for treating a solid cancer comprising an anti-CD43 antibody or an antigen-binding fragment thereof which binds to an epitope located in an extracellular domain of CD43.

Other embodiment provides a method of treating a solid cancer, comprising a step of administering a pharmaceutically effective amount of an anti-CD43 antibody or an antigen-binding fragment thereof which binds to an epitope located in an extracellular domain of CD43 to a subject in need of treating the solid cancer.

Other embodiment provides a use for treating a solid cancer of an anti-CD43 antibody or an antigen-binding fragment thereof which binds to an epitope located in an extracellular domain of CD43.

The epitope may be a polypeptide comprising 6-9 consecutive amino acids in the extracellular domain of CD43 comprising the amino acid sequence of SEQ ID NO: 131. The anti-CD43 antibody or antigen-binding fragment thereof may comprise the afore-mentioned anti-CD43 antibody or the antigen-binding fragment thereof.

The pharmaceutical composition, method and use for treating solid cancer may be characterized for example, by having the inhibitory effect on cancer stem cells of hematologic malignancy or solid cancer. In one embodiment, the solid cancer may be stomach cancer and the hematologic malignancy may be leukemia.

Other embodiment provides a pharmaceutical composition for inhibiting a cancer stem cell, for example, a cancer stem cell of hematologic malignancy or solid cancer, comprising an anti-CD43 antibody or an antigen-binding fragment thereof which binds to an epitope located in an extracellular domain of CD43 as an active ingredient.

Other embodiment provides a method of inhibiting a cancer stem cell, for example, a cancer stem cell of hematologic malignancy or solid cancer, comprising a step of administering a pharmaceutically effective amount of an anti-CD43 antibody or an antigen-binding fragment thereof which binds to an epitope located in an extracellular domain of CD43 to a subject in need of treating hematologic malignancy of the solid cancer.

Other embodiment provides a use for inhibiting a cancer stem cell, for example, a cancer stem cell of hematologic malignancy or solid cancer, of an anti-CD43 antibody or an antigen-binding fragment thereof which binds to an epitope located in an extracellular domain of CD43.

The epitope may be a polypeptide comprising 6-9 consecutive amino acids in the extracellular domain of CD43 comprising the amino acid sequence of SEQ ID NO: 131. The anti-CD43 antibody or antigen-binding fragment thereof may comprise the afore-mentioned anti-CD43 antibody or the antigen-binding fragment thereof. In one embodiment, the solid cancer may be stomach cancer.

Other embodiment provides a conjugate between an anti-CD43 antibody or an antigen-binding fragment thereof which binds to an epitope located in an extracellular domain of CD43, and a cancer stem cell, for example, a cancer stem cell of hematologic malignancy or solid cancer. Other embodiment provides a method for producing a conjugate between an anti-CD43 antibody or an antigen-binding fragment thereof which binds to an epitope located in an extracellular domain of CD43, and a cancer stem cell, for example, a cancer stem cell of hematologic malignancy or solid cancer, wherein the method may comprise a step of administering the anti-CD43 antibody or antigen-binding fragment thereof which binds to an epitope located in an extracellular domain of CD43 into a cancer sample, for example, a solid cancer sample or cancer patient such as a solid cancer patient. The conjugate or method for producing the same may be used for various clinical, diagnostic, and/or experimental purposes as well as cancer treatment.

Other embodiment provides an agent for screening an agent for treating a solid cancer comprising the epitope located in the extracellular domain of CD43. Other embodiment provides a method for screening an agent for treating a solid cancer using the epitope located in the extracellular domain of CD43. Other embodiment provides a use for screening an agent for treating a solid cancer of epitope located in the extracellular domain of CD43. The epitope may be a polypeptide comprising 6-9 consecutive amino acids in the extracellular domain of CD43 comprising the amino acid sequence of SEQ ID NO: 131. The agent for treating a solid cancer screened as described above may be characterized by having an inhibitory effect of cancer stem cell, for example, cancer stem cell of hematologic malignancy or solid cancer. In one embodiment, the solid cancer may be stomach cancer.

Other embodiment provides an agent for screening an agent for inhibiting the cancer stem cell, for example, cancer stem cell of hematologic malignancy or solid cancer, comprising the epitope located in the extracellular domain of CD43.

Other embodiment provides a method for screening an agent for inhibiting the cancer stem cell, for example, cancer stem cell of hematologic malignancy or solid cancer, using the epitope located in the extracellular domain of CD43.

Other embodiment provides a use for screening an agent for inhibiting the cancer stem cell, for example, cancer stem cell of hematologic malignancy or solid cancer, of the epitope located in the extracellular domain of CD43. The epitope may be a polypeptide comprising 6-9 consecutive amino acids in the extracellular domain of CD43 comprising the amino acid sequence of SEQ ID NO: 131. In one embodiment, the solid cancer may be stomach cancer.

Other embodiment provides a novel anti-CD43 antibody or an antigen-binding fragment thereof. The anti-CD43 antibody or antigen-binding fragment thereof may binds to the epitope located in an extracellular domain of CD43. The epitope may be a polypeptide comprising 6-9 consecutive amino acids in the extracellular domain of CD43 comprising the amino acid sequence of SEQ ID NO: 131.

The anti-CD43 antibody or antigen-binding fragment thereof comprises a heavy chain variable region (VH) and a light chain variable region (VL).

The heavy chain variable region may comprise the first complementarity determining region (CDR) (CDR1H), the second CDR (CDR2H) and the third CDR (CDR3H), in order from N-terminus to C-terminus.

In one embodiment, the anti-CD43 antibody or antigen-binding fragment thereof is an essential component of heavy chain variable region, and may comprise CDR1H including the amino acid sequence of GYX$_1$MN (SEQ ID NO: 110; X$_1$ may be selected from all amino acids, and for example, may be F or Y) (for example, GYFMN (SEQ ID NO: 111) or GYYMN (SEQ ID NO: 112)), CDR2H including the amino acid sequence of RINPNX$_2$GDSFYNQKFX$_3$G (SEQ ID NO: 113; X$_2$ and X$_3$ may be selected from all amino acids respectively, and for example, X$_2$ may be N or S, and X$_3$ may be Q or K) (for example, RINPNNGDSFYNQKFQG (SEQ ID NO: 114), RINPNSGDSFYNQKFQG (SEQ ID NO: 115), RINPNNGDSFYNQKFKG (SEQ ID NO: 116), or RINPNSGDSFYNQKFKG (SEQ ID NO: 117)), and CDR3H including the amino acid sequence of EGYYGGRGYALDY (SEQ ID NO: 118).

The light chain variable region may comprise the first CDR (CDR1L), the second CDR (CDR2L) and the third CDR (CDR3L), in order from N-terminus to C-terminus.

In one embodiment, the anti-CD43 antibody or antigen-binding fragment thereof is an essential component of light chain variable region, and may comprise CDR1L including the amino acid sequence of RTSQDISNYLN (SEQ ID NO: 119); CDR2L including the amino acid sequence of X$_4$TX$_5$RLHS (SEQ ID NO: 120; X$_4$ and X$_5$ may be selected from all amino acids respectively, and for example, X$_4$ may be N, Q or A, and X$_5$ may be S or A) (for example, NTSRLHS (SEQ ID NO: 121, NTARLHS (SEQ ID NO: 122), QTSRLHS (SEQ ID NO: 123), or ATSRLHS (SEQ ID NO: 124)); and CDR3L including the amino acid sequence of QQSNMFPY (SEQ ID NO: 125).

Other embodiment provides a pharmaceutical composition for preventing and/or treating cancer comprising the anti-CD43 antibody or antigen-binding fragment thereof, and a pharmaceutically acceptable carrier.

Other embodiment provides a method for preventing and/or treating cancer comprising a step of administering a pharmaceutically effective amount of anti-CD43 antibody or an antigen-binding fragment thereof to a subject in need of preventing and/or treating cancer.

Other embodiment provides a use for prevention and/or treatment, or preparation of anti-cancer agents of the anti-CD43 antibody or antigen-binding fragment thereof.

In one specific embodiment, for the pharmaceutical composition, method and use for preventing and/or treating cancer, the anti-CD43 antibody or antigen-binding fragment thereof may be provided as a single active ingredient, co-administered with cytotoxic material such as anti-cancer agents, or provided in a form of conjugate combined to cytotoxic material such as anti-cancer agents (antibody-drug conjugate; ADC).

Other embodiment provides a method for detecting a cancer cell in a sample using the anti-CD43 antibody or antigen-binding fragment thereof. The detection method may comprise a step of contacting a sample with the anti-CD43 antibody or antigen-binding fragment thereof and a step of detecting the antigen-antibody reaction in the sample.

Other embodiment provides a nucleic acid molecule encoding the anti-CD43 antibody or antigen-binding fragment thereof.

Other embodiment provides a recombinant vector comprising the nucleic acid molecule. The recombinant vector may be used as an expression vector to express the nucleic acid molecule in a host cell.

Other embodiment provides a recombinant cell comprising the nucleic acid molecule or the recombinant vector. The recombinant cell may be obtained by transforming the nucleic acid molecule or the recombinant vector into a host cell.

Other embodiment provides a method for preparing the anti-CD43 antibody or antigen-binding fragment thereof. The preparation method may comprise a step of expressing the nucleic acid molecule in a host cell. The step of expressing may comprise a step of culturing the recombinant cell, and randomly, may further comprise a step of isolating and/or purifying an antibody from the obtained cell cultures.

In one specific embodiment, the preparation method may comprise, (a) a step of preparing a recombinant cell transformed with the nucleic acid molecule or the recombinant vector;

(b) a step of culturing the recombinant cell at the condition and/or period for sufficient expression of the nucleic acid molecule; and (c) a step of isolating and/or purifying an anti-CD43 antibody or an antigen-binding fragment thereof from cultures obtained in the step (b).

Technical Solution

As described above, it is required to develop a technology to inhibit or remove a cancer stem cell in order to completely treat cancer, and for that, it is required to select a cancer stem cell marker which can isolate cancer stem cells from other cells.

Herein, it is suggested for the first time that CD43 is expressed on the surface of a cancer stem cell, for example, a cancer stem cell of hematologic malignancy or solid cancer. CD43 has been known as a specific white blood cell marker restricted to most of white blood cells, hematopoietic stem cells, and thrombocytes, except for red blood cells, but it has not been known that it is expressed on a cancer stem cell, for example, a cancer stem cell of hematologic malignancy or solid cancer.

In addition, it is suggested that an anti-CD43 antibody which specifically recognizes and/or binds to a specific region of extracellular domain of CD43 has an inhibitory efficacy against cancer stem cell, for example, cancer stem cell of hematologic malignancy or solid cancer.

CD43 (cluster of differentiation 43) is called Leukosialin or sialophorin, and is a major transmembrane protein expressed in the surface of most of hematoblasts except for red blood cells. The CD43 may be derived from mammals including primates such as human (*Homo sapiens*), etc., rodents such as mouse (*Mus musculus*), etc. For example, the CD43 may be human CD43 (for example, NCBI Accession No. AAA51949.1 (gene (mRNA): M61827.1), NP_001025459.1 (gene (mRNA): NM_001030288.1), NP_003114.1 (gene: NM_003123.3), etc.), mouse CD43 (for example, NCBI Accession No. NP_001032899.1 (gene: NM_001037810.1), NP_033285.1 (gene: NM_009259.4), etc.) and so on. In this embodiment, the CD43 may be human CD43 (protein: NCBI Accession No. AAA51949.1 (SEQ ID NO: 130); gene (mRNA): M61827.1).

One embodiment of the present invention provides a pharmaceutical composition for treating a solid cancer comprising an anti-CD43 antibody or an antigen-binding fragment thereof which binds to an epitope located in an extracellular domain of CD43 as an active ingredient.

Other embodiment provides a method of treating a solid cancer, comprising a step of administering a pharmaceutically effective amount of an anti-CD43 antibody or an antigen-binding fragment thereof which binds to an epitope located in an extracellular domain of CD43 to a subject in need of treating the solid cancer.

Other embodiment provides a use for treating a solid cancer of an anti-CD43 antibody or an antigen-binding fragment thereof which binds to an epitope located in an extracellular domain of CD43.

The anti-CD43 antibody or antigen-binding fragment thereof which binds to an epitope located in an extracellular domain of CD43 is characterized by exhibiting an inhibitory activity against cancer stem cell, for example, cancer stem cell of hematologic malignancy or solid cancer.

Therefore, other embodiment of the present invention provides a pharmaceutical composition for inhibiting a cancer stem cell, for example, a cancer stem cell of hematologic malignancy or solid cancer, comprising an anti-CD43 antibody or an antigen-binding fragment thereof which binds to an epitope located in an extracellular domain of CD43 as an active ingredient.

Other embodiment provides a method of inhibiting a cancer stem cell, for example, a cancer stem cell of hematologic malignancy or solid cancer, comprising a step of administering a pharmaceutically effective amount of an anti-CD43 antibody or an antigen-binding fragment thereof which binds to an epitope located in an extracellular domain of CD43 to a subject in need of treating the solid cancer.

Other embodiment provides a use for inhibiting a cancer stem cell, for example, a cancer stem cell of hematologic malignancy or solid cancer, of an anti-CD43 antibody or an antigen-binding fragment thereof which binds to an epitope located in an extracellular domain of CD43.

Herein, unless otherwise defined, the epitope located in an extracellular domain of CD43 may mean a polypeptide comprising 6-9 consecutive amino acids in the extracellular domain of CD43 comprising the amino acid sequence of SEQ ID NO: 131:

SEQ ID NO: 131: Pro Leu Trp Thr Ser Ile.

The epitope may be located in an extracellular domain of CD43 protein, but may be not exposed to the external environment in the normal condition, and may be exposed to the outside, if a cell becomes a cancer cell or cancer stem cell. Therefore, the antibody or the antigen-binding fragment thereof specifically recognizing and/or specifically binding to the epitope may specifically target and/or inhibit a cancer cell and/or cancer stem cell.

The extracellular domain of CD43 in which the epitope is located may be the amino acid region from $73^{rd}$ to $81^{st}$ of CD43 (AAA51949.1; SEQ ID NO: 130) (SEQ ID NO: 134). Thus, the epitope may be 6-9 consecutive amino acid region comprising SEQ ID NO: 131 in SEQ ID NO: 134 of CD43 (AAA51949.1).

The epitope may have the amino acid sequence selected from the group consisting of SEQ ID NO: 131 to 134, and for example, may have the amino acid sequence of SEQ ID NO: 134:

SEQ ID NO: 132: Ser Pro Leu Trp Thr Ser Ile;
SEQ ID NO: 133: Gly Ser Pro Leu Trp Thr Ser Ile;
SEQ ID NO: 134: Glu Gly Ser Pro Leu Trp Thr Ser Ile.

The anti-CD43 antibody or antigen-binding fragment thereof may be one or more kinds selected from the group consisting of all antibodies or antigen-binding fragments which recognize the afore-mentioned epitope or specifically bind to it.

Herein, the term "JL-1" is used for meaning CD43 or afore-mentioned epitope of CD43.

Herein, the antibody or antigen-binding fragment thereof may be selected from the group consisting of animal derived antibody, chimeric antibody, humanized antibody and antigen-binding fragments thereof. The antibody may be recombinantly or synthetically produced.

When an antibody produced by immunizing a desired antigen to an animal is administered to human in a therapeutic purpose, immunorejection may generally occur. In order to inhibit the immunorejection, a chimeric antibody has been developed. In the chimeric antibody, the constant region of animal derived antibody causing an anti-isotype reaction is replaced with the constant region of human antibody by genetic engineering. The chimeric antibody has been significantly improved in terms of the anti-isotype reaction compared to the animal derived antibody, but still, it has potential side effects of anti-idiotypic reaction, since animal derived amino acids are present in a variable region. The humanized antibody is developed for improving these side effects. This is constructed by grafting a CDR (complementarity determining region) playing an important role for binding of antigen in variable region of chimeric antibody into a human antibody framework.

The most important thing for the CDR grafting technology for constructing the humanized antibody is selecting optimized human antibody which can receive the CDR of animal derived antibody at best, and for this, the utilization of antibody database, analysis of crystal structure, molecular modeling technology, etc. are utilized. However, the application of additional antibody engineering technology for restoring antigen binding capacity is essential, since amino acids located on the framework of animal derived antibody may affect the antigen binding, despite of grafting the CDR of animal derived antibody into optimized human antibody framework, and therefore there are many cases in which the antigen binding capacity cannot be conserved.

The antibody or antigen-binding fragment may be isolated from a living body (not present in a living body) or may be non-naturally occurring, for example, may be synthetically or recombinantly produced.

Herein, "antibody" means a material produced by stimuli of antigen in an immune system, and its kind is not particularly limited, and may be obtained naturally or non-naturally (for example, synthetically or recombinantly). The antibody is advantageous for massive expression and production, since it is very stable in vitro and in vivo and its half-life is long. In addition, the antibody has a dimer structure, and therefore, its avidity is very high.

The complete antibody has a structure composed of two full length light chains and two full length heavy chains, and each light chain is linked to the heavy chain by disulfide bonds. The constant region of antibody is divided to the heavy chain constant region and light chain invariable region, and the heavy chain invariable region has gamma (γ), mu (μ), alpha (α), delta (δ) and epsilon (ε) types and has gamma1 (γ1), gamma2 (γ2), gamma3 (γ3), gamma4 (γ4), alpha1 (α1) and alpha2 (α2) as subclasses. The constant region of light chain has kappa (κ) and lambda (λ) types.

The term, "heavy chain" is interpreted as comprising all of full length heavy chains comprising variable region domain $V_H$ including the amino acid sequence containing variable region sequence sufficient for giving specificity to an antigen, 3 of constant region domains $C_{H1}$, $C_{H2}$ and $C_{H3}$ and hinge, and fragments thereof. In addition, the term, "light chain" is interpreted as comprising all of full length light chains comprising variable region domain $V_L$ including the amino acid sequence containing variable region sequence sufficient for giving specificity to an antigen, and constant region domain $C_L$, and fragments thereof.

The term, "CDR (complementarity determining region)" means the amino acid sequence of hypervariable region of heavy chain and light chain of immunoglobulin. The heavy chain and light chain may comprise 3 CDRs, respectively (CDRH1, CDRH2, CDRH3 and CDRL1, CDRL2, CDRL3). The CDR may provide a major contact residue for binding of CDR to an antigen or epitope. On the other hand, herein, the term, "specific binding" or "specific recognition" means the same as publicly known to a person skilled in the art, and means that an antigen and antibody specifically interact and perform an immunological reaction.

The term, "antigen-binding fragment" is a fragment in the entire structure of immunoglobulin, and means a part of polypeptide comprising the part where an antigen can binds. For example, it may be scFv, (scFv)$_2$, scFv-Fc, Fab, Fab' or F(ab')$_2$, but not limited thereto.

Fab of antigen-binding fragment is a structure containing variable regions of light chain and heavy chain, constant region of light chain and the first constant region of heavy chain ($C_{H1}$), and has 1 antigen-binding fragment. Fab' differs from Fab in that it has a hinge region comprising one or more cysteine residues at C-terminus of heavy chain $C_{H1}$ domain. F(ab')$_2$ antibody is produced by forming antigen-binding fragment between cysteine residues of hinge region. Fv is a minimum antibody fragment having only heavy variable region and light chain variable region, and the recombination technology of producing Fv fragment is widely known to the public in the art. In the two-chain Fv, the heavy chain variable region and light chain variable region are linked by non-covalent bonds, and in the single-chain Fv, the heavy chain variable region and single chain variable region are linked by covalent bonds generally through a peptide linker or linked directly at C-terminus, thus it may form the same structure as the two-chain Fv. The linker may be a peptide linker consisting of 1 to 100 or 2 to 50 of any amino acids, and appropriate sequences are known in the art. The antigen-binding fragment may be obtained by using a proteinase (for example, when the whole antibody is restrictively digested with papain, Fab may be obtained, and when cleaved by pepsin, F(ab')$_2$ fragment may be obtained), and may be constructed by gene recombination technology.

The term, "hinge region" is a region in the heavy chain of antibody, and is present between CH1 and CH2 regions, meaning a region functioning to provide the flexibility of antigen-binding fragment in the antibody. For example, the hinge may be derived from a human antibody, and specifically, may be derived from IgA, IgE, or IgG, for example, IgG1, IgG2, IgG 3, or IgG4.

The anti-CD43 antibody may be a polyclonal antibody or monoclonal antibody, and for example, may be a monoclonal antibody. The monoclonal antibody may be prepared by the method widely known in the art. For example, it may be prepared by using a phase display technique.

On the other hand, individual monoclonal antibodies may be screened by using a typical ELISA (Enzyme-Linked ImmunoSorbent Assay) format based on the binding capacity to CD43. The inhibitory activity may be tested by functional analyses for testing the molecular interaction of assembly such as competitive ELISA, cell-based assay, Scatchard analysis, or surface plasmon resonance, etc. Then, the affinity to CD43 (Kd values) for each monoclonal antibody members selected based on the strong inhibitory activity may be tested.

For example, the anti-CD43 or an antigen-binding fragment thereof may have the binding affinity (Kd; for example, measured by Scatchard analysis) to CD43 (for example, human CD43, mouse CD43, etc.) or the epitope located in the extracellular domain of CD43 of 1 mM or less, 100 nM or less, 10 nM or less, 5 nM or less, or 3 nM or less, for example, 1 pM to 1 mM, 1 pM to 100 nM, 1 pM to 10 nM, 1 pM to 5 nM, 1 pM to 3 nM, 10 pM to 1 mM, 10 pM to 100 nM, 10 pM to 10 nM, 10 pM to 5 nM, 10 pM to 3 nM, 100 pM to 1 mM, 100 pM to 100 nM, 100 pM to 10 nM, 100 pM to 5 nM, 100 pM to 3 nM, 1 nM to 1 mM, 1 nM to 100 nM, 1 nM to 10 nM, 1 nM to 5 nM, or 1 nM to 3 nM.

Other embodiment provides a hybridoma cell line producing a monoclonal anti-CD43 antibody. The hybridoma cell line may be H-JL1 cell line with accession number KCLRF-BP-00010.

The anti-CD43 or an antigen-binding fragment thereof may be applied with one or more kinds selected from the group consisting of cytotoxic materials, etc.

Therefore, the pharmaceutical composition may further comprise one or more kinds selected from the group consisting of cytotoxic materials, etc., in addition to the anti-CD43 or an antigen-binding fragment thereof. Furthermore, the method of treating and/or inhibiting may further comprise a step of administering one or more kinds selected from the group consisting of cytotoxic materials, etc. in addition to the step of administering the anti-CD43 or an antigen-binding fragment thereof.

Specifically, other embodiment of the present invention provides a pharmaceutical composition for treating a solid cancer comprising (1) the anti-CD43 antibody or an antigen-binding fragment thereof which binds to the epitope located in the extracellular domain of CD43 and (2) one or more kinds selected from the group consisting of cytotoxic materials, etc. as an active ingredient.

Other embodiment provides a method for treating a solid cancer comprising (1) a step of administering a pharmaceutically effective amount of the anti-CD43 antibody or an antigen-binding fragment thereof which binds to the epitope located in the extracellular domain of CD43 to a subject in need of treating the solid cancer, and (2) a step of administering a pharmaceutically effective amount of one or more kinds selected from the group consisting of cytotoxic materials, etc. to a subject in need of treating the solid cancer.

Other embodiment provides a pharmaceutical composition for inhibiting a cancer stem cell, for example, a cancer stem cell in hematologic malignancy or solid cancer, comprising (i) the anti-CD43 antibody or an antigen-binding fragment thereof which binds to the epitope located in the extracellular domain of CD43 and (ii) one or more kinds selected from the group consisting of cytotoxic materials, etc. as an active ingredient.

Other embodiment provides a pharmaceutical composition for inhibiting a cancer stem cell, for example, a cancer stem cell in hematologic malignancy or solid cancer, comprising (i) a step of administering a pharmaceutically effective amount of the anti-CD43 antibody or an antigen-binding fragment thereof which binds to the epitope located in the extracellular domain of CD43 to a cancer patient, for example, a solid cancer patient, and (ii) a step of administering a pharmaceutically effective amount of one or more kinds selected from the group consisting of cytotoxic materials, etc. to a cancer patient, for example, a solid cancer patient.

For the pharmaceutical composition, the anti-CD43 antibody or an antigen-binding fragment thereof and one or more kinds selected from the group consisting of cytotoxic materials, etc. may be formulated as one formulation by conjugated each other or mixed, or formulated as a separate formulation respectively and mixed. For the method, the step of administering the anti-CD43 antibody or an antigen-binding fragment thereof and one or more kinds selected from the group consisting of cytotoxic materials, etc. may be performed simultaneously or in order regardless of order.

The cytotoxic material may be all the materials having toxicity to a cancer cell, particularly, solid cancer cell, and may be one or more kinds selected from the group consisting of radioactive isotope, cytotoxic compound (small molecule), cytotoxic protein, anti-cancer agent, etc., but not limited thereto. The cytotoxic protein may be one or more kinds selected from the group consisting of ricin, saporin, gelonin, momordin, debouganin, diphtheria toxin, *pseudomonas* toxin, etc., but not limited thereto. The radioactive isotope may be one or more kinds selected from the group consisting of $^{131}$I, $^{188}$Rh, $^{90}$Y, etc., but not limited thereto. The cytotoxic compound may be one or more kinds selected from the group consisting of duocarmycin, monomethyl auristatin E (MMAE), monomethyl auristatin F (MMAF), N2'-deacetyl-N2'-(3-mercapto-1-oxopropyl)maytansine (DM1), PBD (Pyrrolobenzodiazepine) dimer, etc., but not limited thereto.

The anti-CD43 antibody or an antigen-binding fragment thereof and one or more kinds selected from the group consisting of cytotoxic materials, etc. may be used in a form of conjugate or fusion protein (in case that the cytotoxic material and/or marker material are proteins) linked each other (for example, by a covalent bond, peptide bond, etc.). The conjugation between antibody (or antigen-binding fragment) and cytotoxic material may be according to the well-known technology in the art to which the present invention belongs.

The active ingredient (anti-CD43 antibody or antigen-binding fragment thereof, and/or cytotoxic material and/or marker material) may be applied (administered) with a pharmaceutically acceptable carrier, and the pharmaceutically acceptable carrier is commonly used for formulation of drug, and may be one or more kinds selected from the group consisting of lactose, dextrose, sucrose, sorbitol, mannitol, starch, acacia rubber, calcium phosphate, alginate, gelatin, calcium silicate, microcystral cellulose, polyvinylpyrrolidone, cellulose, water, syrup, methyl cellulose, methylhydroxybenzoate, propylhydroxybenzoate, talc, magnesium stearate, mineral oil, etc., but not limited thereto. The anti-CD43 antibody may further comprise one or more kinds selected from the group consisting of diluent, excipient, lubricant, humectant, sweetening agent, flavouring agent, emulsifying agent, suspension, preservative, etc. commonly used for preparation of pharmaceutical composition other than the components.

The active ingredient or pharmaceutical composition may be administered orally or parenterally. In case of parenteral administration, it may be administered by intravenous injection, subcutaneous injection, intramuscular injection, intraperitoneal injection, endodermal administration, local administration, intranasal administration, intrapulmonary administration, or intrarectal administration, etc. In case of oral administration, the oral composition should be coated or formulated for an active drug to be protected from degradation in stomach, as protein or peptide is digested. In addition, the anti-CD43 antibody or antigen-binding fragment thereof may be administered by any device with which the active material can be delivered to a target cell.

Herein, "pharmaceutically effective amount" means an amount of exhibiting a pharmaceutically meaningful effect of drug. The pharmaceutically effective amount of active ingredients for a single dose may be diversely prescribed according to factors such as formulation method, administration, age, body weight, gender, morbidity of patient, food, administration time, administration interval, administration route, excretion rate and susceptibility. For example, the pharmaceutically effective amount of active ingredients (for example, the anti-CD43 antibody or antigen-binding fragment thereof) for a single dose may be in the range of 0.001 to 100 mg/kg, or 0.02 to 10 mg/kg, but not limited thereto. The pharmaceutically effective amount a single dose may be formulated as one formulation in a unit capacity form, formulated in proper quantities, or prepared by filling in a multi capacity container.

The solid cancer may mean all non-hematologic malignancy other than hematologic malignancy. For example, the solid cancer may be one or more kinds selected from the group consisting of lung cancer (for example, squamous cell carcinoma, small cell lung cancer, non-small cell lung cancer, adenocarcinoma of lung, squamous cell carcinoma of lung), peritoneal cancer, skin cancer, melanoma in skin or eyeball, rectal cancer, cancer near the anus, esophagus cancer, small intestinal cancer, endocrine gland cancer, parathyroid cancer, adrenal cancer, soft-tissue sarcoma, urethral cancer, gastrointestinal cancer, stomach cancer, pancreatic cancer, glioblastoma, cervical cancer, ovarian cancer, liver cancer, gallbladder cancer, bladder cancer, breast cancer, colon cancer, large intestine cancer, uterine cancer, endometrial cancer, uterine cervical cancer, salivary gland cancer, renal cancer, prostate cancer, vulval cancer, thyroid cancer, head and neck cancer, brain cancer, osteosarcoma, etc., but not limited thereto. For example, the solid cancer may be stomach cancer, breast cancer, lung cancer, large intestine cancer, liver cancer, gallbladder cancer, renal cancer, pancreatic cancer, thyroid cancer, ovarian cancer, uterine cervical cancer, prostate cancer, or bladder cancer. The cancer comprises not only primary cancer but also metastatic cancer. In addition, the solid cancer may be a cancer having resistance to conventional anti-cancer agents (e.g., small molecule anti-cancer agent (anticancer chemical), anti-metabolic agent, alkylating agent, antibiotics, vinca alkaloid, enzyme, hormone, targeted therapeutic agent, and/or antibody therapeutic agent, etc.), and may be a cancer recurred after treatment of conventional anti-cancer agents (e.g., small molecule anti-cancer agent (anticancer chemical), anti-metabolic agent, alkylating agent, antibiotic, vinca alkaloid, enzyme, hormone, targeted therapeutic agent, and/or antibody therapeutic agent, etc.).

The treatment effect on a solid cancer comprises not only growth inhibition (quantitative reduction) and apoptosis of cancer cell (particularly, cancer stem cell) or cancer tissue comprising thereof, but also the inhibitory effect on deterioration of cancer by inhibiting migration, invasion, metastasis, etc.

Herein, "inhibition of a cancer stem cell" means all quantitative and/or functional inhibition of cancer stem cell such as growth inhibition (quantitative reduction), apoptosis, etc. and/or treatment and/or improvement of cancer in which the cancer stem cells are involved.

Herein, "patient" means a patient in need of treatment of cancer (for example, solid cancer or hematologic malignancy), and/or inhibition of cancer stem cell, for example, cancer stem cell in hematologic malignancy or solid cancer, and may be all mammals, for example, human, and may be a patient suffering from cancer, having symptoms of cancer, or at risk of developing cancer, or cells, tissues, body fluids, or cultures thereof isolated therefrom.

Other embodiment provides a conjugate in which the anti-CD43 antibody or antigen-binding fragment thereof which binds to an epitope located in an extracellular domain of CD43 and a cancer stem cell, for example, cancer stem cell in hematologic malignancy or solid cancer, wherein the antibody or antigen-binding fragment binds to the cancer stem cell. Other embodiment provides a method for producing a conjugate in which an anti-CD43 antibody or an antigen-binding fragment thereof which binds to an epitope located in an extracellular domain of CD43, and a cancer stem cell, for example, a cancer stem cell in hematologic malignancy or solid cancer, wherein the antibody or antigen-binding fragment binds to the cancer stem cell, comprising a step of contacting the anti-CD43 antibody or antigen-binding fragment thereof which binds to an epitope located in an extracellular domain of CD43 with a cancer sample, for example, a solid cancer sample or administering it into a cancer patient, such as a solid cancer patient. The method may be performed in vivo or in vitro. The conjugate or method for producing the same may be used for various clinical, diagnostic, and/or experimental purposes as well as treatment of solid cancer. For example, it may be used for confirmation of existence of cancer stem cell, for example, cancer stem cell in hematologic malignancy or solid cancer and/or visualization of cancer stem cell, for example, cancer stem cell in hematologic malignancy or solid cancer, by detecting whether the complex is produced when the anti-CD43 antibody or antigen-binding fragment thereof contacts to a cancer sample. Then, the anti-CD43 antibody or antigen-binding fragment thereof may additionally comprise a marker material. The marker material may be one or more kinds selected from the group consisting of radioactive isotope, fluorescent material, chromogen, dye, etc. The fluorescent material may be all fluorescent materials commonly available, and for example, may be one or more kinds selected from the group consisting of fluorescein isothiocyanate (FITC), phycoerythrin (PE), allophycocyanin (APC) or biotin, but not limited thereto. The marker material may be combined (linked) to the antibody or antigen-binding fragment by common methods (for example, chemical bonds such as covalent bond, coordinate bond, ionic bond, etc.). The combination of antibody (or antigen-binding fragment) and marker material may be according to the well-known technology in the art to which the present invention belongs.

The cancer sample may be cancer cell line or cell, tissue, body fluid, etc. isolated from a cancer patient or cultured artificially. The solid cancer sample may be solid cancer cell line or cell, tissue, body fluid, etc. isolated from a solid cancer patient or cultured artificially.

Other embodiment provides a use as a marker for detecting a cancer stem cell, for example, cancer stem cell of hematologic malignancy or solid cancer of CD43, specifically the epitope located in the extracellular domain of CD43. Specifically, one embodiment provides a composition for detecting a cancer stem cell, for example, cancer stem cell in hematologic malignancy or solid cancer, comprising a material interacting with CD43, specifically the epitope located in the extracellular domain of CD43. Other embodiment provides a method for detecting a cancer stem cell, for example, cancer stem cell in hematologic malignancy or solid cancer comprising a step of contacting a material interacting with CD43, specifically the epitope located in the extracellular domain of CD43, and a step of measuring whether CD34, specifically the epitope located in the extracellular domain of CD43, interacts with the material or degree thereof. In this case, when the interaction between CD43, specifically the epitope located in the extracellular domain of CD43, and the material is present, or its level is high, the cell sample may be decided (determined) to comprise a cancer stem cell, for example, cancer stem cell in hematologic malignancy or solid cancer. The interacting material may be one or more kinds selected from the group consisting of all materials which can interact with CD43, specifically the epitope located in the extracellular domain of CD43, for example, chemical material (small molecular chemical), antibody, antigen-binding fragment of antibody, aptamer, etc. Whether the interaction is present, may be measured by common protein analysis methods using the interacting material, for example, immunochromatography, enzyme linked immunosorbent assay (ELISA), radioimmunoassay (RIA), enzyme immunoassay (EIA), fluorescence immunoassay (FIA), luminescence immunoassay (LIA), western blotting, fluorescent in situ hybridization (FISH)-, flow cytometer, microarray method, etc., but not limited thereto. The cell sample may be a cell, tissue, or culture thereof isolated from mammals, for example, human, and for example, may be a cancer cell, cancer tissue, or culture thereof isolated from a cancer patient, for example of solid cancer patient.

Other embodiment provides a use of screening solid cancer therapeutics of the epitope located in the extracellular domain of CD43.

Other embodiment provides an agent for screening anti-solid cancer agents comprising the epitope located in the extracellular domain of CD43.

Other embodiment provides a method for screening anti-solid cancer agents comprising a step of contacting a candidate compound to the epitope located in the extracellular domain of CD43, and a step of selecting the candidate compound binding to the epitope to determine it as a solid cancer therapeutic candidate.

The solid cancer therapeutic agent screened as above may be characterized by having an effect of inhibiting a cancer stem cell, for example, cancer stem cell in hematologic malignancy or solid cancer.

Thus, other embodiment provides a use for screening an agent for inhibiting a cancer stem cell, for example, cancer stem cell of hematologic malignancy or solid cancer, of epitope located in the extracellular domain of CD43.

Other embodiment provides an agent for screening an agent for inhibiting a cancer stem cell, for example, cancer stem cell of hematologic malignancy or solid cancer, of epitope located in the extracellular domain of CD43.

Other embodiment provides a method for screening an agent for inhibiting a cancer stem cell, for example, cancer stem cell in hematologic malignancy or solid cancer, comprising a step of contacting a candidate compound to the epitope located in the extracellular domain of CD43, and a step of selecting the candidate compound binding to the epitope to determine it as the candidate material of agent for inhibiting a cancer stem cell, for example, cancer stem cell in hematologic malignancy or solid cancer.

The candidate compound binding to the epitope may have the binding affinity to the epitope (Kd; for example, measured by Scatchard analysis) of 1 mM or less, 100 nM or less, 10 nM or less, 5 nM or less, or 3 nM or less, for example, 1 pM to 1 mM, 1 pM to 100 nM, 1 pM to 10 nM, 1 pM to 5 nM, 1 pM to 3 nM, 10 pM to 1 mM, 10 pM to 100 nM, 10 pM to 10 nM, 10 pM to 5 nM, 10 pM to 3 nM, 100 pM to 1 mM, 100 pM to 100 nM, 100 pM to 10 nM, 100 pM to 5 nM, 100 pM to 3 nM, 1 nM to 1 mM, 1 nM to 100 nM, 1 nM to 10 nM, 1 nM to 5 nM, or 1 nM to 3 nM.

The epitope is as aforementioned and may have the amino acid sequence selected in SEQ ID NO: 131 to 134. The epitope may be provided as the entire CD43 protein or a part comprising the epitope, or synthesized chemically or produced recombinantly.

The candidate compound may be artificially synthesized or may be one or more kinds selected from the group consisting of natural, various kinds of compounds, polypeptide, oligopeptide, peptide structure or protein structure (for example, antibody, antigen-binding fragment of antibody, peptibody, nanobody, etc.), polynucleotide, oligonucleotide, antisense-RNA, shRNA (short hairpin RNA), siRNA (small interference RNA), aptamer, natural extract, etc.

The combination of candidate compound and epitope may be performed by confirming the formation of complex of candidate compound and epitope, and it may be carried out by various methods known publicly in the art. For example, it may be measured by common enzymatic reaction, fluorescence, luminescence and/or radiation detection, and specifically, may be measured by a method selected from the group consisting of immunochromatography, immunohistochemistry, enzyme linked immunosorbent assay (ELISA), radioimmunoassay (RIA), enzyme immunoassay (EIA), Fluorescence immunoassay (FIA), luminescence immunoassay (LIA), western blotting, etc., but not limited thereto.

In one embodiment, the agent for treating a solid cancer or the agent for inhibiting a cancer stem cell screened as above may be one or more kinds selected from the group consisting of antibody, antigen-binding fragment of antibody, antibody-like protein structure (for example, peptibody, nanobody), etc.

In other embodiment, a pharmaceutical composition for treating a solid cancer comprising the agent for treating a solid cancer screened as above is provided. Other embodiment provides a method for treating a solid cancer comprising a step of administrating a pharmaceutically effective amount of screened agent for treating a solid cancer to a patient in need of treating a solid cancer. In one embodiment, the solid cancer may be stomach cancer.

Other embodiment provides a pharmaceutical composition for inhibiting a cancer stem cell, for example, cancer stem cell in hematologic malignancy or solid cancer comprising the agent for inhibiting the cancer stem cell screened as above. Other embodiment provides a method for inhibiting a cancer stem cell, for example, cancer stem cell in hematologic malignancy or solid cancer comprising a step of administering a pharmaceutically effective amount of agent for inhibiting the cancer stem cell as above to a cancer patient, for example, solid cancer patient. In one embodiment, the solid cancer may be stomach cancer.

Other embodiment provides a novel anti-CD43 antibody or an antigen-binding fragment thereof. The anti-CD43 antibody or antigen-binding fragment thereof may binds to the epitope located in an extracellular domain of CD43. The epitope may be a polypeptide comprising 6-9 consecutive amino acids in the extracellular domain of CD43 comprising the amino acid sequence of SEQ ID NO: 131.

The anti-CD43 antibody or antigen-binding fragment thereof comprises a heavy chain variable region (VH) and a light chain variable region (VL). The anti-CD43 antibody or antigen-binding fragment thereof may be animal derived antibody (for example, mouse antibody), chimeric antibody, or humanized antibody, and may be a monoclonal antibody or polyclonal antibody, and it may be non-naturally (for example, chemical or biological synthesis, recombinant method, etc.) produced.

The heavy chain variable region may comprise the first complemetarity determining region (CDR) (CDR1H), the second CDR (CDR2H) and the third CDR (CDR3H), in order from N-terminus to C-terminus.

In one embodiment, the anti-CD43 antibody or antigen-binding fragment thereof may comprise CDR1H including the amino acid sequence of GYX$_1$MN (SEQ ID NO: 110; X$_1$ may be selected from all amino acids, and for example, may be F or Y) (for example, GYFMN (SEQ ID NO: 111) or GYYMN (SEQ ID NO: 112)), CDR2H including the amino acid sequence of RINPNX$_2$GDSFYNQKFX$_3$G (SEQ ID NO: 113; X$_2$ and X$_3$ may be selected from all amino acids respectively, and for example, X$_2$ may be N or S, and X$_3$ may be Q or K) (for example, RINPNNGDSFYNQKFQG (SEQ ID NO: 114), RINPNSGDSFYNQKFQG (SEQ ID NO: 115), RINPNNGDSFYNQKFKG (SEQ ID NO: 116), or RINPNSGDSFYNQKFKG (SEQ ID NO: 117)), and CDR3H including the amino acid sequence of EGYYGGR-GYALDY (SEQ ID NO: 118) as an essential component of heavy chain variable region.

The heavy chain variable region may further comprise a framework of immunoglobulin at N-terminus and/or C-terminus of afore-mentioned complementarity determining regions (CDR). More specifically, the heavy chain variable region may comprise the first framework (FR1H), the first complementarity determining region (CDR) (CDR1H), the second framework (FR2H), the second CDR (CDR2H), the third framework (FR3H), the third CDR (CDR3H), and the fourth framework (FR4H) in order from N-terminus to C-terminus.

In one specific embodiment, the anti-CD43 antibody or antigen-binding fragment thereof is humanized, and (i) FR1H may be comprise the amino acid sequence from no. 1 to no. 30 of one of SEQ ID NO: 83 to SEQ ID NO: 94, or the amino acid sequence having 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more of sequence homology with the amino acid sequence above;

(ii) CDR1H may comprise the amino acid sequence of GYX$_1$MN (SEQ ID NO: 110; X$_1$ may be selected among all amino acids, and for example, may be F or Y), and for example, may comprise the amino acid sequence of GYFMN (SEQ ID NO: 111) or GYYMN (SEQ ID NO: 112);

(iii) FR2H may be comprise the amino acid sequence from no. 36 to no. 49 of one of SEQ ID NO: 83 to SEQ ID NO: 94, or the amino acid sequence having 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more of sequence homology with the above amino acid sequence;

(iv) CDR2H may comprise the amino acid sequence of RINPNX$_2$GDSFYNQKFX$_3$G (SEQ ID NO: 113; each of X$_2$ and X$_3$ may be independently selected from all amino acids, and for example, X$_2$ may be N or S, X$_3$ may be Q or K), and for example, may comprise the amino acid sequence of RINPNNGDSFYNQKFQG (SEQ ID NO: 114), RINPNSGDSFYNQKFQG (SEQ ID NO: 115), RINPNNGDSFYNQKFKG (SEQ ID NO: 116), or RINPNSGDSFYNQKFKG (SEQ ID NO: 117);

(v) FR3H may be comprise the amino acid sequence from no. 67 to no. 98 of one of SEQ ID NO: 83 to SEQ ID NO: 94, or the amino acid sequence having 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more of sequence homology with the above amino acid sequence;

(vi) CDR3H may comprise the amino acid sequence of EGYYGGRGYALDY (SEQ ID NO: 118);

(vii) FR4H may be comprise the amino acid sequence from no. 112 to no. 122 of one of SEQ ID NO: 83 to SEQ ID NO: 94, or the amino acid sequence having 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more of sequence homology with the amino acid sequence.

The light chain variable region may comprise the first CDR (CDR1L), the second CDR (CDR2L) and the third CDR (CDR3L), in order from N-terminus to C-terminus.

In one embodiment, the anti-CD43 antibody or antigen-binding fragment thereof may comprise CDR1L including the amino acid sequence of RTSQDISNYLN (SEQ ID NO: 119); CDR2L including the amino acid sequence of X$_4$TX$_5$RLHS (SEQ ID NO: 120; X$_4$ and X$_5$ may be selected from all amino acids respectively, and for example, X$_4$ may be N, Q or A, and X$_5$ may be S or A) (for example, NTSRLHS (SEQ ID NO: 121, NTARLHS (SEQ ID NO: 122), QTSRLHS (SEQ ID NO: 123), or ATSRLHS (SEQ ID NO: 124)); and CDR3L including the amino acid sequence of QQSNMFPY (SEQ ID NO: 125) as an essential component of light chain variable region.

The light chain variable region may further comprise a framework of immunoglobulin at N-terminus and/or C-terminus of afore-mentioned complementarity determining regions (CDR). More specifically, the light chain variable region may comprise the first framework (FR1L), the first complementarity determining region (CDR) (CDR1 L), the second framework (FR2 L), the second CDR (CDR2 L), the third framework (FR3 L), the third CDR (CDR3 L), and the fourth framework (FR4 L) in order from N-terminus to C-terminus.

In one specific embodiment, (viii) FR1L may be comprise the amino acid sequence from no. 1 to no. 23 of one of SEQ ID NO: 95 to SEQ ID NO: 109, or the amino acid sequence having 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more of sequence homology with the amino acid sequence above;

(ix) CDR1L may comprise the amino acid sequence of RTSQDISNYLN (SEQ ID NO: 119);

(x) FR2L may comprise the amino acid sequence from no. 35 to no. 49 of one of SEQ ID NO: 95 to SEQ ID NO: 109, or the amino acid sequence having 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more of sequence homology with the amino acid sequence above;

(xi) CDR2L may comprise the amino acid sequence of $X_4TX_5RLHS$ (SEQ ID NO: 120; each of $X_4$ and $X_5$ may be independently selected from all amino acids, and, for example, $X_4$ may be N, Q, or A, and $X_5$ may be S or A), and for example, may comprise NTSRLHS (SEQ ID NO: 121, NTARLHS (SEQ ID NO: 122), QTSRLHS (SEQ ID NO: 123), or ATSRLHS ((SEQ ID NO: 124).

(xii) FR3L may comprise the amino acid sequence from no. 57 to no. 88 of one of SEQ ID NO: 95 to SEQ ID NO: 109, or the amino acid sequence having 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more of sequence homology with the amino acid sequence above.

(xiii) CDR3L may comprise the amino acid sequence of QQSNMFPY (SEQ ID NO: 125);

(xiv) FR4L may comprise the amino acid sequence from no. 97 to no. 108 of one of SEQ ID NO: 95 to SEQ ID NO: 109, or the amino acid sequence having 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more of sequence homology with the above amino acid sequence.

In one embodiment, the anti-CD43 antibody or antigen-binding fragment thereof may comprise a heavy chain variable region and a light chain variable region. The heavy chain variable region may comprise the amino acid sequence of SEQ ID NO: 2, 6, 10, 14, 18, 22, 26, 30, 83, 84, 85, 86, 87, 88, 89, 90, 91, 92, 93, or 94. The light chain variable region may comprise the amino acid sequence of SEQ ID NO: 4, 8, 12, 16, 20, 24, 28, 32, 95, 96, 97, 98, 99, 100, 101, 102, 103, 104, 105, 106, 107, 108, or 109.

For example, the anti-CD43 antibody or antigen-binding fragment thereof may be humanized, and may be illustrated to comprise the heavy chain variable region and light chain variable region defined as follows:

(a) heavy chain variable region comprising the amino acid sequence of SEQ ID NO: 83 and light chain variable region comprising the amino acid sequence of SEQ ID NO: 95;

(b) heavy chain variable region comprising the amino acid sequence of SEQ ID NO: 84 and light chain variable region comprising the amino acid sequence of SEQ ID NO: 96;

(c) heavy chain variable region comprising the amino acid sequence of SEQ ID NO: 85 and light chain variable region comprising the amino acid sequence of SEQ ID NO: 97;

(d) heavy chain variable region comprising the amino acid sequence of SEQ ID NO: 86 and light chain variable region comprising the amino acid sequence of SEQ ID NO: 98;

(e) heavy chain variable region comprising the amino acid sequence of SEQ ID NO: 87 and light chain variable region comprising the amino acid sequence of SEQ ID NO: 99;

(f) heavy chain variable region comprising the amino acid sequence of SEQ ID NO: 88 and light chain variable region comprising the amino acid sequence of SEQ ID NO: 100;

(g) heavy chain variable region comprising the amino acid sequence of SEQ ID NO: 89 and light chain variable region comprising the amino acid sequence of SEQ ID NO: 101;

(h) heavy chain variable region comprising the amino acid sequence of SEQ ID NO: 90 and light chain variable region comprising the amino acid sequence of SEQ ID NO: 102;

(i) heavy chain variable region comprising the amino acid sequence of SEQ ID NO: 91 and light chain variable region comprising the amino acid sequence of SEQ ID NO: 103;

(j) heavy chain variable region comprising the amino acid sequence of SEQ ID NO: 93 and light chain variable region comprising the amino acid sequence of SEQ ID NO: 103;

(k) heavy chain variable region comprising the amino acid sequence of SEQ ID NO: 94 and light chain variable region comprising the amino acid sequence of SEQ ID NO: 106;

(l) heavy chain variable region comprising the amino acid sequence of SEQ ID NO: 91 and light chain variable region comprising the amino acid sequence of SEQ ID NO: 97;

(m) heavy chain variable region comprising the amino acid sequence of SEQ ID NO: 85 and light chain variable region comprising the amino acid sequence of SEQ ID NO: 103;

(n) heavy chain variable region comprising the amino acid sequence of SEQ ID NO: 93 and light chain variable region comprising the amino acid sequence of SEQ ID NO: 107;

(o) heavy chain variable region comprising the amino acid sequence of SEQ ID NO: 93 and light chain variable region comprising the amino acid sequence of SEQ ID NO: 108; or (p) heavy chain variable region comprising the amino acid sequence of SEQ ID NO: 93 and light chain variable region comprising the amino acid sequence of SEQ ID NO: 109.

One specific embodiment, the amino acid sequence of framework comprised in the humanized anti-CD43 antibody or antigen-binding fragment thereof may be illustrated as follows, but not limited thereto:

(i) FR1H may comprise the amino acid residue from no. 1 to no. 30 of one of SEQ ID NOs: 83 to 94;

(ii) FR2H may comprise the amino acid residue from no. 36 to no. 49 of one of SEQ ID NOs: 83 to 94;

(iii) FR3H may comprise the amino acid residue from no. 67 to no. 98 of one of SEQ ID NOs: 83 to 94;

(iv) FR4H may comprise the amino acid residue from no. 112 to no. 122 of one of SEQ ID NOs: 83 to 94;

(v) FR1L may comprise the amino acid residue from no. 1 to no. 23 of one of SEQ ID NOs: 95 to 109;

(vi) FR2L may comprise the amino acid residue from no. 35 to no. 49 of one of SEQ ID NOs: 95 to 109;

(vii) FR3L may comprise the amino acid residue from no. 57 to no. 88 of one of SEQ ID NOs: 95 to 109;

(viii) FR4L may comprise the amino acid residue from no. 97 to no. 108 of one of SEQ ID NOs: 95 to 109.

In other example, the anti-CD43 antibody or antigen-binding fragment thereof may further comprise a human heavy chain constant region and/or human light chain constant region induced from a human immunoglobulin. The human immunoglobulin may be selected from the group consisting of IgA, IgD, IgE, IgG (IgG1, IgG2, IgG3, IgG4), IgM, etc. For example, the human heavy chain constant region may comprise the amino acid sequence of no. 123-452 of SEQ ID NO: 40 or the amino acid sequence having 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more of sequence homology with the amino acid sequence above; and the human light chain constant region may comprise the amino acid sequence of no. 108-214 of SEQ ID NO: 48 or the amino acid sequence having 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more of sequence homology with the amino acid sequence above.

In other embodiment, the anti-CD43 antibody or antigen-binding fragment thereof may be characterized in that the amino acid residue is not glycosylated. For this, when a glycosylation motif, for example, N-glycosylation motif (e.g., "N-X-S/T" (X may be all amino acid residues)) is in the antibody, in particular, heavy chain variable region and/or light chain variable region, the motif may be modified. For example, when the N-glycosylation motif is "N-X-S/T" (X may be all amino acid residues), "N", "S/T" or both of them in the motif may be substituted with an amino acid different from the original, respectively. In one embodiment, the unglycosylated anti-CD43 antibody or an antigen-binding fragment thereof may comprise NTARLHS (SEQ ID NO: 122), QTSRLHS (SEQ ID NO: 123), or ATSRLHS (SEQ ID NO: 124) as CDR2L. As other embodiment, the unglycosylated anti-CD43 antibody or an antigen-binding fragment thereof may comprise the amino acid sequence of SEQ ID NO: 107, 108, or 109 as a light chain variable region.

The anti-CD43 antibody or antigen-binding fragment thereof specifically binds to the aforementioned specific epitope of CD43, and may be selected from the group consisting of animal antibody (for example, mouse antibody), chimeric antibody, humanized antibody and antigen-binding fragments thereof. The animal antibody may be derived from animal species other than human, and for example, may be derived from rat, mouse, goat, guinea pig, donkey, rabbit, horse, llama, camel, birds (for example, chicken, duck, etc.), and so on, but not limited thereto. The technique to construct a chimeric antibody and/or humanized antibody from the animal antibody has been well known in the art. The humanized antibody may be IgG (IgG1, IgG2, IgG3, IgG4), IgM, IgA, IgD, IgE or any appropriate isotype such as any subclass.

Herein, the binding specificity to CD43 of antibody may mean that the antibody has higher affinity to CD43 than non-CD43 peptide, or has higher affinity to the aforementioned epitope of CD43 compared to other region of CD43 or other extracellular region.

The binding of antibody and antigen (more specifically, epitope) (antigen-antibody binding) may be measured by all methods known in the art. For example, the antigen-antibody binding may be measured by one or more kinds of methods selected from the group consisting of ELISA, flow cytometer, immunochemical staining, BIAcore optical biosensor, etc., but not limited thereto.

The term of antigen binding fragment used herein means a part (fragment) of antibody having an ability to specifically recognize the antigen (CD43) or the aforementioned epitope of CD43 and/or specifically binds to it. For example, the antigen binding fragment may be selected from the group consisting of Fab, F(ab)2, Fv, scFv, scFv-Fc fragments, etc.

In one embodiment, the epitope of anti-CD43 may be anti-CD43 scFv. The anti-CD43 scFv may comprise aforementioned CDRH1, CDRH2, CDRH3, CDRL1, CDRL2, and CDRL3, or comprise aforementioned heavy chain variable region and light chain variable region.

For the anti-CD43 scFv, the aforementioned heavy chain variable region and light chain variable region may be linked by an appropriate linker. The linker may be a peptide linker consisting of 1 to 100 or 2 to 50 of any amino acids, and appropriate sequences are known in the art. In one embodiment, the peptide linker may be expressed as GGGX$_6$S (X$_6$ is G or A; SEQ ID NO: 126) or (GGGX$_6$S)n (n is an integer from 1 to 5, and X$_6$ included in each repeating unit is independently G or A), and for example, may comprise the amino acid sequence of GGGASGGGGSGGGGS (SEQ ID NO: 127) or GGGGSGGGGSGGGAS (SEQ ID NO: 128), but not limited thereto.

In one embodiment, the anti-CD43 scFv may comprise the amino acid sequence of SEQ ID NOs: 50, 52, 54, 56, or 58, but not limited thereto.

In one embodiment, the anti-CD43 antibody or antigen-binding fragment thereof may exhibit cytotoxicity to a target cell by being conjugated with a cytotoxic material which can induce cell death (for example, including programmed cell death such as apoptosis). The cytotoxic material may be one or more selected from the group consisting of all the compounds (small molecular compound; anti-cancer agent, etc.), protein, peptide, oligonucleotide, polynucleotide, etc. known to exhibit toxicity to a cell, particularly, cancer cell in the art, and for example, may be one or more kinds selected from the group consisting of radioactive isotope, cytotoxin compound (small molecule), cytotoxic protein, anti-cancer agent, etc. The cytotoxin protein may be one or more kinds selected from the group consisting of ricin, saporin, gelonin, momordin, debouganin, diphtheria toxin, pseudomonas toxin, etc., but not limited thereto. The radioactive isotope may be one or more kinds selected from the group consisting of $^{131}$I, $^{188}$Rh, $^{90}$Y, etc., but not limited thereto. The cytotoxin compound may be one or more kinds selected from the group consisting of duocarmycin, monomethyl auristatin E (MMAE), monomethyl auristatin F (MMAF), N2'-deacetyl-N2'-(3-mercapto-1-oxopropyl)maytansine (DM1), PBD (Pyrrolobenzodiazepine) dimer, etc., but not limited thereto.

In other embodiment, the anti-CD43 antibody or antigen-binding fragment thereof may be provided as a conjugate form in which a detectable marker is conjugated. The conjugate may be usefully used for detecting the presence of CD43 or the afore-mentioned epitope of CD43 in vitro or in vivo. The detectable marker may be selected from all marker materials commonly known in the art, and for example, may be one or more selected from the group consisting of radioactive marker (for example, $^3$H, $^{14}$C, $^{35}$S, $^{90}$Y, $^{99}$Tc, $^{111}$In, $^{125}$I, $^{131}$I, $^{177}$Lu, $^{166}$Ho, $^{153}$Sm, etc.), enzyme, fluorescent label, luminescent label, bioluminescent label, magnetic label, chemical materials such as biotin, etc, but not limited thereto. To choose an appropriate label according to the use of antibody or epitope is obvious to a person skilled in the art.

Other embodiment provides a pharmaceutical composition for preventing and/or treating cancer comprising the anti-CD43 antibody or antigen-binding fragment thereof as an active ingredient. Other embodiment provides a pharmaceutical composition for inhibiting a cancer stem cell comprising the anti-CD43 antibody or antigen-binding fragment thereof as an active ingredient. Other embodiment provides a method for preventing and/or treating cancer comprising a step of administering a pharmaceutically effective amount of anti-CD43 antibody or antigen-binding fragment thereof to a subject in need of preventing and/or treating cancer. Other embodiment provides a method for inhibiting a cancer stem cell, comprising a step of administering a pharmaceutically effective amount of anti-CD43 antibody or antigen-binding fragment thereof to a subject in need of preventing and/or treating cancer. The pharmaceutically effective amount means the amount effective to obtain a desired anti-cancer effect, for example, therapeutic effect (for example, increasing cell death of cancer cell, reducing cancer tissues, inhibiting cancer metastasis, etc.) in the subject to be administered. For the pharmaceutical composition and method, the anti-CD43 antibody or antigen-binding fragment thereof may be used alone or in a form of conjugate linked to a cytotoxic material. The cytotoxic material is same as described above.

The cancer may be specific to all the cancer expressing the aforementioned epitope of CD43. In one embodiment, the cancer may be hematologic malignancy, and for example, may be one or more kinds selected from the group consisting of acute myeloid leukemia, acute lymphoblastic leukemia, acute monocytic leukemia, Hodgkin's lymphoma, non-Hodgkin's lymphoma, etc. In other embodiment, the cancer may be one or more kinds selected among the aftermentioned solid cancers.

The antibody or antigen-binding fragment may be administered in a sufficient amount to bind to CD43 on a cell surface, particularly, the afore-mentioned CD43 or CD43 epitope on a tumor cell expressing CD43 epitope, and the amount may be determined without difficulty by a person skilled in the art.

The aforementioned pharmaceutically effective amount or sufficient amount means an amount for providing an expected effect in a subject to be administered. The expected effect will accompany the binding of antibody to CD43 (or the epitope of CD43) expressed on a cell surface, and the binding may be exhibit cytotoxicity (for example, antibody-dependent cellular cytotoxicity (ADCC) or complement-dependent cytotoxicity (CDC)) through antibody, antigen-binding fragment or the cytotoxic material conjugated to the antibody or fragment. In other embodiment, the expected effect induces the binding of antibody to CD43 expressed on the surface of cell with little or no cytotoxicity by other antibodies, and thereby the binding may let a person skilled in the art detecting and selectively removing (for example, leukapheresis) from CD43+ cells and CD43+ cells in a patient (for example, the antibody or fragment is labeled with a detectable marker). The amount of antibody molecule required may differ depending on patient, race, age and general condition of patient, administration of specific compound, administration method, etc. in a patient. Therefore, it may be not possible to designate "accurate sufficient amount". However, in any individual case, the appropriate amount may be determined with a usual technique by using a regular experiment. In addition, the dose may be adjusted to the urgency of situation and may be adjusted to deduct the optimal dosage. For example, several doses may be provided daily, weekly, monthly or in other appropriate time interval.

The aforementioned pharmaceutically effective amount or sufficient amount may be determined by monitoring the antibody binding to a cell in a biological sample (for example, body fluid sample (for example, blood sample, etc.), cell/tissue sample (for example, tumor cell/tissue sample, etc.), and so on obtained from a patient to which the antibody or antigen-binding fragment thereof is administered or is to be administered. The biological sample may be collected from a patient at a specific time after administering the antibody or fragment (for example, about 5, 10, 15 or 20 min after administration). The presence of antibody or fragment on the cell surface in a sample (that is, antibody or antigen-binding fragment bound to CD43 or epitope thereof on the cell surface by the antigen-antibody reaction) may be analyzed by using well-known methods in the art. In addition, the obtained biological sample may be used for the general analysis for measuring the cell viability or number of living cells in the sample. Based on the fact that the number of CD43-positive cells are decreased after administration of antibody or fragment (for example, decrease in the number of living cells in the sample in which the antibody or fragment is administered, compared to the control sample like a sample obtained before administration of antibody or fragment, etc.), the antibody-mediated cytotoxicity may be measured. The cytotoxicity may be mediated by the antibody alone (for example, non-conjugated antibody which is not liked to a cytotoxic material or antigen-binding fragment) and/or may be mediated by a cytotoxic material conjugated to the antibody or fragment.

The anti-CD43 antibody or antigen-binding fragment thereof which specifically binds to CD43 epitope provided herein may reduce 10% or more, 20% or more, 30% or more, 40% or more, 50% or more, 60% or more, 70% or more, 80% or more or 90% or more of level of target CD43-positive cell in a sample of patient administered, compared to the level of CD43-positive cell in a control sample (for example, the sample obtained from a patient before administration of antibody or fragment). In one embodiment, the CD43 positive cell may be a cancer cell, for example, a malignant hematopoietic cell (for example, leukemic cell), and/or a cancer stem cell.

In other embodiment, the dosage (pharmaceutically effective amount) of antibody or antigen-binding fragment may be estimated and determined by in vitro cell-based assay. For example, in order to determine a concentration of antibody or fragment for reducing the number of CD43-positive cell which is the target of antibody or fragment, in vitro cell-based assay using a CD43-positive cell (e.g., CEM7 cell line) may be performed. The concentration of antibody or fragment determined for reducing the number of cells in vitro (for example, reducing at least 10%, 20%, 30%, 40%, 50%, 60%, 70%, 80% or 90%, compared to the number of cells when the antibody or fragment is not present) may be adopted as the basis to determine the dosage sufficient to reduce the number of CD43 positive cells required in vivo. In addition, the dosage may be determined in consideration of factors such as body weight of patient, blood volume, clearance rate, etc.

The term, "subject or patient" used herein may be selected among animals including mammals like human, gorilla, chimpanzee, etc., or may be a cell, tissue, body fluid isolated from the animals or cultures thereof. The mammals may comprise human. The invention provided herein may be applied for specific targeting of CD43-positive cell in a human or veterinary field, and this has the content clearly understandable to a person skilled in the art. Commonly, "animal" is used for collectively calling not only primates like human, monkey, etc. but also domestic animals and companion animals like cow, horse, sheep, pig, camel, goat, donkey, dog, cat, etc., and laboratory animals like mouse, rat, etc. In case of horse, a horse used for the racing industry as well as entertainment or domestic animal industry.

As necessary, the method provided herein may further comprise performing the second therapeutic means (for example, therapeutic agent). For example, the method of the present invention may comprise administering other chemotherapeutic compound (the second active ingredient) to a subject in need. The administration of the second active ingredient may be simultaneously performed with the administration of antibody or antigen-binding fragment provided herein, or may be performed in any order (before or after administration of antibody, etc.).

In another aspect, a use of cancer treatment; preparation of anti-cancer agent; inhibition of cancer stem cell; and/or preparation of agent for inhibiting cancer stem cell of the anti-CD43 antibody or antigen-binding fragment provided herein.

For the pharmaceutical composition, method and use disclosed herein, the cancer may be a solid cancer or hematopoietic cancer, and may be a primary cancer or metastatic cancer. In one embodiment, the cancer may be a hematologic malignancy. The hematologic malignancy may be acute myeloid leukemia, acute lymphoblastic leukemia, acute monocytic leukemia or Hodgkin's lymphoma, but not limited thereto. The hematologic malignancy may be a cancer comprising a cancer stem cell.

In other embodiment, the cancer may be a solid cancer. The solid cancer may be one or more kinds selected from the group consisting of lung cancer (for example, squamous cell carcinoma, small cell lung cancer, non-small cell lung cancer, adenocarcinoma of lung, squamous cell carcinoma of lung), peritoneal cancer, skin cancer, melanoma in skin or eyeball, rectal cancer, cancer near the anus, esophagus cancer, small intestinal cancer, endocrine gland cancer, parathyroid cancer, adrenal cancer, soft-tissue sarcoma, urethral cancer, gastrointestinal cancer, stomach cancer, pancreatic cancer, glioblastoma, cervical cancer, ovarian cancer, liver cancer, gallbladder cancer, bladder cancer, breast cancer, colon cancer, large intestine cancer, uterine cancer, endometrial cancer, uterine cervical cancer, salivary gland cancer, renal cancer, prostate cancer, vulval cancer, thyroid cancer, head and neck cancer, brain cancer, osteosarcoma, etc., but not limited thereto. For example, the solid cancer may be stomach cancer, breast cancer, lung cancer, large intestine cancer, liver cancer, gallbladder cancer, renal cancer, pancreatic cancer, thyroid cancer, ovarian cancer, uterine cervical cancer, prostate cancer, or bladder cancer. The cancer comprises not only primary cancer but also metastatic cancer. In addition, the solid cancer may be cancer having resistance to conventional anti-cancer agents (e.g., small molecular anti-cancer agent (anticancer chemical), anti-metabolite, alkylating agent, antibiotics, vinca alkaloid, enzyme, hormone, targeted therapeutic agent, and/or antibody therapeutic agent, etc.), and may be cancer recurred after treatment of conventional anti-cancer agents (e.g., small molecular anti-cancer agent (anticancer chemical), anti-metabolite, alkylating agent, antibiotics, vinca alkaloid, enzyme, hormone, targeted therapeutic agent, and/or antibody therapeutic agent, etc.). The solid cancer may be cancer comprising a cancer stem cell.

The effect of treating a solid cancer comprises not only growth inhibition (quantitative reduction) and apoptosis of cancer cell (particularly, cancer stem cell) or cancer tissue comprising thereof, but also the effect of inhibiting the deterioration of cancer by inhibiting migration, invasion, metastasis, etc.

The anti-CD43 antibody or antigen-binding fragment thereof provided herein may be administered in various routes, and may be administered orally or parenterally. For example, as proper examples of administration routes, there are intravenous injection, intra-arterial injection, intramuscular injection or infusion, etc., and in one embodiment, it may be administered by intravenous injection, but not limited thereto.

In one embodiment, the anti-CD43 antibody or antigen-binding fragment thereof may be formulated in a form to be administered alone or together with the second therapeutic compound (e.g., chemotherapeutic compound).

In another aspect, a pharmaceutical composition comprising the anti-CD43 antibody or antigen-binding fragment thereof provided herein and one or more kinds of additives selected from the group consisting of pharmaceutically acceptable carrier, diluent, and excipient is provided. In one embodiment, the antibody comprised in the pharmaceutical composition may comprise the form in which a cytotoxic material is linked or conjugated. The appropriate pharmaceutically acceptable carrier, diluent, and excipient are well-known to a person skilled in the art, and as the examples, there are saline solution, solvent (for example, injection solvent), dispersion media, anti-fungal and/or anti-microbial agent, surfactant, isotonic agent, adsorptive agent, etc., but not limited thereto.

In one embodiment, the pharmaceutical composition may be formulated as various forms of formulations such as in various dose unit forms of injectable formulation, etc.

The formulation and follow-up administration of the pharmaceutical composition may be in accordance with conventional techniques in the art. The administration depends on the condition of subject to the treatment, drug reactivity, etc., but it is desirable to be continued, if the desirable effect lasts. The dosage, administration method and repeating frequency of the pharmaceutical composition may be determined in consideration of age, gender, morbidity, drug reactivity, etc., and this is obvious to a person skilled in the art.

Another embodiment provides a preparation method for the anti-CD43 antibody or antigen-binding fragment thereof. The preparation method may comprise a step of expressing the nucleic acid molecule in a host cell. The step of expressing may comprise a step of culturing the recombinant cell, and randomly, may further comprise a step of isolating and/or purifying the antibody from the obtained cell cultures.

In one specific embodiment, the preparation method, may comprise, a step of culturing a recombinant cell transformed with a nucleic acid encoding the anti-CD43 antibody or antigen-binding fragment thereof or a recombinant vector comprising the same under the condition and/or period for sufficient expression of the nucleic acid; and a step of isolating and/or purifying the anti-CD43 antibody or antigen-binding fragment thereof from the cultured cell or obtained cultures.

The recombinant cell may be obtained by transforming a host cell with a nucleic acid encoding the anti-CD43 antibody or antigen-binding fragment thereof or a recombinant vector comprising the same.

Other embodiment provides purified anti-CD43 antibody or antigen-binding fragment thereof obtained from the step of isolating and/or purifying. The obtained antibody or antigen-binding fragment may be a recombinant molecule isolated from other components linked when expressed in the cell or secreted outside the cell. In one embodiment, the isolated and/or purified antibody or antigen-binding fragment may has the purity of 50% or more, 60% or more, 70% or more, 75% or more, 80% or more, 85% or more, 90% or more, 95% or more, 96% or more, 97% or more, 98% or more, or 99% or more. A person skilled in the art may clearly understand that the degree of isolation and/or purification depends on purpose of use and/or form of use of the antibody or antigen-binding fragment. For example, when it is intended to be administered in an animal, particularly, in a human body, the purification purity of antibody or antigen-binding fragment may be required at relatively high level, and when used for in vitro experiments, acceptable impurities (for example, components derived from a host cell and/or cultures (protein, etc.) and so on) may be included.

Other embodiment provides a nucleic acid molecule encoding the anti-CD43 antibody or antigen-binding fragment thereof. In one specific embodiment, the nucleic acid may comprise a nucleic acid molecule encoding a heavy chain variable region (VH binding domain) of the antibody or antigen-binding fragment, a nucleic acid molecule encoding a light chain variable region (VL binding domain), or combinations thereof. The nucleic acid molecule encoding the heavy chain variable region may comprise a nucleotide sequence selected from the group consisting of SEQ ID NOs: 1, 5, 9, 13, 17, 21, 25, and 29. The nucleic acid molecule encoding the light chain variable region may comprise a nucleotide sequence selected from the group consisting of SEQ ID NOs: 3, 7, 11, 15, 19, 23, 27, and 31.

The nucleic acid may be comprised in an appropriate expression vector. The expression vector may be all vectors commonly used for expressing an foreign gene in a host cell, and for example, may be illustrated as pTT5, pAPEX3p, pcDNA3.2(−), etc., but not limited thereto.

Other embodiment provides a recombinant cell comprising a nucleic acid molecule encoding the anti-CD43 antibody or antigen-binding fragment thereof or a recombinant vector comprising the same (or expression vector). The recombinant cell is obtained by introducing the nucleic acid molecule or recombinant vector into a host cell, and a cell which can express the nucleic acid molecule. As an example of host cell, there are prokaryotic cell (e.g., E. Co/i, etc.) or protozoan cell, and eukaryotic cell such as animal cell (e.g., CHO, COS, HEK-293E, HEK-293T cell, specific gene modified (for example, deleted cell thereof, etc.), plant cell, fungal cell (e.g., *Saccharomyces cerevisiae*, etc.), insect cell (e.g., Sf9 cell, etc.), but not limited thereto, and may be selected among all cells which can express an foreign gene.

Other embodiment provides a method for detecting CD43 or a method for detecting CD43 positive cell, comprising a step of contacting the anti-CD43 antibody or antigen-binding fragment thereof to a cell sample and a step of confirming whether the antigen-antibody binding is in the sample. By the method, whether CD43 is expressed on the cell surface in the cell sample may be confirmed, and thus, the method may be applied for diagnosis of disease related to expression of CD43. Therefore, other embodiment provides a method for diagnosing a CD43-related disease or a method for providing information for diagnosis of CD43-related diseases, comprising a step of contacting the anti-CD43 antibody or antigen-binding fragment thereof to a cell sample and a step of confirming whether the antigen-antibody binding is in the sample. The CD43-related disease is a disease related to the presence of CD43 or increment of CD43, and may be a cancer, and the cancer may be a solid cancer or hematologic malignancy, and particularly, may be a hematologic malignancy related to increment of CD43 (for example, acute lymphoblastic leukemia, acute myeloid leukemia). In other specific embodiment, the CD43-related disease may be a cancer comprising a cancer stem cell.

In the method, the antigen-antibody binding may be confirmed by detecting whether the complex between the antibody (or antigen-binding fragment thereof) and CD43 protein forms (that is, when the formation of antibody-CD43 protein complex is detected, it is confirmed that the antigen-antibody binding is present). Then, for a relative comparison, it may be compared with the result obtained from the test cell sample by performing the same experiment for the control cell sample. The control cell sample may be selected among well-known CD43 negative cell, or normal cell (non-cancer or non-tumor cells).

In one embodiment, the detection method or diagnosis method, may comprise, (1) a step of contacting the antibody or antigen-binding fragment to the test cell sample and control cell sample; and (2) a step of measuring whether the formation of complex between the antibody or antigen-binding fragment and the cell or its level. Then, when the presence of complex in the test cell sample or the relatively high level of complex compared with the control cell sample is measured, it may be confirmed that CD43 is present in the test cell sample or that the cell is a cell expressing CD43 (that is, CD43 positive cell). The cell sample may be isolated from a living body, and the method may be performed in vitro.

Other embodiment provides a composition for detecting or visualizing (imaging) CD43 comprising the anti-CD43 antibody or antigen-binding fragment thereof. Another embodiment provides a method for detecting or visualizing (imaging) CD43 by using the anti-CD43 antibody or antigen-binding fragment thereof. The composition and method may be applied for detection and/or visualization of CD43 in vivo as well as in vitro. For the composition and method, the antibody or antigen-binding fragment may be a form conjugated with a detectable label, and for example, the detectable label may be one or more kinds selected from the group consisting of radioactive label (for example, $^3$H, $^{14}$C, $^{35}$S, $^{90}$Y, $^{99}$Tc, $^{111}$In, $^{125}$I, $^{131}$I, $^{177}$Lu, $^{166}$Ho, $^{153}$Sm, etc.), enzyme, fluorescent label, luminescent label, bioluminescent label, magnetic label, chemical material like biotin, etc., but not limited thereto, and may be all labels detectable by common detection methodsclearly known in the art. As described above, the detection and/or visualization of CD43 in vitro and/or in vivo may be used for diagnosis of diseases related to the increment of the number of CD43 positive cell, for example, cancer, more specifically cancer or hematologic malignancy comprising a cancer stem cell.

The method of detection and/or visualization of CD43 (in vivo) may comprise the followings:

(i) a step of administering the anti-CD43 antibody or antigen-binding fragment thereof to a test subject; and (ii) a step of measuring the formation of complex of antibody or antigen-binding fragment or degree (level) of formation of complex.

The complex may be a complex of the antibody or antigen-binding fragment thereof and CD43 expressed on the cell surface in the body of test subject or a complex formed by antigen-antibody binding between the antibody or antigen-binding fragment thereof and cells expressing CD43 (CD43-positive cells). The antibody or antigen-binding fragment thereof may be used in a form conjugated with the afore-mentioned detectable label. The visualization method may be applied for visualization of the cell expressing CD43, for example, cancer stem cell.

Whether the complex of antibody or antigen-binding fragment is formed in the administration subject or level of formation may be relatively estimated by comparing to whether the complex is formed in the control subject (for example, subject not having a CD43-related disease or subject not comprising a cell (over)expressing CD43) or level of formation. For this comparison, the method may comprise, (i-1) a step of administering the anti-CD43 antibody or antigen-binding fragment thereof to a test subject and control subject, respectively;

(ii-1) a step of measuring whether the complex of antibody or antigen-binding fragment is formed or degree (level) of formation in the test subject and control subject, respectively; and (iii) a step of comparing the result measured in the test subject with the result in the control subject.

The method may be applied for diagnosis of CD43-related diseases of test subject or confirmation (detection) of cancer stem cell expressing CD43. In this case, when the formation of complex or the increment of level of formation of complex compared to the control subject in the step (ii) or (ii-1) is measured, the test subject may be determined as a patient of CD43-related disease or may be determined that the test subject has a cancer stem cell.

The formation of in vivo or in vitro antigen (or cell expressing the antigen on the surface)-antibody complex may be measured by common means in the art, and these common means are obvious to a person skilled in the art. For example, the complex may be confirmed by labeling the antibody or antigen-binding fragment with an appropriate detectable label and measuring the signal of the label or by proper detection methods. The proper detection method may be all the common methods in the art, and for example, may be ELISA, flow activated cytometry system (FACS), immunohistochemical staining, etc., but not limited thereto.

It will be clearly understood by a person skilled in the art that further variations and/or modifications for the invention provided herein other than described above may be made. The invention provided herein should be understood to comprise all variations and/or modifications within the spirit and/or scope disclosed. In addition, the invention provided herein may respectively or wholly comprise all steps, characteristics, compositions and/or compounds clearly described or referred herein.

Specific embodiments will be described by referring to the following embodiment, but these examples are designed only for the purpose of illustration, and do not limit the afore-mentioned scope of the invention.

As appreciated, the nucleotide sequences developed and described herein are modified by well-known methods in the art, for example, the affinity maturation or method reducing the immunogenicity and increasing the binding capacity by predicting and removing the motif for binding to MHC class 2. The usefulness of therapeutic agent from nucleotide sequences developed and described herein may be enhanced by controlling functional properties by antibody dependent cell-mediated cytotoxicity (ADCC), complement dependent cytotoxicity (CDC), serum half-life, isotype, Fc receptor binding or combinations of these actions. These variations may be performed by protein engineering, glycan engineering or chemical methods. According to the required application of therapeutic agent, the increase or decrease of these activities may be advantageous.

Numerous methods for affinity maturation of antibody are known in the art. Most these are based on the general strategy of producing a library of mutant panel or modified protein, and screening and selecting, in order to increase the affinity. Mutagenesis is often performed at the DNA level, for example by error prone PCR, by gene shuffling, by use of mutagenic chemicals or irradiation, by use of 'mutator' strains with error prone replication machinery, or by somatic hypermutation approaches that harness natural affinity maturation machinery. Mutagenesis can also be performed at the RNA level, for example by use of replicase. Library-based methods allowing screening for improved variant proteins can be based on various display technologies such as phage, yeast, ribosome, bacterial or mammalian cells, and are well known in the art. Affinity maturation can be achieved by more directed/predictive methods for example by site-directed mutagenesis or gene synthesis guided by findings from 3D protein. Methods of increasing ADCC or CDC will be known to persons skilled in the art.

A number of methods of modulating the serum half-life and the distribution of antibody in living body changes the interaction between the antibody and neonatal Fc receptors playing an important role for preventing IgG from catabolism, and maintaining the high serum antibody concentration. For example, the patents of U.S. Pat. Nos. 6,277,375; 6,821,505; 7,083,784, 7,217,797 and WO 2000/4207 may be referred. Other example of substitution of amino acids in constant regions regulating the binding capacity of Fc receptor and this receptor-mediated function such as binding capacity to FcRn and serum half-life is described in the patent of U.S. Pat. Application Nos 20090142340; 20090068175; and 20090092599.

The glycan linked to the antibody molecule affects the activity of antibody including the serum half-life by affecting the interaction of Fc receptor and glycan receptor. Therefore, the glycan type controlling the activity of antibody may give advantages to therapeutic agent. The method for producing the controlled glycan type is well-known in the art, but it is not limited to that disclosed in U.S. Pat. Nos. 6,602,684; 7,326,681; 7,388,081; and WO 2008/006554.

The method for extending the half-life by adding polyethylene glycol (PEG) is used for extending the serum half-life of protein.

The term "% identical" is used herein to describe a number of sequences. As would be understood, the term "% identical" means that in a comparison of two sequences over the specified region the two sequences have the specified number of identical residues in the same position.

The % identity of one polypeptide to the other polypeptide may be determined by GAP analysis with a gap creation penalty=5, and a gap extension penalty=0.3. The query sequence is at least 50 amino acids, and the GAP analysis adjusts the region of two sequences in at least 50 amino acids. More preferably, the length of query is at least 100 amino acids, and GAP analysis adjusts the region of two sequences in at least 100 amino acids. Even more preferably, the length of query is at least 250 amino acids, and GAP analysis arranges two sequences on the region of at least 250 amino acids. The most preferably, GAP analysis arranges the amino acid sequence of the total length of two polypeptides debated.

With regard to a defined polypeptide, it will be appreciated that % identity figures higher than those provided will encompass preferred embodiments. Therefore, if possible, it is preferable that in light of at least % identity, the polypeptide comprises the amino acid sequence related to SEQ ID NO having identity of amino acid preferably at least 95% or more, more preferably at least 97% or more, even more preferably at least 98% or more, further more preferably at least 99% or more, more preferably at least 99.1% or more, more preferably at least 99.2% or more, more preferably at least 99.3% or more, more preferably at least 99.4% or more, more preferably at least 99.5% or more, more preferably at least 99.6% or more, more preferably at least 99.7% or more, more preferably at least 99.8% or more, even more preferably at least 99.9% or more.

Herein the amino acid and nucleotide sequence variation may be introduced and produced through the change of nucleotides by mutation of nucleic acid in vivo by chemical or radioactive treatment. The example of this mutation includes deletion, insertion or substitution of residues of amino acid sequence. The polynucleotides of the invention may be subjected to DNA shuffling techniques as described by Harayama, 1998 or other in vitro methods to produce altered polynucleotides which encode polypeptide variants. This DNA shuffling technique may use the gene sequence related to the present invention such as Rht-B1 from plant species other than wheat The product obtained from mutant/ modified DNA, may be screened by using the technique disclosed herein to determine if they possess, for example, overgrowth phenotype. For example, the deletion of amino acid sequence may comprise the deletion of generally about 1 to 15 amino acid residues, for example, 1 to 10 amino acid residues or consecutive 1 to 5 amino acid residues.

For example, the substitution of amino acid sequence may comprise that one or more amino acid residues in the polypeptide are deleted and one or more amino acid residues which are different from the original amino acid residues are inserted at the position.

As used herein, "comprise (comprises or comprising)" may be used as an open type meaning comprising disclosed components, steps, numerical values, etc., and is not interpreted as an intent to exclude components, steps, numerical values, etc. other than them, and according to circumstances, it may not be excluded to mean "consisting essentially of".

All literatures mentioned herein are included herein as a reference.

Effect of the Invention

The present invention provides an antibody which is capable of treating a cancer stem cell as well as hematologic malignancy or solid cancer, and an epitope which the antibody recognizes and an antibody recognizing the same or antigen-binding fragment thereof, thereby treating cancer more strongly and radically and contributing to the development of effective cancer therapeutic agents.

BRIEF DESCRIPTION OF DRAWINGS

FIG. 21 is the image obtained at 2 hours after antibody treatment.

FIGS. 25A-15B are the graphs showing the therapeutic effect of anti-JL1 antibody itself and toxin-conjugated anti-JL1 antibody in a leukemia ALL heterograft model, wherein FIG. 25A shows the result in CEM7 leukemia model and FIG. 25B shows the result in NALM-6 model (Cell line: NALM6 (B-ALL)), respectively. The test was performed under the following conditions: Mice: NOD-SCID (8/group); inoculation: 0 day $10^7$ cells; administration: 15 μg/injection+100 μg bulk IgG i.v. 1×/week starting day 8; end point: paralysis state.

FIGS. 27A-27B is the graph showing the apoptosis effect by chimeric humanized JL-1 (ADCC and CDC), wherein FIG. 27A is the result of measuring the cytotoxicity by using Cell Titer Glo. CEM7 cell line cultured with the effector cell (PBMC) and then JL-1 chimeric antibody or control antibody was added, and FIG. 27B is the result of measuring the cytotoxicity by using Cell Titer Glo. CEM7 cell line was culture with the culturing media and JL1 chimeric antibody was added together with the rabbit complement. As the control group, the IgG1 isotype antibody irrelevant to the experiment is used.

FIG. 35 shows the result of internalization cytotoxicity analysis of the final 3 modified antibodies, and the cytotoxicity was measured at 3 days after mixing the antibody or antihuman IgG-saporin.

DETAILED DESCRIPTION OF THE EMBODIMENTS

Figure 1:
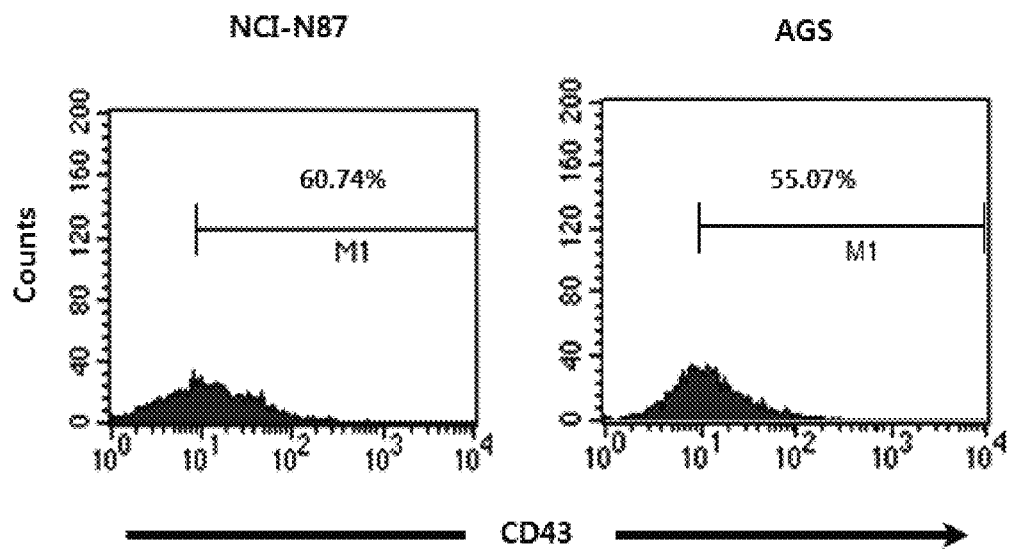
FIG. 1 is the result of confirming the expression of CD43 in human stomach cancer cell line NCI-N87 (left) and AGS (right) by the immunostaining method (X axis: CD43 expression rate, Y axis: Reading cell numbers).
Figure 2A:
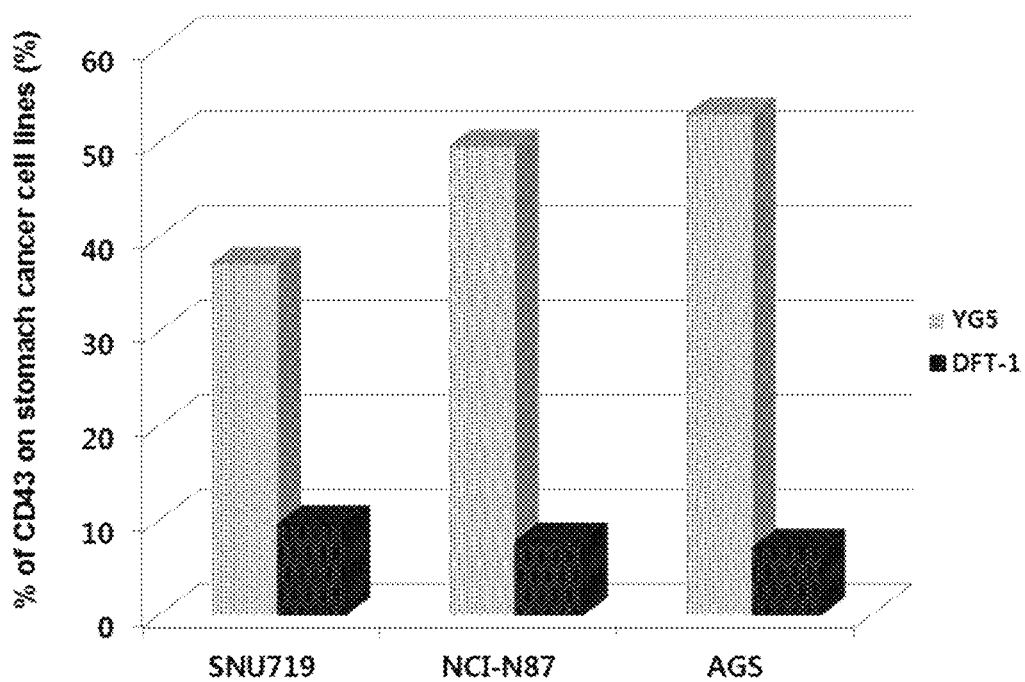
FIGS. 2A-2C are the results of confirming the expression of CD43 in various solid cancer cell lines by the immunostaining method (2A: stomach cancer cell line; 2B: rectal cancer cell line; 2C: liver cancer cell line).
Figure 2B:
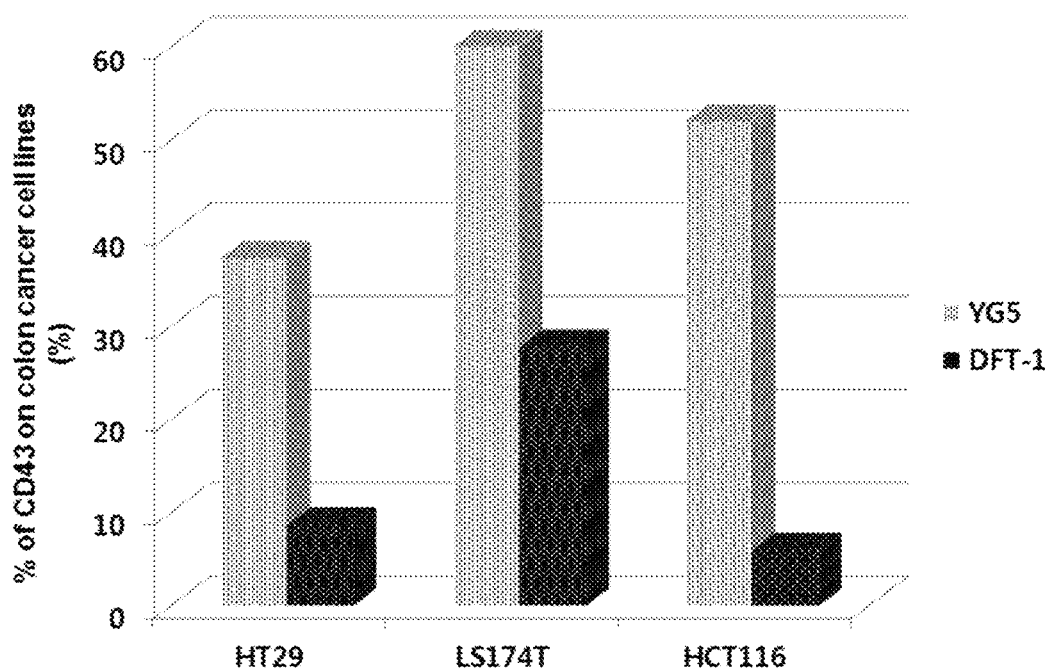
Figure 2C:
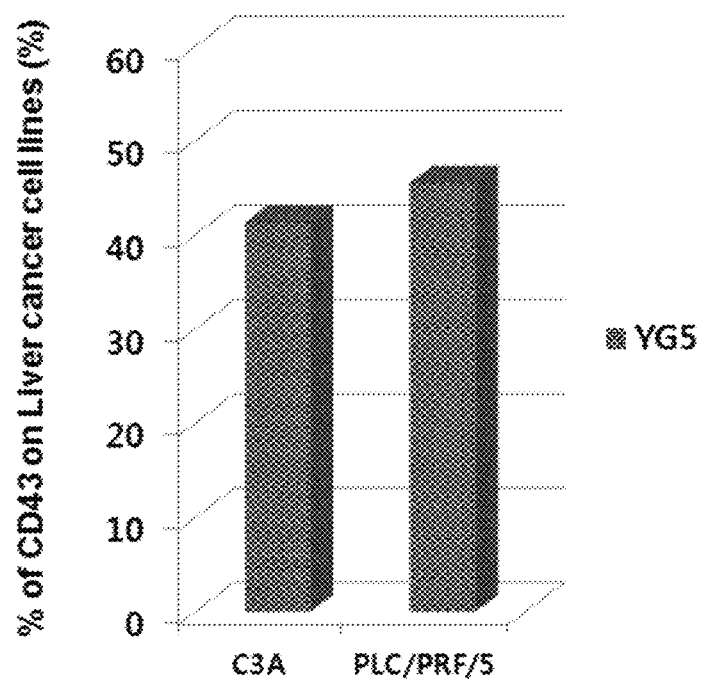

Hereinafter, the present invention will be described in more detail with examples, but these examples are only for illustrative purpose and are not intended to limit the scope of the invention. It is obvious to a person skilled in the art that the examples described below may be modified without departing from the spirit of the invention.

Example 1. Preparation of Anti-CD43 Antibody 1-1. Preparation of Mouse Antibody 1-1-1. Preparation of Cell Producing Monoclonal Antibody It was prepared by the fusion of splenocyte of Balb/c white mouse in which a human thymocyte was injected as an antigen and myeloma cell line SP2/0-Ag14 (ATCC, CRL-1581) of 8-azaguanine resistant mouse.

$10^7$ of human thymocytes (Seoul National University Hospital) were intraperitoneally injected into Balb/c white mouse per 2 weeks for 6 weeks to induce an immune response, and the spleen was extracted at 3 days after the last additional inoculation to prepare cell suspension. According to the method of Koeler & Milstein (1975), $10^8$ of splenocytes and $10^7$ of myeloma cells were under cell fusion by using 400 of polyethylene glycol. The fused cells were washed and then suspended in DMEM culture solution supplemented with 100 uM hypoxanthine, 0.44 uM animopterin and 16 uM thymidine (HAT culture solution), and cells were aliquoted in a 96-well plate, and cultured in a culture medium in which 37° C., 5% $CO_2$ were supplied.

When the formation of colony was observed after 2 weeks, the supernatant was collected and the antibody titer was measured by using immunohistochemistry and flowcytometry.

The positive group meant the case in which $10^5$ or more of cells were formed per well. The monoclonal cells with high antibody titer were harvested by collecting cells in the well in which the colony with high antibody titer of supernatant, was formed and subcloned according to the limiting dilution assay method. The culture solution of monoclonal cells was stored by collecting the supernatant for the later experiments.

1-1-2. Screening of Monoclonal Cell Producing Antibody to Cell Surface Protein of Thymocyte Frozen tissues of thymus (Seoul National University Hospital) and paraffin embedded tissues (Seoul National University Hospital) were sectioned in 4 micrometer thickness to use. After passing the process of removing paraffin and then adding a normal goat serum (BioGenex company product), the paraffin embedded tissues were left for 1 hr at the room temperature. After administering each primary antibody (Dinona) to the tissues and then leaving them in 4° C. cold chamber overnight to react, they were washed 3 times with phosphate-buffered saline the next day. They were incubated for 1 hr at the room temperature with biotinylated goat anti-mouse immunoglobulin (2 drops, DAKO) as the second antibody, and then washed 3 times with phosphate-buffered saline, and the streptavidin-HRP conjugate was treated. After administering $H_2O_2$-aminoethyl carbazole solution for 20 min, they were washed 3 times with phosphate-buffered saline, and the color development was observed in the optical microscope.

As a result, the monoclonal cell line H-JL1 producing an antibody which specifically reacts only to a human thymocyte could be sorted. The obtained cell line was donated to Korean Cell Line Research Foundation (KCLRF) located in Yeongeon-dong, Jongno-gu, Seoul, Korea in Jan. 13, 1997, and the accession number KCLRF-BP-00010 was given.

Figure 10:
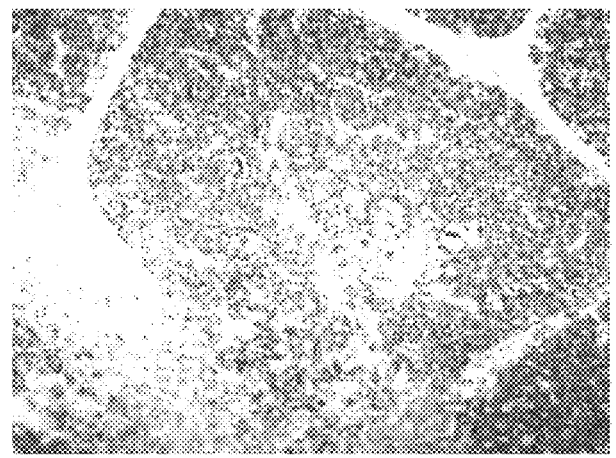
FIG. 10 is the result of immunohistochemical staining of thymic tissue with the anti-CD43 monoclonal antibody (YG5).

The thymus tissues were immunohistochemically stained with the supernatant of the selected monoclonal cell line, and it was confirmed that the thymocyte was stained as positive (FIG. 10). In addition, the thymocyte stained as positive exhibited the aspect of being strongly stained in periphery of cell, and thereby it was demonstrated that the monoclonal cell line produced the antibody to the cell surface protein.

Figure 11:
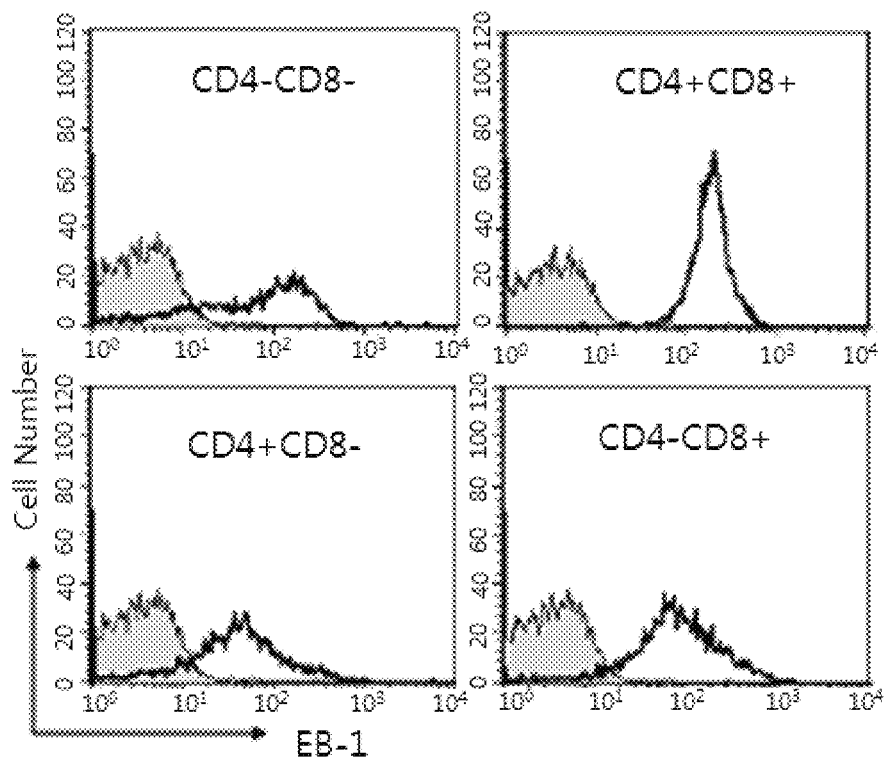
FIG. 11 is the graph of flow activated cytometry system measuring the reactivity of anti-CD43 monoclonal antibody (YG5) to the thymic cell.

In order to confirm the reaction of the antibody in the development stage of thymocyte, the flow cytometry was carried out. The thymus of human extracted for heart surgery was cut into small fragments and grounded with a glass slide, and the thymocyte was collected. After reacting the antibody (1*10^5 cell/antibody 10 μg/mL) for 30 min at 4° C. in the isolated thymocyte, it was washed with cold phosphate-buffered saline, and FITC (Fluorescein Isothiocyanate)-linked goat anti-mouse immunoglobulin antibody (Jackson ImmunoResearch) was reacted for 30 min at 4° C. It was then washed with cold phosphate-buffered saline and 5 μL of each PE (phycoerythrin)-linked anti-CD8 antibody (BD Bioscience) and APC-linked anti-CD4 antibody (BD Bioscience) were added and reacted for 30 min at 4° C. It was washed with cold phosphate-buffered saline and the flow cytometry was conducted by using FACSCalibur (Becton Dickinson, Mountain View, Calif.). The thymocytes were classified to CD4-CD8-thymocyte→CD4+CD8+ thymocyte→CD4+CD8- or CD4-CD8+ thymocyte according to the expression aspect of CD4 and CD8, and the antibody reacted to all 4 kinds of thymocytes, but in particular, it reacted to CD4+CD8+ thymocyte highly (refer to FIG. 11). The grey region in FIG. 11 was the negative control group, and the solid line was the graph of staining with the sorted antibody.

1-1-3. Production of Monoclonal Antibody from Sorted Monoclonal Cell Line of Balb/c mouse was intraperitoneally injected with 0.5 mL of pristane before 3 weeks, and $10^7$ of monoclonal cells were cultured in DMEM medium comprising 10% fetal bovine serum and injected in peritoneal cavity of those mice, and then hydrops abdominis of mouse was collected after 2-3 weeks. 5-10 mg/mL of high concentration antibodies were obtained from the hydrops abdominis.

To purity antibodies from the hydrops abdominis, Q-sepharose (Pharmacia product) chromatography and hydroxylapatite (Bio-gel HTP Gel, Pharmacia product) chromatography were conducted. 3.14 g of ammonium sulfate ((NH4)2SO4) per 10 mL of hydrops abdominis was added and dissolved on ice slowly (50% (NH4)2SO4 precipitation). This mixture was centrifuged at 15,000 rpm for 30 min, and the precipitate was dissolved in deionized water, and then was dialyzed in 1 L of buffer solution (20 mM phosphate, pH 7.4).

The solution passed Q-sepharose column equilibrated with a buffer solution (20 mM phosphate, pH 7.4) in advance and was adsorbed, and then the concentration gradient of NaCl was flowed to a linear gradient from 0 M to 0.8 M by using buffer solution I (20 mM phosphate, pH 7.4) and buffer solution II (20 mM phosphate, 0.5M NaCl, pH 7.4), to obtain eluates. Each fraction was the collected fraction containing plenty of antibodies by 15% SDS-PAGE. The fraction was dialyzed with buffer solution (20 mM phosphate, pH 6.8), and adsorbed by passing the hydroxylapatite column equilibrated with buffer solution (20 mM phosphate, pH 6.8) in advance, and then the concentration gradient of phosphate was flowed to a linear gradient from 0 M to 0.3 M by using buffer solution III (20 mM phosphate, pH 6.8) and buffer solution IV (300 mM phosphate, pH 6.8), to obtain eluates. The fraction was collected only in the fraction having 95% or more of purity of antibody by 15% SDS-PAGE. By the experiment, 5-10 mg of monoclonal antibody per 1 ml of hydrops abdominis could be collected.

The obtained antibody was called YG5.

1-1-4. Analysis of Epitope of CD43

<Construction of Structure Comprising CD43 Partial Fragment>

Figure 12:
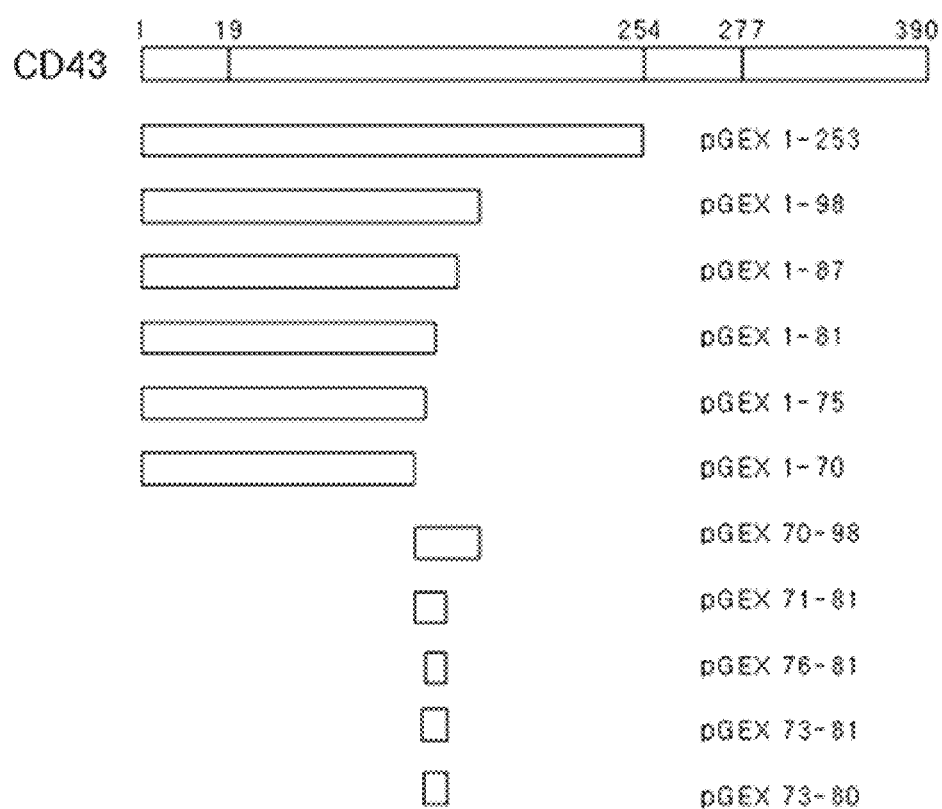
FIG. 12 is a figure schematically showing 11 kinds of CD43 deletion mutants.

As shown in FIG. 12, each CD43 deletion mutant was constructed, and the reactivity of YG5 antibody to the deletion mutant was tested, and analyzed for the epitope of CD43. CD43 protein (NCBI Accession No. M61827.1) was composed of the total 400 amino acids, and the amino acid sequence from no. 1 to no. 19 was the signal sequence, and the amino acid sequence form no. 20 to no. 254 was the extracellular domain, and the amino acid sequence from no. 255 to no. 277 was the transmembrane domain, and the amino acid sequence from no. 278 to no. 400 was the intracellular domain.

After constructing a DNA structure in order that each deletion mutant was expressed at the C-terminus of Glutathione-S-transferase (GST), it was inserted to pGEX-2T (Pharmacia Biotech Inc., Piscataway, N.J.) vector. Hereinafter, the vector comprising the amino acid sequence from no. 1 to no. 253 of CD43 protein was called pGEX1-253, and the vector comprising the amino acid sequence from no. 1 to no. 87 was called pGEX1-87, and the vector comprising the amino acid sequence from no. 1 to no. 87 of CD43 protein was called pGEX1-81, and the vector comprising the amino acid sequence from no. 1 to no. 75 of CD43 protein was called pGEX1-75, and the vector comprising the amino acid sequence from no. 1 to no. 70 of CD43 protein was called pGEX1-70, and the vector comprising the amino acid sequence from no. 70 to no. 98 of CD43 protein was called pGEX70-98, and pGEX71-81, pGEX76-81, pGEX73-81, and pGEX73-80 were named under the same principle as above.

The sequence encoding the deletion mutant was amplified from human CD43 cDNA, and PCR primers were constructed from the sequence on Genebank, and BamHI/EcoRI or BamHI/BglII restriction enzyme site was included. PCR products were cut with BamHI/EcoRI or BamHI/BglII and linked to pGEX-2T of same restriction enzyme site, and then transformed into *E. coli* competent TOP10F' cell [F' [laclq, Tn10(TetR)], mcrA, D(mrr-hsdRMS-mcrBC), 80lacZDM15, lacX74, deoR, recA1, araD139 D(ara-leu) 7697, galK, rpsL(StrR), endA1, nupG]. The sequence of transformant was analyzed, thereby reconfirmed the sequence of deletion mutant.

<Expression of GST-CD43 Deletion Mutant Fusion Protein>

The transformed *E. coli* TOP10 cell was cultured at 37° C. in LB medium in which 50 μg/mL of ampicillin was added overnight and the cultured cell was diluted 20-fold with LB medium, and then it was cultured for 3 to 4 hours to be OD 0.6. IPTG (Sigma Chemical Co., St. Louis, Mo.) was added to cultures at the final concentration 1 mM and it was cultured for additional 4 hours, and then it was centrifuged at 6,000 g for 15 min. After collecting cells only cells and which was suspended with 3 ml of lysis buffer solution (50 mM Tris, pH 8.0, 1 mM EDTA, 100 mM NaCl) per 1 g cell, the final concentration 0.2 mM of phenylmethylsulfonyl fluoride (Sigma Chemical Co.) was added and then placed on ice for 30 min.

<CD43 Epitope Analysis>

After the lysates of each transformants expressing the total 11 kinds of deletion mutants were subjected for 10% SDS-PAGE, western blot was performed with YG5 antibody and anti-GST antibody, respectively.

Figure 13A:
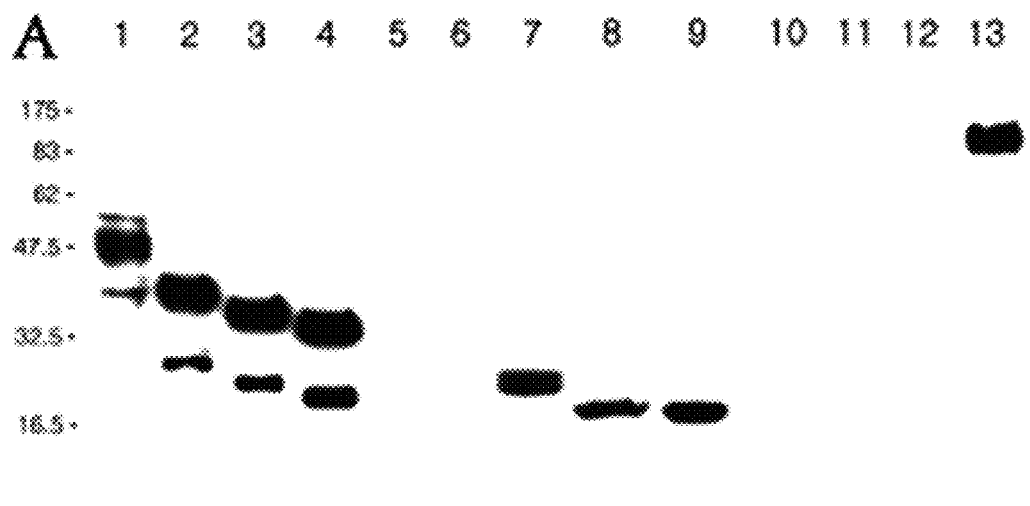
FIG. 13A-13B are the western blot results of confirming the reactivity of anti-CD43 (YG5) monoclonal antibody to 11 kinds of CD43 deletion mutants.
Figure 13B:
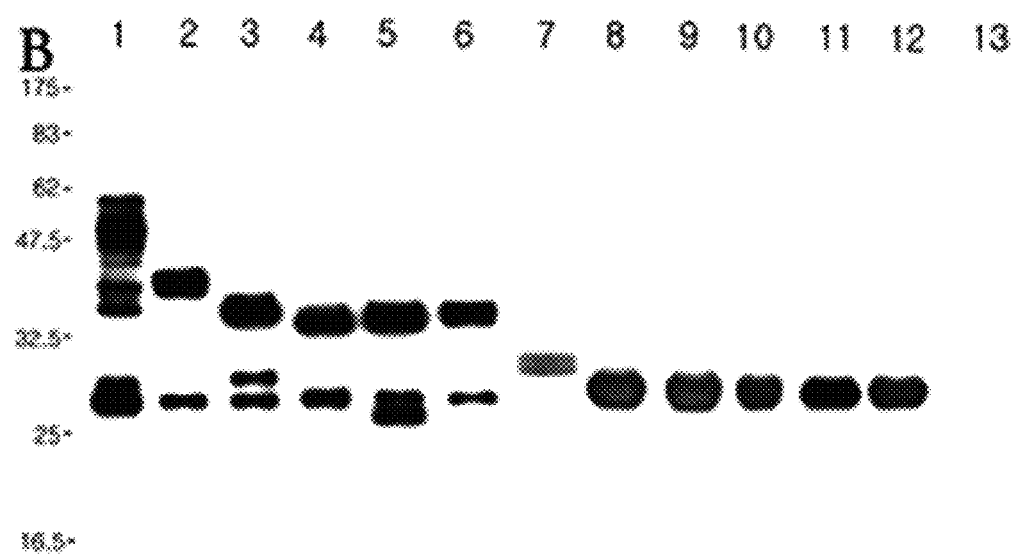

FIG. 13 is the western blot confirming the reactivity of YG5 antibody to 11 kinds of deletion mutants, where A is the case of using YG5 antibody, and B is the case of using GST antibody. In addition, lane 1 was pGEX1-253, and lane 2 was pGEX1-98, and lane 3 was pGEX1-87, and lane 4 was pGEX1-81, and lane 5 was pGEX1-75, and lane 6 was pGEX1-70, and lane 7 was pGEX70-98, and lane 8 was pGEX71-81, and lane 9 was pGEX73-81, and lane 10 was pGEX76-81, and lane 11 was pGEX73-80, and lane 12 was pGEX-2T, and lane 13 was human thymocyte. As shown in FIG. 13, the minimum unit of deletion mutant having the reactivity to YG5 antibody was confirmed as pGEX73-81, and thereby it was demonstrated that the antigenic determinant of CD43 was the amino acid sequence from no. 73 to no. 81 (Glu Gly Ser Pro Leu Trp Thr Ser Ile; SEQ ID NO: 4).

To sum up the examples, it was demonstrated that YG5 directly recognized the amino acid sequence from no. 73 to no. 81, not glycocomponent of CD43 glycoprotein, that is different from conventional other antibodies. This sequence was exposed mainly in lymphocyte progenitor cell and thymocyte in the development stages of hemoblast, and thereby YG5 antibody recognized it, and it was covered by glycosylation or structural changes around the amino acid sequence from no. 73 to no. 81 in hematopoietic stem cell, but mature white blood cell and thrombocyte, and thus YG5 antibody could not recognize it.

1-2. Chimeric Antibody Preparation

Based on the amino acid sequence of the constructed anti-CD43 mouse antibody YG5, the anti-CD43 chimeric antibody was prepared.

1-2-1. Plasmid Preparation

For the expression of anti-CD43 chimeric antibody, the plasmid for heavy chain expression and light chain expression were prepared, respectively. The pOptiVEC (Invitrogen Company) vector was used for the plasmid for heavy chain expression, and pcDNA3.3 (Invitrogen Company) vector was used for the plasmid for light chain expression. cDNA coding variable regions of heavy chain and light chain for antibody expression was cloned by using Ig-Primer sets (Novagen Company), and it was inserted to pGem-T vector (Promega Company), and then DNA sequence was confirmed by sequencing, and the mouse antibody gene was confirmed by IMGT site.

Figure 14:
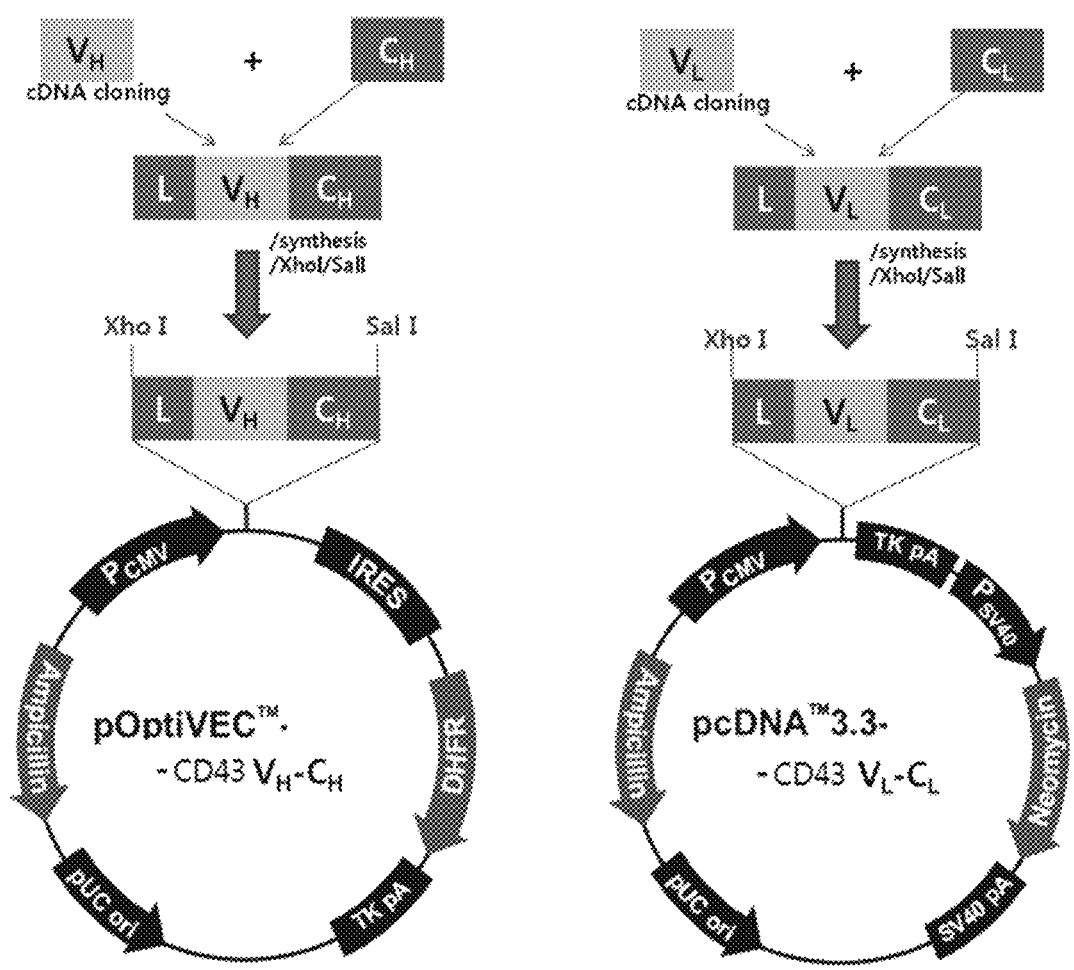
FIG. 14 is a schematic diagram illustratively showing the process for preparing the heavy chain and light chain expression plasmids of anti-CD43 antibody.

In order to express cDNA coding variable region and cDNA encoding invariable region of each antibody as a consecutive amino acid sequence without insertion of additional amino acid, the gene fragments in which the coding sequence of the cloned variable region linked with known human IgG1 invariable region (heavy chain) and kappa invariable region (light chain) coding sequence were synthesized (Bioneer Inc), respectively. After the heavy chain and light chain expressed genes synthesized as above were cut with restriction enzymes Xho I and Sal I, the heavy chain gene fragment was ligated into pOptiVec vector, and the light chain gene fragment was ligated into pcDNA3.3 vector, respectively, thereby constructing the complete plasmid for antibody expression (pcDNA3.3-anti-CD43 light chain expression plasmid and pOptiVEC-anti-CD43 heavy chain expression plasmid). The process of construction of the heavy chain and light chain expression plasmids was schematically shown in FIG. 14.

2-1-2. Transformation

The transformation process was performed by transfecting the constructed pcDNA3.3-anti-CD43 light chain expression plasmid and pOptiVEC-anti-CD43 heavy chain expression plasmid into DG44 cell (Invitrogen) derived from CHO.

At first, suspended DG44 cell was adapted to MEMα medium containing 5% FBS at 3 days before transfection, thereby converting it to adsorbed cell to be adapted for increasing the efficiency of transfection. The transfection was conducted in 6 well plate by using Effectene transfection regent (QIAGEN Company). The adapted DG44 cell subcultured at the concentration of $1 \times 10^5$ cells/well one day before transfection was prepared, and the amount of DNA used for transfection was used in the same amount of 2 μg each of pcDNA3.3-anti-CD43 light chain expression plasmid and pOptiVEC-anti-CD43 heavy chain expression plasmid. The transfection was performed for 48 hours. To sort the transfected cell group, flow cytometer and Enzyme Linked Immunosorbent Assay (ELIA) were conducted, as a result, two clones of E #4, E #5 were selected. The selected cell group was cultured in MEMα selection medium comprising 5% Dialyzed Fetal Bovine Serum containing 30 nM Methotrexate (MTX) and 400 μg/mL of G418 (Geneticin) and the concentration of MTX and G418 was increased gradually to select the transformed cell group.

2-1-3. Transformed Cell Culture and Antibody Purification

The transfected cell group selected above (24.0×10$^5$ cells/mL or more, viability (%) 90% or more) was cultured until the expression level reached by 600 mg/L (according to IPC (in-process control) standard) in power CH02 CDM (Lonza; final medium amount 880 L) under the condition of 37° C. and 5% $CO_2$.

After cell clarification (using POD filter (1.1/0.2 μm)) process by collecting 800 L of culture solution obtained as above, the antibody was purified by 3 stages column process (Protein A affinity chromatography (stationary phase: ProteinA, equilibrium buffer solution: 50 mM Sodium phosphate, 50 mM sodium chloride, pH 7.5, elution buffer solution: 20 mM sodium citrate pH3.0); cation exchange chromatography (stationary phase: SP FF, equilibrium buffer solution: 20 mM sodium citrate pH 5.5, elution buffer solution: 20 mM Sodium citrate, 150 mM, sodium chloride, pH 6.1); anion exchange chromatography (stationary phase: Q FF, equilibrium buffer solution: 20 mM Sodium citrate, pH 6.5)).

The chromatography condition was as follows:

|  | Protein A | Cation exchange | Anion exchange |
| --- | --- | --- | --- |
| Colum type | Mabselect sure | SP FF | Q FF |
| Colum controller | 6 mm Bioprocess (CL-3271) | 10 mm Bioprocess (CL-3201) | 10 mm Bioprocess (CL-3201) |
| Column size | BPG 200 | BPG 300 | BPG 300 |
| Column volume | 6.5 L | 14.0 L | 14.0 L |
| Column Height | 20 cm | 20 cm | 20 cm |
| Flow rate | 62.8 L/hr | 141 L/hr | 141 L/hr |

The formulation of the final crude liquid was completed by simultaneously performing buffer change and concentration processes through ultrafiltration/diafiltration (UF/DF) process, and the concentration of the final protein was adjusted to 11.5 mg/mL.

The anti-CD43 chimeric antibody was obtained by the process as above, and named DNP001.

2-1-4. Confirmation of Binding Capacity of Epitope Region of Chimeric Antibody

In order to confirm that the prepared chimeric antibody DNP001 (having the same CDR region as mouse antibody) bound to the same epitope as the mouse antibody, the synthesized epitope peptide was chemically combined to bovine serum albumin (BSA) protein, and then ELISA was conducted.

epitope peptide synthesis sequence (named DN2)
EG<u>SPLWTSIGASTGS</u>C (SEQ ID NO: 129; epitope was represented by underlining)

The DN2 peptide-BSA conjugate was prepared by conjugating the synthesized DN2 peptide into BSA protein through EDC linker. Then, the molar ratio of peptide:BSA protein was 15:1.

After coating the prepared DN2 peptide-BSA conjugate at 50 μg/mL per well, the chimeric antibody DNP001 was incubated at various concentration gradients. Next, the antibody linked to the conjugate was detected by measuring the reactivity of the chimeric antibody to the DN2 peptide-BSA conjugate. The linked antibody was detected by anti-human antibody-HRP (anti-human Ig-HRP), and the OD values at 450 nm were measured and shown in the following table and FIG. 42.

| Chi. Ab (ug/ml) | OD value |
| --- | --- |
| 100 | 1.878 |
| 50 | 1.398 |
| 25 | 0.803 |
| 12.5 | 0.5 |
| 6.25 | 0.327 |
| 3.13 | 0.204 |
| 1.56 | 0.137 |
| 0 | 0.007 |

Figure 42:
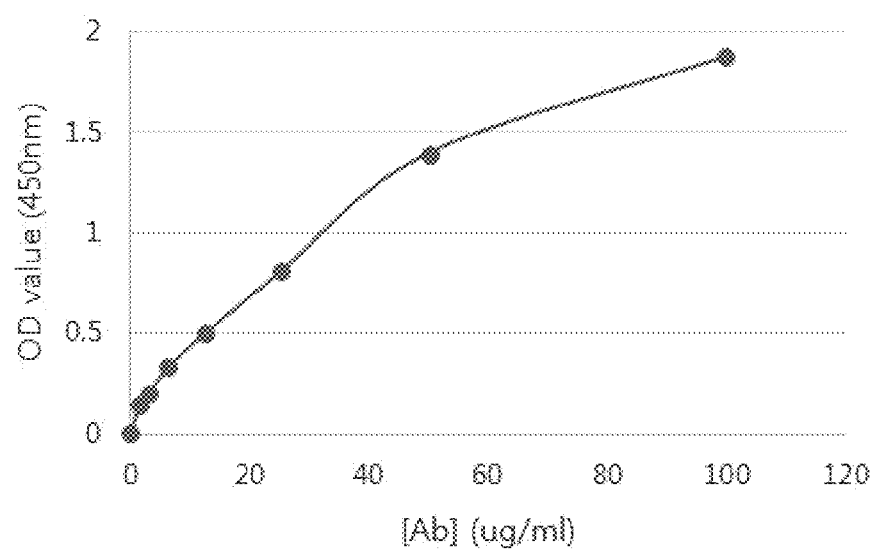
FIG. 42 is the graph showing the epitope binding activity of chimeric antibody DNP001.

As shown in the result of the table and FIG. 42, it was demonstrated that chimeric antibody DNP001 bound to the epitope peptide in a concentration dependent manner.

Example 2: Investigation of Expression Level of CD43 Epitope in Human Solid Cancer Cell Lines In order to investigate the expression level of CD43 in various solid cancer cell lines, immunostaining and flow cytometry were conducted.

The information of cell lines used for analysis was as follows:

| Name | Origin | Histopathology | Accession NO. |
| --- | --- | --- | --- |
| SNU-1 | stomach, gastric | adenocarcinoma | ATCC, CRL-5971 |
| SNU-719 | stomach | adenocarcinoma, primary | KCLB, No. 00719 |
| NCI-N87 | stomach | carcinoma; metastatic to liver | ATCC, CRL-5822 |
| AGS | stomach | adenocarcinoma | ATCC, CRL-1739 |
| HT29 | colon | adenocarcinoma | ATCC, HTB-38 |
| LS174T | colon | Dukes' type B, colorectal adenocarcinoma | ATCC, CL-188 |
| HCT116 | colon | colorectal carcinoma | ATCC, CCL-247 |
| C3A | liver | hepatocellular carcinoma | ATCC, CRL-10741 |
| HepG2 | liver | hepatoblastoma | ATCC, HB-8065 |
| PLC/PRF/5 | liver | hepatoma | ATCC, CRL-8024 |

Specifically, each cell line was inoculated and cultured in 100 mm of cell culture container, and when 70~80% of surface was concentrated with the culture cell, the culture cell was washed with phosphate-buffered solution and then treated with Trypsin-EDTA (Invitrogen), and dissociated, and then centrifuged. The precipitated cell was suspended in buffer solution again and aliquoted 1×10$^5$ each, and 1.5 μL of the anti-CD43 antibody (YG5)-phycoerythrin (PE) prepared in the example 1-1 was added and reacted in a 4° C. refrigerator for 20 min. After reaction at 4° C. for 20 min, cell was washed with 4 ml of buffer solution (1× Phosphate Buffered Saline, PBS buffer) again, then it was analyzed with Flow Cytometer (Becton, Dickinson and Company, Franklin Lakes, N.J., USA). For comparison, the same test using DFT-1 antibody (2 μL, Ancell corporation) instead of the anti-CD43 antibody was performed.

The obtained results were shown in FIG. 1 and FIGS. 2A-2C. In FIG. 1, X axis showed the expression level of antigen CD43 which reacts to the antibody YG5 in quoted cell line and Y axis indicated Reading cell numbers (counts).

As shown in FIG. 1 and FIGS. 2A-2C, approximately 60% of expression level was shown in Duke's type B adenocarcinoma (LS174T) in rectal cancer, and approximately 50, 37% of expression level was shown in HCT116, HT29, and the expression of CD43 (epitope) was confirmed in other various kinds of solid cancer cell lines.

Example 3: Test of Cytotoxicity of Anti-CD43 Antibody to Cancer Cell (In Vitro)

3-1. Preparation of Antibody-Toxin Conjugate

The saporin (Sigma, St. Louis, Mo.) conjugation of monoclonal antibody was conducted according to the conventional method (Polito et al., 2004). After dissolving the antibody (DNP001; prepared in example 1-2) and saporin at the concentration of 2 mg/mL (antibody concentration) and 8 mg/mL (saporin concentration), respectively in 50 mM sodium borate buffer (pH 9.0), 2-iminothiolane (Sigma) was treated at the concentration of 0.4 mM and 1.0 mM, respectively. Afterward, the antibody and saporin were mixed at the ratio of 10:1 and reacted at the room temperature for 16 hours, and the antibody-saporin conjugate was purified by gel filtration. Hereinafter, the prepared conjugate was described as anti-CD43-saporin conjugate.

Referring the method above, anti-CD43-MMAE conjugate in which anti-CD43 antibody (DNP001; prepared in example 1-2) and monomethyl auristatin E (MMAE; Creative Biolabs) were conjugated, anti-CD43-DM1 conjugate in which anti-CD43 antibody (DNP001) and N2'-diacetyl-N2'-(3-mercapto-1-oxopropyl) maytansine (DM1; The Chemistry Research Solution LLC) were conjugated, and anti-CD43-Duocarmycin conjugate in which anti-CD43 antibody (DNP001) and Duocarmycin (The Chemistry Research Solution LLC) were conjugated, and anti-CD43 antibody (DNP001)-DM1 conjugate were prepared, respectively.

3-2. Cytotoxicity of Anti-CD43 Antibody-Toxin Conjugate to Stomach Cancer Cell

The cytotoxicity of the antibody-toxin conjugates prepared in the example 3-1 (anti-CD43-saporin conjugate, anti-CD43-DM1 conjugate, anti-CD43-MMAE conjugate, and anti-CD43-Duocarmycin conjugate) to the stomach cancer cell was tested.

The day before the test, stomach cancer cell lines NCI-N87, AGS, and SNU719 were respectively plated at $4\times10^3$ per well. The each antibody-toxin conjugate was treated to each stomach cell line at the concentration of 10000 ng/mL (in case of (anti-CD43 antibody)-MMAE conjugate and (anti-CD43)-DM1 conjugate) or 1000 ng/mL (in case of (anti-CD43)-Duocarmycin conjugate). Afterward, 10 μL of EzCytox (Daeil lab, Korea) was added to each well after 24 hours, 48 hours, and 72 hours, and cells were cultured in a 37° C. $CO_2$ container, and then their viability were measured by microspectrophotometry.

Figure 3:
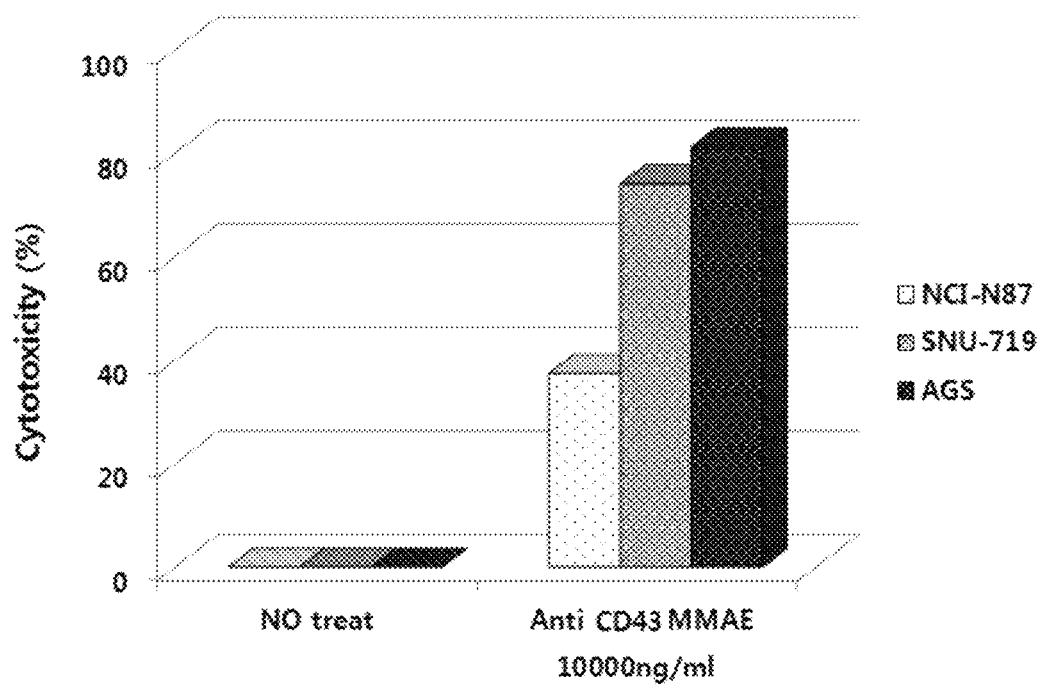
FIG. 3 is the result of confirming the cytotoxicity of (anti-CD43 antibody)-MMAE conjugate to human stomach cell lines NCI-N87, SNU-719, and AGS.
Figure 4:
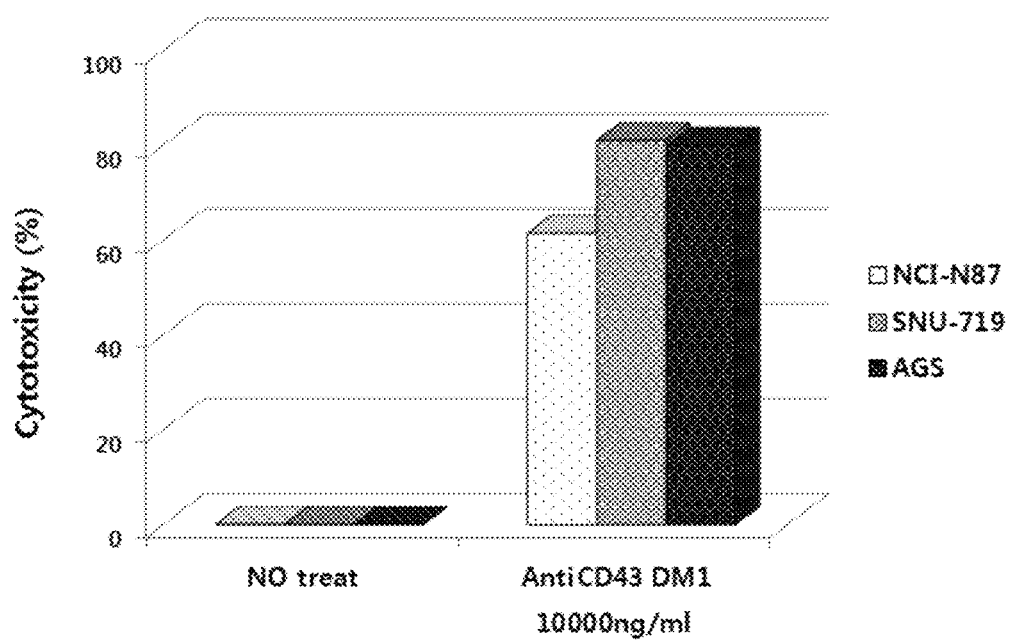
FIG. 4 is the result of confirming the cytotoxicity of (anti-CD43 antibody)-DM1 conjugate to human stomach cell lines NCI-N87, SNU-719, and AGS.
Figure 5:
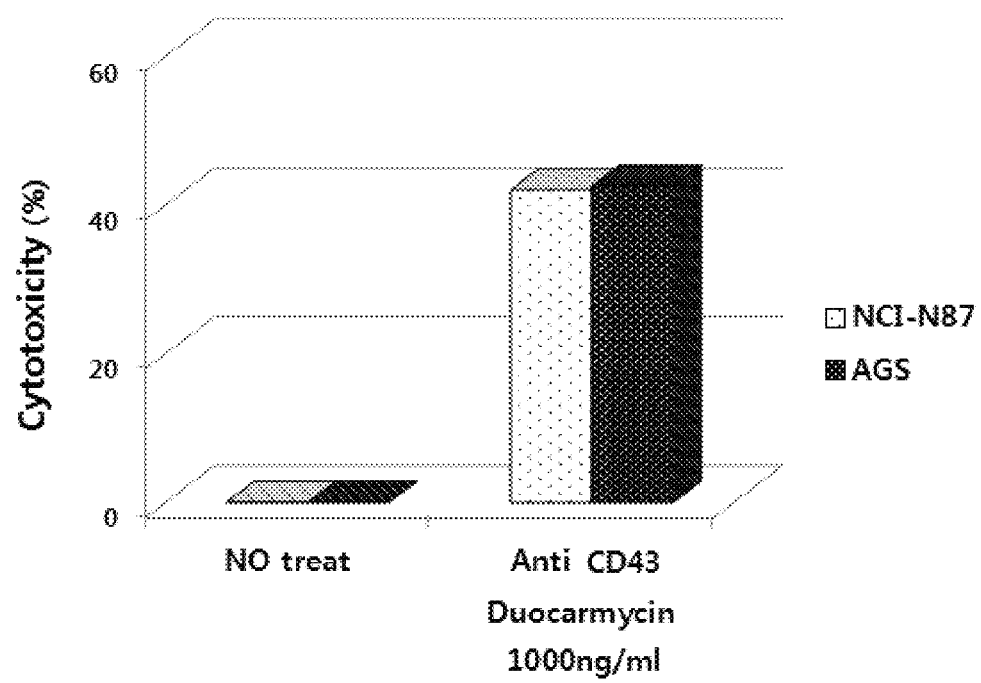
FIG. 5 is the result of confirming the cytotoxicity of (anti-CD43 antibody)-Duocarmycin conjugate to human stomach cell lines NCI-N87 and AGS.

The cytotoxicity of each conjugate obtained was shown in FIG. 3 ((anti-CD43 antibody)-MMAE conjugate), FIG. 4 ((anti-CD43)-DM1 conjugate) and FIG. 5 ((anti-CD43)-Duocarmycin conjugate). The cytotoxicity was calculated with the following equation:

$$\text{Cytotoxicity (\%)} = [1-(\text{the number of survived cells}/\text{the number of initial cells})] \times 100$$

As shown in FIGS. 3, 4 and 5, it was confirmed that the anti-CD43-DM1 conjugate and anti-CD43-MMAE conjugate showed the cytotoxicity in all 3 kinds of cell lines, and the anti-CD43-Duocarmycin conjugate showed the cytotoxicity in NCI-N87 and AGS.

Example 4: Test of Anti-Cancer Effect of Anti-CD43 Antibody in Animal Model (In Vivo)

4-1. Preparation of Stomach Cancer Animal Model (Tumorigenesis)

The stomach cancer model was prepared by using the cell lines in which CD43 expression was confirmed in the result of example 2 (NCI-N87; ATCC, CRL-5822). At first, $2.8\times10^7$ of NCI-N87 cells were prepared. The prepared cells were subcutaneously inoculated $5\times10^6$ cells/100 μL (RPMI) into the right side of nude mice. The inoculated nude mice were arranged into the control group (PBS administration) and test group, and the anti-CD43 antibody (DNP001) prepared in the example 1-2 was injected into the tail vein in an amount of 12 mg/kg 2 times per week for 3 weeks at 3 days, or 0.2 mg/kg of the anti-CD43-Duocarmycin conjugate (DNP001-Duocarmycin) prepared in the example 3-1 was intraperitoneally injected once per week for 3 weeks, after inoculating the cancer cell. The size of tumor was measured before administrating the therapeutic agent 2 times per week, and the size of tumor was calculated by the following equation:

$$\text{Tumor size (mm}^3) = (\text{major axis} \times \text{minor axis}^2)/2$$

Figure 6:
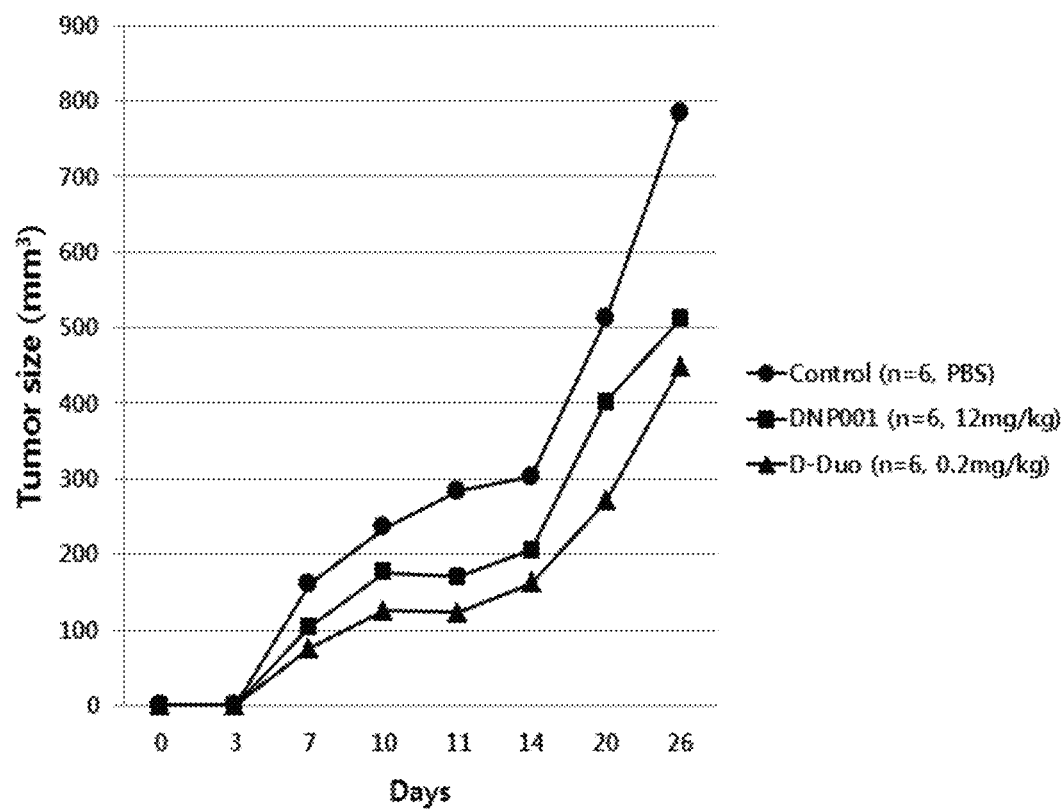
FIG. 6 is the result of confirming the anti-cancer effect of anti-CD43 antibody alone (DNP001) and anti-CD43 antibody-Duocarmycin conjugate (D-Duo) in the stomach cancer animal model in which the human stomach cancer cell line is grafted.

The obtained result was shown in FIG. 6. As shown in FIG. 6, it was confirmed that the growth of tumor began to be inhibited in DNP001-Duocarmycin administration group (D-Duo) compared to the control group from 7th day after starting the test. 26 days after starting the test, the mean tumor sizes of mice administered with DNP001-Duocarmycin, DNP001 alone, and PBS were 447.2 mm$^3$, 510.9 mm$^3$, 784.6 mm$^3$, respectively. In case of the group in which the anti-CD43-Duocarmycin conjugate and anti-CD43 antibody were administered, the growth of tumor was suppressed by approximately 43% and 34%, respectively, compared to the control group. This result exhibited the significant inhibitory effect of growth of stomach cancer of the anti-CD43 antibody alone and anti-CD43-Duocarmycin conjugate.

Example 5: Investigation of Distribution of CD43 in Human Solid Cancer Tissue

In addition to stomach cancer, to confirm the expression of CD43 and the possibility to test the therapeutic efficacy in various solid cancer, (stomach cancer, signet ring cell stomach cancer, breast cancer, ductal infiltrating adenocarcinoma among breast cancer, renal cancer, pancreatic cancer, gallbladder cancer, cervical cancer, uterine cervix cancer, bladder cancer, granulocytic sarcoma) targeting CD43, immunohistochemistry was performed in various human origin tumor tissues.

The immunohistochemical staining was progressed in the following order. As the solid cancer tissue, the paraffin embedded solid cancer tissue (Chungbuk National University Hospital) was used. At first, the paraffin solid cancer slide was under the de-paraffin process of 3 times of xylene for 10 min each, twice of 100% alcohol for 5 min each, 80% alcohol for 3 min, 50% alcohol for 1 min, 20% alcohol for 1 min, and then washed with running water twice. Then, it was soaked in 1×TBS (Tris-buffered saline) for 10 min. To regenerate antigen in tissue, 10 mM HEPES (4-(2-hydroxyethyl)-1-piperazineethanesulfonic acid, pH 8.0) buffer was added and proceeded in a microwave for 15 min and rapidly cooled in running water, and the slide was then soaked in 1×TBS for 20 min. The endogenous peroxidase was removed with 0.1% $H_2O_2$+100% methanol for 10 min and washed with running water twice. Then, to remove the non-specific reaction of biotin and antigen-antibody, the blocking process was proceeded. The blocking process was performed by dropping 4 drops of biotin solution and reacted at the room temperature for 15 min. After dropping 4 drops of avidin solution (VECTOR laboratories) to the tissue, it was reacted at the room temperature for 15 min and then washed with 1×PBS.

10 μg/mL, 5 μg/mL each of the anti-CD43 (YG5) antibody and DFT-1 antibody (control group; Ancell corporation) prepared in the example 1-1 were suspended in 150 μL of 1×TBS to cover the tissue, and it was reacted at the room temperature for 30 min. After washing it with 1×TBST (1×TBS+0.1% tween 20) 3 times for 15 min each, the second antibody (anti-mouse/rabbit HRP; DAKO) was covered to the tissue 2 drops each, and reacted at the room temperature for 30 min. Then, after washing it with 1×TBST (1×TBS+0.1% tween 20) 3 times for 15 min each, the color development reaction was carried out with DAB (Diaminobenzidine). After washing it with 1×TBS for 5 min twice and counter staining, it was washed with running water. Then, after the dehydration process was proceeded, it was mounted.

Figure 7:
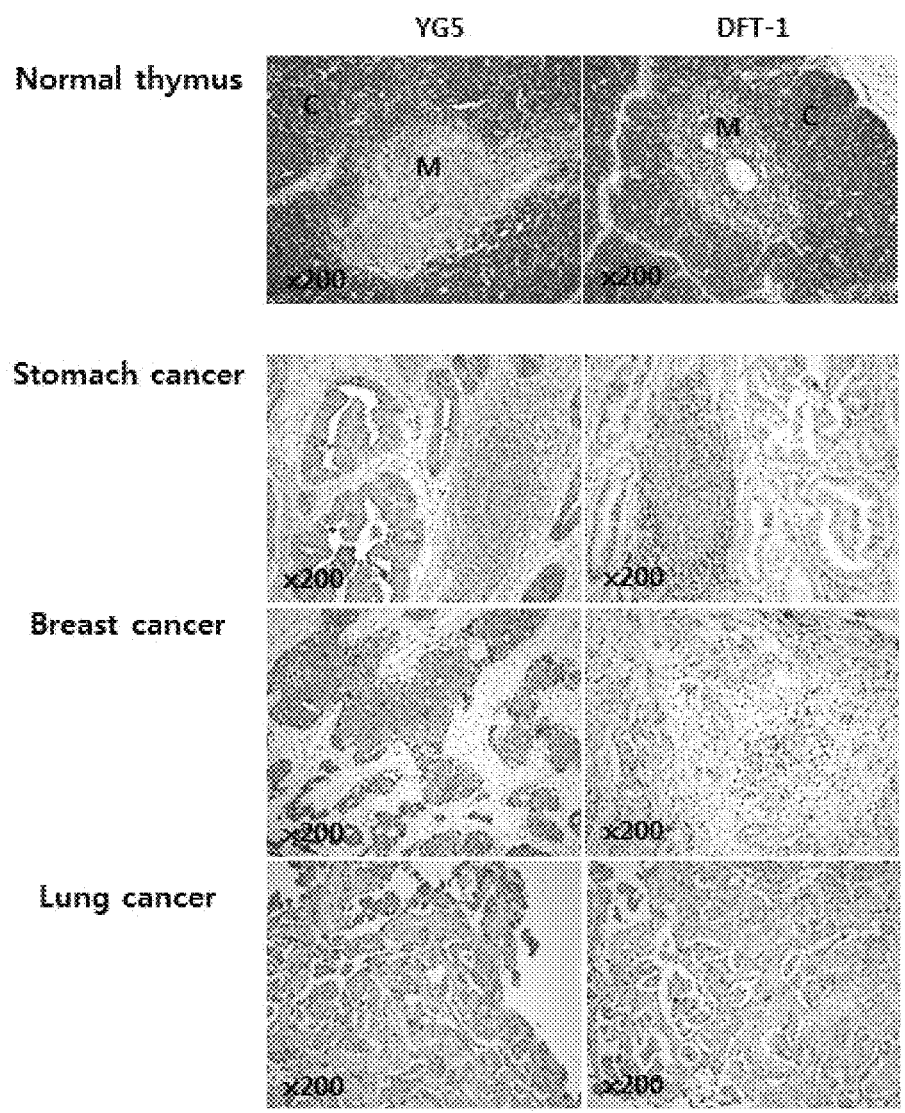
FIG. 7 is the result of confirming the expression of CD43 epitope in various solid cancer tissues originated from human by the immunohistochemistry method (M; medulla, C; cortex).
Figure 8:
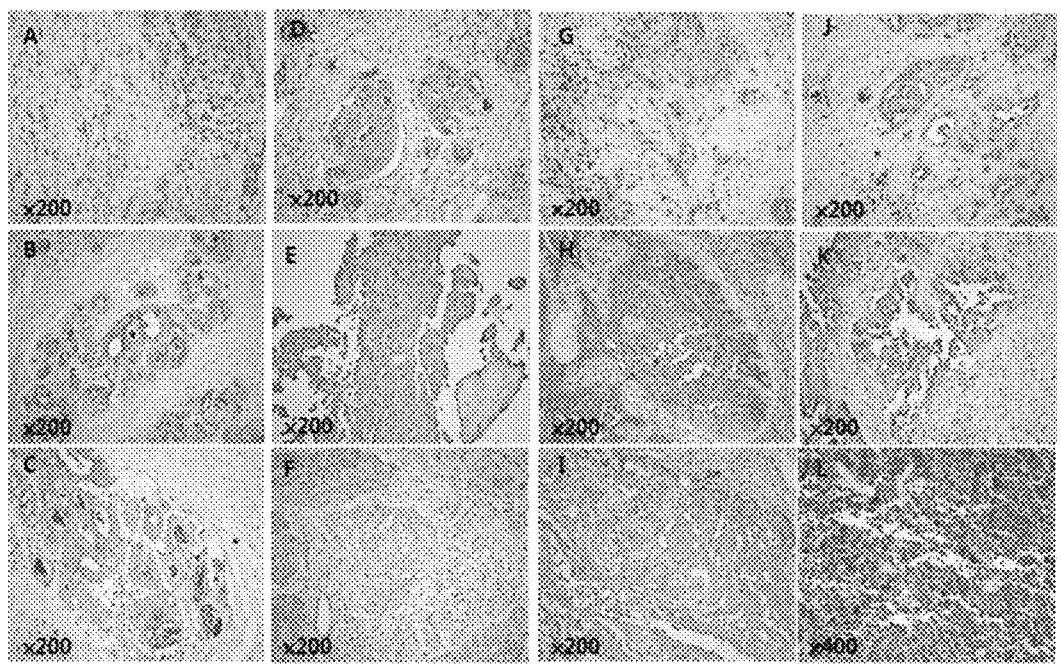
FIG. 8 is the result of confirming the expression of CD43 epitope according to the disease of various solid cancers originated from human by the immunohistochemistry method (A; signet ring cell (Stomach signet ring cell carcinoma), B; Breast infiltrating duct adenocarcinoma, C; Pancreas adenocarcinoma, D; Kidney renal cell carcinoma, E; lung Adenocarcinoma, F; LarynX squamous cell carcinoma, G; Gall bladder carcinoma, H; Cervix squamous cell carcinoma, I; Uterus squamous cell carcinoma, J; Urinary bladder cancer, K; Lung squamous cell carcinoma, L; Ear granulocytic sarcoma).

The obtained result was shown in FIG. 7 and FIG. 8 and Table 1. The criteria to determine the CD43 positivity in each tissue were as follows: negative: 0, positive: classified into 1 to 3 grades according to the level of staining of YG5 in the tumor region.

TABLE 1

Expression of CD43 in various cancer tissue section

| Origin | Total (n) | Positive (n) | %, positivity |
|---|---|---|---|
| Stomach | 213 | 179 | 84 |
| Breast | 231 | 90 | 39 |
| Lung | 28 | 13 | 46 |
| Kidney | 54 | 5 | 9 |
| Pancreas | 30 | 3 | 10 |
| Thyroid | 21 | 1 | 5 |
| Gall bladder | 4 | 1 | 25 |
| Uterus | 2 | 1 | 50 |
| Urinary bladder | 5 | 2 | 40 |
| Cervix | 4 | 1 | 25 |

(In the table 1,

Positivity means the numerical value obtained by dividing the number of positive tissue except for the negative tissues in which YG5 was not stained by the number of total tissues of corresponding cancer;

Total means the total number of tissues used for staining;

Positive means the number of tissues showing a positive reaction to YG5 among tissues used, respectively)

As confirmed in table 1, FIG. 7 and FIG. 8, it was demonstrated that CD43 was expressed in tumors which occurred in an epithelial cell mainly such as stomach cancer, signet ring cell stomach cancer, breast cancer, ductal infiltrating adenocarcinoma among breast cancer, renal cancer, pancreatic cancer, gallbladder cancer, cervical cancer, uterine cervix cancer, bladder cancer, granulocytic sarcoma, etc.

Example 6: CD43 Expression in Cancer Stem Cell of Stomach Cancer

The level of expression of CD43 in cancer stem cells of various tumors was tested. CD44 and CD133 (Prominin-1) were publicly known cancer stem cell markers. The cancer stem cell markers CD44 and CD133 were triple-stained to confirm the CD43 expression, thereby demonstrating that CD43 was expressed in CD44 or $CD44^+CD133^+$ positive group. NCI-N87 cell was inoculated and cultured in 100 mm of cell culture container, and when 70~80% of surface was concentrated with the culture cell, the culture cell was washed with phosphate-buffered solution and then treated with Trypsin-EDTA (Invitrogen), and dissociated, and then centrifuged. The precipitated cell was suspended in buffer solution again. After reacting them with anti-CD44-allophycocyanin (APC) (10 μL, Miltenyi Biotec), anti-CD133-fluorescein isothiocyanate (FITC) (10 μL, Miltenyi Biotec), and anti-CD43 antibody (prepared in example 1; YG5)-phycoerythrin (PE; 1.5 μL, Dinona) in a 4° C. refrigerator for 20 min, the unreacted antibody was washed and fixed with 1% paraformaldehyde. Cells were then analyzed by Flow Cytometer (Becton, Dickinson and Company, Franklin Lakes, N.J., USA). The same test using mouse IgG1 instead of the anti-CD44 antibody and anti-CD133 antibody as a negative control group was performed.

Figure 9:
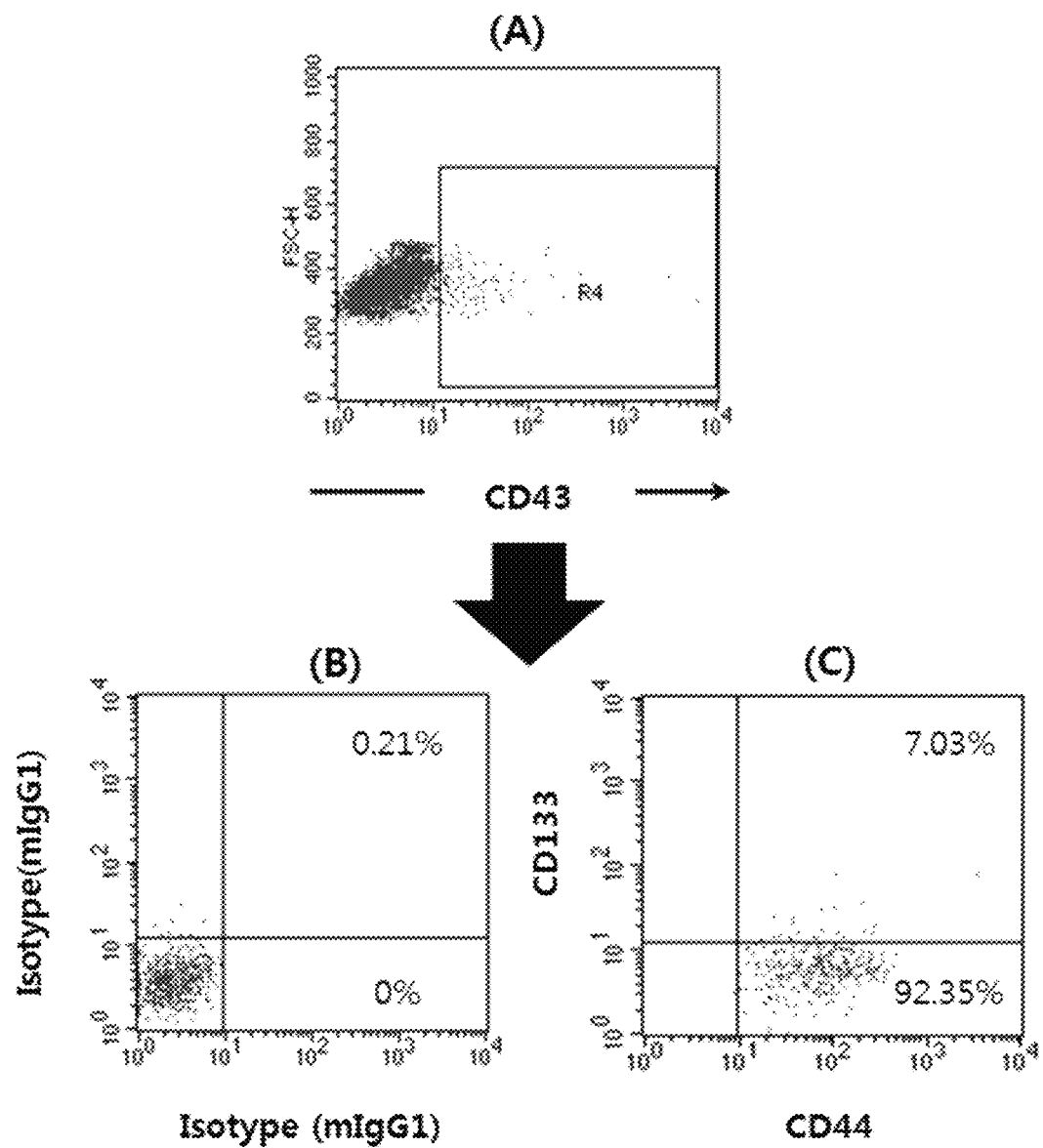
FIGS. 9A-9C are the results of confirming the expression of CD43, CD44, and CD133 in the cancer stem cell of human stomach cancer cell line NCI-N87 by the immunostaining method.

The obtained result was shown in FIGS. 9A-9C.

As shown in FIGS. 9A-9C, as the result of confirming the expression of CD43 in cancer stem cells of stomach cancer, it was confirmed that CD43 was positive in cells in which markers differentiating cancer stem cells of stomach cancer (CD44 or CD133) were positive. This result showed that the anti-CD43 antibody according to the present invention could specifically bind to CD43 expressed on the surface of cancer stem cells of stomach cancer.

Example 7: Investigation of Expression of CD43 in Various Solid Cancer Stem Cells The expression of CD43 in cancer stem cells of CD43 positive solid cancer quoted in the example 5 was confirmed by the same method quoted in the example 6.

Cells originated from each CD43 positive tissue disclosed in the example 5 (breast cancer, lung cancer, rectal cancer, liver cancer and gallbladder cancer, renal cancer, pancreatic cancer, thyroid cancer, prostate cancer, cervical cancer, uterine cervix cancer, bladder cancer-originated cell lines) were used. Each cell was inoculated and cultured in 100 mm of cell culture container, and when 70~80% of surface was concentrated with the culture cell, the culture cell was washed with phosphate-buffered solution and then treated with Trypsin-EDTA (Invitrogen), and dissociated, and then centrifuged. The precipitated cell mass was suspended in buffer solution again and reacted with 100-fold diluted anti-CD44-allophycocyanin (APC), anti-CD44-allophycocyanin (APC), anti-CD326 (EpCAM)-allophycocyanin (APC), anti-CD133-fluorescein isothiocyanate (FITC), anti-CD43 antibody-phycoerythrin (PE) in a 4° C. refrigerator for 20 min. The unreacted antibody was washed and fixed with 1% paraformaldehyde, and then cells were analyzed by Flow Cytometer (Becton, Dickinson and Company, Franklin Lakes, N.J., USA).

As a result, as the result of confirming the CD43 expression in cancer stem cells of CD43 positive tissue originated cells in the example 5, it was confirmed that CD43 was positive in cells in which markers differentiating each cancer stem cell (CD44, CD133, or EpCAM) were positive.

Example 8: Test of CD43 Expression in Cancer Stem Cell of Fresh Cancer Tissue of Patient Based on the result of the example 5, the expression of CD43 was tested after classification using cancer stem cell markers in cancer tissues of patient.

The fresh cancer tissue of patient was finely monoclonalized. The monoclonalized tumor cell was centrifuged at 1700 rpm for 3 min and then the supernatant was removed, and it was resuspended to 10 mL medium containing 10% FBS and then centrifuged at 1700 rpm for 3 min. The supernatant was removed and it was resuspended with 10 mL 1×PBS, and then counted. Cells were distributed to FACS tubes, and then after reacting them with anti-CD44-allophycocyanin (APC), anti-CD44-allophycocyanin (APC), anti-CD326 (EpCAM)-allophycocyanin (APC), anti-CD133-fluorescein isothiocyanate (FITC), anti-CD43 antibody-phycoerythrin (PE) in a 4° C. refrigerator for 20 min, the unreacted antibody was washed and fixed with 1% paraformaldehyde, and then cells were analyzed by Flow Cytometer (Becton, Dickinson and Company, Franklin Lakes, N.J., USA).

As above, as the result of testing the CD43 expression in cancer stem cells of stomach cancer in cancer stem cells of cancer tissues of patient, it was confirmed that CD43 was positive in cancer stem cells originated from cancer tissues of patient.

Example 9: Inhibition of Colony Formation of Cancer Stem Cell by Anti-CD43 Antibody (In Vitro)

It was confirmed that the colony formation of CD43 positive stem cells in the CD43-positive solid tumor presented in Example 5 was inhibited by the anti-CD43 antibody was confirmed in Example 6. Cells originated from each CD43 positive tissue disclosed in the example 5 (breast cancer, lung cancer, rectal cancer, liver cancer and gallbladder cancer, renal cancer, pancreatic cancer, thyroid cancer, prostate cancer, cervical cancer, uterine cervix cancer, bladder cancer-originated cell lines) were used. Each cell line was inoculated and cultured in 100 mm of cell culture container, and when 70~80% of surface was concentrated with the culture cell, the culture cell was washed with phosphate-buffered solution and then treated with Trypsin-EDTA (Invitrogen), and dissociated, and then centrifuged. The precipitated cell mass was suspended in buffer solution again and the anti-CD43 antibody was added at the concentration of 20 μg/mL per $10^7$ of tumor cells and reacted in a 4° C. refrigerator for 20 min, and then unreacted antibody was washed with 1×PBS. After adding 20 μL of magnetic bead-boung IgG, it was reacted in a 4° C. refrigerator for 15 min and then washed with 1×PBS, and CD43 positive cells were classified by MACS separating system.

After reacting the classified CD43 positive cells or negative cells with anti-CD44-allophycocyanin (APC), anti-CD326(EpCAM)-allophycocyanin (APC), anti-CD133-fluorescein isothiocyanate (FITC), anti-Mignetic Bead antibody-phycoerythrin (PE, 20ul, Miltenyi Biotec) in a 4° C. refrigerator for 15 min, it was washed and fixed with 1% paraformaldehyde, and then analyzed by Flow Cytometer (Becton, Dickinson and Company, Franklin Lakes, N.J., USA).

The CD43 positive cells or negative cells obtained from the examples were added in ultra low attachment 6-well plates (Corning Inc., Corning, N.Y., USA) at the number of 5,000 per well in the well containing serum-free media (100 IU/ml penicillin G, 100 μg/mL streptomycin, 20 ng/mL human recombinant epidermal growth factor (hrEGF), 10 ng/ml human recombinant basic fibroblast growth factor (hrbFGF), 2% B27 supplement without vitamin A, 1% N2 supplement (Invitrogen, Carlsbad, Calif., USA) were comprised). Then, the anti-CD43 antibody and control antibody were added 100 μg/mL each and cultured. Afterward, spheres were observed. The same experiment was conducted by classifying CD43 positive cells in fresh cancer tissues of patient.

As a result, it was confirmed that the tumorigenesis of cancer stem cell was inhibited, compared to the control group, as the result of administering the anti-CD43 antibody to CD43 positive cancer stem cells of various tumors and cancer tissues of patient. This result showed the significant inhibitory effect of oncogenesis of cancer stem cell of anti-CD43 antibody.

Example 10: Test of Anti-Cancer Effect of Anti-CD43 Antibody in Various Cancer Animal Models (In Vivo)

The animal model was prepared by using cell lines in which CD43 expression was confirmed in the results of the examples 7 and 8 and fresh cancer tissues, and the method was same as the example 4. The mice were randomly assigned into the control group (PBS administration), and test group, and the anti-CD43 antibody (DNP001 mAb) prepared in the example 2 was injected into the tail vein in an amount of 8 mg/kg 2 times per week for 3 weeks, or 0.2 mg/kg, 0.5 mg/kg, 1 mg/kg, 5 mg/kg of the anti-CD43-saporin, DM1, MMAE, Duocarmycin conjugate prepared in the example 3-1 was intraperitoneally injected once per week for 3 weeks, at 3 days after inoculating cancer cells.

Example 11: Test of Change of Binding Capacity to Normal Blood Cell after Neuraminidase Treatment It was confirmed whether there was change of binding capacity to the normal lymphocyte in which the antibody recognizing CD43 expressed in normal blood (DFT-1) and the anti-CD43 antibody (YG5) recognizing tumor-specific CD43 were treated with neuraminidase.

10 mL of blood was gathered from health people, and 40 mL of red blood cell lysis solution (RBC lysis solution; NH4Cl, NaHCO$_3$, EDTA pH8.0) was added into the blood, and lysed at the room temperature for 10 min. The blood in which red blood cells were lysed was centrifuged at 1700 rpm for 5 min and then the supernatant was removed, and it was washed with 10 mL of PBS twice. 3*$10^6$ of lymphocytes were suspended in 130 μL of the obtained red blood cell lysis solution above, and 50 μL of neuminidase (ELPIS, Korea) and 20 μL of buffer were added. And then, cell was reacted at 37° C. for 50 min, and washed with PBS. In order to confirm whether there was change of epitope of antibody recognizing CD43 by the neuraminidase, FITC and PE-bound DFT-1 and YG5 antibodies were added into the cell and after reacting at 4° C. for 15 min, the cell was then washed with 4 ml of PBS. The cell was then measured with flow cytometry and the titer to the normal lymphocyte was measured.

Figure 15:
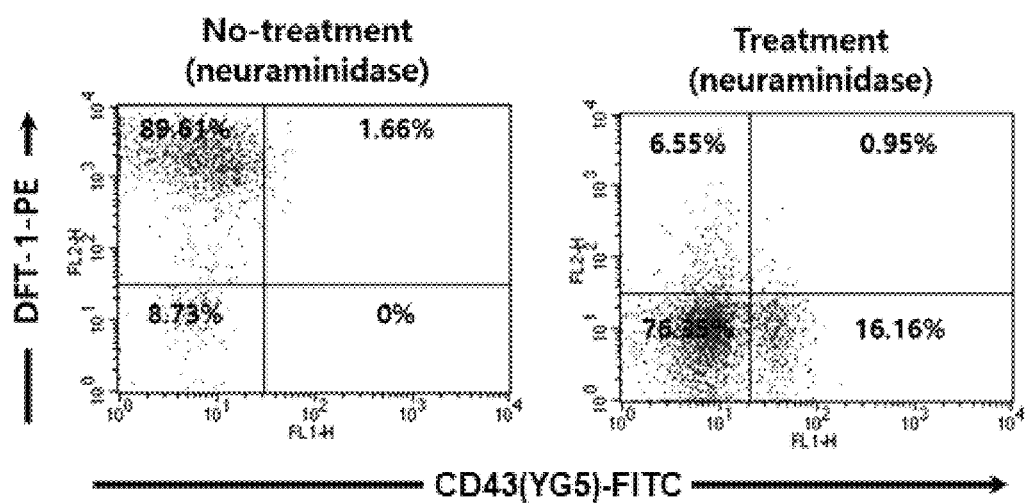
FIG. 15 is the graph showing the binding capacity of anti-CD43 antibody to CD43 epitope, after treating neuraminidase to a normal blood cell.

The result of confirming the titers of two antibodies to CD43 obtained above (DFT-1 and YG5) was shown in FIG. 15. As shown in FIG. 15, it was confirmed that DFT-1 showed high titer before treating the neuraminidase, but did not after treating the neuraminidase, whereas, YG5 did not exhibit the titer before treating the neuraminidase, but 16.16% of titer was shown after treating the neuraminidase. As a result, it was confirmed that the anti-CD43 antibody (YG5) according to the present invention did not recognize the sialylated epitope of CD43 protein, and this showed that the anti-CD43 antibody according to the present invention did not bind to the normal cell and specifically bound to the cancer cell, in particular, cancer stem cell.

Example 12: Test of Cross-Reactivity to CEACAM5 and CEACAM6

5F1 clone known to recognize CD43 protein was known to simultaneously recognize CD43 and CEACAM6 and bind to fucosylated position of two proteins. It was tested that the anti-CD43 antibody showed the cross-reactivity with CEACAM5 and CEACAM6, and the change of the binding capacity of anti-CD43 antibody by the glycosylation change of CD43 epitope by kifunensine and fucosidase was tested.

After rCEACAM5-hFC (Sinobiologics, Cat. No: 11077-H03H-50) and rCEACAM6-hFC (DinonA inc.) recombinant proteins were added to maxisorp ELISA plate at 200 μL per well and reacted at 37° C. for 1 hour, thereby blocking. IgG1, YG5, DFT-1, 9A6, or 8F5 monoclonal antibodies (8F5: Biomaterials, 2015 October, 67, 32-41, 9A6: Santa-Cruz Biotechnology, Cat. No: sc-59899) were added at 100 ng per well, respectively, to the well coated with rCEACAM5-hFC and rCEACAM6-hFC proteins and reacted at 37° C. for 1 hour, and then washed with PBS, to remove unbound antibodies. Then, goat anti-mouse IgG-HRP (Jackson) was diluted and added, and it was reacted for 30 min and then washed with PBS, and TMB solution was added at 50 μL per well and it was reacted for 10 min, and then 50 μL of sulfuric acid was added to ceasing the reaction and the absorbance at 450 nm was measured.

Figure 16:
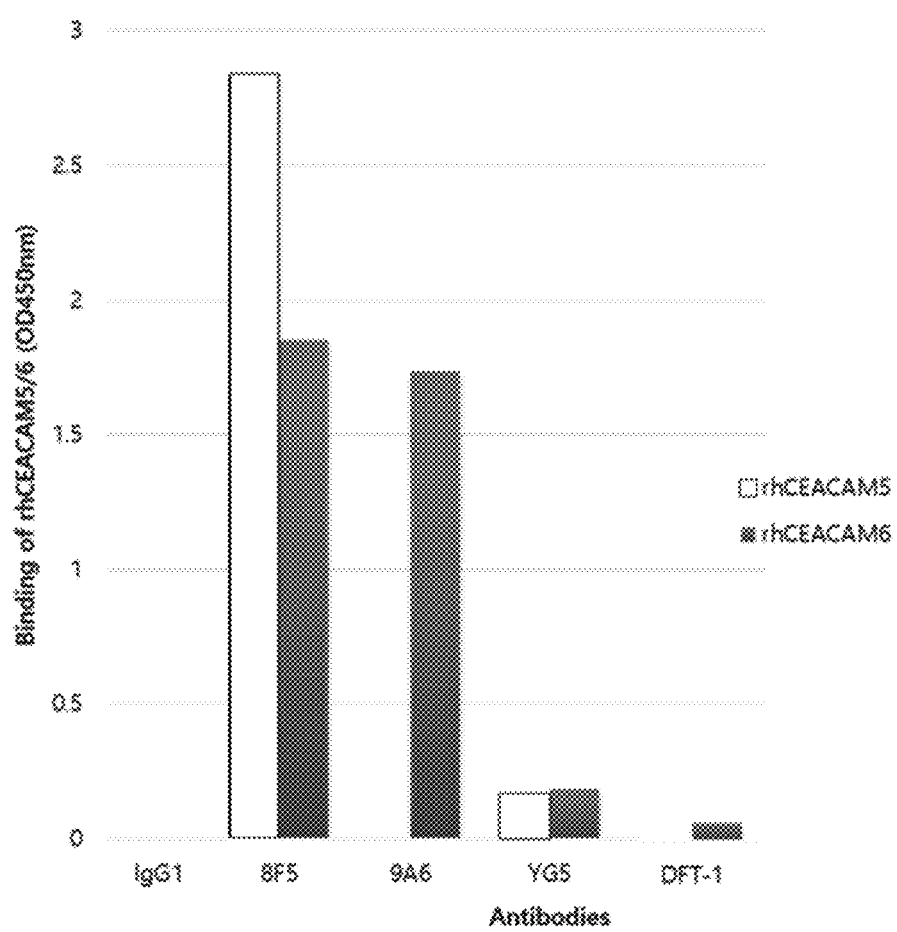
FIG. 16 is the graph showing the result of measuring the cross-reactivity of anti-CD43 antibodies to the recombinant CEACAM5 and CEACAM6.

The obtained result was shown in FIG. 16. As shown in FIG. 16, it was demonstrated that the anti-CD43 antibody (YG5) had little reactivity to the recombinant proteins CEACAM5 and CEACAM6.

In addition, there was no the change of binding capacity of anti-CD43 antibody to the fucosidase and kifunensine treated CEM7 cell (cell sorted as having 50% or more increased level of cell surface expression of CD43 compared to the original cell by single cell culturing CCRF-CEM cell obtained from ATCC (CCL-119); same hereinafter). The result showed that the antibody provided in the present invention (for example, (anti-CD43 antibody (YG5)) kept the binding capacity with CD43 even under the condition in which the sugar condition of CD43 was changed, and this means that the epitope of antibody was not independent to sugar. On the other hand, the conventional CD43 antibody, 5F1 was known to show the sugar-dependent epitope binding capacity, and thereby it was demonstrated that the antibody provided in the present invention had discrimination from the conventional antibody.

Example 13: 3-Dimensional Culture Experiment of Stomach Cancer Cell (Tumor Sphere Assay)

The stomach cancer cell line, NCI-N87 cell was prepared to be 80~90% of 150 mm dish before the experiment. NCI-N87 cell was suspended by treating 1×Trypsin•EDTA and then washed. The prepared NCI-N87 cell was resuspended with media (DMEM/F12 (GIBCO), B27 (Invitrogen), EGF & bFGF (Invitrogen)) and then aliquoted with $1*10^5/2$ ml in 6 well (ultra-low attached plate), and then cultured in a 37° C. $CO_2$ incubator for 5 days. After photographing cells of each well with the optical microscope, cells were separated to single cells by 1×TE 200 μL and then washed with PBS. 1/50 of the normal mouse serum was added into cells, and it was blocked at 4° C. for 10 min. Subsequently, cells were aliquoted into flow cytometry tubes at 100 μL each, and the anti-CD44 antibody (eBioscience, Cat. No: 17-0441-82) and anti-CD43 antibody (YG5, DFT-1) were added at 10 μL, 1 μL, respectively, and it was reacted at 4° C. for 25 min. After washing by the same method as above, 1% (w/v) paraform aldehyde was added per sample to fix cells, and then the flow cytometry was carried out.

Figure 17A:
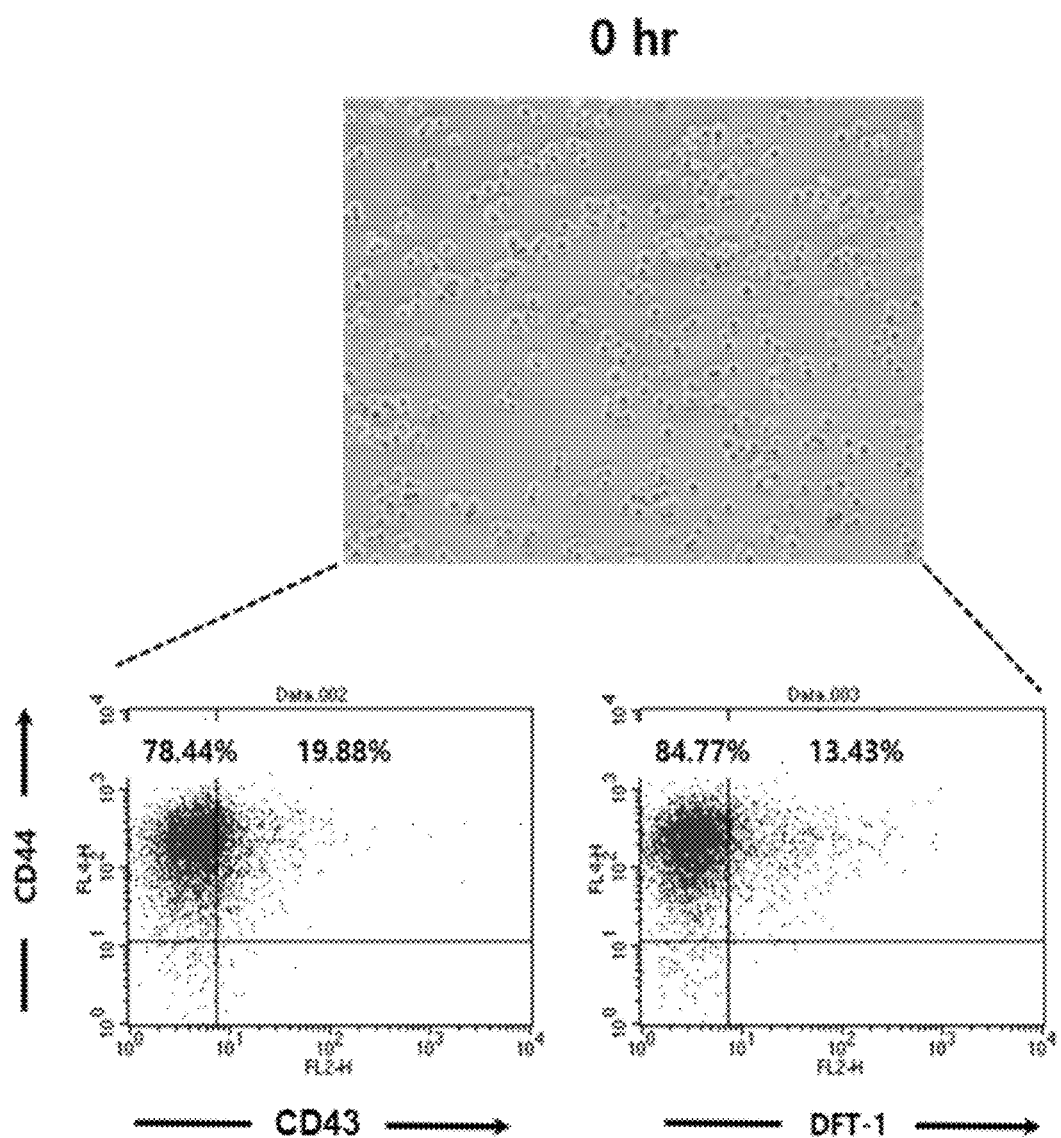
FIGS. 17A-17B are the graphs showing the degree of expression of CD43 epitope in the tumor stem cell (tumor sphere).
Figure 17B:
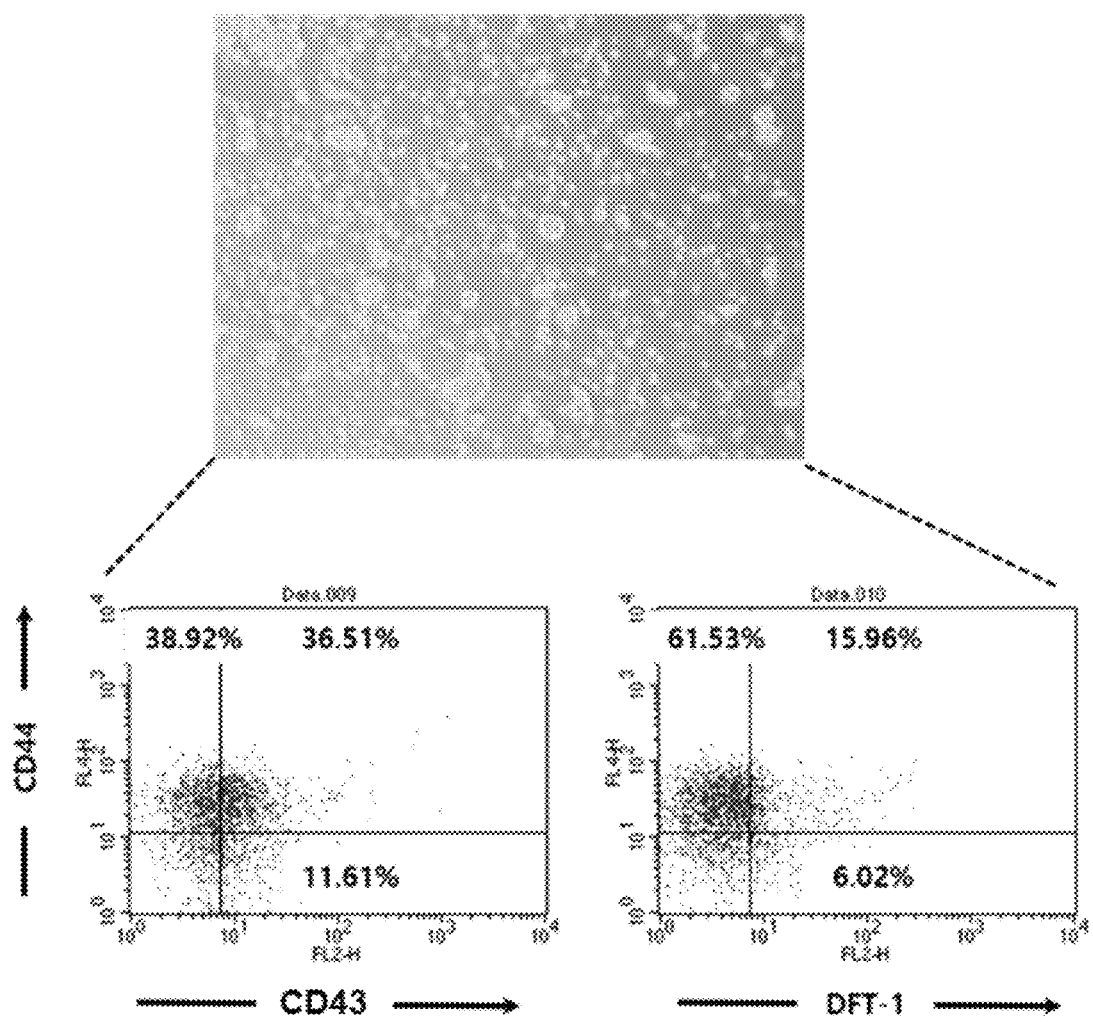

The obtained result was shown in FIGS. 17A (result at culturing) and 17B (result after culturing for 5 days). The top of each figure was the microscopic image and the bottom was the graph showing the result of flow cytometry. As shown in FIGS. 17A and 17B, the increment of CD44 and CD43 double positive cells was confirmed in NCI-B87 tumor sphere cultured for 5 days by using flow cytometry, and it was confirmed that the tumor colony was formed over time. In addition, it was confirmed that CD43 expression was increased by forming the tumor sphere. This result showed that CD43 expression was increased specifically in tumor stem cells.

Example 14: ELISA Protocol Measuring Modified Cell Binding Capacity by Using Suspended Cells in Suspension This analysis was designed as a pilot research to confirm binding capacity of scFv or IgG to suspended cells in suspension by using ELISA experiment with reduced the background signal in the poly-D-lysine plate.

Method:
1. Step of collecting cells.
  a. Cells were pelleted by putting cells in 50 mL falcon tube and centrifuging at 500×g for 5 min (pelleting);
  b. Cells were pelleted by washing the obtained cell pellets with 10 ml PBS once and centrifuging at 500×g for 5 min (pelleting);
  c. Cells were counted after resuspending cells with 1 mL PBS (counting cells);
  d. Cells were diluted with blocking buffer (PBS+3% FCS) (cell dilution concentration: $5×10^5$ cell/well ($10×10^6$ cells/mL));
  e. Cell stock 50 μL per well was added to the V-bottomed 96-well plate.
2. 50 μL per well of cytoplasmic extract (anti-CD43 scFv) or IgG1 (desired final concentration×2-fold concentrated stock; for example, when 25 μg/mL of final concentration was desired, preparing 50 μg/mL stock) was added (according to Layout analysis, prepared in duplicate or triplicate). The samples were mixed by pipetting 4 times carefully.
3. They were cultured at the room temperature for 1 hour.
4. They were centrifuged at 500×g for 5 min, to pellet cells.
5. The supernatant was removed by turning the plate inside out or aspiration.
6. Cells were washed with 200 μL blocking buffer and samples were mixed by pipetting 4 times.
7. Cells were pelleted by centrifugation at 500×g for 5 min.
8. The supernatant was removed by turning the plate inside out carefully or aspiration.
9. 100 μL of anti-Flag HRP-conjugated antibody diluted by 1:1,500 in the blocking buffer was added to cell pellets and resuspended carefully, and cultured at the room temperature for 30 min.
10. Cells were pelleted by centrifugation at 500×g for 5 min.
11. The supernatant was removed by turning the plate inside out carefully or aspiration.

12. Cells were carefully washed by adding 200 µL blocking buffer and the obtained samples were mixed by pipetting 4 times.

13. Cells were pelleted by centrifugation at 500×g for 5 min.

14. The supernatant was removed by turning the plate inside out carefully or aspiration.

15. Cells were carefully washed by adding 200 µL blocking buffer and the obtained samples were mixed by pipetting 4 times.

16. Cells were pelleted by centrifugation at 500×g for 5 min.

17. Cells were carefully resuspended to SureBlue™ TMB Microwell Peroxidase substrate 80 µL and cultured at the room temperature for 5 min, and then the reaction was ceased by 1 M HCl.

18. Samples of 100 µL each were transferred to the standard 96-well plate.

19. The plate (absorbance) at 450 nm was read.

Example 15: FACS Protocol Measuring Modified Cell Binding Capacity by Using Suspended Cells in Suspension This analysis was designed as another method for FCAS experiment to reduce the background signal in the poly-D-lysine plate and evaluate the binding capacity of scFv or IgG.

Method:
1. Flow cytometry:
  a. Step of collecting cell:
    i. Cells were pelleted in 50 mL falcon tube by centrifuging at 500×g for 5 min (pelleting);
    ii. Cells were pelleted by washing the obtained cell pellets with 10 mL PBS once and centrifuging at 500×g for 5 min (pelleting);
    iii. Cells were counted after resuspending cells with 1 mL PBS (counting cells);
    iv. Cells were diluted with blocking buffer (PBS+3% FCS) (cell dilution concentration: $5×10^5$ cell/well ($10×10^6$ cells/mL));
    v. Cell stock 50 µL per well was added to the V-bottomed 96-well plates. 2. According to Layout analysis, cells were added with 50 µL per well of IgG in duplicate or triplicate (desired final concentration×2-fold stock; for example, when 25 µg/mL of final concentration was desired, preparing 50 µg/ml stock), the obtained samples were mixed by pipetting 4 times.
3. They were incubated at the room temperature for 30 min. 4. Blocking buffer 200 µL was added.
5. Cells were pelleted by centrifugation at 500×g for 5 min.
6. The supernatant was removed by turning the plate inside out carefully or aspiration.
7. 200 µL blocking buffer was added and cells were softly washed out, and then evenly mixed about 4 times by using the pipet.
8. Cells were pelleted by centrifugation at 500×g for 5 min.
9. Medium was removed.
10. Goat anti-human IgG Alexa Fluor 488 200 µL diluted by 1:20 in the blocking buffer was added to cell pellets and they were carefully resuspended, and left on ice for 1 hour where the light was blocked.
11. Cells were pelleted by centrifugation at 500×g for 5 min.
12. Medium was removed.

13. 200 µL blocking buffer was added and cells were softly washed out, and then evenly mixed by using the pipet about 4 times.
14. Cells were pelleted by centrifugation at 500×g for 5 min.
15. Blocking buffer 200 µL was added and cells were softly resuspended.
16. The plate was read by using flow cytometer.

Example 16: scFv Flow Cytometry Using Soluble scFv Preparations

The present example tested the level of binding of scFv to CEM7 and U937 cell (ATCC® CRL1593.2™), and used soluble scFvs expressed in *E. coli* periplasm, and designed for scFv cell binding analysis by flow cytometry.

Method:
Day 1: Clone Inoculation
1. Starter culture plate:
  a. 200 µL 2YT (2×yeast extract)+5% (w/v) glucose+ amphicilin was filled in the 96-well culture plate.
  b. scFvs which could be the comparison group together with desired clones (anti-CD43 (mJL1) scFv coding DNA: SEQ ID NO: 49; Sh741-112 scFv coding DNA: SEQ ID NO: 51; Sh145-112 scFv coding DNA: SEQ ID NO: 53; Sh146-112: SEQ ID NO: 55; or Sh434-112 scFv coding DNA: SEQ ID NO: 57) were inoculated to the well.
2. They were cultured overnight as shaking them under the condition of 650 rpm, 37° C.

Day 2: Expression of scFvs
Periplasmic Extract Cultures:
3. According to the final use of inoculate expression plates: periplasmic extract, one or more wells per sample could be inoculated.
  a. 96 deep-well plate was filled with 1.0 mL/well of 2YT+Amp (no glucose).
  b. After diluting the starter cultures to have 0.1 value at $OD_{600}$, they were inoculated to the 96 well plate. They were cultured as shaking under the condition of 650 rpm, 30° C. for 2-4 hours. Periodically, the turbidity at $OD_{600}$ was measured by collecting the samples. Cells were raised to have $OD_{600}$ value between 0.7 and 1.0.
4. Induction of scFv expression in expression plates:
  a. To induce the expression of periplasmic extract culture, 100 µL 2YT+Amp in which IPTG (diluting stock IPTG by 1:100) was added to the expression plates each.
  b. They were cultured over night shaking under the condition of 650 rpm and 22° C.

Day 3: Preparation of Periplasmic Extract and Flow Cytometry
Periplasmic Extractions:
5. Preparation of periplasmic extract:
  a. Cells were pelleted by centrifugation at 2000×g for 10 min.
  b. The supernatant in the expression plate was dusted to the container containing a bleaching agent, and the medium left in the plate was removed by putting it up on the paper towel.
  c. 75 µL cold PPB (Potassium Phosphate Buffer)+protease inhibitor (1 tablet per 50 mL; complete; Roche, Cat. No: 04693116001) was put into each well, and resuspended by pipetting 4 times, and then cultured under the condition of 1000 rpm and 4° C. for 10 min.
  d. was put into each well, and resuspended by pipetting 4 times, and then cultured under the condition of 1000 rpm and 4° C. for 1 hour under shaking.
  e. Plate was centrifuged at 3000×g for 10 min.

f. Periplasmic extracts (approximately 270 μL) was transferred and put filter into the stack (ensure A1 orientation corresponds).
  i. Top part: 1.2 μm 96 well filter plate
  ii. Middle part: 100 K 96 well filter plate
  iii. Bottom part: 96-well, flat based standard plate.
g. Plate was centrifuged at 4000 rpm for 20 min.
h. (If necessary) for preparing flow cytometry analysis, samples for each clone were collected.
6. Flow Cytometry:
  a. scFv samples: use of periplasmic extracts
  b. collection of cells:
    i. Cells were pelleted by putting into 50 mL falcon tube and centrifuging at 500×g for 5 min (pelleting).
    ii. Cells were pelted by washing cell pellets once by using 10 mL PBS and centrifuging at 500×g for 5 min.
    iii. Cells were counted, after resuspending cells in 1 mL PBS (counting cells).
    iv. Cells were diluted with $0.5 \times 10^5$ cells/well ($2.5 \times 10^6$ cells/mL).
    v. 20 μL cell stock per well was added to V-bottomed 96-well plates.
  c. 20 μL per well of periplasmic extract was added in duplicate (scFv).
And samples were mixed softly by pipetting about 4 times.
  d. They were left at the room temperature for 30 min.
  e. 180 μL Blocking buffer was added.
  f. Cells were pelleted by centrifugation at 500×g for 5 min.
  g. The supernatant was removed by turning the plate inside out or aspiration.
  h. 200 μL blocking buffer was added and cells were softly washed out, and then evenly mixed by pipetting about 4 times.
  i. Cells were pelleted by centrifugation at 500×g for 5 min.
  j. Medium was removed.
  k. Cells were softly resuspended by adding 50 μL of 5 μg/mL anti-Flag PE-conjugated antibody (BioLegend, Cat. No: 637310) to the readily prepared binding buffer. The plates should be protected from light at maximum, since the antibody was sensitive to light. They were left on ice for 30 min under the condition of protection from light.
  l. Cells were pelleted by centrifugation at 500×g for 5 min.
  m. Medium was removed.
  n. 200 μL blocking buffer was added and cells were softly washed out, and then evenly mixed by pipetting about 4 times.
  o. Cells were pelleted by centrifugation at 500×g for 5 min.
  p. 200 μL blocking buffer was added and cells were softly resuspended.
  q. The plate was read by using Guava flow cytometer (Merckmillipore). The flow cytometry should be prepared in advance to recognize the yellow fluorescence.

Example 17: Functional Properties of Murine Anti-CD43 Antibody being Template

The present experiment was performed to demonstrate the target epitope proper for antibody treatment (JL-1). In the present experiment, the mouse anti-CD43 monoclonal antibody binding the epitope (heavy chain: SEQ ID NO: 34; heavy chain coding DNA: SEQ ID NO: 33; heavy chain expression vector (pTT5 based): SEQ ID NO: 35; light chain: SEQ ID NO: 37, light chain coding DNA: SEQ ID NO: 36; light chain expression vector (pTT5 based): SEQ ID NO: 37) was used.

It was confirmed that the significant amount of antigen was not sheded from the cell, when JL-1 antigen (CD43) was cultured at 37° C. for 4 hours. It was demonstrated that there was no large difference in the aspect of size, when the anti-CD43 antibody mixed in the buffer and the anti-CD43 antibody mixed in the supernatant of the actual Molt-4 (CD43+ acute lymphocytic leukemia cell line; ATCC, CRL-1582) or HL-60 (ATCC) were compared by western blot analysis.

In addition, it was confirmed that the amount of JL-1 antigen (CD43) circulating in the serum of normal human was not sufficient to significantly interrupt the binding of anti-CD43 antibody to the target. The effect of 50% human serum to the anti-CD43 antibody binding to the leukemia cell was evaluated in vitro (measuring IF (immunofluorescence) reactivity). The obtained result was shown in table 2.

TABLE 2

Effect of normal human serum for binding of JL-1(CD43) to leukemia cell

| Cell line | JL-1 (CD43) ug/mL | IF reactivity | |
|---|---|---|---|
| | | No human serum | 50% human serum |
| Molt-4 | 50 | ++ | ND* |
| " | 25 | ++ | ND |
| " | 12.5 | ++ | ++ |
| " | 6.25 | +/++ | +/++ |
| HL-60 | 50 | + | ND |
| " | 25 | + | ND |
| " | 12.5 | + | +/− |
| " | 6.25 | +/− | +/− |

*ND, Not determined

As shown in the table 2, it was confirmed that the serum did not interrupt the binding of the anti-CD43 antibody to Molt-4 cell or HL-60 cell.

In addition, it was tested that the naked anti-CD43 antibody which was not conjugated had no direct cytotoxic effect to the isolated target cell. For this, CD43+ CEM7 cell (represented as CEM7-high antigen) and CCRF-CEM cell (original CEM cell (ATCC); represented as CEM7-medium antigen) were added to 96-well plate in amount of 40,000 cells/well, respectively, and the mouse CD43 antibody (mouse anti-CD43 monoclonal antibody prepared in advance) was serially diluted and treated, and the cytotoxicity was determined by using Cell Titer Glo (Promega™) at the 3rd day of culturing. The same experiment to H9K cell (H9K-low antigen) expressing CD43 at the low concentration was carried out for comparison.

Figure 18:
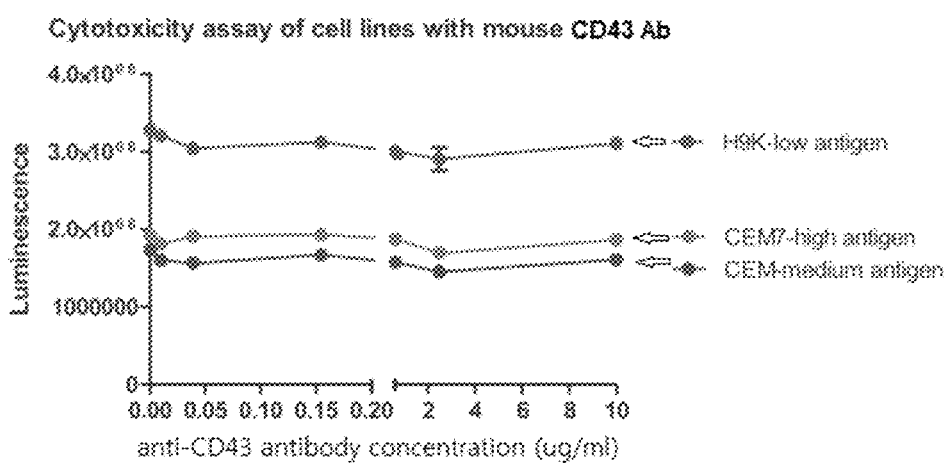
FIG. 18 is the graph showing the cytotoxicity of anti-CD43 antibody to CEM7 or CCRF-CEM cell (low CD43 epitope expression), and shows that the anti-CD43 antibody has not direct cytotoxicity.

The obtained result was shown in FIG. 18. As shown in FIG. 18, it was demonstrated that the mouse CD43 antibody did not exhibit the cytotoxicity to CD43+ CEM7 (CEM7-high antigen) or CCRF-CEM cell (CEM-medium antigen; CD43 was less expressed, compared to CEM7 cell).

The cell lines such as CEM7, CCRRF-CEM, Nalm6 (ATCC, CRL-3273) and HL-60 (ATCC, CCL-240), etc. exhibited individually different JL-1 antigen (CD43) expression level (from high expression to low expression in the order described). The saporin-conjugated anti-CD43 antibody (refer to the example 3-1 for construction of conjugate; the anti-CD43 antibody was the mouse anti-CD43 monoclonal antibody prepared in advance) or isotype control was treated at the diluted concentration from 20 μg/mL to each cell (20,000 cells), and the cell viability was measured by using Cell Titer Glom at the 3rd day of culturing. The mouse IgG1 was used as the isotype control used for the comparison.

Figure 19:
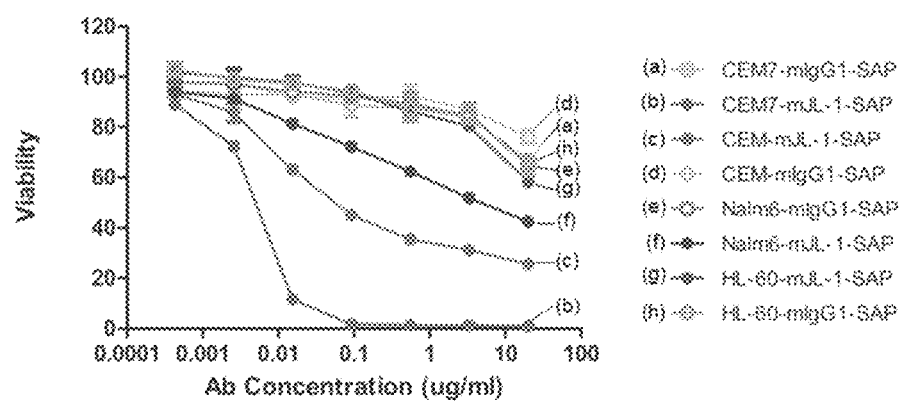
FIG. 19 is the graph showing the viability of target cell treated with the toxin-adhered anti-JL-1 antibody (saporin conjugated anti-JL-1 antibody), and show that the apoptosis is occurred by the saporin conjugated anti-JL-1 antibody.

The obtained result was shown in FIG. 19. As shown in FIG. 19, it was observed that the cell viability of CEM7 was decreased the largest, when the saporin-conjugate anti-CD43 antibody (represented as mJL-1 in FIG. 19) was treated, and CEM and NALM6 cells were followed. The lowest cytotoxicity (the lowest cell viability reduction) in HL-60 which did not express the target was observed. As FIG. 19, the toxin-linked anti-CD43 antibody induced the death of target cell. The anti-CD43 antibody-treated CEM7, CCRF-CEM, NALM6 and HL-60 cells exhibited the activity to effectively kill cells, compared to the expression level of antigen present in cells. Saporin displayed the cytotoxic effect only in the case of induced inside the cell.

The internalization of anti-CD43 antibody was tested. The mouse anti-CD43 antibody (the mouse anti-CD43 monoclonal antibody prepared in advance) was treated to cells (CEM7) in the refrigerated condition for 30 min, and transferred to the condition of 37° C., and then $10^6$ cells were collected at the respective time represented in the X axis of FIG. 20, and the anti-mouse IgG-PE second antibody (Santa cruz biotechnology, Cat. No: SC3738) was treated at the refrigerated temperature for 10 min, and cells were washed and fixed, and then analyzed by flow cytometry (refer to example 15).

Figure 20:
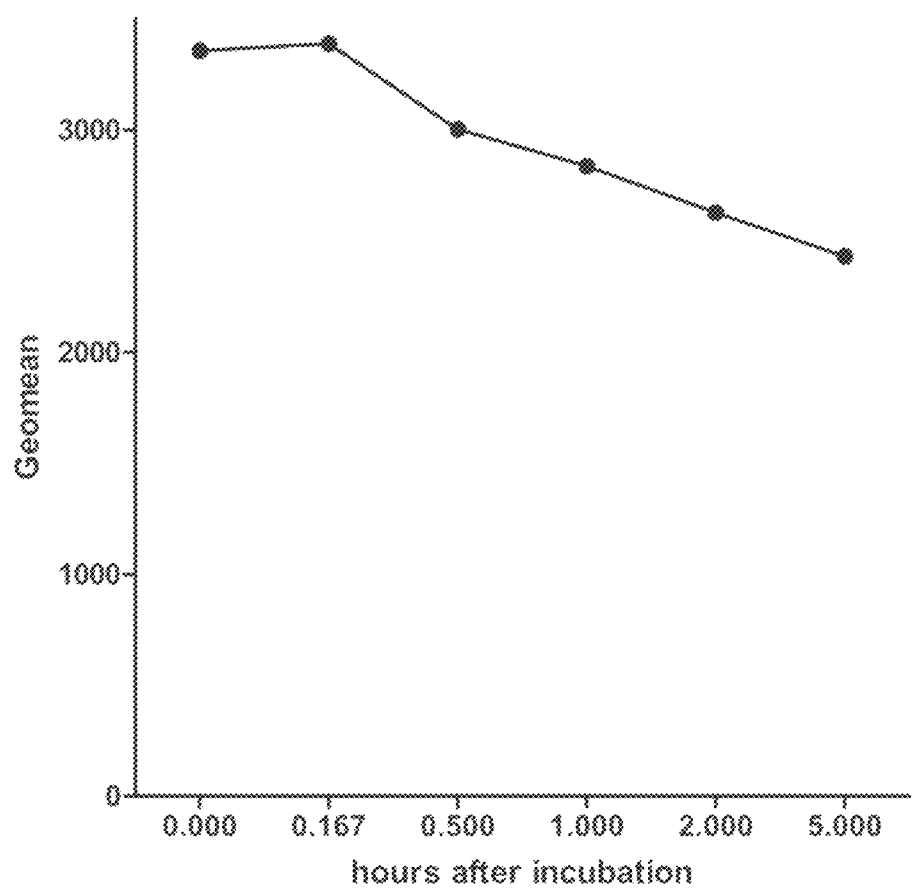
FIG. 20 is the graph showing the internalization phenomenon of anti-JL-1 antibody (anti-CD43 antibody) (rodent, human antibodies both) in the apoptosis test described in FIG. 19, and the result obtained by analysis with a flow cytometry apparatus. For this, the mouse JL-1 antibody is treated to the cell in refrigeration for 30 min and moved at 37° C. condition, and then $10^6$ cells are collected at each time represented in X axis of the graph and the anti-mouse IgG-PE second antibody is treated at the refrigerated temperature for 10 min, and cells are washed and fixed.

The obtained result was shown in FIG. 20. As shown in FIG. 20, the anti-CD43 antibody entered the cell when bound to antigen, and the corresponding data showed the level that the antibody on the cell surface entered the cell and disappeared over time. The data demonstrated the internalization of anti-CD43 antibody (both of mouse antibody and humanized antibody) for apoptosis analysis, as referred in FIG. 19.

Figure 21:
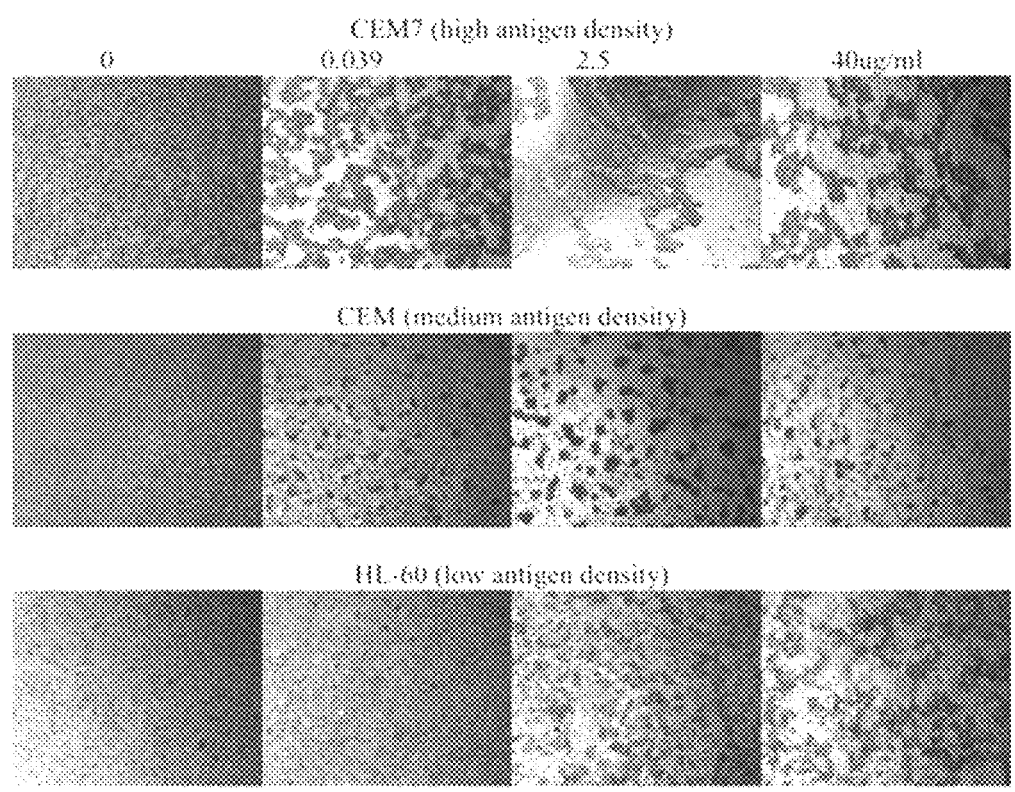
FIG. 21 is the image showing the homotypic aggregation phenomenon induced by the anti-JL-1 antibody in the cell expressing the CD43 antigen. The image is obtained by taking microscopic photographs according to the arranged time, after treating the anti-JI-1 antibody to 300,000 cells respectively at the start concentration of 40 pg/mL and culturing them under the condition of 37° C. and 5% $CO_2$.

On the other hand, the homotypic aggregation phenomenon induced by the anti-CD43 antibody in cells expressing antigen was tested. For this, the anti-CD43 antibody (mouse anti-CD43 monoclonal antibody prepared in advance) was treated at the start concentration of 40 μg/mL to 300,000 cells (CEM7, CCRRF-CEM, or HL-60) and cultured in the condition of 37° C., 5% $CO_2$, and then images were obtained by taking microscopic photographs at the arranged time (2 hours after antibody treatment). The obtained image was shown in FIG. 21. FIG. 21 was the image showing the homotypic aggregation phenomenon induced by the anti-CD43 antibody (represented as anti-JL-1 antibody), indicating that the anti-CD43 antibody induced the homotypic aggregation of cell expressing CD43 in vitro and the level of homotypic aggregation was related to the expression level of antigen (CD43).

In addition, the CD43 expression in human normal bone marrow cells was tested. The monocytes of normal bone marrow were stained with mouse anti-CD43 antibody (mouse anti-CD43 monoclonal antibody prepared in advance), and then stained with goat-anti-mouse IgG F(ab)2-PE (Jackson, Cat. No: 115-035-072), and was observed by the method disclosed in the example 15.

Figure 22:
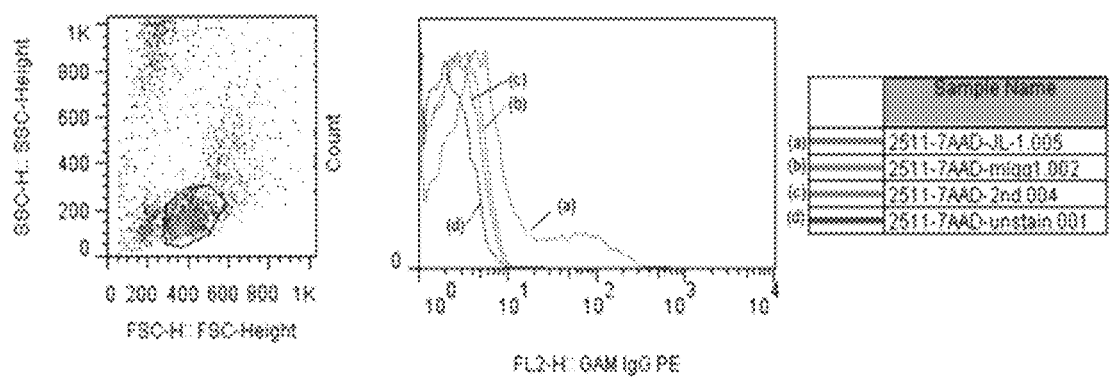
FIG. 22 is the result showing the low and heterogeneous JL-1 antigen expressing in a normal bone marrow cell. Monocytes of normal bone marrow are stained with mouse anti-JL-1 antibody, and then stained with goat-anti-mouse IgG F(ab)2-PE, and observed. Histogram overlay is represented by limiting to lymphocytes.

The obtained result was shown in FIG. 22. In FIG. 22, the histogram overlay was represented the limited lymphocytes. As shown in FIG. 22, low level of heterogeneous CD43 expression was confirmed in various normal bone marrow samples, by anti-CD43 antibody (represented as JL1) staining, and it also confirmed in several peripheral blood cells. In other words, the result shows low level of heterogeneous CD43 expression in normal bone marrow cells.

On the other hand, CD43 expression was measured in CD34+CD38− cell (hemopoietic cell sorted as CD43 expression and CD38 non-expression cell by the test with FACS; same hereinafter) from various human normal bone marrow samples (Seoul National University Hospital) by flow cytometry, and it was confirmed that the CD43 protein expression was lacked in hematopoietic stem cell and precursor cell that formed colony in bone marrow. The method of confirmation was simply described as follows: The umbilical cord hematopoietic stem cells were inoculated to 30 NSG mice (NOD/SCID×common g chain deficiency) at 0 day. After 12 weeks, PBL (Peripheral Blood Lymphocyte) of all mice was analyzed with the finally differentiated immune cell. The immune system of all mice used in the test was ingrafted, and the anti-CD43 antibody (mouse anti-CD43 monoclonal antibody prepared in advance)-toxin (saporin) conjugate or vehicle (PBS) was administered for 4 weeks. At 4 weeks after the treatment, the presence of human immune cells were analyzed in immunized animal. For comparison, the same test was performed using the mouse IgG1-toxin (saporin) conjugate instead of anti-CD43 antibody.

The obtained result was shown in the following Table 3:

TABLE 3

| | % of viable cells (SD) | | | |
|---|---|---|---|---|
| | B cells | T cells | Monocytes | PMNs |
| 16 weeks PBL | | | | |
| JL1-Toxin | 32 (11) | 16 (4) | 2.9 (2) | 1.7 (1.2) |
| Isotype-Toxin | 31 (5) | 17 (6) | 4.5 (4) | 2.1 (1.0) |
| Vehicle | 28 (8) | 20 (9) | 2.8 (1) | 1.4 (0.4) |
| 16 weeks LN | | | | |
| JL1-Toxin | 36 (15) | 31 (11) | 0.3 (0.8) | 1.6 (1.0) |
| Isotype-Toxin | 38 (10) | 39 (10) | 0.1 (0.2) | 0.9 (0.4) |
| Vehicle | 34 (13) | 37 (15) | 0.2 (0.3) | 1.3 (1.6) |

(In the table, JL1 represents CD43; PMN: polymorphonuclear leukocyte; LN: lymph node)

As shown in the table 3, when NSG mice were engrafted with normal human Hematopoietic stem cells (HSCs) obtained from the cord blood stem cell and the anti-CD43 antibody-toxin (saporin) conjugate was treated for 4 weeks, any loss of hematopoietic section was not observed. This result showed that the anti-CD43 antibody-toxin (saporin) conjugate did not kill the hematopoietic stem cell or intermediate progenitor cell.

The immunohistochemical staining (IHC) was performed by using the mouse anti-CD43 antibody in various human normal tissues, and the obtained result was shown in the following table 4.

TABLE 4

| Tissue type | # positive | Intensity |
|---|---|---|
| Cerebellum | 0/3 | |
| Adrenal gland | 0/3 | |
| Ovary | 0/3 | |
| Pancreas | 0 3 | |
| Parathyroid gland | 0/3 | |
| Pituitary gland | 0/3 | |
| Testis | 0/3 | |
| Thyroid | 0/3 | |
| Breast | 0/3 | |
| Spleen | 0/3 | |
| Tonsil | 0/3 | |

TABLE 4-continued

| Tissue type | # positive | Intensity |
| --- | --- | --- |
| Thymus gland | 3/3 | +++ |
| Bone marrow | 0 3 | |
| Lung | 0/3 | |
| Heart | 0/3 | |
| Esophagus | 0/3 | |
| Stomach | 0/3 | |
| Sm. Intestine* | 0/3 | |
| Colon* | 0/3 | |
| Liver | 0/3 | |
| Salivary gland | 0/3 | |
| Kidney | 0/3 | |
| Prostate | 0/3 | |

*mucin staining

As shown in the Table 4, CD43-specific staining was not found in any other tissues than the thymus.

Figure 23:
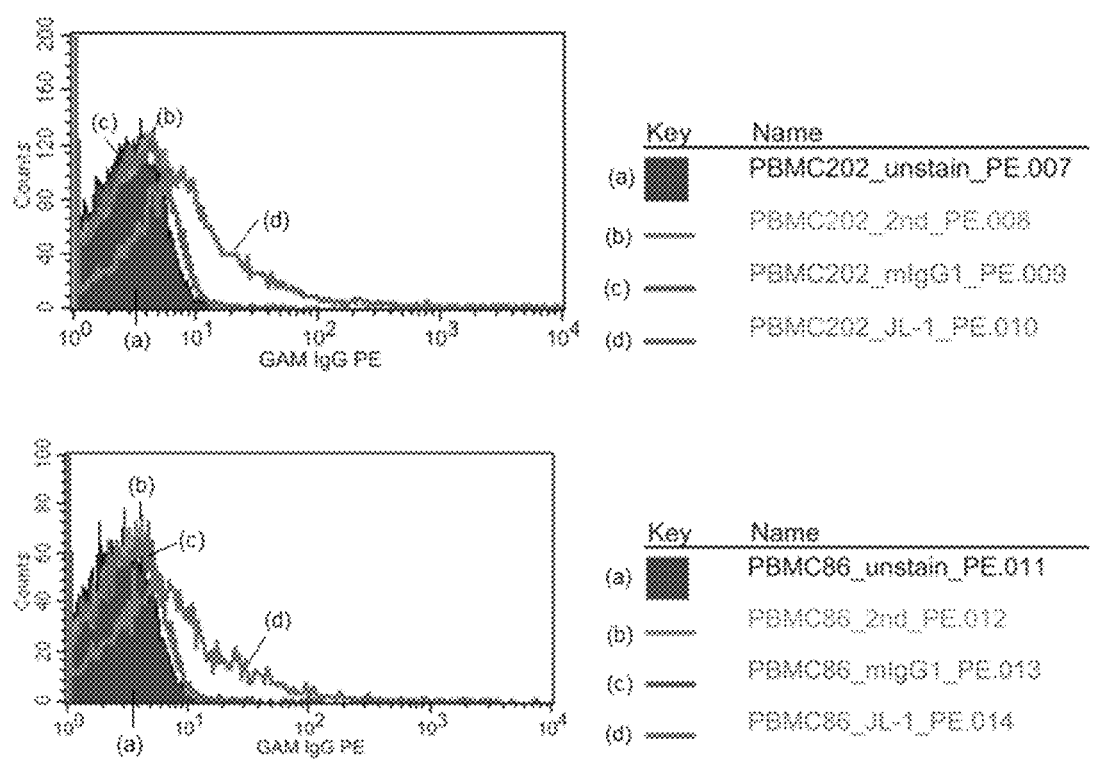
FIG. 23 shows the expression rate of JL-1 antigen in a peripheral blood cell. Two normal human PBMC samples were stained with mouse anti-human JL-1 (blue line: (d)), and low expression of JL1 antigen was observed

The expression rate of CD43 antigen was measured by staining two normal human PBMCs (peripheral blood mononuclear cells) with mouse anti-human CD43 (represented as JL-1: (d)) (refer to example 15 (FACS), and result was shown in FIG. 23. As shown in FIG. 23, the low expression rate of CD43 was confirmed.

Figure 24:
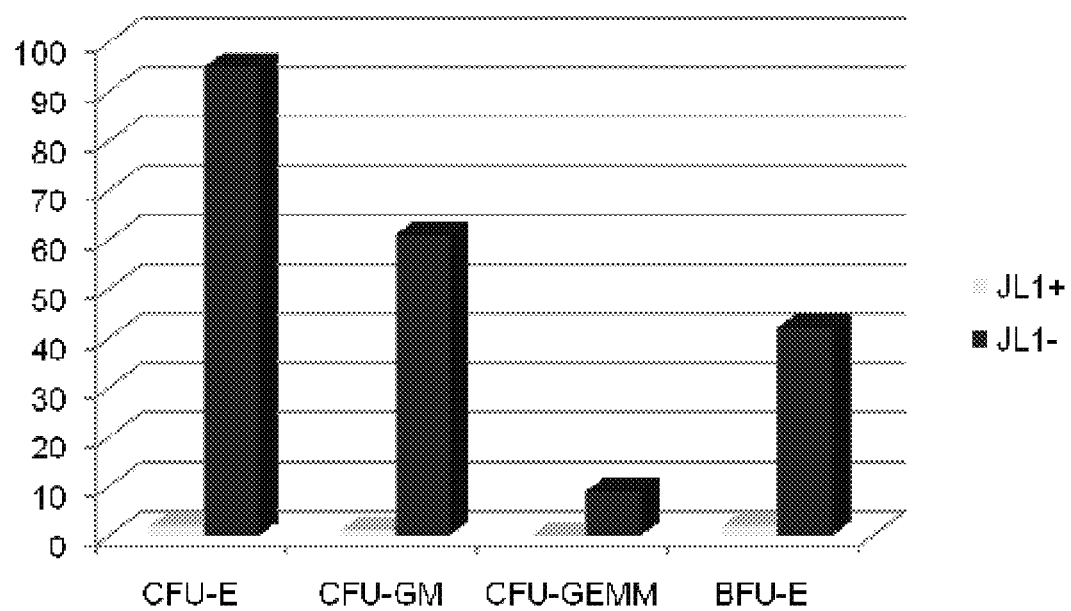
FIG. 24 is the graph showing the result of measuring the level of colony formation of bone marrow subsets of the case of treating anti-JL-1 antibody linked with saporin to a normal bone marrow cell in pretreatment (JL1+) and the case of no treating. It is confirmed that the colony of bone marrow subsets is not formed in case of pre-treating saporin-conjugated anti-JL-1 antibody to a normal bone marrow cell. The result was measured after isolating bone marrow and harvesting white blood cells, and isolating and harvesting CD34+ cells by classifying into JL-1 positive and negative, and putting harvested cells into MethoCult with a cytokine.

Saporin-conjugated mouse anti-CD43 antibody (10 µL/mL) was treated to normal bone marrow cell in advance (JL1+) and the case of not treating (JL1−), and the colony formation level of these bone marrow subsets was measured. The bone marrow was isolated from human white blood cells, and CD34+ cells were isolated and harvested by dividing into JL-1 (CD43) positive and negative. Harvested cells were then put into Methocult together with the cytokine and the colony formation was measured. The obtained result was shown in FIG. 24. As shown in FIG. 24, it was confirmed that the colony of bone marrow subsets were not formed in case of treating saporin-conjugated mouse anti-CD43 antibody (10 µL/mL) in advance (JL1+).

Figure 25A:
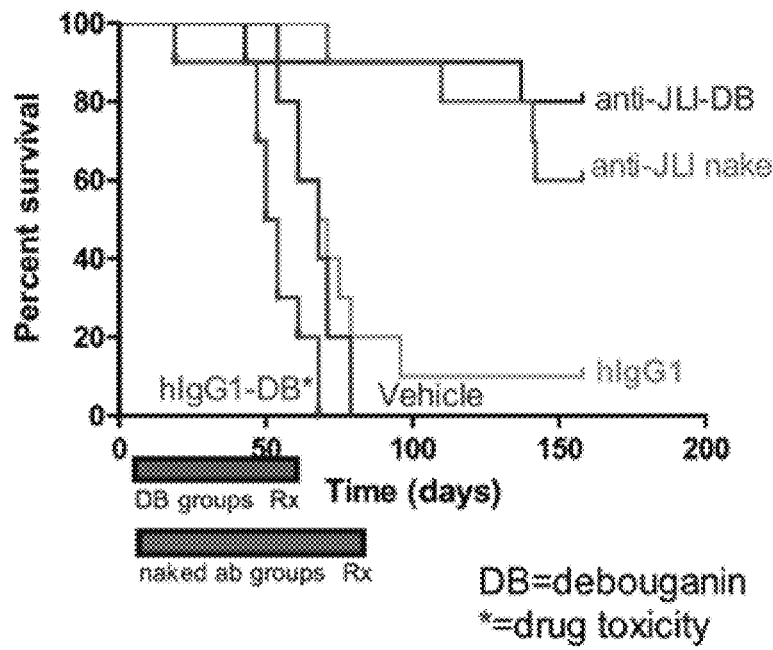
Figure 25B:
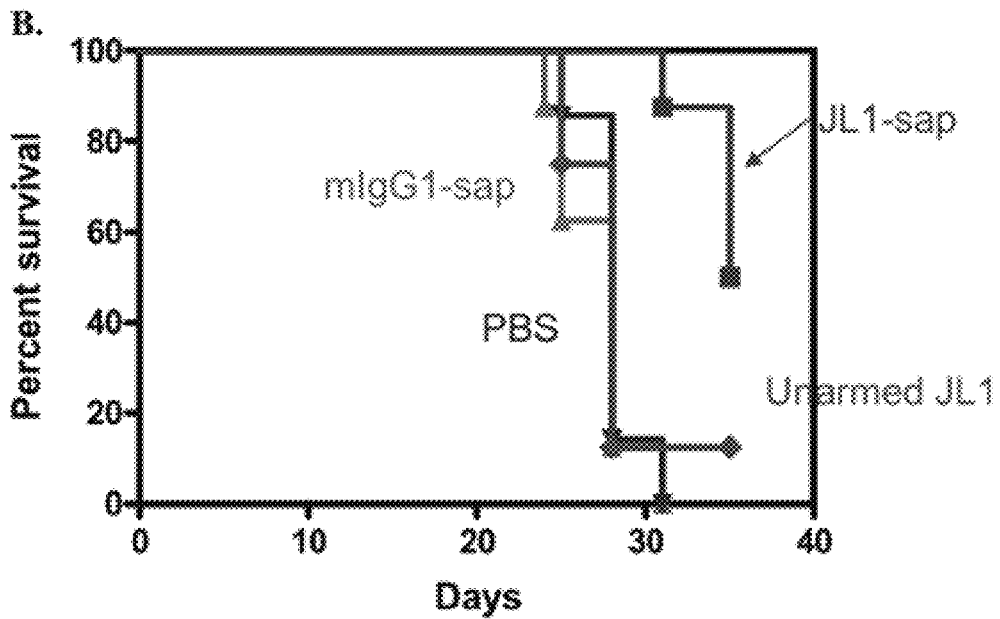

On the other hand, the therapeutic effect of the anti-CD43 antibody itself (naked) and toxin-bound anti-CD43 antibody-toxin (debouganin) conjugate was tested in the leukemia ALL xenograft mouse model using the cell line (acute leukemia mouse model obtained by grafting CEM7 cell to mouse). The mouse anti-CD43 monoclonal antibody prepared in advance as the anti-CD43 antibody was used. The obtained result was shown in FIGS. 25A-25B. In FIGS. 25A-25B, the anti-CD43 antibody was represented as JL1. In FIGS. 25A-25B, (25A) showed the result in CEM7 leukemia model and (25B) showed the result in NALM-6 model (Cell line: NALM6 (B-ALL)), respectively, and the test was performed under the following condition: Mice: NOD-SCID (8/group); inoculation: $10^7$ cells at 0 day; administration: 15 µg/injection+100 µg bulk IgG i.v. 1x/week starting day 8; end point: paralysis state. As shown in FIGS. 25A-25B, when the naked (non-conjugate) anti-CD43 antibody was treated to CEM7 or NALM-6 cell-inoculated ALL xenograft model mouse, the disease was not occurred or delayed.

Figure 26:
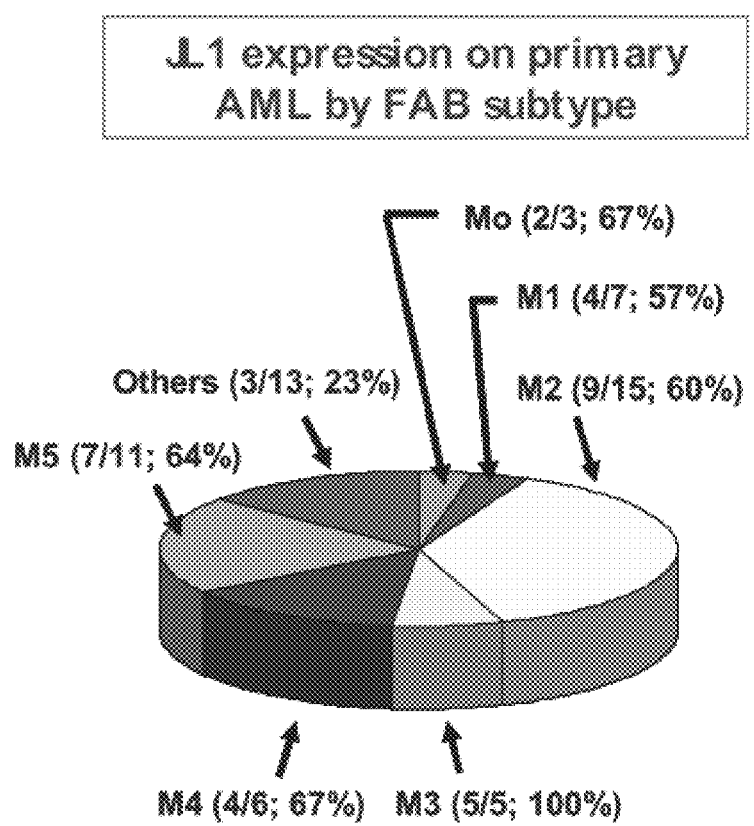
FIG. 26 shows the level of expression of JL-1 in the major AML blast and subset.

On the other hand, the CD43 expression level in major AML (Acute myeloid leukemia) blast and subsets was measured. The result was shown in FIG. 26. As shown in FIG. 26, the CD43 protein (represented as JL-1) expression was analyzed in primary AML blast and prevalence of specific subsets. CD43 was expressed in approximately 60% of AML group.

Example 18: Construction of Humanized Anti-CD43 Monoclonal Antibody

Based on the sequence of gremlin maintaining the mouse CD43 antibody (heavy chain: SEQ ID NO: 34; heavy chain coding DNA: SEQ ID NO: 33; heavy chain expression vector: SEQ ID NO: 35, light chain: SEQ ID NO: 37; light chain coding DNA: SEQ ID NO: 36; light chain expression vector (pTT5 based): CDR region sequence of heavy chain and light chain each of SEQ ID NO: 38) (CDRH1: SEQ ID NO: 111 (GYFMN); CDRH2: SEQ ID NO: 114 (RINPNNGDSFYNQKFQG); CDRH3: SEQ ID NO: 118 (EGYYGGRGYALDY); CDRL1: SEQ ID NO: 119 (RTSQDISNYLN); CDRL2: SEQ ID NO: 121 (NTSRLHS); CDRL3: SEQ ID NO: 125 (QQSNMFPY)) and coding human antibody gene, the scFv type of recombinant humanized antibody library, in which the sequence of region to framework region was recombined, was constructed.

The constructed scFv antibody library was expressed and screened by the common phage display method, and the positive clone was constructed as the sub-library expressing variants which were substituted in region except CDR or partial sequence of region in CDR, thereby repeating the screening.

By repeating various cycles of these constructions of library and display method, the humanized antibody variant sequences showing the antigen affinity very similar to parent clone were secured.

The heavy chain sequences of the secured humanized anti-CD43 antibody were shown in SEQ ID NOs: 40, 42, 44, and 46, and the light chain sequence was shown in SEQ ID NO: 48, and the heavy chain variable regions and light chain variable regions were shown in SEQ ID NO: 2, 6, 10, 14, 18, 22, 26, 30, and 83 (heavy chain variable region), and SEQ ID NO: 4, 8, 12, 16, 20, 24, 28, 32, and 83 (light chain variable region), respectively.

In addition, the heavy chain variable regions and light chain variable regions of mutant humanized anti-CD43 antibody from modified SEQ ID NO: 83 (heavy chain variable region) and SEQ ID NO: 95 (light chain variable region) were shown in SEQ ID NOs: 84 to 94 (heavy chain variable region) and SEQ ID NOs: 96 to 106 (light chain variable region), respectively.

The scFv type of antibody was prepared by linking the obtained heavy chain variable region and light chain variable region with GGGASGGGGSGGGGS (SEQ ID NO: 127) or GGGGSGGGGSGGGAS (SEQ ID NO: 128).

Figure 27A:
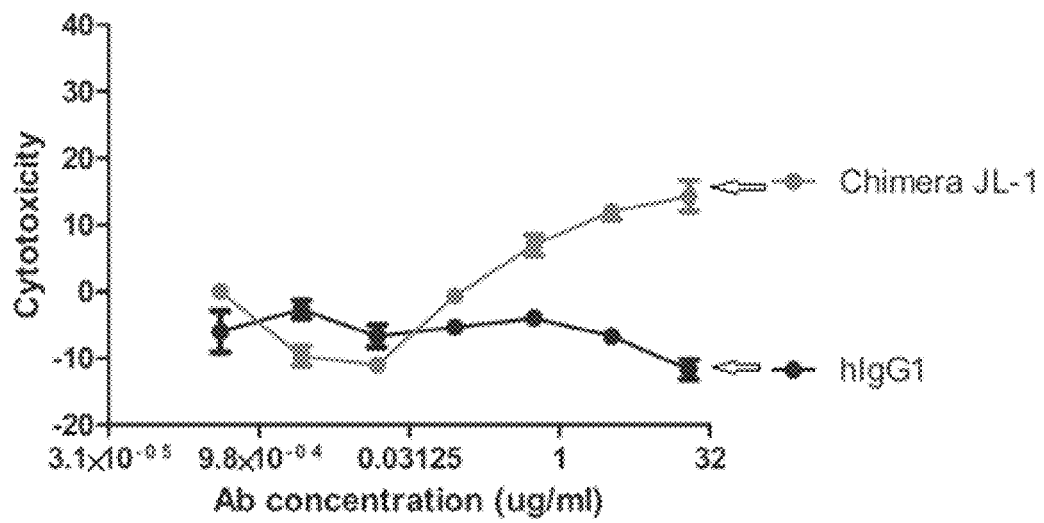
Figure 27B:
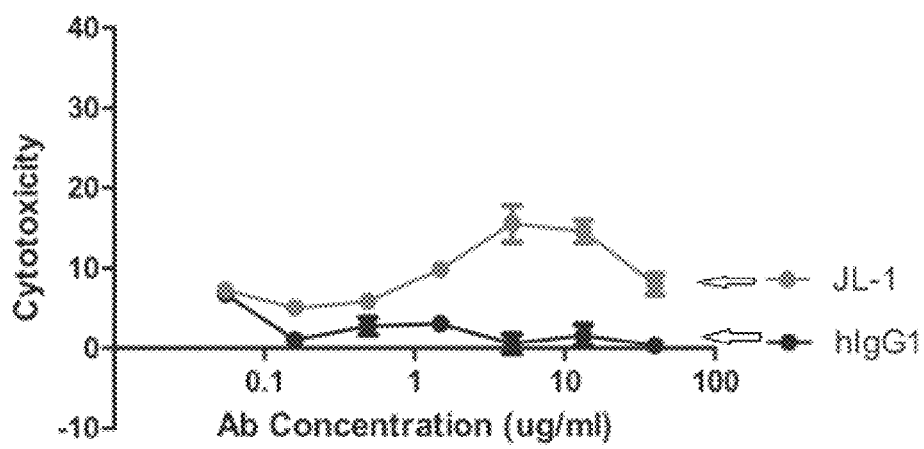

Example 19: Antibody-Dependent Cell Cytoxicity (ADCC) and Complement-Dependent Cytotoxicity (CDC) by Humanized or Chimeric Anti-CD43 Monoclonal Antibody The apoptosis effect (ADCC and CDC) by the prepared chimeric anti-CD43 antibody (DNP001; Example 2-1-3) was tested. At first, CEM7 cell line effector cell (PBMC; peripheral blood mononuclear cell) was co-cultured with anti-CD43 chimeric or control antibody (human IgG1) for 4 hours, and then the cytotoxicity was measured by using Cell Titer Glo, and the result was shown in FIG. 27A. The CEM7 cell line was cultured with culturing medium and anti-CD43 chimeric antibody together with rabbit complement (cedarlane, Cat. No: CL3051), and then the cytotoxicity was measured by using Cell Titer Glo, and the result was shown in FIG. 27B. The anti-CD43 chimeric antibody was represented as JL-1 in FIGS. 27A-27B. As shown in FIGS. 27A-27B, it was confirmed that the chimeric anti-CD43 antibody induced the effector-mediated killing (ADCC and CDC) in the in vitro level, compared to the human IgG1 control antibody.

Figure 28:
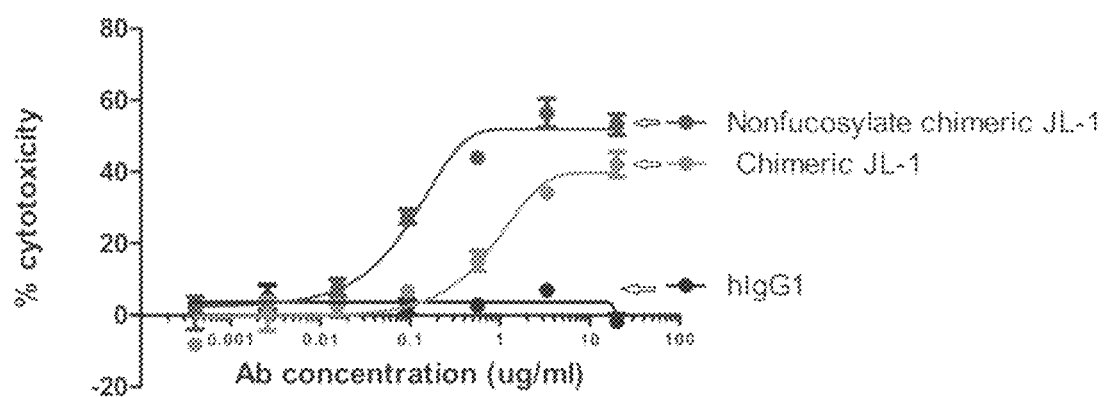
FIG. 28 is the result of showing that the ADCC activity of JL-1 chimeric antibody is increased when defucosylated.

FIG. 28 showed that the defucosylated (defucosylated by treating kifunensine to antibody) chimeric anti-CD43 antibody (represented as JL-1) enhanced the ADCC activity to CEM7 in the in vitro level.

Figure 29:
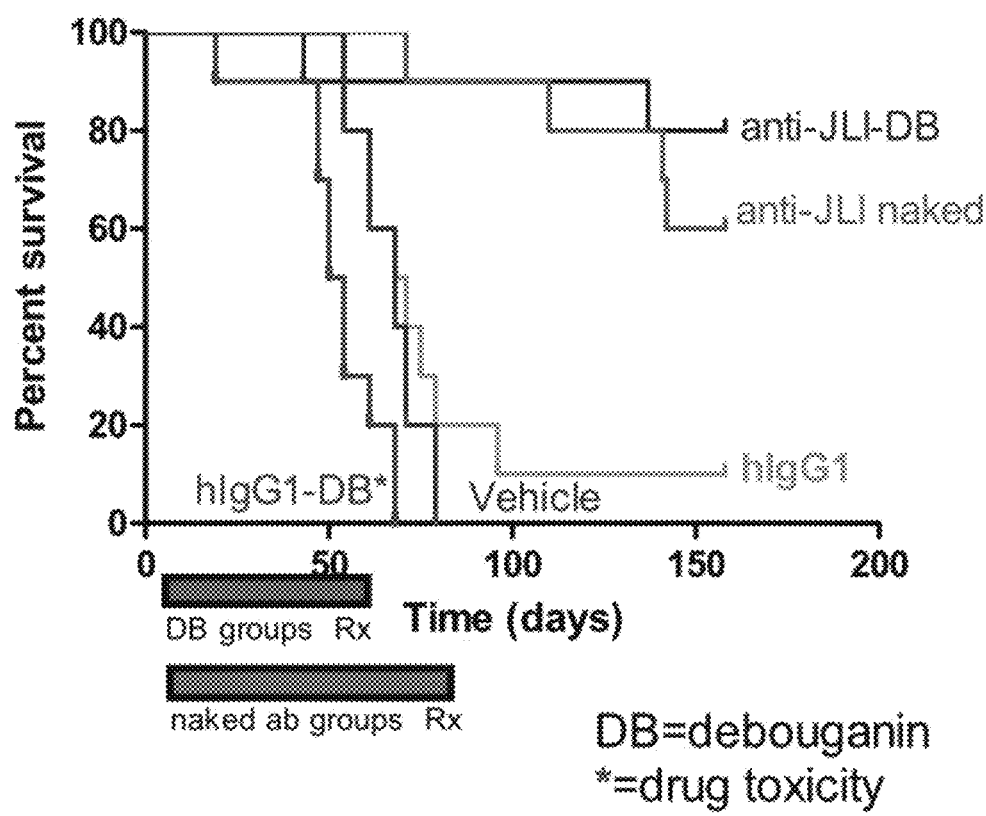
FIG. 29 is the graph showing the effect of naked-chimeric antibody in CEM7 cell line in vivo.

FIG. 29 is the graph showing the effect of naked-chimeric antibody which did not bind to anything itself in CEM7 cell line in vivo. As shown in FIG. 29, it was confirmed that the naked (non-conjugated) and debouganin-conjugated chimeric anti-CD43 antibodies enhanced the survival of CEM7 cell-inoculated animal (ALL (acute lymphocytic leukemia) leukemia model).

Figure 30:
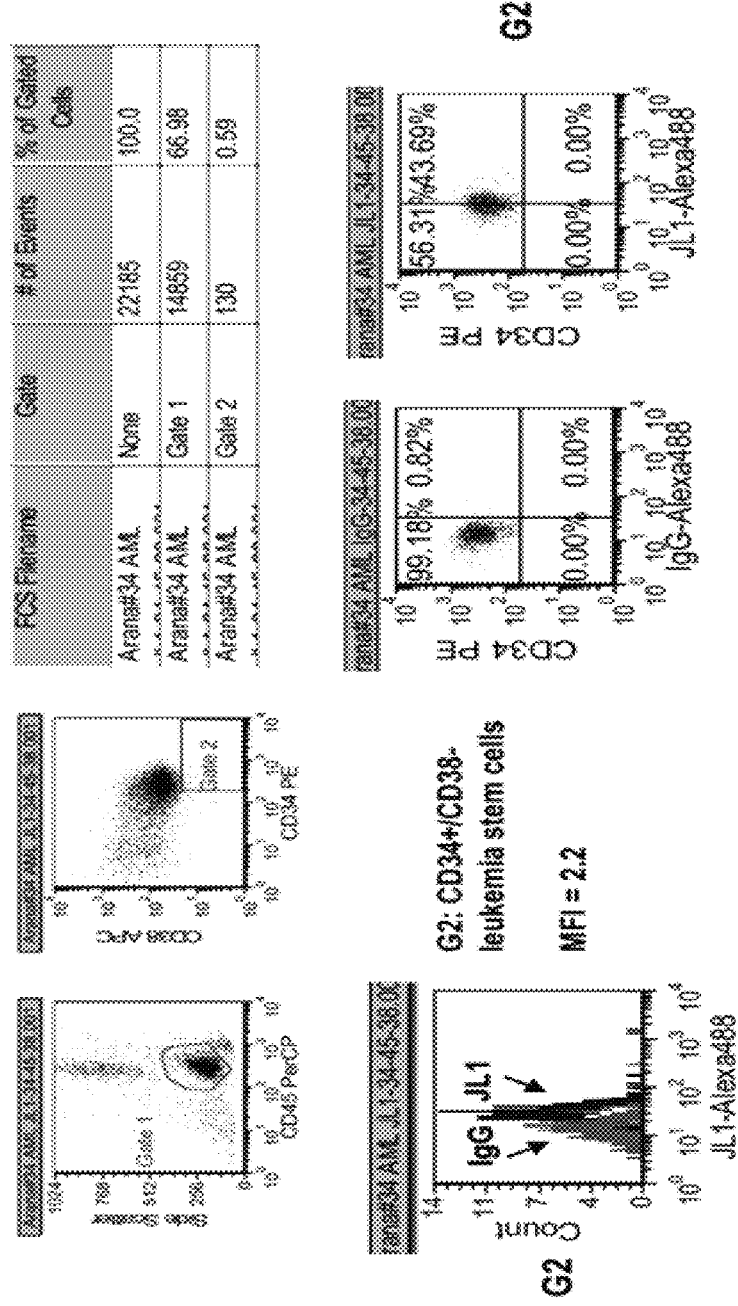
FIG. 30 is the result showing the expression of JL1 in the leukemia stem cell (LSC) subset.

The CD43 expression in Leukemia stem cell (LSC) subsets was tested. AML (Acute myeloid leukemia) patient bone marrow was stained with CD45 antibody (BD), CD34 antibody (BD), CD38 antibody (BD), CD43 antibody (DNP001), or mIgG1 (control) with Alexa488, and the CD43 expression level was evaluated by sorting CD34+ CD38− leukemia stem cells, and they were compared to the control group. The result was shown in FIG. 30 (JL1: CD43). As shown in FIG. 30, the CD43 antigen was expressed in leukemia-initiating cell (LSC) subsets (CD34+/CD38-).

The mean number of colonies treated with the chimeric anti-CD43 antibody conjugated with toxin (saporin: SAP) (CCC) was measured in vitro and shown in FIG. 31. The result showed the apoptosis effect of antigen-positive AML, which was added with the CD43 antibody-saporin conjugate or mouse IgG1-saporin conjugate to the stem cell colony matrix.

In addition, the effect of the chimeric anti-CD43 antibody conjugated with toxin (saporin: SAP) (CCC) on the proliferation of antigen-positive, major AML was measured in vitro and shown in FIGS. 32A-32B. The result showed that the CCC decreased the proliferation of major AML. The result was obtained by putting the major AML blasts to the culturing medium comprising the CD43 antibody-saporin conjugate or mouse IgG1-saporin conjugate and measuring the level of cell proliferation after 3 days, and from the result, it was confirmed that the cell growth was slowed when cultured in the medium comprising JL1-saporin (32A) and the ratio of dead cells was increased (32B).

Figure 31:
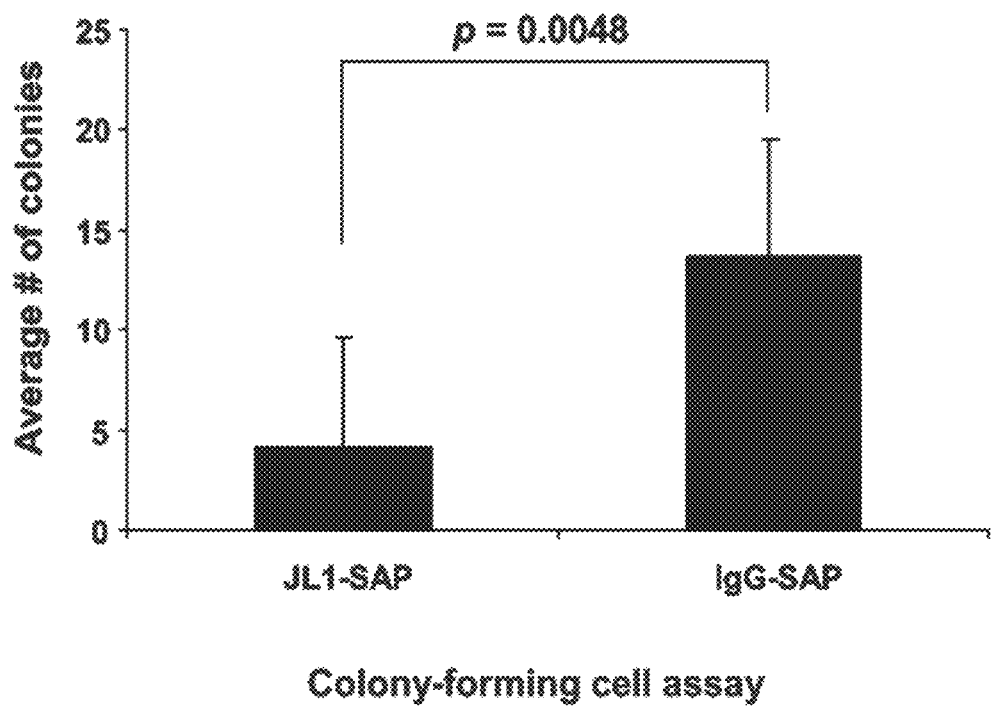
FIG. 31 is the graph showing the result of colony forming analysis by the anti-JL1 antibody conjugated with the toxin (saporin: SAP) in vitro (CCC) (colony mean number), and it shows the increased apoptosis effect of antigen-positive AML. The cell was put into the stem cell colony matrix with JL1-saporin or mouse IgG1-saporin and colony forming was observed.
Figure 32A:
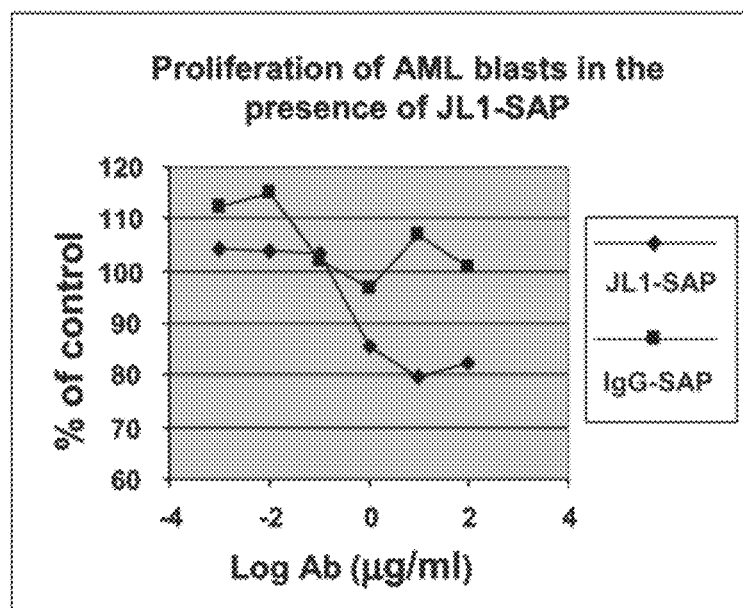
FIGS. 32A-32B are the graphs showing the effect that the anti-JL1 antibody conjugated with the toxin (saporin: SAP) in vitro (CCC) influences the proliferation of antigen-positive major AML.
Figure 32B:
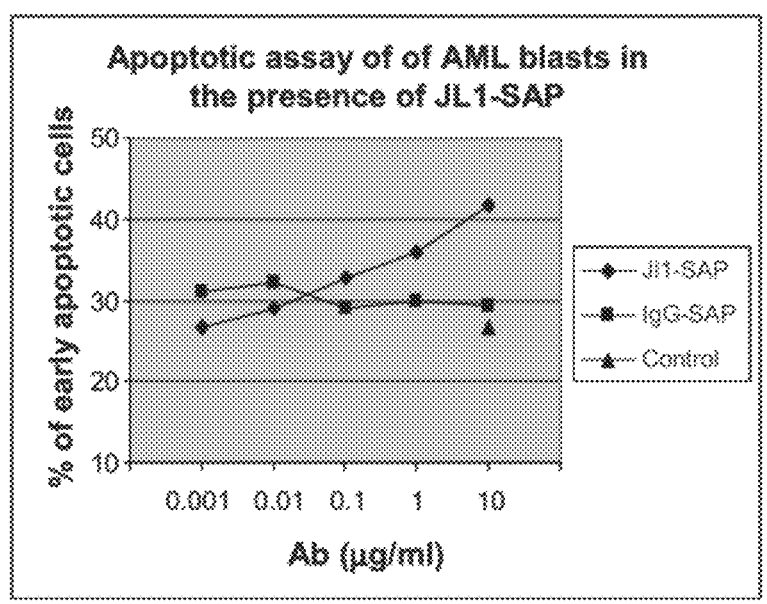

As shown in FIGS. 31 and 32A-32B, when confirmed by colony assay (FIG. 31) and proliferation assay (FIGS. 32A-32B) in vitro, the toxin-conjugated humanized chimeric antibody had the cytotoxicity to CD43-positive primary AML.

Figure 33:
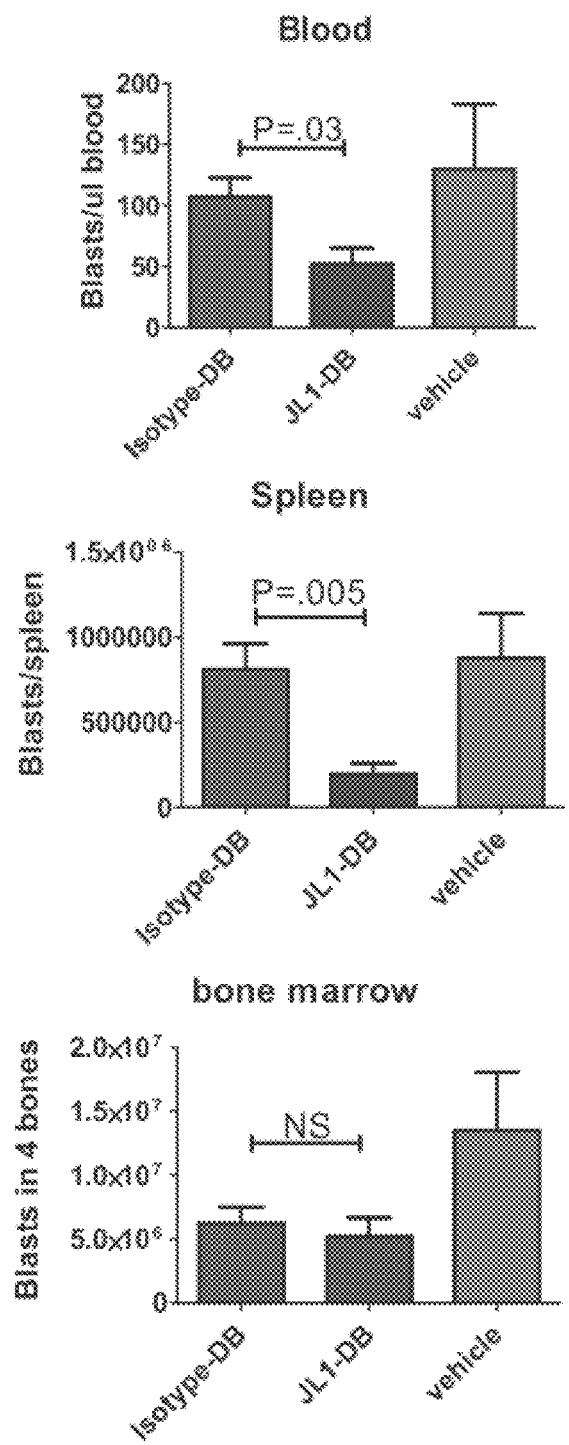
FIG. 33 is the graph showing the inhibitory effect of major AML cancer cell growth by the antibody linked with the toxin in NSG mouse (in vitro), 5×$10^7$ of bone marrow cells was harvested from JL-1+ AML patient and intravenously injected to 30 NSG mice irradiated. After 8 weeks, 45 μg dose of JL1-debouganin (DB), hIgG1-DB, or PBS were administered to the mice every week, and the bone marrow and spleen were harvested, and subjected to the engraftment and tumor production were observed.

The inhibitory effect on major AML cancer cell growth by the toxin-conjugated antibody in NSG mouse (in vivo) was tested. $5 \times 10^7$ of bone marrow cells were harvested from CD43+ AML patient, and they were intravenously injected to 30 NSG mice irradiated and after 8 weeks, the chimeric CD43 antibody-debouganin (DB) conjugate (represented as JL1-DB), hIgG1-DB conjugate (represented as Isotype-DB), or PBS (vehicle) was administered into those mice in 45 μg dose every week for 4 weeks. Blood, bone marrow and spleen were then collected form those mice, and engraftment and tumor production were observed. The obtained result was shown in FIG. 33. As shown in FIG. 33, the growth of primary AML cancer cell was inhibited by toxin-conjugated anti-CD43 humanized chimeric antibody in NSG mice in the in vivo level.

Figure 34:
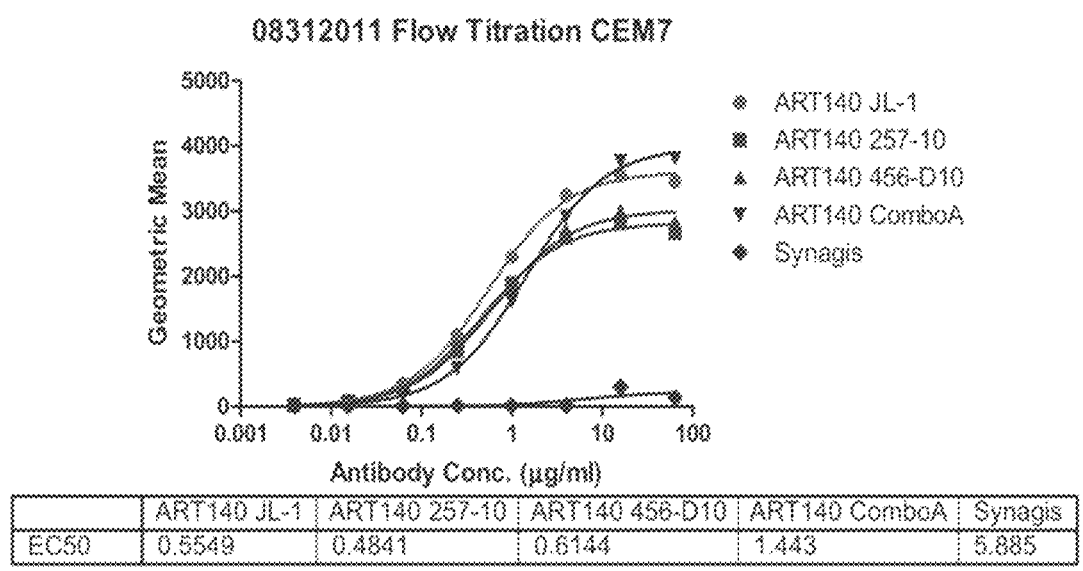
FIG. 34 and FIG. 35 are the results of confirming that various humanized/optimized modified antibodies show the equal binding profile, compared to the original (mouse) JL-1 antibody. CEM7 cell was stained with the parent original JL-1 antibody or 3 kinds of antibodies modified by humanization to observe. As results, FIG. 43 indicates that the modified "Combo A" showed the best profile, but all other test antibodies showed the significant level of cytotoxicity in CEM7 cell.
Figure 35:
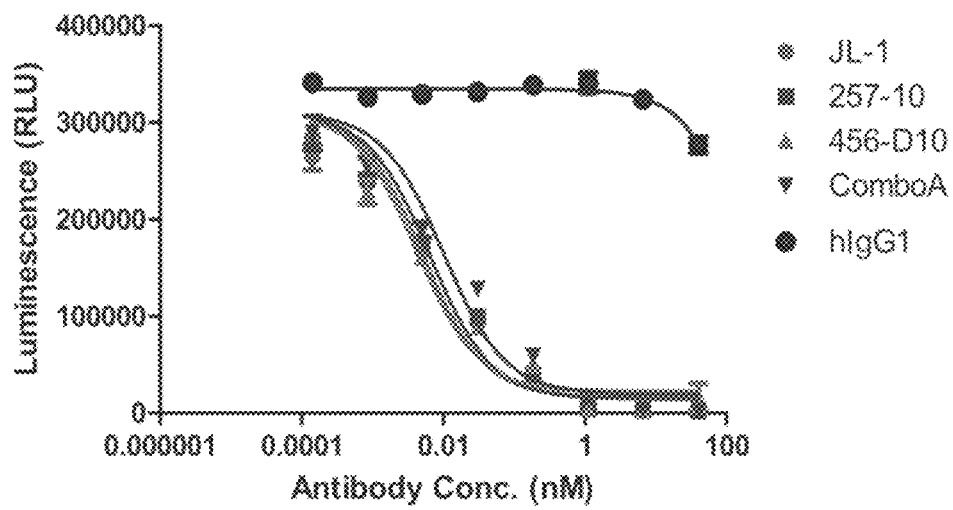

FIGS. 34 and 35 confirmed that various humanized/optimized modified antibodies showed equivalent binding profile compared to the template (mouse) CD43 antibody. CEM7 cell was stained with parent template CD43 antibody (ART140 JL1; mouse anti-CD43 antibody; heavy chain: SEQ ID NO: 34; light chain: SEQ ID NO: 37) and 3 kinds of humanized antibodies (257-10 (SEQ ID NO: 93 & 105); 456-D10 (SEQ ID NO: 94 & 106); ComboA (SEQ ID NO: 2 & 4)), thereby measuring the fluorescence intensity, and the result was shown in FIG. 34. As shown in FIG. 34, it was confirmed that modified "Combo A" showed the best profile, but all of other test antibodies showed significant level of cytotoxicity in CEM7 cell. In order to test the cell internalization of antibody conjugated with cytotoxic materials, 3 kinds of humanized antibodies precomplexed with anti-human IgG-saporin were treated to CEM7 cell, and the cytotoxicity was measured after 3 days, and shown in FIG. 35. As shown in FIG. 35, when the conjugate of 3 kinds of modified antibodies and saporin was used, the cytotoxicity was significantly high.

As shown in FIGS. 34 and 35, the binding level and the cytotoxicity level of various humanized anti-CD43 antibody variants were equal, compared to murine CD43 antibody (ART140 JL1) in vitro. Synagis (Medimmune Company) which was the humanized monoclonal antibody (IgG) for the antigen determinant on A antigenic site of RSV F protein was used as the control group.

Figure 36:
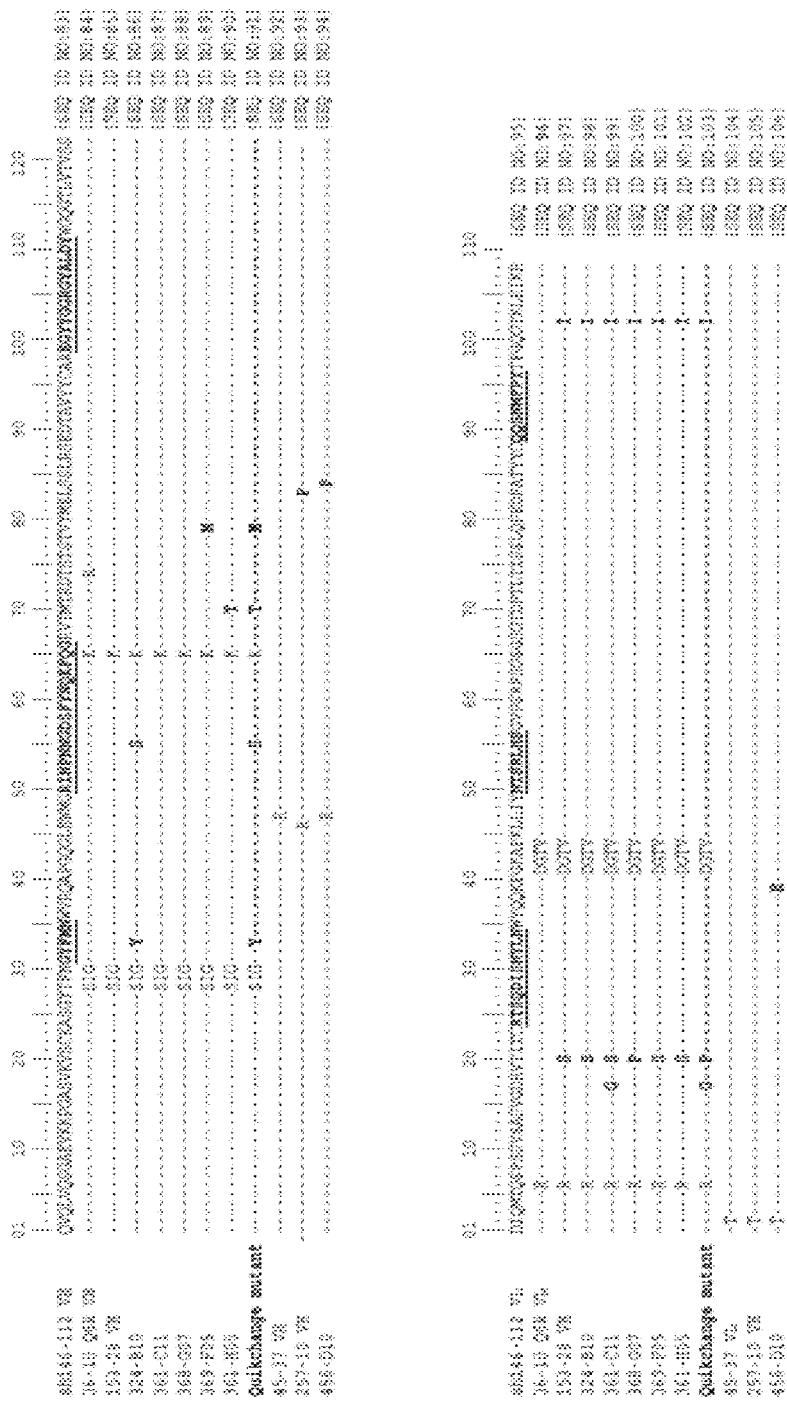
FIG. 36 shows the result of amino acid sequence arrangement of the best 2 round and 3 round clones, which are the comparison of amino acid sequences of parent clone and more humanized clone, respectively. Among them, 153-28 is derived from 36-10 Q6R, and 257-10 is derived from 45-37. CDRs are represented in bold and underlined fonts.
Figure 37A:
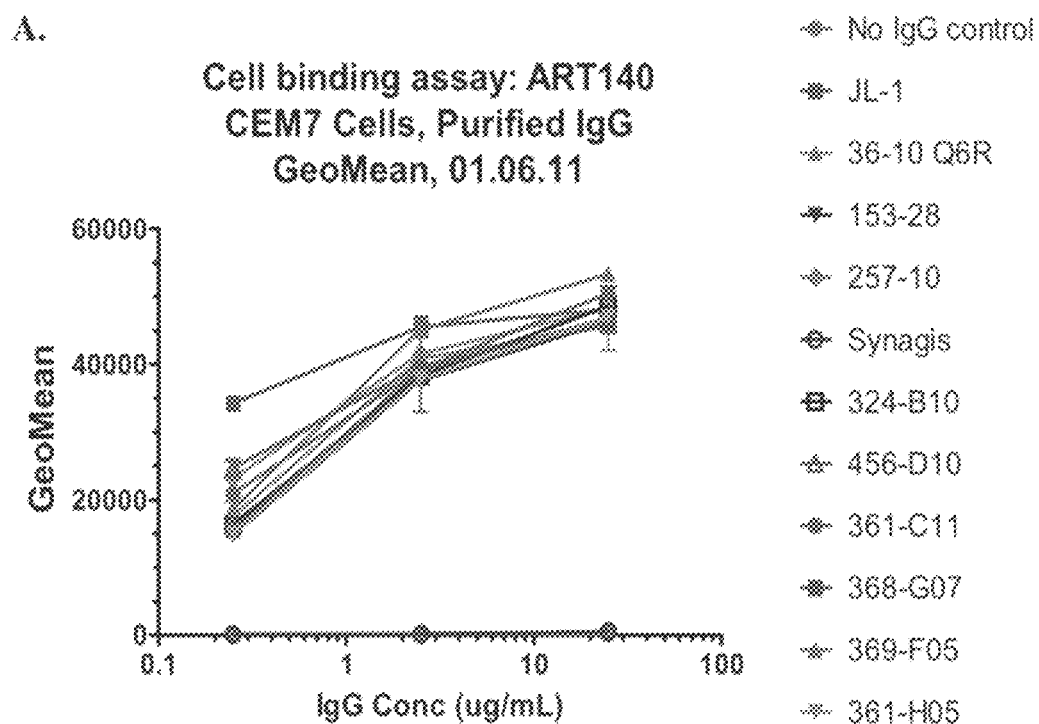
FIG. 37A is the graph showing the level of binding of ART140 lead candidate to IgG in JL-1 positive CEM7 cell by flow cytometry.
Figure 37B:
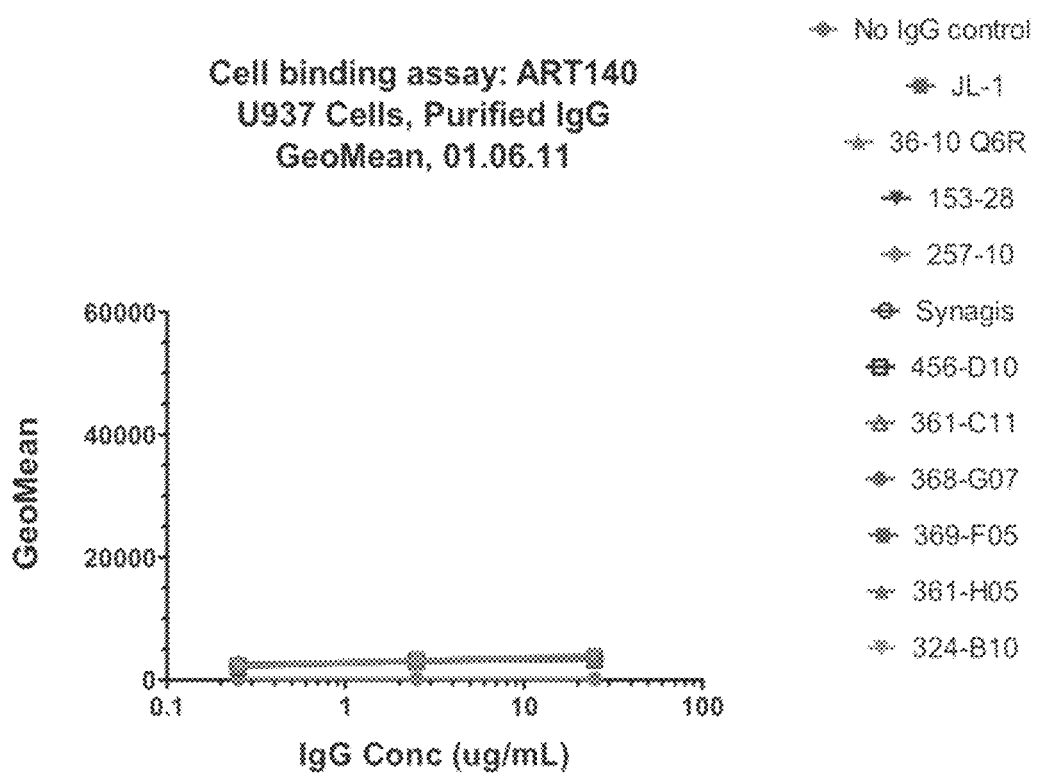
FIG. 37B is the graph showing the result in the negative control group, U937 cell.

FIGS. 37A and 37B showed a number of humanized anti-CD43 antibody variants (refer to FIG. 36) bound to CD43 antigen on the cell surface, in comparison to murine CD43 antibody (ART140 JL1) by flow cytometry. U937 cell was used as the negative control in which the expression of CD43 antigen on the surface was deficient.

Figure 38A:
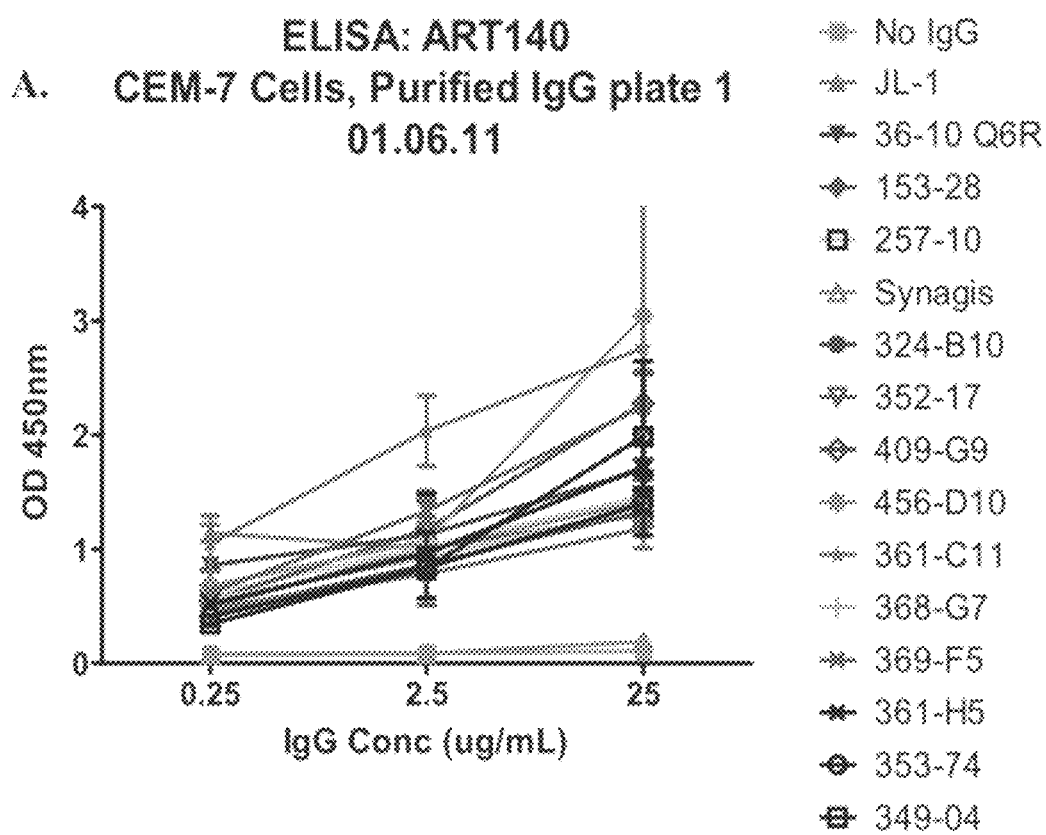
FIG. 38A is the graph showing the level of binding of ART140 lead candidate to IgG in JL-1 positive CEM7 cell by cell-based ELISA (living cell in suspension) and FIG. 38B is the graph showing the result in the negative control group, U937 cell.
Figure 38B:
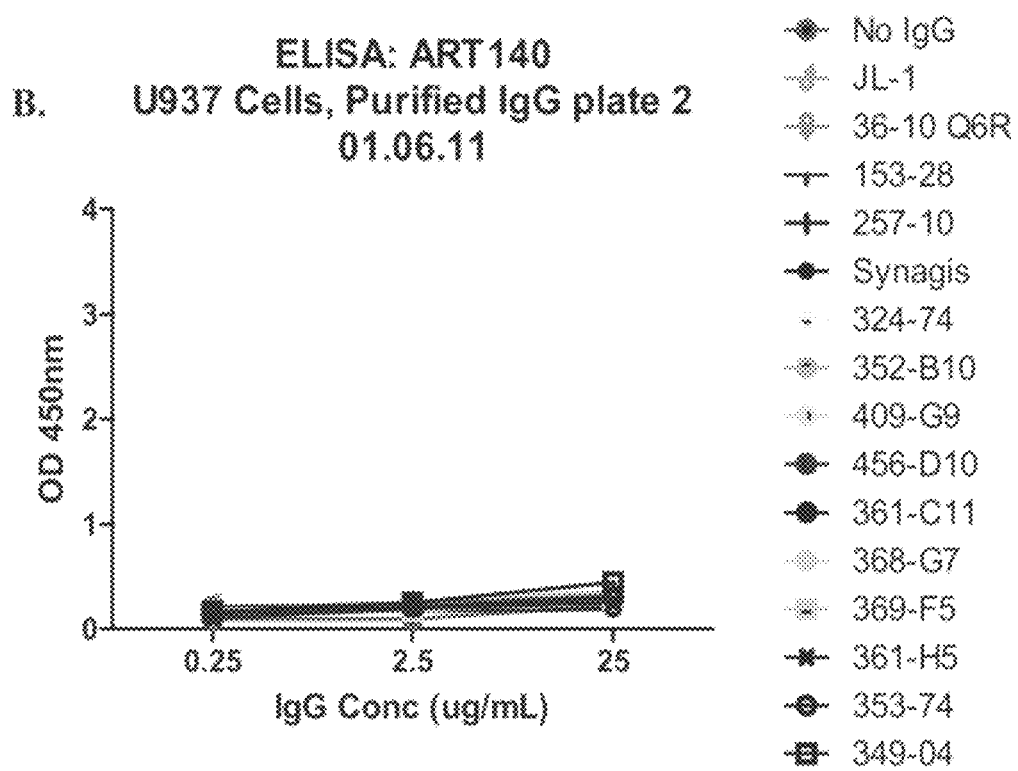

FIGS. 38A and 38B showed that a number of humanized anti-J CD43 antibody variants (refer to FIG. 36) bound to CD43 antigen on the cell surface, compared to murine CD43 antibody (ART140 JL1) by enzyme linked immunosorbent assay (ELISA). U937 cell was used as the negative control in which the expression of CD43 antigen on the surface was deficient.

Figure 39A:
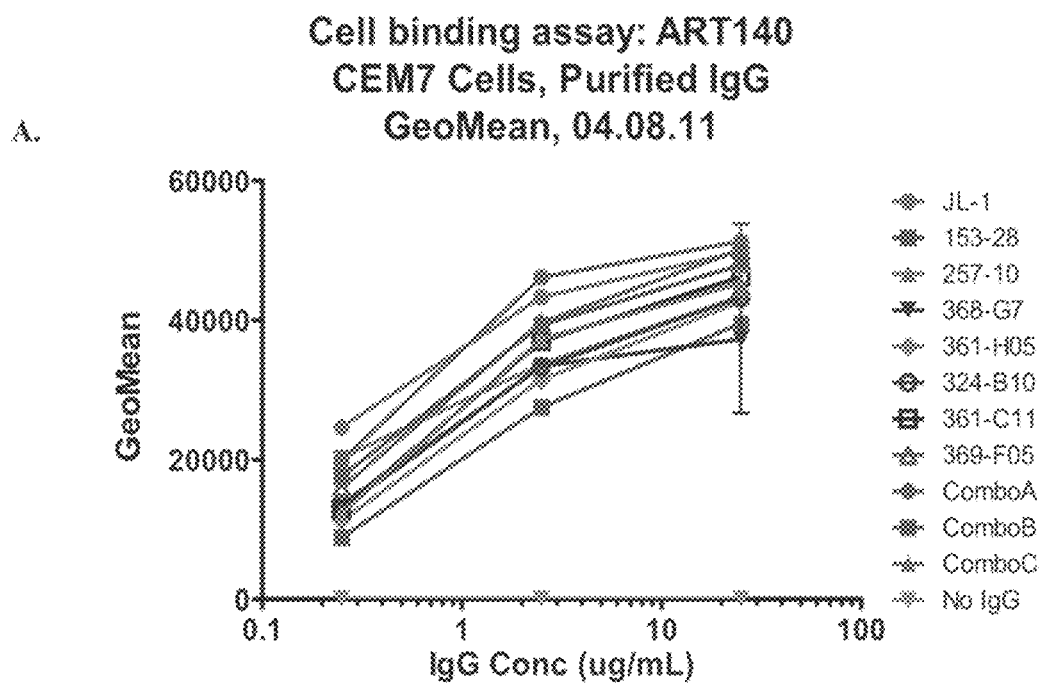
FIG. 39A is the graph showing the level of binding of lead candidate group and IgG of Quikchange mutant to JL-1 positive CEM by flow cytometry.
Figure 39B:
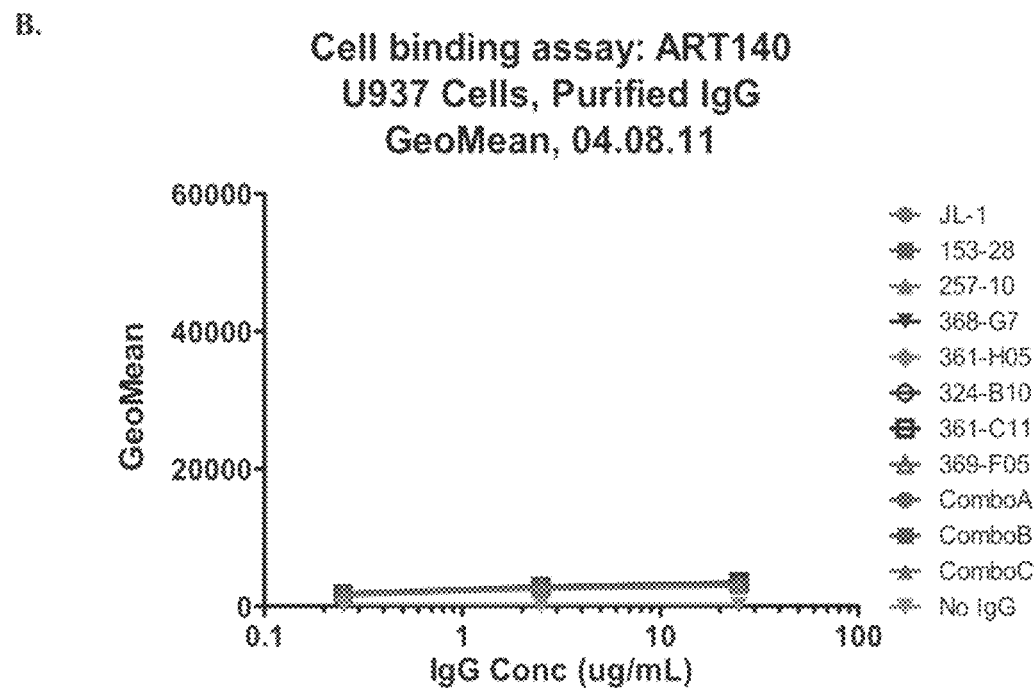
FIG. 39B is the graph showing the result in the negative control group, U937 cell.
Figure 40A:
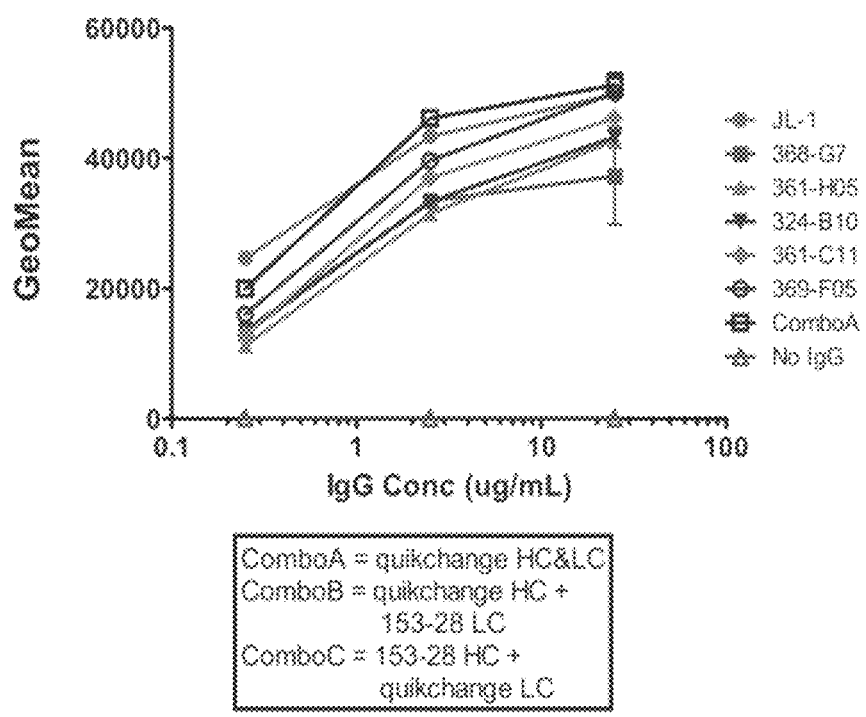
FIGS. 40A-40C are the graphs showing the level of binding of IgG of Quikchange mutant to JL-1 positive CEM by flow cytometry.
Figure 40B:
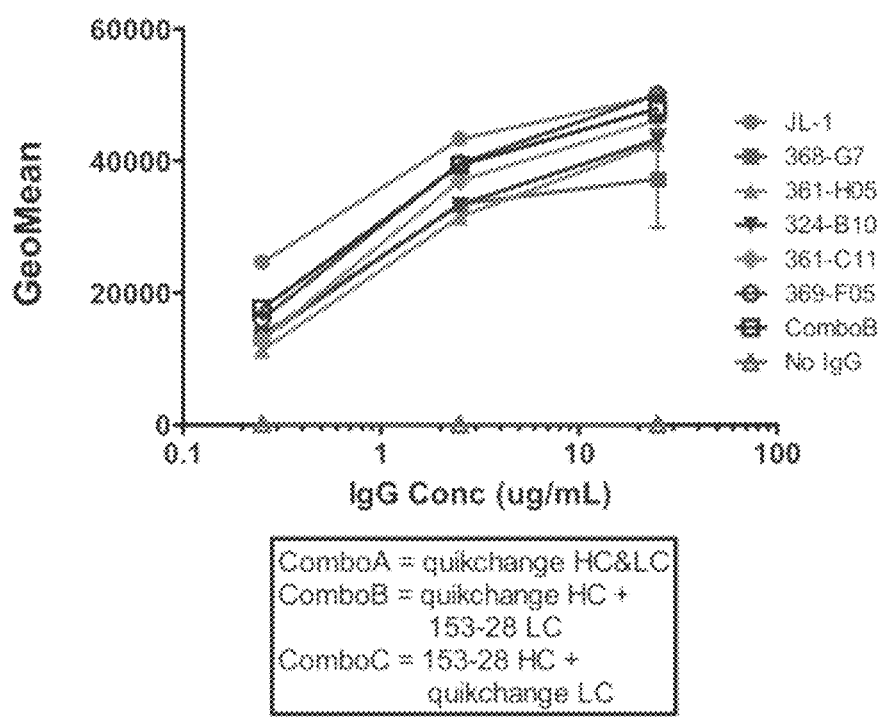
Figure 40C:
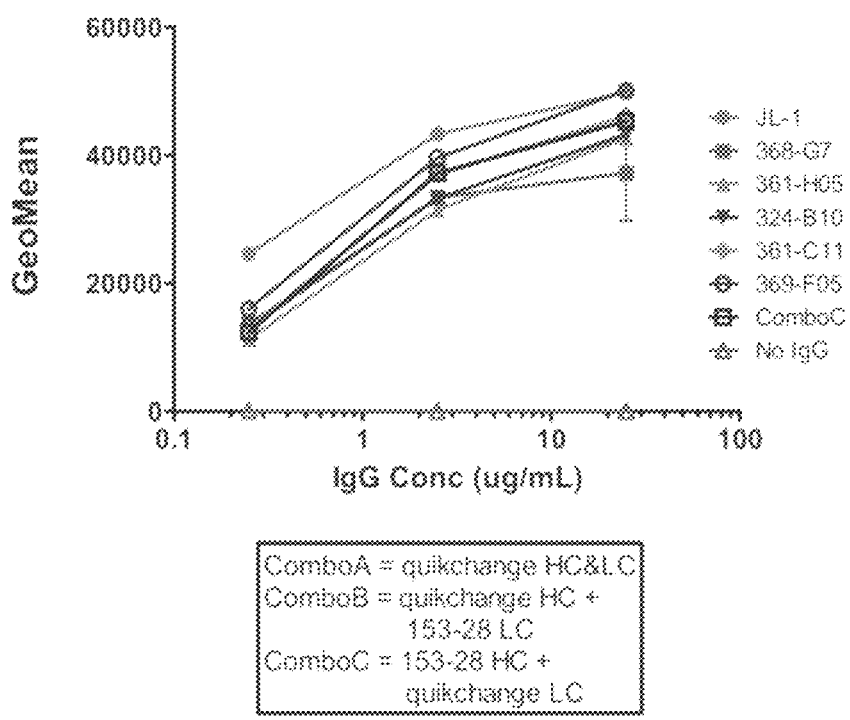

FIGS. 39A and 39B showed that Quikchange mutant humanized anti-CD43 antibody variants (Combo A (SEQ ID NO: 91 (heavy chain variable region); SEQ ID NO: 103 (light chain variable region)), Combo B (SEQ ID NO: 91 (heavy chain variable region); SEQ ID NO: 103 (light chain variable region)), Combo C(SEQ ID NO: 85 (heavy chain variable region); SEQ ID NO: 97 (light chain variable region))) bound to CD43 on the cell surface, compared to murine CD43 antibody (ART140 JL1) and round 3 parental framework by flow cytometry.

Figure 41A:
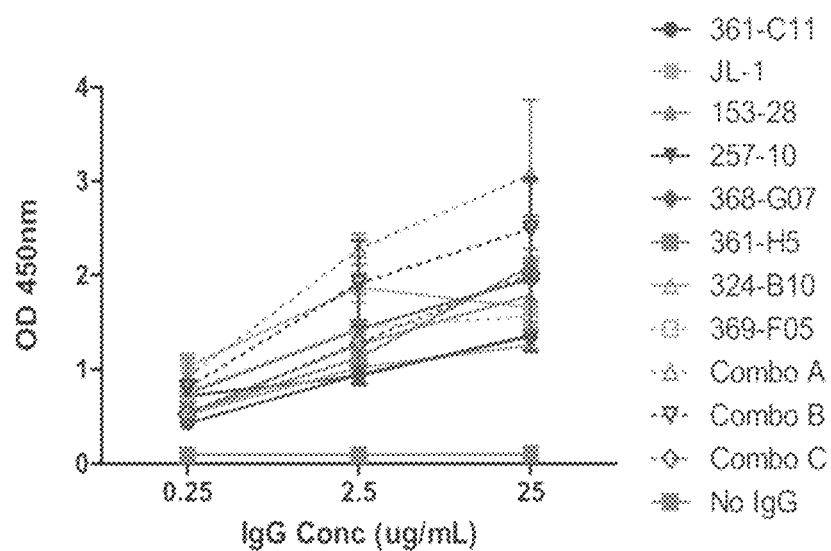
FIGS. 41A-41C are the graphs showing the result of confirming IgG of Quikchange mutant which binds to JL-1 positive CEM7 by cell-based ELISA (living cell in suspension).
Figure 41B:
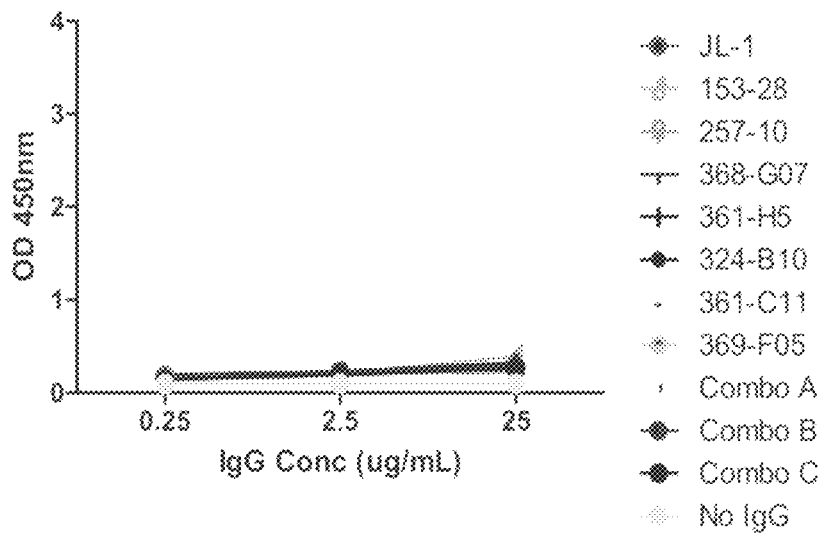
Figure 41C:
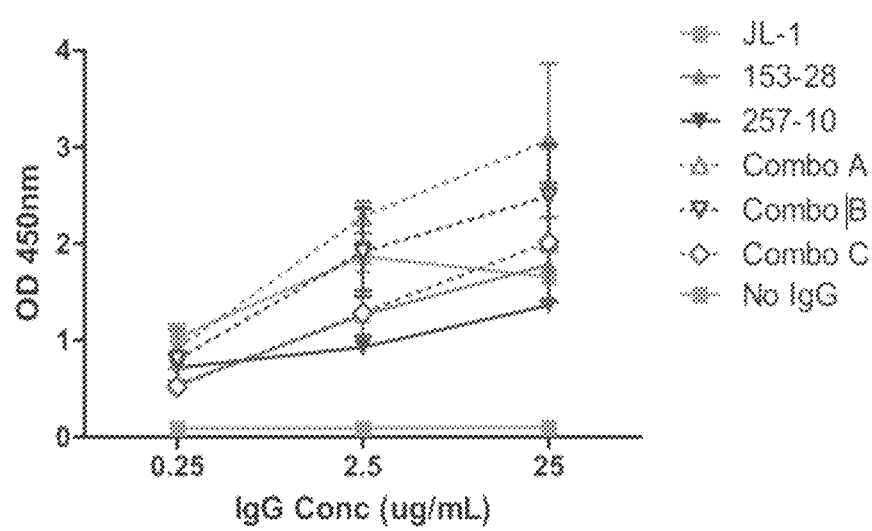

FIGS. 41A-41C showed that Quikchange mutant humanized anti-CD43 antibody variants (Combo A, Combo B, Combo C) bound to JL1 antigen on the cell surface, compared to murine CD43 antibody (ART140 JL1) and round 3 parental framework.

Example 20: Preparation of Modified Antibody Removing Amino Acid Residue of Glycosylated Region of Humanized Antibody It was found that there was the amino acid sequence having the possibility of glycosylation in the light chain variable region (SEQ ID NO: 105) of the humanized anti-CD43 antibody obtained from the example 18 (257-10; comprising SEQ ID NO: 93 (heavy chain variable region)+SEQ ID NO: 105 (light chain variable region)), and the mutant antibody was prepared to remove it.

Since the glycosylation of light chain epitope (light chain variable region) is highly likely to cause negative effects on the antigen binding capacity and physical properties of antibody, and may affect the productivity degradation in the subsequent mass production, the possibility of antibody development as a therapeutic agent was increased by substituting the amino acid having the potential possibility of glycosylation into other amino acids.

Figures 43, 44:
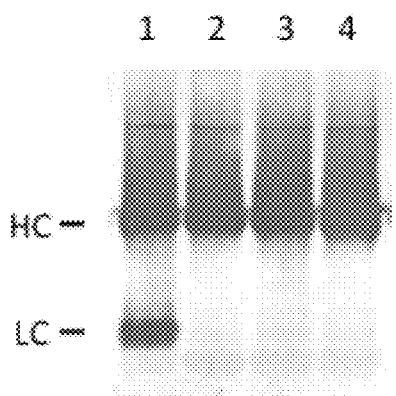
FIG. 43 illustratively shows the amino acid of glycan region in light chain variable region to be substituted for preparing the antibody with the variation in which amino acid residues of glycan region of humanized antibody are deleted.
FIG. 44 is the result of western blotting variants by using Concanavalin A-HRP binding to glycan region for the antibody with the variation in which amino acid residues of glycan region of humanized antibody are deleted.

The 50th position of amino acid residue asparagine (Asn, N) and the 52th position of amino acid residue serine (Ser, S) were selected as the amino acids having the possibility of glycosylation of light chain variable region (SEQ ID NO: 105) of humanized anti-CD43 antibody (refer to FIG. 43). The mutant antibody was prepared by substituting the 50th position of amino acid residue asparagine (Asn, N) of SEQ ID NO: 8 into glutamine (Gln, Q) or alanine (Ala, A), and/or substituting the 52th position of amino acid residue serine (Ser, S) into alanine (Ala, A), and the light chain variable regions of mutant antibody obtained as above were shown in SEQ ID NOs: 107 (S52A), 108 (N50Q), and 109 (N50A).

[SEQ ID NO 107 (S52A)]
DTQMTQSPSSVSASVGDRVTITCRTSQDISNYLNWYQQKPGKAPKLLIYN

T<u>A</u>RLHSGVPSRFSGSGSGTDFTLTISSLQPEDFATYYCQQSNMFPYTFGQ

GTKLEIK

[SEQ ID NO 108 (N50Q)]
DTQMTQSPSSVSASVGDRVTITCRTSQDISNYLNWYQQKPGKAPKLLIY<u>Q</u>

TSRLHSGVPSRFSGSGSGTDFTLTISSLQPEDFATYYCQQSNMFPYTFGQ

GTKLEIK

[SEQ ID NO 109 (N50A)]
DTQMTQSPSSVSASVGDRVTITCRTSQDISNYLNWYQQKPGKAPKLLIY<u>A</u>

TSRLHSGVPSRFSGSGSGTDFTLTISSLQPEDFATYYCQQSNMFPYTFGQ

GTKLEIK

The IgG1 type antibody comprising the heavy chain variable region (SEQ ID NO: 93) and the light chain variable region of the obtained modified antibody 55 was prepared, and western blotting was performed by using Concanavalin A-HRP binding to glycosylated region (Sigma-Aldrich).

The obtained result was shown in FIG. 44. As shown in FIG. 44, it was confirmed that Concanavalin A bound to all of light chain region and heavy chain region in the antibody in which amino acids of glycosylated region were not modified (comprising SEQ ID NO: 93 and SEQ ID NO: 105; wild type), but the binding in the light chain region did not occur in the three kinds of modified antibodies (scFv). This result means that the glycosylation of light chain region of antibody was removed.

Figure 45:
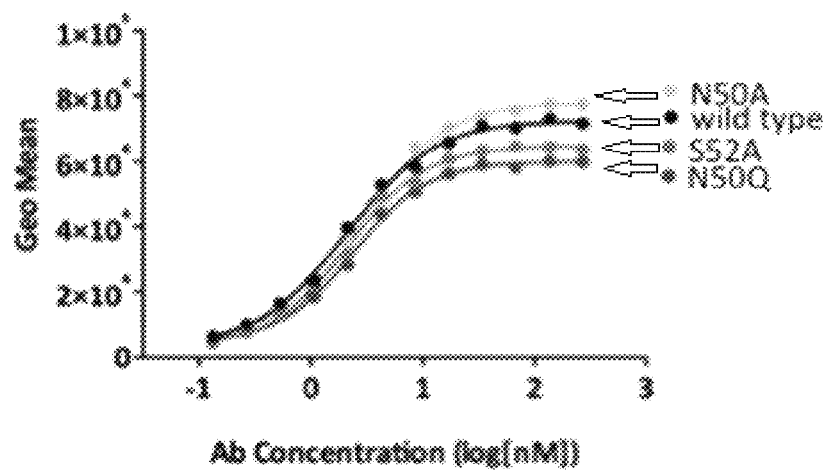
FIG. 45 is the graph showing the binding capacity of the antibody with the variation in which amino acid residues of glycan region of humanized antibody are deleted.

In addition, by measuring the binding capacity of the antibody to the CD43 positive cell, CEM7 cell, the antigen binding capacity was analyzed. The obtained result was shown in FIG. 45. As shown in FIG. 45, the modified antibody showed equivalent antigen binding capacity to wild type.

Figure 46:
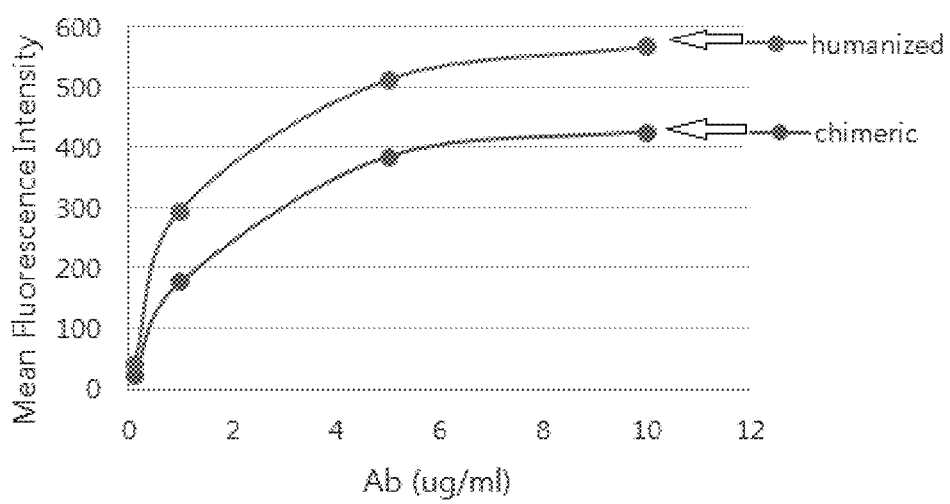
FIG. 46 is the graph showing the binding capacity of chimeric anti-CD43 antibody and humanized anti-CD43 antibody in which amino acid residues of glycan region are deleted with the antigen (CD43) positive cell, CEM7 cell.

The chimeric antibody (DNP001) and modified humanized antibody removing glycosylation (heavy chain variable region; SEQ ID NO: 93; light chain variable region: SEQ ID NO: 109) were bound to antigen (CD43) positive cell, CEM7 cell, and they were analyzed by flow cytometry. The obtained result was shown in FIG. 46. As shown in FIG. 46, it was confirmed that the modified humanized antibody showed more enhanced CD43 expression cell binding capacity than the chimeric antibody.

The invention claimed is:

1. A method of treating a cancer or inhibiting a cancer stem cell, comprising administering a pharmaceutically effective amount of an anti-CD43 antibody or an antigen-binding fragment thereof to a subject in need of treating the cancer or inhibiting a cancer stem cell, wherein the anti-CD43 antibody or the antigen-binding fragment thereof comprises:
  a CDR1H of SEQ ID NO: 111,
  a CDR2H of SEQ ID NO: 114,
  a CDR3H of SEQ ID NO: 118,
  a CDR1L of SEQ ID NO: 119,
  a CDR2L of SEQ ID NO: 122, 123, or 124, and
  a CDR3L of SEQ ID NO: 125.

2. The method of claim 1, wherein the anti-CD43 antibody or an antigen-binding fragment thereof comprises:
  a CDR1H of SEQ ID NO: 111,
  a CDR2H of SEQ ID NO: 114,
  a CDR3H of SEQ ID NO: 118,
  a CDR1L of SEQ ID NO: 119,
  a CDR2L of SEQ ID NO: 124, and
  a CDR3L of SEQ ID NO: 125.

3. The method of claim 1, wherein the cancer is a hematopoietic malignancy.

4. The method of claim 3, wherein the hematopoietic malignancy is acute myeloid leukemia, acute lymphoblastic leukemia, acute monocytic leukemia, Hodgkin's lymphoma, or non-Hodgkin's lymphoma.

5. The method of claim 1, wherein the cancer is a solid cancer.

6. The method of claim 5, wherein the solid cancer is gastric cancer, breast cancer, lung cancer, colon cancer, liver cancer, gallbladder cancer, renal cancer, pancreatic cancer, thyroid cancer, prostatic cancer, ovarian cancer, cervical cancer, or bladder cancer.

7. The method of claim 1, wherein the cancer stem cell is a cancer stem cell in hematopoietic malignancy or solid cancer.

8. The method of claim 1, wherein the anti-CD43 antibody or the antigen-binding fragment thereof is administered together with a cytotoxic material.

9. The method of claim 8, wherein the cytotoxic material is at least one selected from the group consisting of ricin, saporin, gelonin, momordin, debouganin, diphtheria toxin, *pseudomonas* toxin, radioisotopes, duocarmycin, monomethyl auristatin E (MMAE), monomethyl auristatin F (MMAF), N2'-deacetyl-N2'-(3-mercapto-1-oxopropyl)maytansine (DM1), and pyrrolobenzodiazepine (PBD) dimer.

* * * * *